United States Patent
Zhang et al.

(10) Patent No.: US 12,428,396 B2
(45) Date of Patent: Sep. 30, 2025

(54) FUSED PYRIDINE RING DERIVATIVE, PREPARATION METHOD THEREFOR, AND PHARMACEUTICAL USE THEREOF

(71) Applicants: JIANGSU HENGRUI MEDICINE CO., LTD., Jiangsu (CN); SHANGHAI HENGRUI PHARMACEUTICAL CO., LTD., Shanghai (CN)

(72) Inventors: Xiaomin Zhang, Shanghai (CN); Weimin Hu, Shanghai (CN); Feng He, Shanghai (CN); Chaobaihui Ye, Shanghai (CN)

(73) Assignees: Jiangsu Hengrui Medicine Co., Ltd., Lianyungang Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 335 days.

(21) Appl. No.: 17/756,545

(22) PCT Filed: Nov. 27, 2020

(86) PCT No.: PCT/CN2020/132026
§ 371 (c)(1),
(2) Date: May 26, 2022

(87) PCT Pub. No.: WO2021/104413
PCT Pub. Date: Jun. 3, 2021

(65) Prior Publication Data
US 2023/0023968 A1    Jan. 26, 2023

(30) Foreign Application Priority Data

| Nov. 29, 2019 | (CN) | 201911198968.9 |
| Feb. 20, 2020 | (CN) | 202010104095.7 |
| Jun. 4, 2020 | (CN) | 202010500013.0 |
| Jul. 9, 2020 | (CN) | 202010656009.3 |

(51) Int. Cl.
*C07D 401/14*    (2006.01)

(52) U.S. Cl.
CPC .................. *C07D 401/14* (2013.01)

(58) Field of Classification Search
CPC ..... C07D 401/14; C07D 401/04; A61P 31/18; A61K 31/435; A61K 31/4725
See application file for complete search history.

(56) References Cited

FOREIGN PATENT DOCUMENTS

| CN | 1720043 A | 1/2006 |
| CN | 101010299 A | 8/2007 |
| CN | 105705500 A | 6/2016 |
| CN | 109890808 A | 6/2019 |
| WO | 03035076 A1 | 5/2003 |
| WO | 2013006738 A1 | 1/2013 |
| WO | 2014110297 A1 | 7/2014 |
| WO | 2014134566 A2 | 9/2014 |
| WO | 2016033243 A1 | 3/2016 |
| WO | 2018035359 A1 | 2/2018 |
| WO | WO-2018203235 A1 * | 11/2018 ............. A61P 31/18 |
| WO | 2019035904 A1 | 2/2019 |
| WO | 2019161017 A1 | 8/2019 |

OTHER PUBLICATIONS

International Search Report issued Mar. 3, 2021 in PCT/CN2020/132026.
Engelman, A., et al., "The structural biology of HIV-1: mechanistic and therapeutic insights," Nature Reviews, Microbiology, vol. 10, pp. 279-290, Apr. 2012.
Flexner, Charles, "HIV drug development: the next 25 years," Nature Reviews, Drug Discovery, vol. 6, pp. 959-966, Dec. 2007.
Grant, Robert M., et al., "Time Trends in Primary HIV-1 Drug Resistance Among Recently Infected Persons," American Medical Association, JAMA, vol. 288, No. 2, pp. 181-188, Jul. 10, 2002.
Smith, Robert J., "Evolutionary Dynamics of Complex Networks of HIV Drug-Resistant Strains: The Case of San Francisco," Science, vol. 327, pp. 697-701, Feb. 5, 2010.
Bednarova, Eva, et al., "A Ruthenium Complex-Catalyzed Cyclotrimerization of Halo-diynes with Nitriles. Synthesis of 2- and 3-Haopyridines," Advanced Synthesis & Catalysis, vol. 358, pp. 1916-1923, 2016.
Hartmann, Eduard, et al., "Two-Directional Desymmetrization by Double 1,4-Addition of Silicon and Boron Nucelophiles," Organic Letters, vol. 14, No. 9, pp. 2406-2409, Apr. 16, 2012.

* cited by examiner

*Primary Examiner* — Joseph K McKane
*Assistant Examiner* — Meghan C Heasley
(74) *Attorney, Agent, or Firm* — Ice Miller LLP

(57) ABSTRACT

A fused pyridine ring derivative represented by general formula (I), a preparation method therefor, a pharmaceutical composition containing the derivative, and a use thereof as a therapeutic agent, particularly, in preparation of drugs for preventing and/or treating HIV infection.

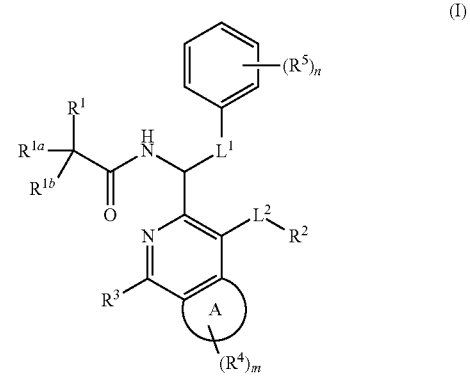

19 Claims, 3 Drawing Sheets

FUSED PYRIDINE RING DERIVATIVE, PREPARATION METHOD THEREFOR, AND PHARMACEUTICAL USE THEREOF

CROSS-REFERENCE TO RELATED APPLICATION

This application is a Section 371 of International Application No. PCT/CN2020/132026 filed Nov. 27, 2020, which was published in the Chinese language Jun. 3, 2021, under International Publication No. WO 2021/104413 A1, which claims priority to Chinese Patent Application No. 201911198968.9 filed Nov. 29, 2019, Chinese Patent Application No. 202010104095.7 filed Feb. 20, 2020, Chinese Patent Application No. 202010500013.0 filed Jun. 4, 2020, and Chinese Patent Application No. 20201065009.3 filed Jul. 9, 2020, the disclosures of which are incorporated herein by reference in their entireties.

TECHNICAL FIELD

The present disclosure belongs to the field of pharmaceutics and relates to a fused pyridine ring derivative of general formula (I), a preparation method therefor, a pharmaceutical composition containing the derivative, and use of the derivative as a therapeutic agent, and in particular to use of the derivative in the preparation of a medicament for preventing and/or treating HIV infection.

BACKGROUND

AIDS (acquired immune deficiency syndrome), which is a fatal infectious disease caused by human immunodeficiency virus (HIV), has the pathogenesis that the functions of $CD4^+T$ lymphocytes are damaged and largely destroyed under the direct and indirect action of the HIV virus, causing cellular immunodeficiency and various serious opportunistic infections and tumorigenesis. Today, over 35 million of people worldwide have been infected with the HIV virus.

Current therapy for HIV infected patients is composed of combinations of highly active antiretroviral drugs (HAART) mainly including nucleotide reverse transcriptase inhibitors (NRTIs), non-nucleotide reverse transcriptase inhibitors (NNRTIs), protease inhibitors (PIs), integrase strand transfer inhibitors (INIs) or entry inhibitors. These drugs effectively inhibit viral load and rate of transmission by targeting viral enzymes or viral proteins at various stages in the HIV viral replication cycle, thus significantly delaying the progression of the disease, thereby prolonging the life of the patient (Engelman, A., Cherepanov, P., *Nature Reviews* 2012, 10, 279-290; Flexner, C., *Nature Rev Drug Discov.* 2007, 6, 959-966).

However, these combination therapies are susceptible to the development of drug-resistant strains of HIV due to the rapid replication and high mutation rate of human immunodeficiency virus type 1 (HIV-1), which ultimately leads to drug failure, viral escape and exacerbation (Grant, R. M., Hecht, F. M., Warmerdam, M., *JAMA* 2002, 288, 181-188-559; Smith, R. J., Okano, J. T., Kahn, J. S., Bodine, E. N., Blower, S., *Science* 2010, 327, 697-701). Therefore, there is an urgent need to develop novel antiretroviral drugs that are active against the newly emerging drug-resistant HIV variants. In particular, novel developed drugs demonstrate high genetic disorder on drug resistance and have higher safety and patient compliance than the existing drugs.

Patent applications for treatment of HIV infection that have been disclosed include WO2013006738, WO2014110297, WO2014134566, WO2018035359, WO2019035904, WO2018203235 and the like.

SUMMARY

The present disclosure is intended to provide a compound of general formula (I) or an atropisomer, tautomer, mesomer, racemate, enantiomer, diastereomer thereof or a mixture thereof, or a pharmaceutically acceptable salt thereof,

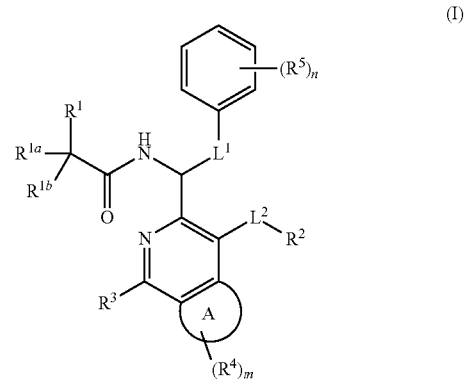

wherein,
ring A is selected from the group consisting of cycloalkyl, heterocyclyl and aryl;
$L^1$ is alkylene;
$L^2$ is absent or selected from the group consisting of —$CH_2$—, —O—, —S— and —$NR^6$—;
$R^1$ is selected from the group consisting of cycloalkyl, heterocyclyl, aryl and heteroaryl, wherein the cycloalkyl, heterocyclyl, aryl and heteroaryl are each independently optionally substituted with one or more substituents selected from the group consisting of oxo, halogen, alkyl, haloalkyl, cyano, amino, nitro, hydroxy, hydroxyalkyl and cycloalkyl;
$R^{1a}$ and $R^{1b}$ are identical or different and are each independently selected from the group consisting of hydrogen, halogen, alkyl and haloalkyl;
$R^2$ is selected from the group consisting of cycloalkyl, heterocyclyl, aryl and heteroaryl, wherein the cycloalkyl, heterocyclyl, aryl and heteroaryl are each independently optionally substituted with one or more substituents selected from the group consisting of oxo, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O)R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$;
$R^3$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$S(O)_rR^9$, —$C(O)R^9$ and —$C(O)NR^{10}R^{11}$, wherein the alkyl, alkenyl, alkynyl, alkoxy, haloalkyl, hydroxyalkyl, cycloalkyl, heterocyclyl, aryl and heteroaryl are each independently optionally substituted with one or more substituents selected from the group consisting of oxo, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR$^9$, —OC(O)R$^9$, —OC(O)NR$^{10}$R$^{11}$, —NHS(O)$_r$R$^9$, —NHS(O)$_2$OR$^9$, —NHS(O)$_2$NR$^{10}$R$^{11}$, —C(O)R$^9$, —C(O)OR$^9$, —C(O)NR$^{10}$R$^{11}$, —S(O)$_r$R$^9$, —S(O)$_r$NR$^{10}$R$^{11}$, —NR$^{10}$R$^{11}$, —NHC(O)R$^9$, —NHC(O)OR$^9$, —NHC(O)NR$^{10}$R$^{11}$ and —NHC(O)NHOR$^9$;

R$^4$ is identical or different and is each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;

R$^5$ is identical or different and is each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;

R$^6$ and R$^9$ are identical or different and are each independently selected from the group consisting of hydrogen, alkyl, cycloalkyl, heterocyclyl, aryl and heteroaryl, wherein the alkyl, cycloalkyl, heterocyclyl, aryl or heteroaryl is each independently optionally substituted with one or more substituents selected from the group consisting of alkyl, halogen, hydroxy, alkoxy, cycloalkyl, heterocyclyl, aryl and heteroaryl;

R$^7$, R$^8$, R$^{10}$ and R$^{11}$ are identical or different and are each independently selected from the group consisting of hydrogen, alkyl, cycloalkyl, heterocyclyl, aryl, heteroaryl, —C(O)R$^6$ and —S(O)$_r$R$^6$, wherein the alkyl, cycloalkyl, heterocyclyl, aryl and heteroaryl are each independently optionally substituted with one or more substituents selected from the group consisting of alkyl, halogen, hydroxy, alkoxy, cycloalkyl, heterocyclyl, aryl and heteroaryl;

m is 0, 1, 2, 3, 4, 5 or 6;

n is 0, 1, 2, 3, 4 or 5; and r is 0, 1 or 2.

In some embodiments of the present disclosure, the compound of general formula (I) or the atropisomer, tautomer, mesomer, racemate, enantiomer, diastereomer thereof or the mixture thereof, or the pharmaceutically acceptable salt thereof according to the present disclosure is a compound of general formula (I-1) or general formula (1-2) or an atropisomer, tautomer, mesomer, racemate, enantiomer, diastereomer thereof, or a mixture thereof, or a pharmaceutically acceptable salt thereof,

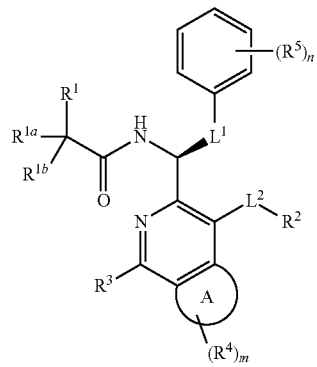

(I-1)

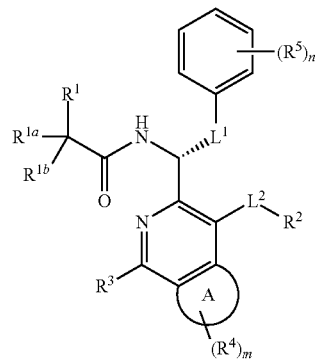

(I-2)

wherein, ring A, L$^1$, L$^2$, R$^1$-R$^5$, R$^{1a}$, R$^{1b}$, m and n are as defined in general formula (I).

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, L$^1$ is methylene.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, L$^2$ is absent.

In some embodiments of the present disclosure, the compound of general formula (I) or the atropisomer, tautomer, mesomer, racemate, enantiomer, diastereomer thereof or the mixture thereof, or the pharmaceutically acceptable salt thereof according to the present disclosure is a compound of general formula (II), general formula (II-1) or general formula (II-2) or an atropisomer, tautomer, mesomer, racemate, enantiomer, diastereomer thereof or a mixture thereof or a pharmaceutically acceptable salt thereof,

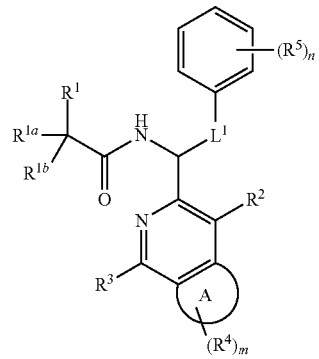

(II)

-continued (II-1)

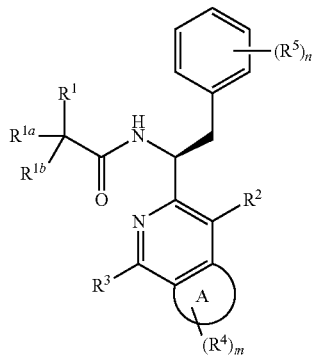

(II-2)

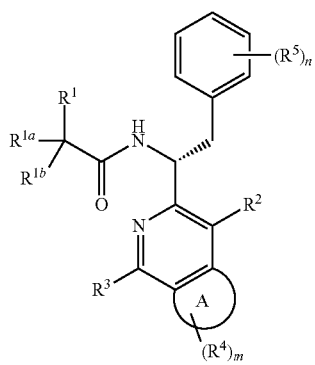

wherein, ring A, $R^1$-$R^5$, $R^{1a}$, $R^{1b}$, m and n are as defined in general formula (I).

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{1a}$ and $R^{1b}$ are each independently hydrogen.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^1$ is

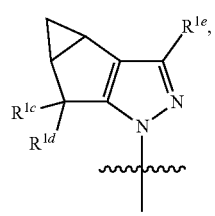

and preferably is

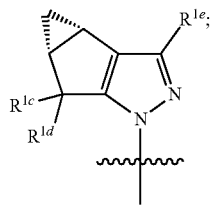

$R^{1c}$, $R^{1d}$ and $R^{1e}$ are identical or different and are each independently selected from the group consisting of hydrogen, halogen, alkyl, haloalkyl, cyano, amino, nitro, hydroxy, hydroxyalkyl and cycloalkyl; preferably, $R^{1c}$ and $R^{1d}$ are identical or different and are each independently hydrogen or halogen; $R^{1e}$ is selected from the group consisting of hydrogen, halogen, $C_{1-6}$ alkyl and halogenated $C_{1-6}$ alkyl.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^2$ is

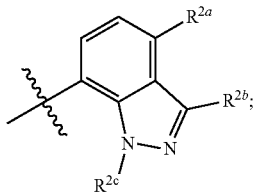

$R^{2a}$, $R^{2b}$ and $R^{2c}$ are identical or different and are each independently selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O)R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$; $R^6$-$R^8$ and r are as defined in general formula (I); preferably, $R^{2a}$ is selected from the group consisting of hydrogen, halogen and $C_{1-6}$ alkyl; $R^{2b}$ is —$NHS(O)_2R^6$, $R^6$ is $C_{1-6}$ alkyl or $C_{3-6}$ cycloalkyl; preferably, $R^6$ is $C_{1-6}$ alkyl; $R^{2c}$ is $C_{1-6}$ alkyl or halogenated $C_{1-6}$ alkyl.

In some embodiments of the present disclosure, the compound of general formula (I) or the atropisomer, tautomer, mesomer, racemate, enantiomer, diastereomer thereof or the mixture thereof, or the pharmaceutically acceptable salt thereof according to the present disclosure is a compound of general formula (III), general formula (III-1) or general formula (III-2) or an atropisomer, tautomer, mesomer, racemate, enantiomer, diastereomer thereof, or a mixture thereof, or a pharmaceutically acceptable salt thereof,

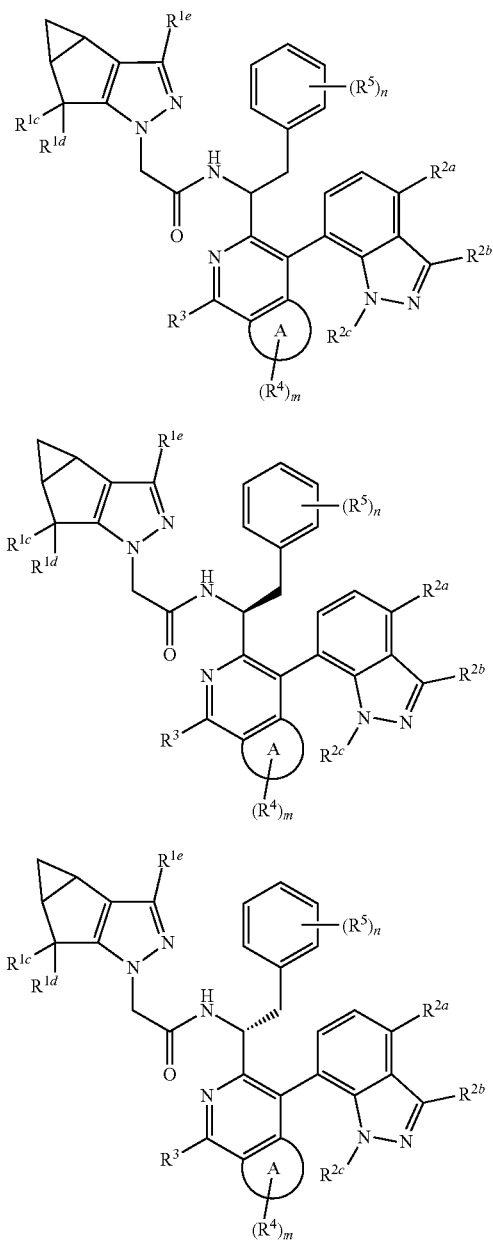

(III)

(III-1)

(III-2)

wherein, $R^{1c}$, $R^{1d}$ and $R^{1e}$ are identical or different and are each independently selected from the group consisting of hydrogen, halogen, alkyl, haloalkyl, cyano, amino, nitro, hydroxy, hydroxyalkyl and cycloalkyl;

$R^{2a}$, $R^{2b}$ and $R^{2c}$ are identical or different and are each independently selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O)R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$; and ring A, $R^3$-$R^8$, m, n and r are as defined in general formula (I).

In some embodiments of the present disclosure, the compound of general formula (I) or the atropisomer, tautomer, mesomer, racemate, enantiomer, diastereomer thereof or the mixture thereof, or the pharmaceutically acceptable salt thereof according to the present disclosure is a compound of general formula (III-1a) or general formula (III-1b) or an atropisomer, tautomer, mesomer, racemate, enantiomer, diastereomer thereof, or a mixture thereof, or a pharmaceutically acceptable salt thereof,

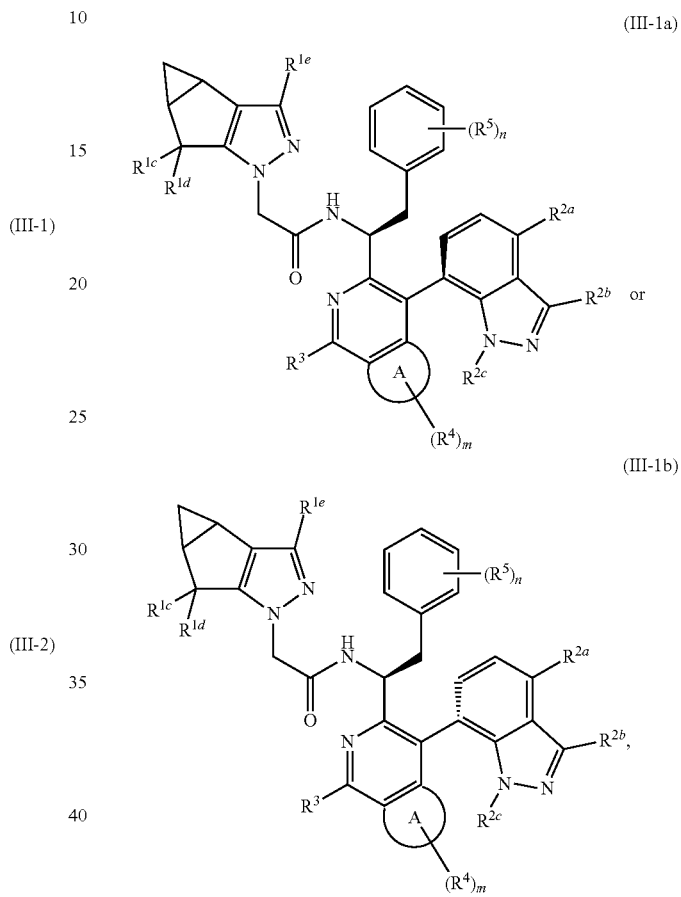

(III-1a)

(III-1b)

wherein, ring A, $R^{1c}$, $R^{1d}$, $R^{1e}$, $R^{2a}$, $R^{2b}$, $R^{2c}$, $R^3$-$R^5$, m and n are as defined in general formula (III).

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, the structure

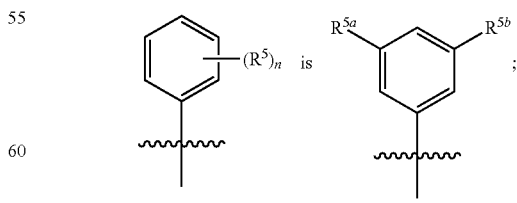

$R^{5a}$ and $R^{5b}$ are identical or different and are each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl; preferably, $R^{5a}$ and $R^{5b}$ are identical or different and are each independently halogen.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, ring A is selected from the group consisting of cycloalkyl, heterocyclyl and aryl, and the heterocyclyl is a saturated or partially unsaturated monocyclic or polycyclic hydrocarbon substituent.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, ring A is selected from the group consisting of $C_{3-6}$ cycloalkyl, phenyl and 3-6 membered heterocyclyl; preferably, ring A is selected from the group consisting of

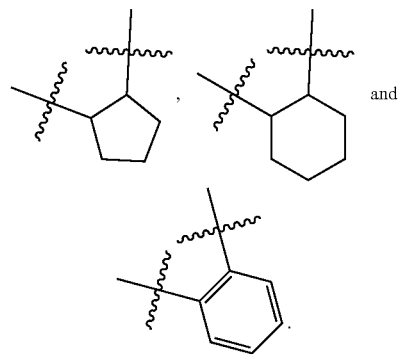

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, ring A is selected from the group consisting of $C_{3-6}$ cycloalkyl and 3-6 membered heterocyclyl, preferably

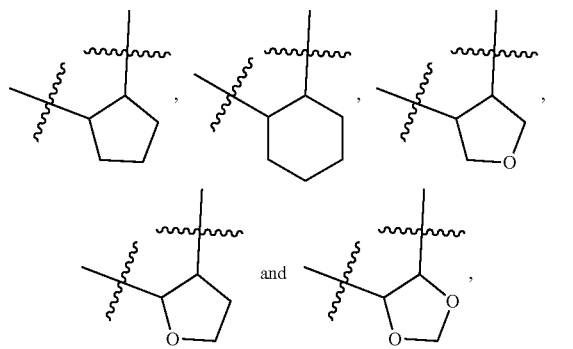

and more preferably,

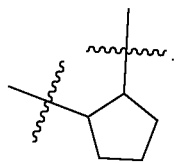 [SMILES: *C1CCCC1*]

In some embodiments of the present disclosure, the compound of general formula (I) or the atropisomer, tautomer, mesomer, racemate, enantiomer, diastereomer thereof or the mixture thereof, or the pharmaceutically acceptable salt thereof according to the present disclosure is a compound of general formula (IV), general formula (IV-1) or general formula (IV-2) or an atropisomer, tautomer, mesomer, racemate, enantiomer, diastereomer thereof, or a mixture thereof, or a pharmaceutically acceptable salt thereof,

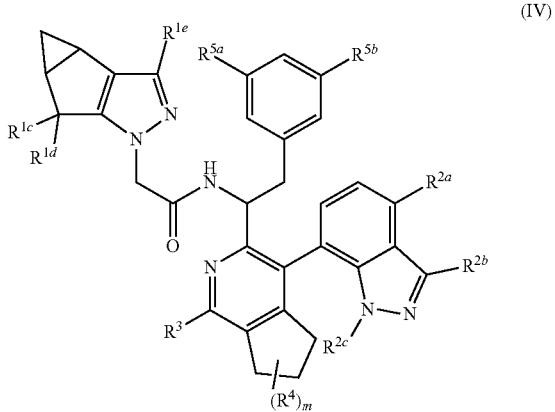

(IV)

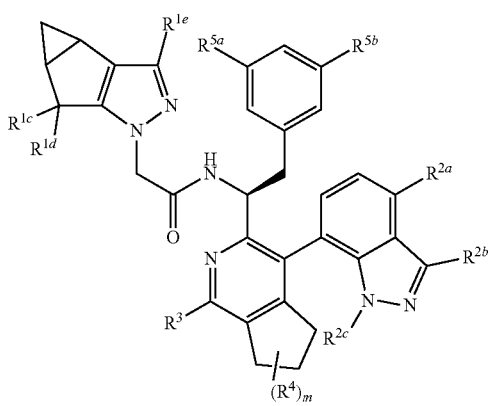

(IV-1)

(IV-2)

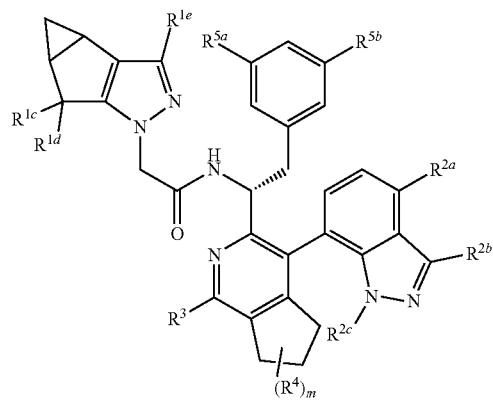

wherein, $R^{5a}$ and $R^{5b}$ are identical or different and are each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl; and $R^{1c}$, $R^{1d}$, $R^{1e}$, $R^{2a}$, $R^{2b}$, $R^{2c}$, $R^3$, $R^4$ and m are as defined in general formula (III).

In some embodiments of the present disclosure, the compound of general formula (I) or the atropisomer, tautomer, mesomer, racemate, enantiomer, diastereomer thereof or the mixture thereof, or the pharmaceutically acceptable salt thereof according to the present disclosure is a compound of general formula (IV-1a) or general formula (IV-1b) or an atropisomer, tautomer, mesomer, racemate, enantiomer, diastereomer thereof, or a mixture thereof, or a pharmaceutically acceptable salt thereof, (IV-1a)

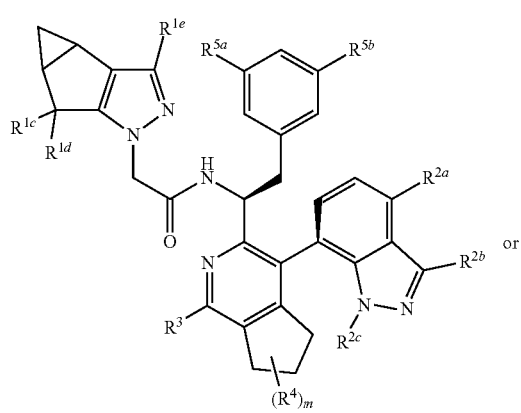

or (IV-1b)

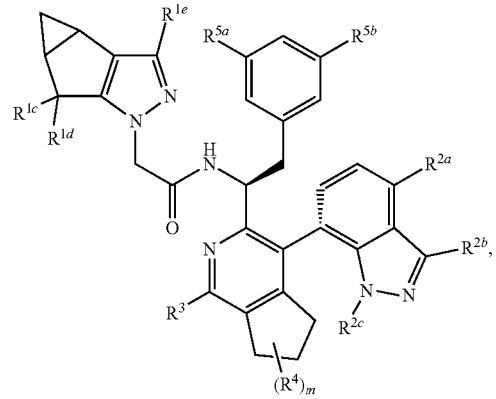

wherein, $R^{1c}$, $R^{1d}$, $R^{1e}$, $R^{2a}$, $R^{2b}$, $R^{2c}$, $R^3$, $R^4$, $R^{5a}$, $R^{5b}$ and m are as defined in general formula (IV).

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{2b}$ is —NHS(O)$_2$R$^6$; R$^6$ is C$_{1-6}$ alkyl or C$_{3-6}$ cycloalkyl; preferably, R$^6$ is C$_{1-6}$ alkyl.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{2b}$ is —NHS(O)$_2$R$^6$; R$^6$ is as defined in general formula (I) and R$^6$ is preferably alkyl.

In some embodiments of the present disclosure, the compound of general formula (I) or the atropisomer, tautomer, mesomer, racemate, enantiomer, diastereomer thereof or the mixture thereof, or the pharmaceutically acceptable salt thereof according to the present disclosure is a compound of general formula (V), general formula (V-1) or general formula (V-2) or an atropisomer, tautomer, mesomer, racemate, enantiomer, diastereomer thereof, or a mixture thereof, or a pharmaceutically acceptable salt thereof, (V)

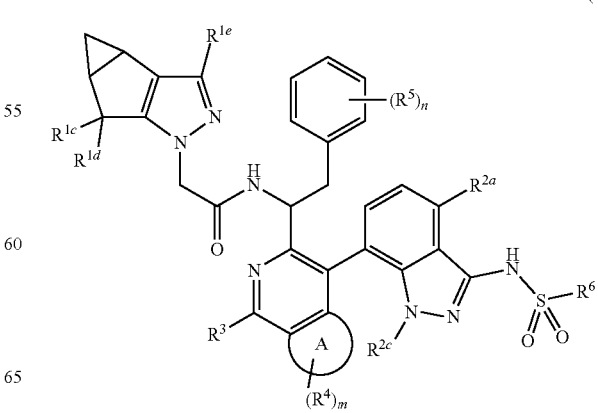

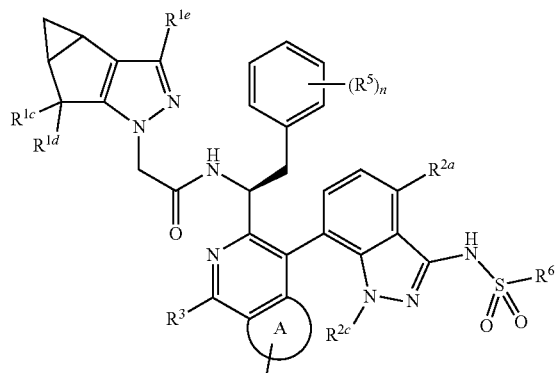

(V-1)

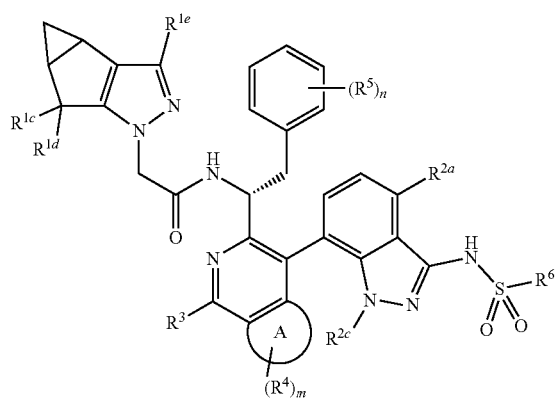

(V-2)

wherein $R^6$ is $C_{1-6}$ alkyl or $C_{3-6}$ cycloalkyl; preferably, $R^6$ is $C_{1-6}$ alkyl;

$R^{1c}$, $R^{1d}$, $R^{1e}$, $R^{2a}$, $R^{2c}$, $R^3$-$R^5$, m and n are as defined in general formula (III).

In some embodiments of the present disclosure, the compound of general formula (I) or the atropisomer, tautomer, mesomer, racemate, enantiomer, diastereomer thereof or the mixture thereof, or the pharmaceutically acceptable salt thereof according to the present disclosure is a compound of general formula (VI), general formula (VI-1) or general formula (VI-2) or an atropisomer, tautomer, mesomer, racemate, enantiomer, diastereomer thereof, or a mixture thereof, or a pharmaceutically acceptable salt thereof,

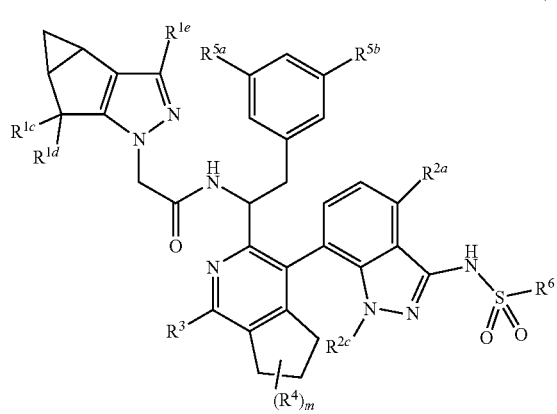

(VI)

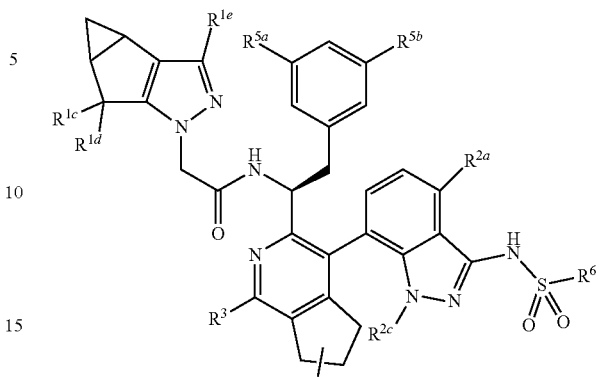

(VI-1)

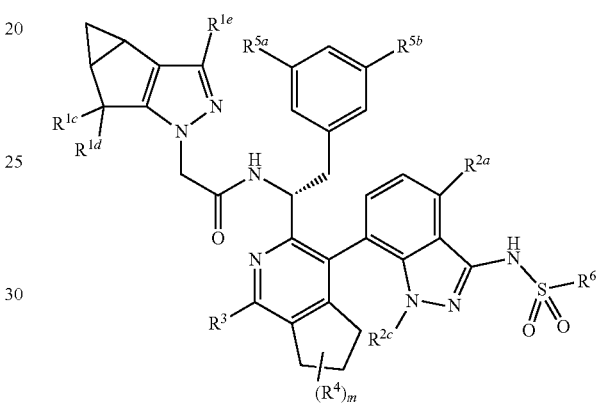

(VI-2)

wherein $R^6$ is $C_{1-6}$ alkyl or $C_{3-6}$ cycloalkyl; preferably, $R^6$ is $C_{1-6}$ alkyl;

$R^{1c}$, $R^{1d}$, $R^{1e}$, $R^{2a}$, $R^{2c}$, $R^{5a}$, $R^{5b}$, $R^3$, $R^4$ and m are as defined in general formula (IV).

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{1c}$ and $R^{1d}$ are each independently halogen, and preferably fluorine.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{1e}$ is haloalkyl, and preferably, $R^{1e}$ is halogenated $C_{1-6}$ alkyl; more preferably, $R^{1e}$ is $CF_3$.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{1e}$ is haloalkyl, and preferably $CF_3$.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{2a}$ is halogen, and preferably chlorine.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{2c}$ is haloalkyl, and preferably, $R^{2c}$ is halogenated $C_{1-6}$ alkyl; more preferably, $R^{2c}$ is —$CH_2CF_3$.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^2$ is haloalkyl, and preferably —$CH_2CF_3$.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^{5a}$ and $R^{5b}$ are identical or different and are each independently halogen, and preferably fluorine.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^6$ is $C_{1-6}$ alkyl or $C_{3-6}$ cycloalkyl; preferably, $R^6$ is $C_{1-6}$ alkyl.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^6$ is alkyl.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^3$ is $C_{2-12}$ alkynyl, the $C_{2-12}$ alkynyl being optionally substituted with one or more —$S(O)_2R^9$; $R^9$ is $C_{1-6}$ alkyl or $C_{3-6}$ cycloalkyl; preferably, $R^3$ is

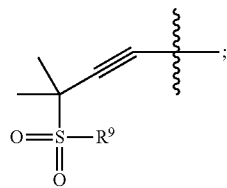

$R^9$ is $C_{1-6}$ alkyl or $C_{3-6}$ cycloalkyl; more preferably, $R^9$ is $C_{1-6}$ alkyl.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^3$ is alkynyl, the alkynyl being optionally substituted with one or more —$S(O)_2R^9$; $R^3$ is preferably

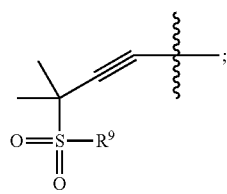

$R^9$ is alkyl.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^4$ is identical or different and is each independently hydrogen or halogen.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^4$ is hydrogen.

In some embodiments of the present disclosure, for the compound of general formula (I) or the atropisomer, tautomer, mesomer, racemate, enantiomer, diastereomer thereof or the mixture thereof, or the pharmaceutically acceptable salt thereof according to the present disclosure, $R^5$ is identical or different and is each independently selected from the group consisting of hydrogen and halogen, preferably halogen, and more preferably fluorine.

Typical compounds disclosed herein include, but are not limited to:

| Example | Structure and name of compound |
|---|---|
| | 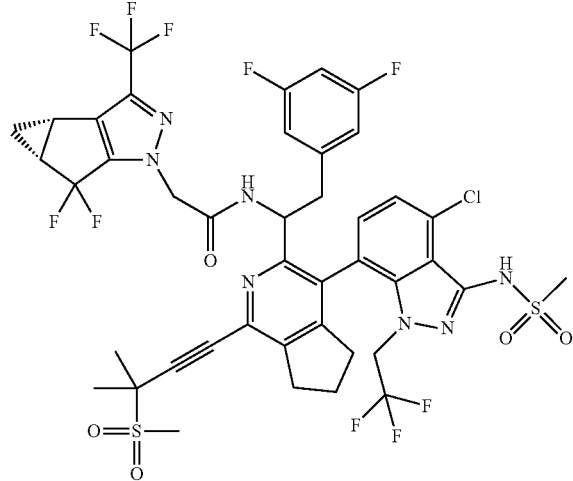<br>N-(1-(-4-(4-chloro-3-(methanesulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |
| | 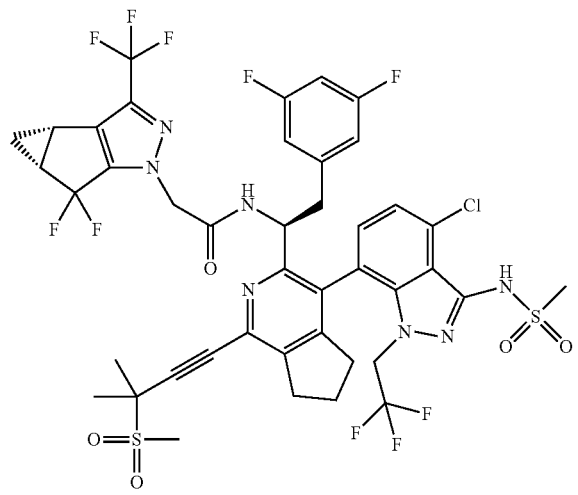 [SMILES: CC(C)(C#Cc1nc([C@H](Cc2cc(F)cc(F)c2)NC(=O)Cn2nc(C(F)(F)F)c3c2C(F)(F)[C@@H]2C[C@H]32)c(-c2ccc(Cl)c3c(NS(C)(=O)=O)nn(CC(F)(F)F)c23)c2c1CCC2)S(C)(=O)=O]<br>N-((S)-1-(-4-(4-chloro-3-(methanesulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |

| Example | Structure and name of compound |
|---|---|
|  | 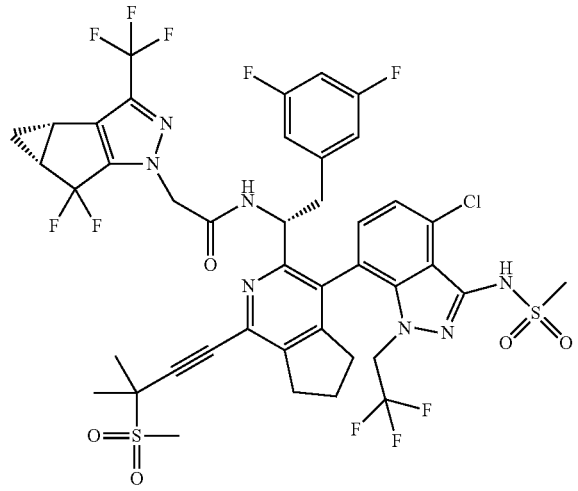 [SMILES: CC(C)(C#Cc1nc([C@@H](Cc2cc(F)cc(F)c2)NC(=O)Cn2nc(C(F)(F)F)c3c2C(F)(F)[C@@H]2C[C@H]32)c(-c2ccc(Cl)c3c(NS(C)(=O)=O)nn(CC(F)(F)F)c23)c2c1CCC2)S(C)(=O)=O]<br>N-((R)-1-(-4-(4-chloro-3-(methanesulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |
| 1-2 | 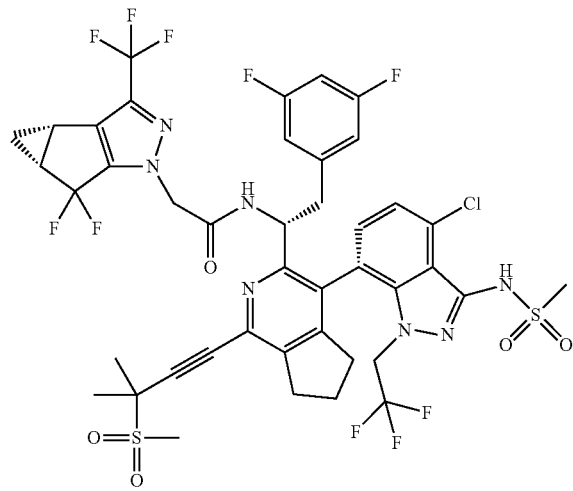<br>1-2<br>N-((R)-1-((S)-4-(4-chloro-3-(methanesulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 1-2 |

| Example | Structure and name of compound |
|---|---|
| 1-1/1-1a | 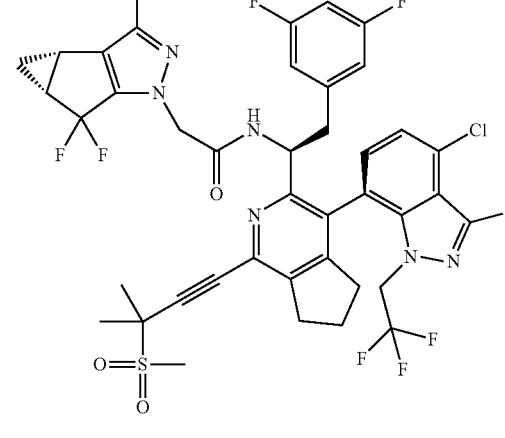<br>1-1a<br><br>N-((S)-1-((R)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 1-1/1-1a |
| 1-1b | 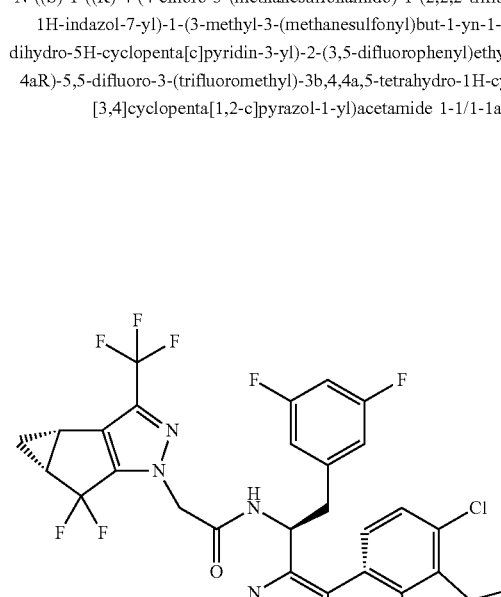<br>1-1b<br><br>N-((S)-1-((S)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 1-1b |

| Example | Structure and name of compound |
|---|---|
| | 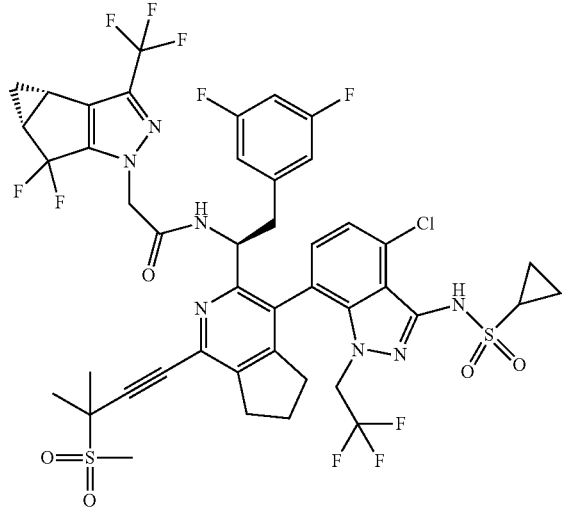<br>N-((S)-1-(-4-(4-chloro-3-(cyclopropylsulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS, 4aR)-5,5-difluoro-3-(trifluoromethyl)-3b,4,4a,5-tetrahydro-1H-cyclopropa[3,4]cyclopenta[1,2-c]pyrazol-1-yl)acetamide |
| 2 | 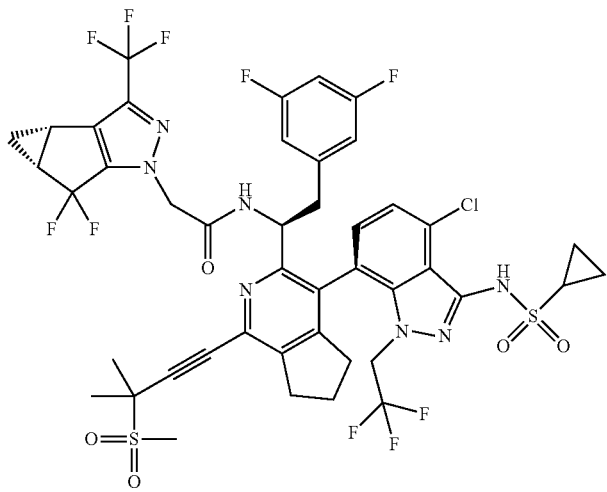<br>2<br>N-((S)-1-((R)-4-(4-chloro-3-(cyclopropylsulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS, 4aR)-5,5-difluoro-3-(trifluoromethyl)-3b,4,4a,5-tetrahydro-1H-cyclopropa[3,4]cyclopenta[1,2-c]pyrazol-1-yl)acetamide 2 |

| Example | Structure and name of compound |
| --- | --- |
| | 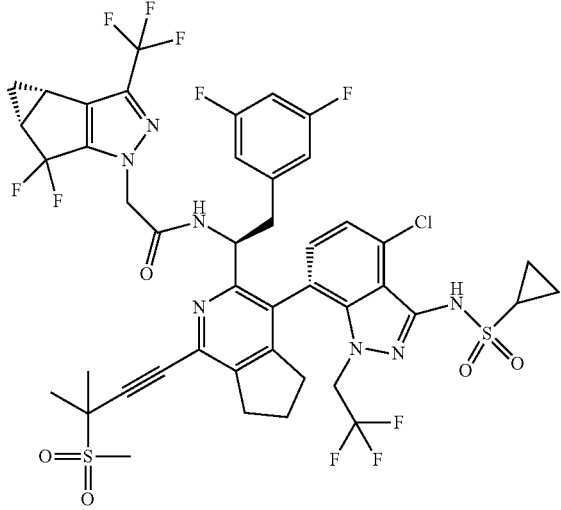

N-((S)-1-((S)-4-(4-chloro-3-(cyclopropylsulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |
| | 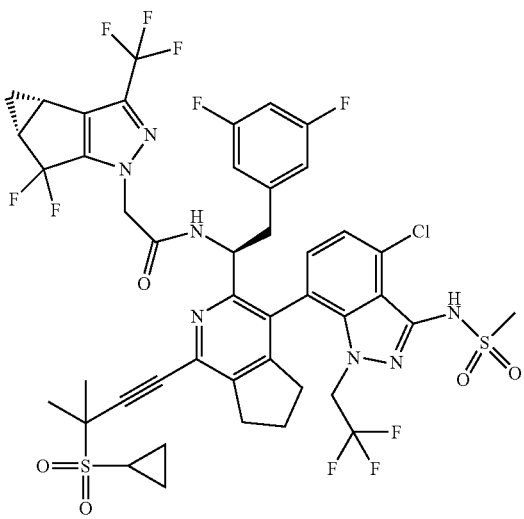 [SMILES: CC(C)(C#Cc1nc([C@H](Cc2cc(F)cc(F)c2)NC(=O)Cn2nc(C(F)(F)F)c3c2C(F)(F)[C@@H]2C[C@H]32)c(-c2ccc(Cl)c3c(NS(C)(=O)=O)nn(CC(F)(F)F)c23)c2c1CCC2)S(=O)(=O)C1CC1]

N-((S)-1-(-4-(4-chloro-3-(methanesulfonamido)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |

| Example | Structure and name of compound |
|---|---|
| 3 | 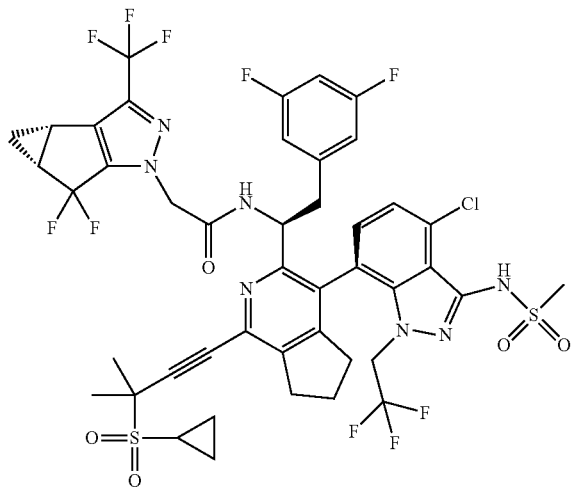

3

N-((S)-1-((R)-4-(4-chloro-3-(methanesulfonamido)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 3

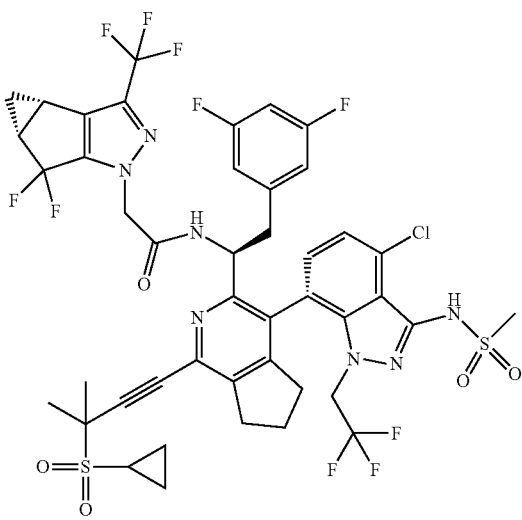

N-((S)-1-((S)-4-(4-chloro-3-(methanesulfonamido)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |

| Example | Structure and name of compound |
|---|---|
| | 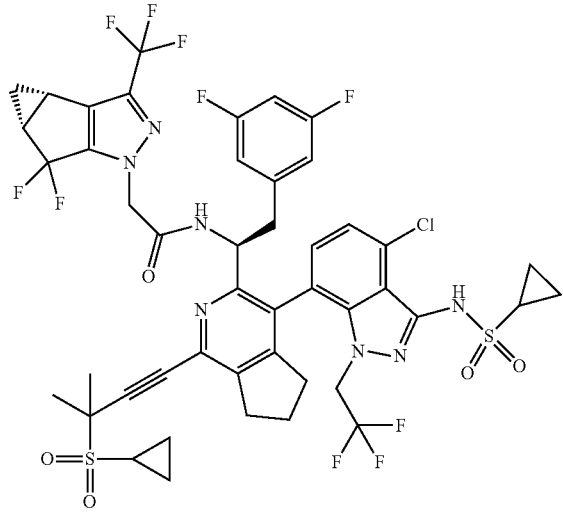 [SMILES: CC(C)(C#Cc1nc([C@H](Cc2cc(F)cc(F)c2)NC(=O)Cn2nc(C(F)(F)F)c3c2C(F)(F)[C@@H]2C[C@H]32)c(-c2ccc(Cl)c3c(NS(=O)(=O)C4CC4)nn(CC(F)(F)F)c23)c2c1CCC2)S(=O)(=O)C1CC1]

N-((S)-1-(-4-(4-chloro-3-(cyclopropylsulfonamide)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |
| 4 | 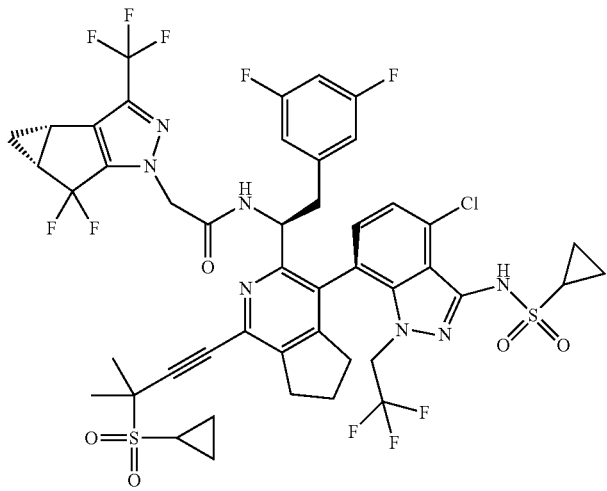

N-((S)-1-((R)-4-(4-chloro-3-(cyclopropylsulfonamide)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 4 |

| Example | Structure and name of compound |
| --- | --- |

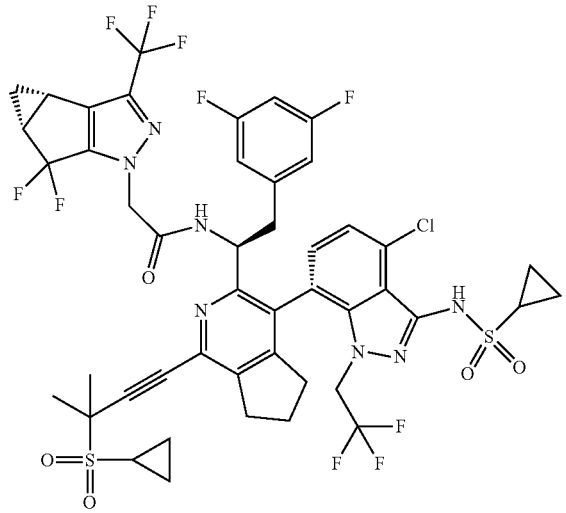

N-((S)-1-((S)-4-(4-chloro-3-(cyclopropylsulfonamide)-1-(2,2,2-trifluoroethyl)-
1H-indazol-7-yl)-1-(3-(cyclopropylsulfonyl)-3-methyl-but-1-yn-1-yl)-
6,7-dihydro-5H-cyclopenta[c]pyridin-3-yl)-2-(3,5-difluorophenyl)ethyl)-
2-((3bS,4aR)-5,5-difluoro-3-(trifluoromethyl)-3b,4,4a,5-tetrahydro-1H-
cyclopropa[3,4]cyclopenta[1,2-c]pyrazol-1-yl)acetamide

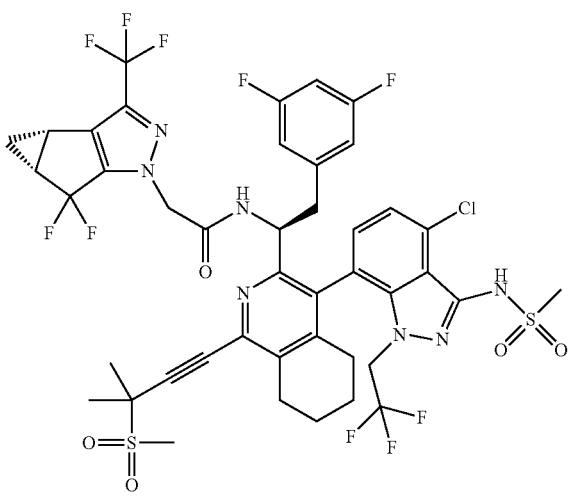

N-((S)-1-(-4-(4-chloro-3-(methanesulfonamido)-1-(2,2,2-trifluoroethyl)-1H
indazol-7-yl)-1-(3-methyl-3-(methanesulfonyl)but-1-yn-1-yl)-5,6,7,8-
tetrahydroisoquinolin-3-yl)-2-(3,5-difluorophenyl)ethyl)-2-((3bS,4aR)-5,5-
difluoro-3-(trifluoromethyl)-3b,4,4a,5-tetrahydro-1H-cyclopropa[3,4]
cyclopenta[1,2-c]pyrazol-1-yl)acetamide

| Example | Structure and name of compound |
|---|---|
| 5-1 | 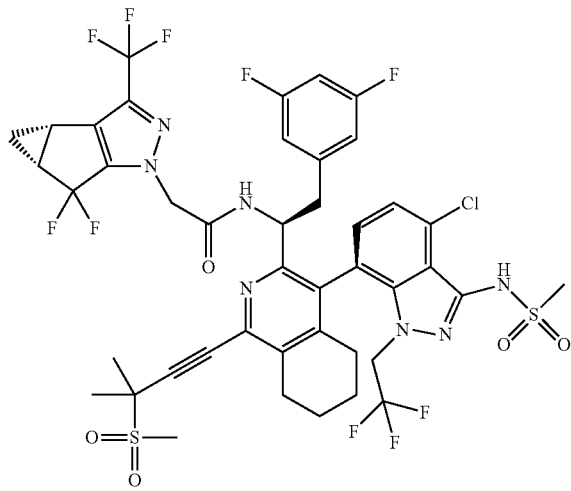<br>5-1<br><br>N-((S)-1-((R)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-5,6,7,8-tetrahydroisoquinolin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 5-1 |
| 5-2 | 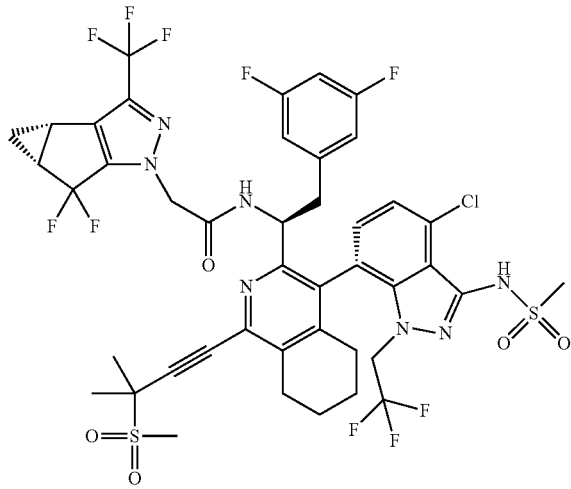 [SMILES: CC(C)(C#Cc1nc([C@H](Cc2cc(F)cc(F)c2)NC(=O)Cn2nc(C(F)(F)F)c3c2C(F)(F)[C@@H]2C[C@H]32)c(-c2ccc(Cl)c3c(NS(C)(=O)=O)nn(CC(F)(F)F)c23)c2c1CCCC2)S(C)(=O)=O]<br>5-2<br><br>N-((S)-1-((S)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-5,6,7,8-tetrahydroisoquinolin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 5-2 |

| Example | Structure and name of compound |
|---------|-------------------------------|
|  | 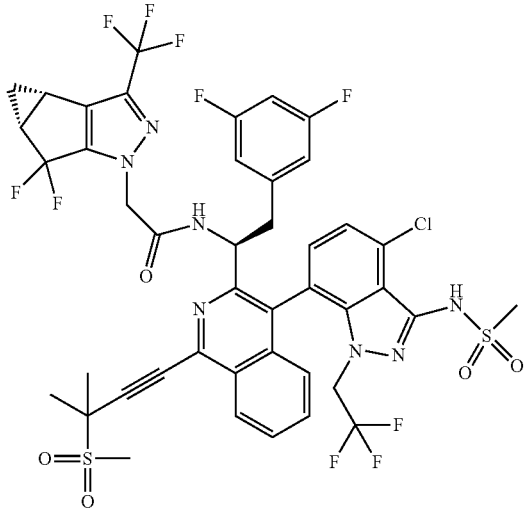 [SMILES: CC(C)(C#Cc1nc([C@H](Cc2cc(F)cc(F)c2)NC(=O)Cn2nc(C(F)(F)F)c3c2C(F)(F)[C@@H]2C[C@H]32)c(-c2ccc(Cl)c3c(NS(C)(=O)=O)nn(CC(F)(F)F)c23)c2ccccc12)S(C)(=O)=O]<br>N-((S)-1-(-4-(4-chloro-3-(methanesulfonamido)-1-(2,2,2-trifluoroethyl)-1H-indazol-7-yl)-1-(3-methyl-3-(methanesulfonyl)but-1-yn-1-yl)isoquinolin-3-yl)-2-(3,5-difluorophenyl)ethyl)-2-((3bS,4aR)-5,5-difluoro-3-(trifluromethyl)-3b,4,4a,5-tetrahydro-1H-cyclopropa[3,4]cyclopenta[1,2-c]pyrazol-1-yl)acetamide |
| 6 | 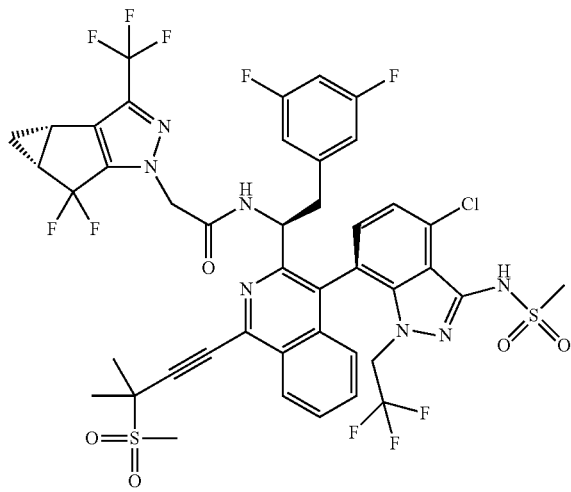<br>6<br>N-((S)-1-((R)-4-(4-chloro-3-(methanesulfonamido)-1-(2,2,2-trifluoroethyl)-1H-indazol-7-yl)-1-(3-methyl-3-(methanesulfonyl)but-1-yn-1-yl)isouinolin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 6 |

| Example | Structure and name of compound |
|---|---|
| | 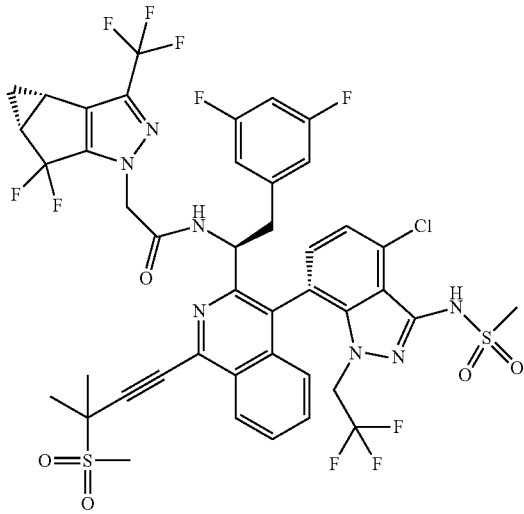<br>N-((S)-1-((S)-4-(4-chloro-3-(methanesulfonamido)-1-(2,2,2-trifluoroethyl)-1H-indazol-7-yl)-1-(3-methyl-3-(methanesulfonyl)but-1-yn-1-yl)isoquinolin-3-yl)-2-(3,5-difluorophenyl)ethyl)-2-((3bS,4aR)-5,5-difluoro-3-(triifluoromethyl)-3b,4,4a,5-tetrahydro-1H-cyclopropa[3,4]cyclopenta[1,2-c]pyrazol-1-yl)acetamide |
| 7-1 | 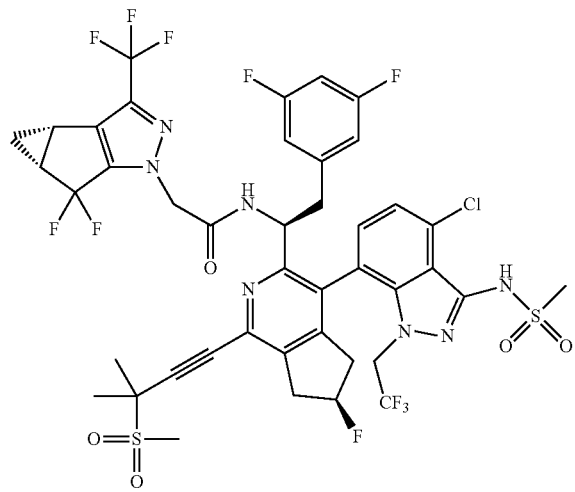<br>N-((1S)-1-((6R)-4-(4-chloro-3-(methanesulfonamido)-1-(2,2,2-trifluoroethyl)-1H-indazol-7-yl)-6-fluoro-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |

| Example | Structure and name of compound |
|---|---|
| 7-1 | 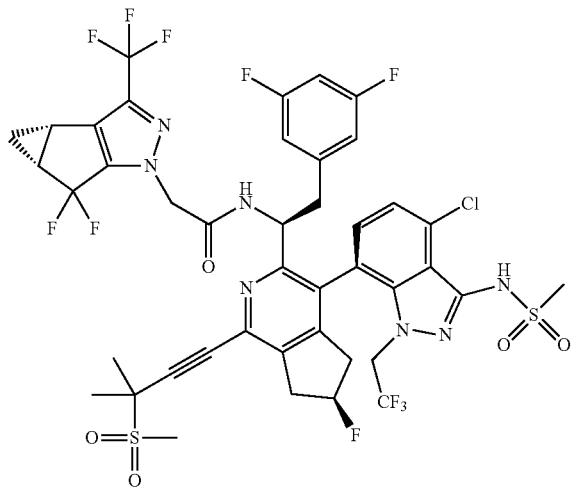

7-1

N-((1S)-1-((4R,6R)-4-(4-chloro-3-(methanesulfonamido)-1-(2,2,2-trifluroroethyl)-1H-indazol-7-yl)-6-fluoro-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 7-1 |
| | 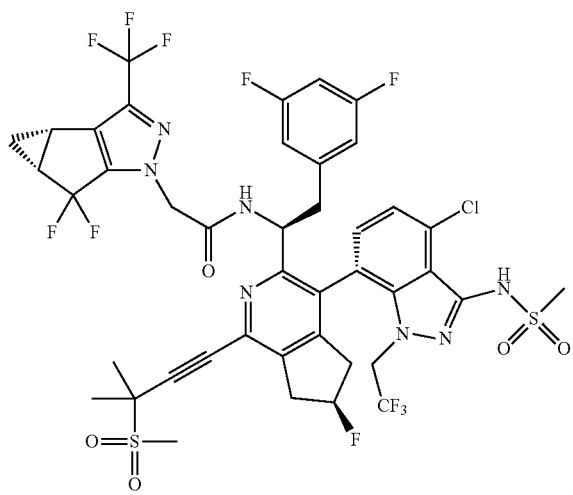

N-((1S)-1-((4S,6R)-4-(4-chloro-3-(methanesulfonamido)-1-(2,2,2-trifluoroethyl)-1H-indazol-7-yl)-6-fluoro-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |

| Example | Structure and name of compound |
|---|---|
| | 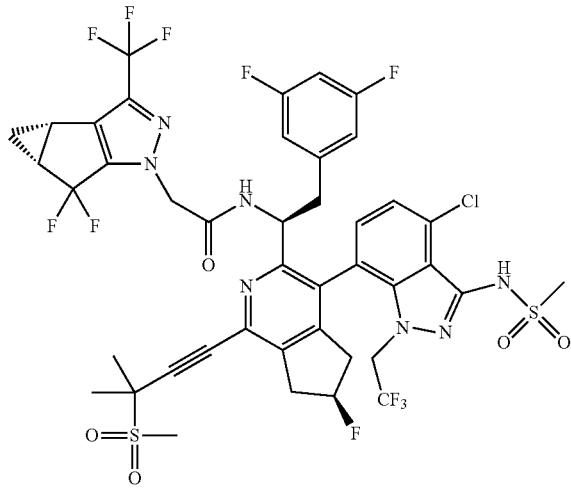<br>7-2<br><br>N-((1S)-1-((6S)-4-(4-chloro-3-(methanesulfonamido)-1-(2,2,2-trifluoroethyl)-1H-indazol-7-yl)-6-fluoro-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |
| 7-2 | 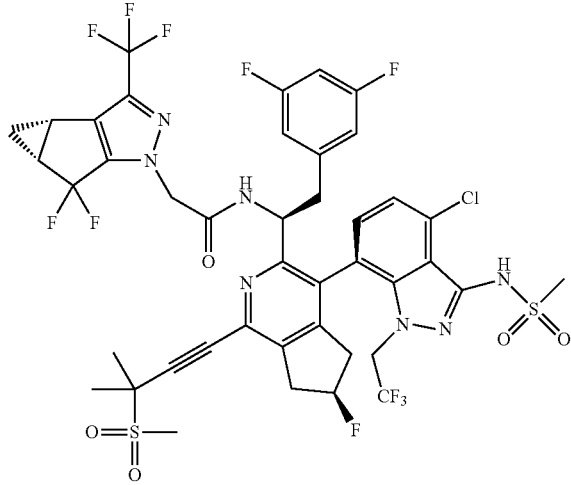<br>7-2<br><br>N-((1S)-1-((4R,6S)-4-(4-chloro-3-(methanesulfonamido)-1-(2,2,2-trifluoroethyl)-1H-indazol-7-yl)-6-fluoro-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 7-2 |

| Example | Structure and name of compound |
|---|---|
| | 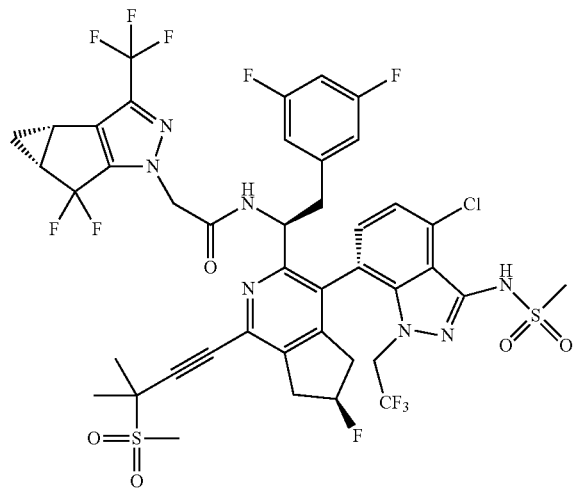<br>N-((1S)-1-((4S,6S)-4-(4-chloro-3-(methanesulfonamido)-1-(2,2,2-trifluoroethyl)-1H-indazol-7-yl)-6-fluoro-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide |

Non-limiting examples of compounds that exist in atropisomeric forms include, but are not limited to, the following compounds:

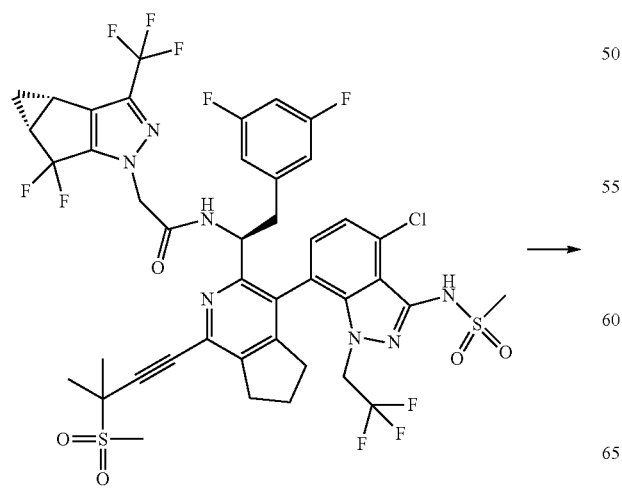

45
-continued
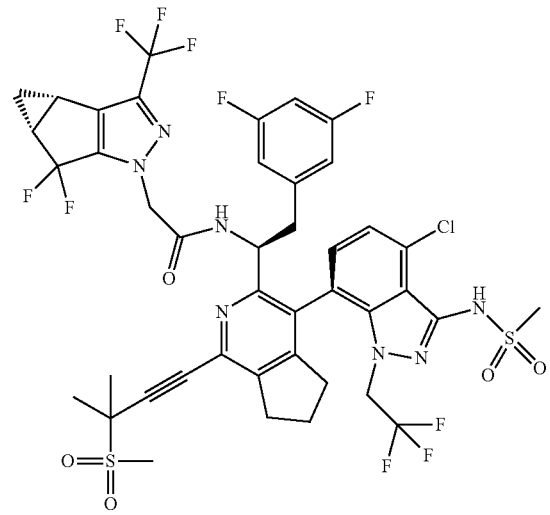
R-atropisomer
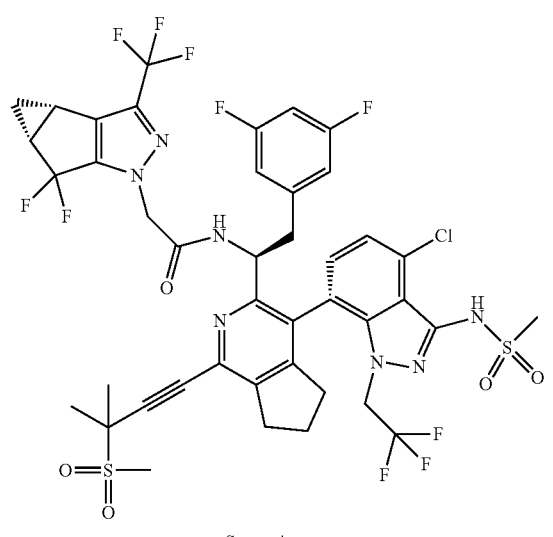
S-atropisomer
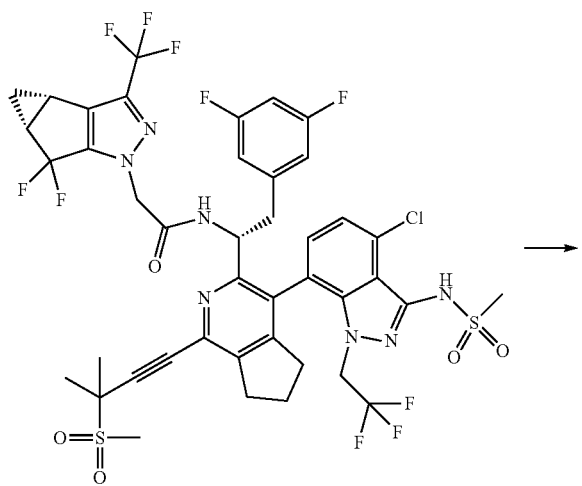
→
46
-continued
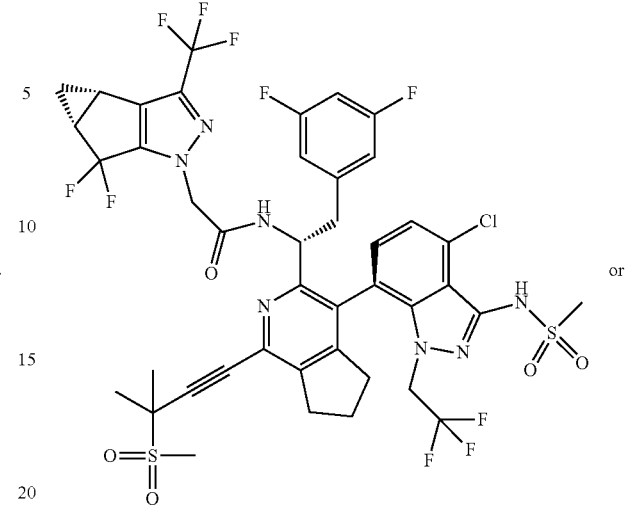
R-atropisomer
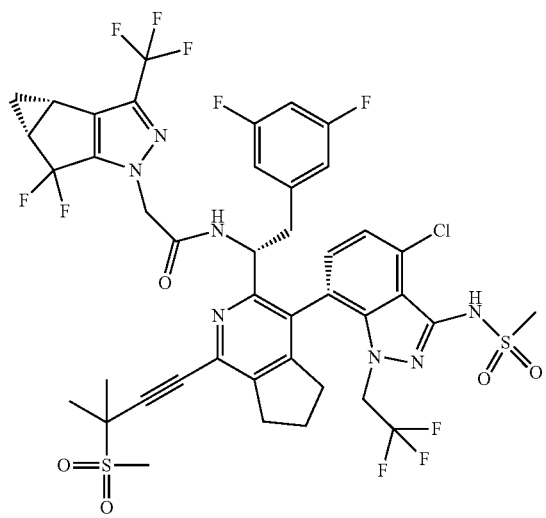
S-atropisomer
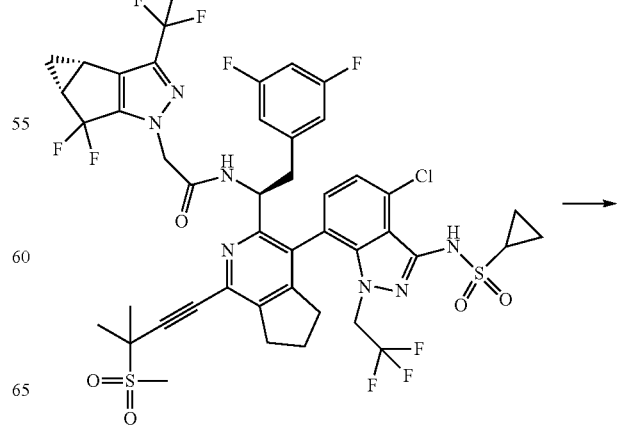
→

47
-continued
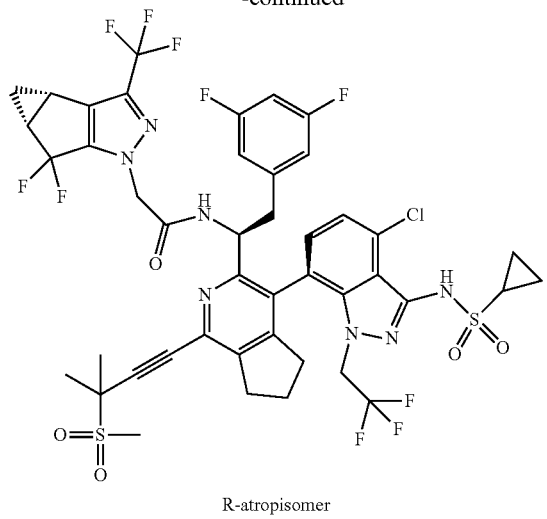
R-atropisomer
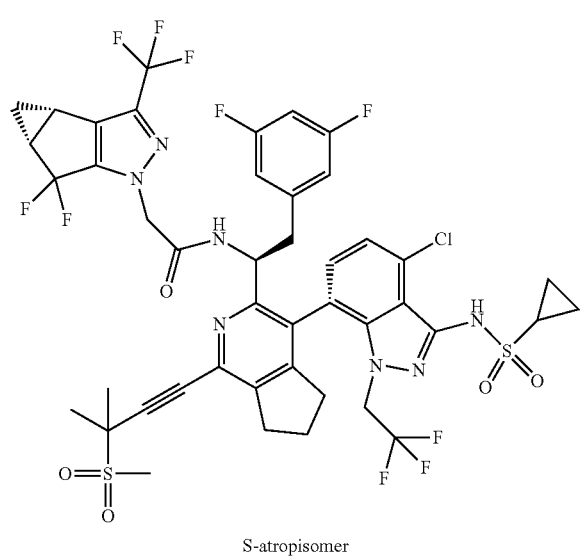
S-atropisomer
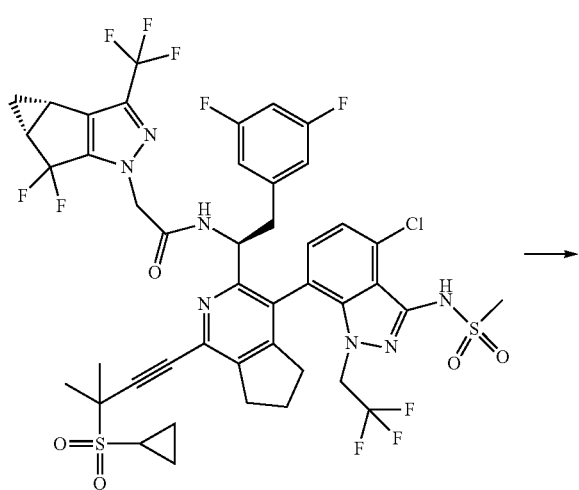
→
48
-continued
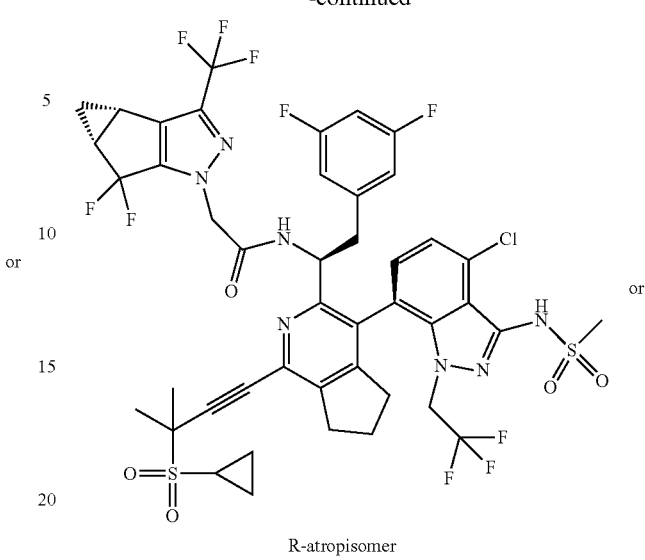
or
R-atropisomer
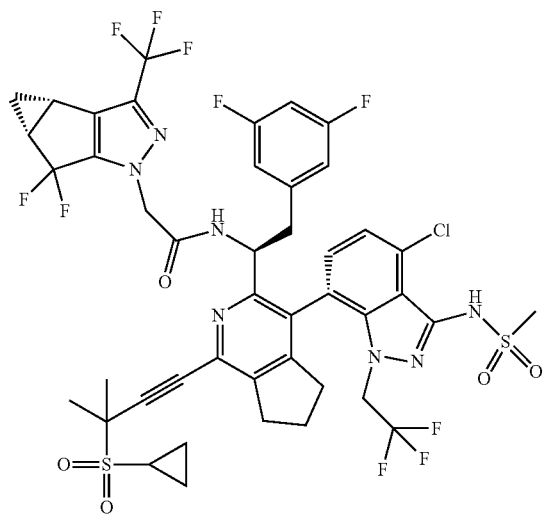
S-atropisomer
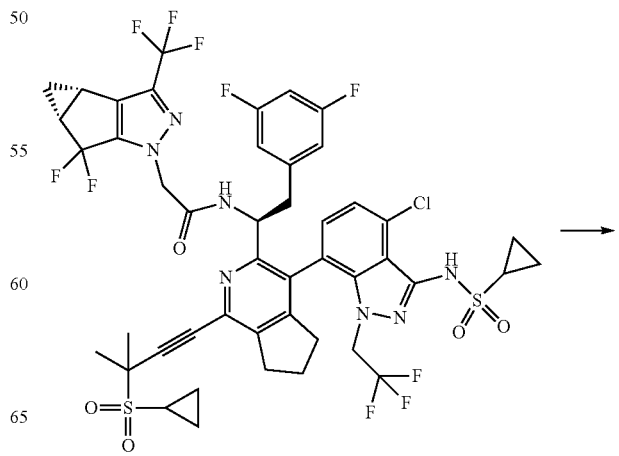
→

49
-continued
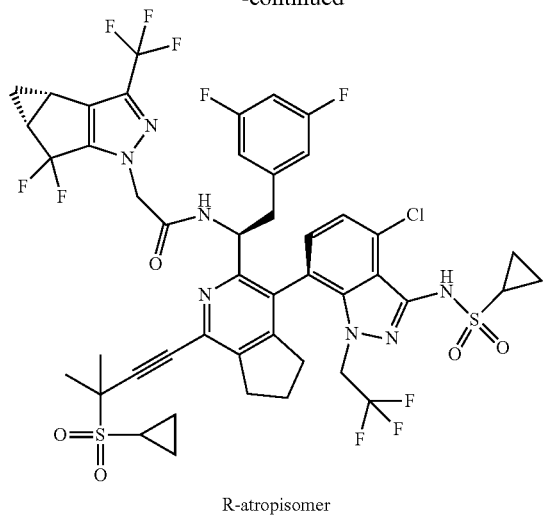
R-atropisomer
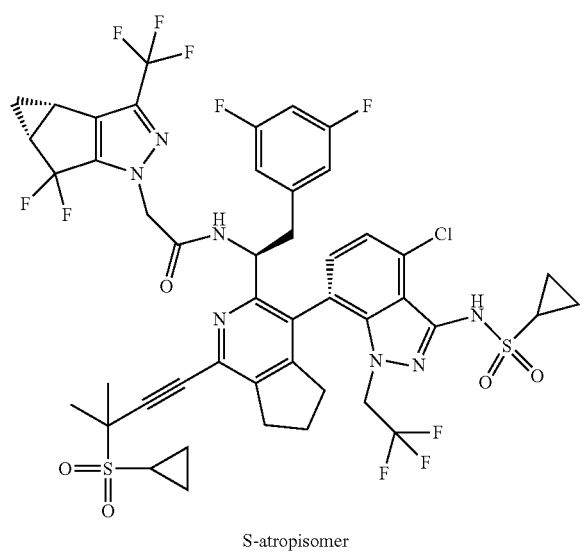
S-atropisomer
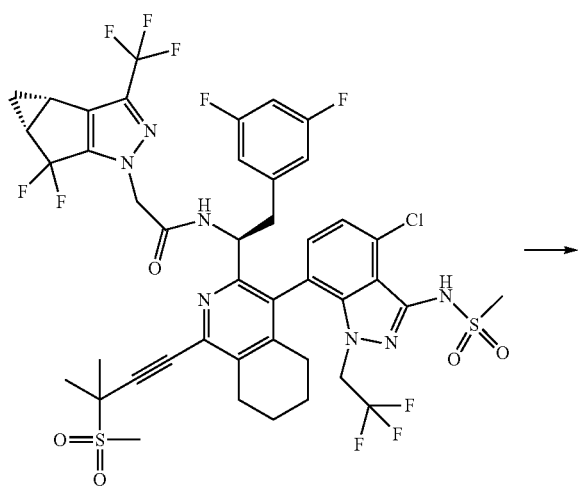
→
50
-continued
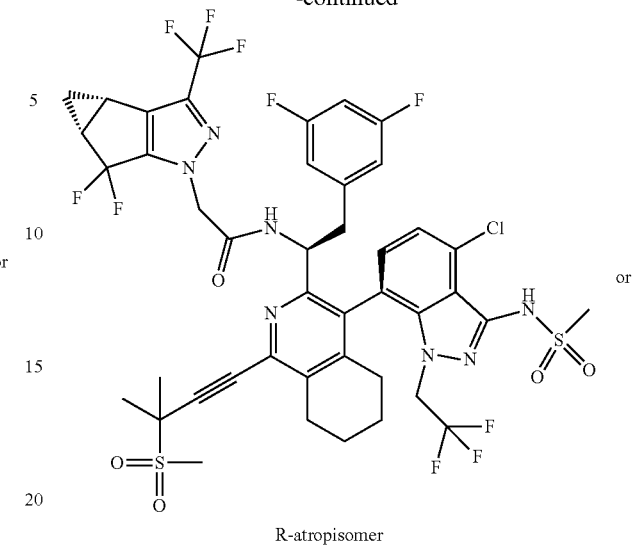
or
R-atropisomer
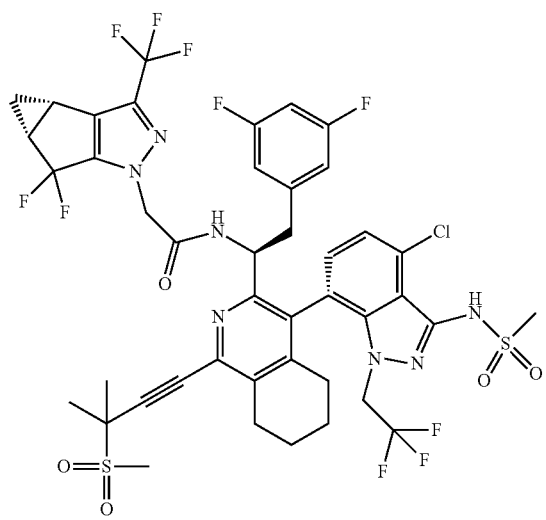
or
S-atropisomer
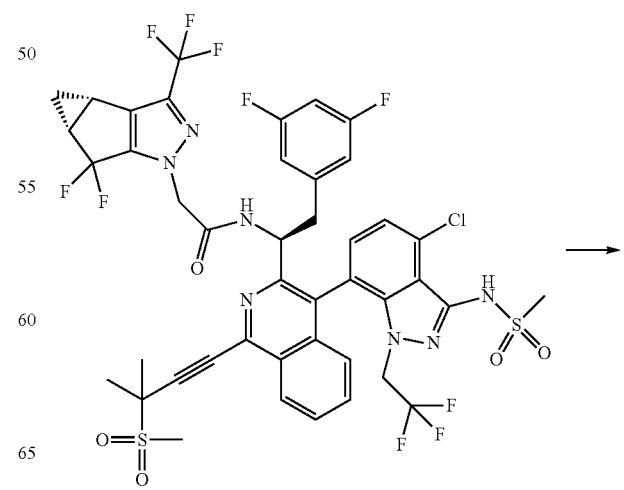
→

51
-continued
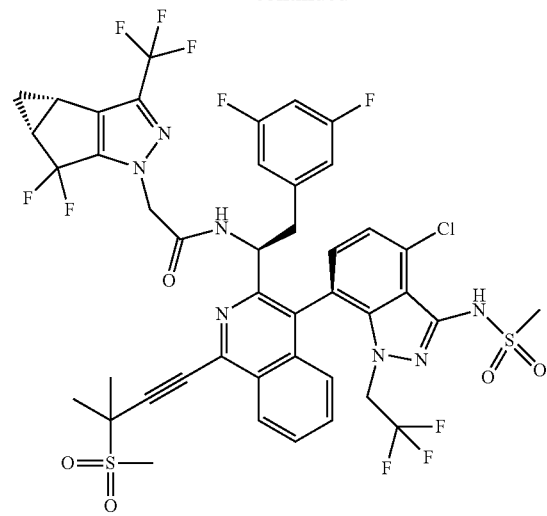
R-atropisomer
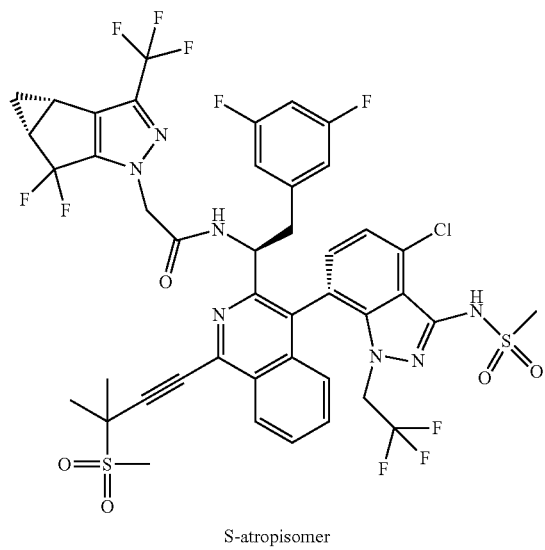
S-atropisomer
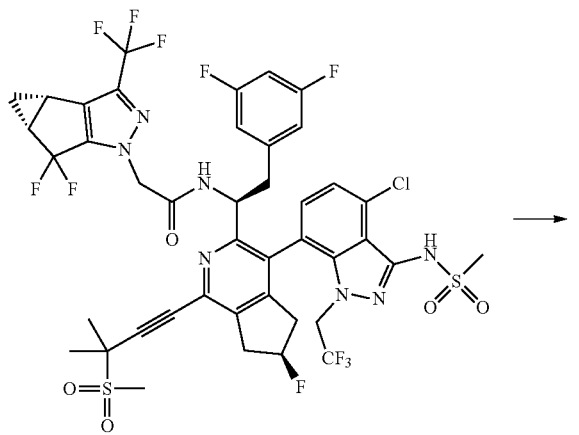
→
52
-continued
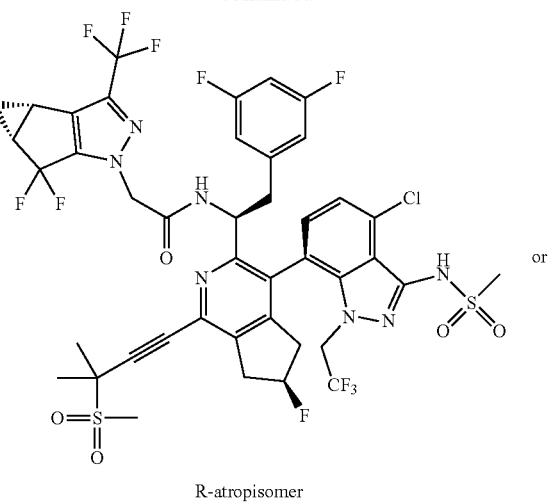
R-atropisomer
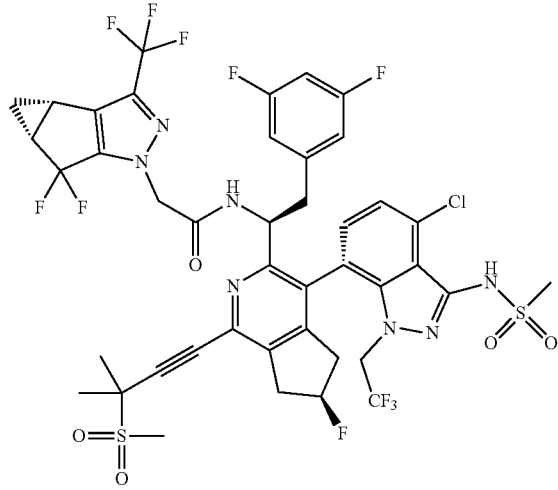
S-atropisomer
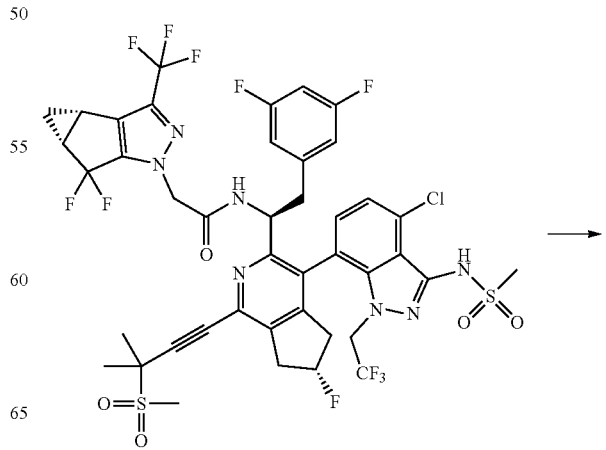
→

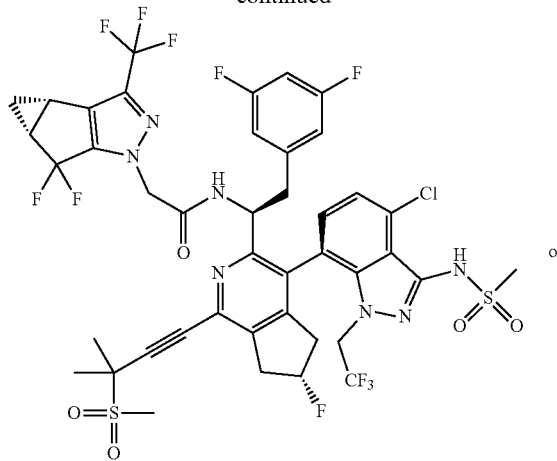

R-atropisomer

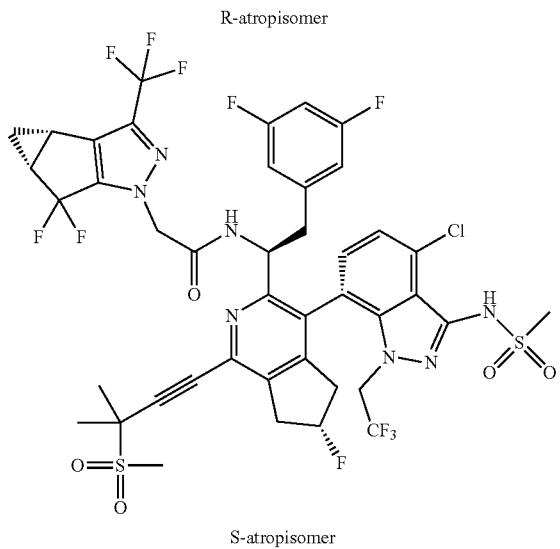

S-atropisomer

Another aspect of the present disclosure relates to a compound of general formula (IA) or an atropisomer, tautomer, mesomer, racemate, enantiomer, diastereomer thereof or a mixture thereof, or a pharmaceutically acceptable salt thereof,

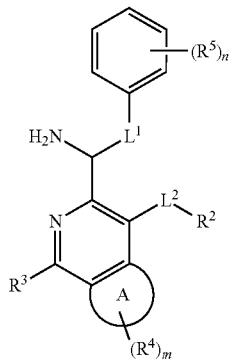

(IA)

wherein,
ring A is selected from the group consisting of cycloalkyl, heterocyclyl and aryl;
$L^1$ is alkylene;
$L^2$ is absent or selected from the group consisting of —$CH_2$—, —O—, —S— and —$NR^6$—;
$R^2$ is selected from the group consisting of cycloalkyl, heterocyclyl, aryl and heteroaryl, wherein the cycloalkyl, heterocyclyl, aryl and heteroaryl are each independently optionally substituted with one or more substituents selected from the group consisting of oxo, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O)R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$;
$R^3$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$S(O)_rR^9$, —$C(O)R^9$ and —$C(O)NR^{10}R^{11}$, wherein the alkyl, alkenyl, alkynyl, alkoxy, haloalkyl, hydroxyalkyl, cycloalkyl, heterocyclyl, aryl and heteroaryl are each independently optionally substituted with one or more substituents selected from the group consisting of oxo, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^9$, —$OC(O)R^9$, —$OC(O)NR^{10}R^{11}$, —$NHS(O)_rR^9$, —$NHS(O)_2OR^9$, —$NHS(O)_2NR^{10}R^{11}$, —$C(O)R^9$, —$C(O)OR^9$, —$C(O)NR^{10}R^{11}$, —$S(O)_rR^9$, —$S(O)_rNR^{10}R^{11}$, —$NR^{10}R^{11}$, —$NHC(O)R^9$, —$NHC(O)OR^9$, —$NHC(O)NR^{10}R^{11}$ and —$NHC(O)NHOR^9$;
$R^4$ is identical or different and is each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;
$R^5$ is identical or different and is each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;
$R^6$ and $R^9$ are identical or different and are each independently selected from the group consisting of hydrogen, alkyl, cycloalkyl, heterocyclyl, aryl and heteroaryl, wherein the alkyl, cycloalkyl, heterocyclyl, aryl or heteroaryl is each independently optionally substituted with one or more substituents selected from the group consisting of alkyl, halogen, hydroxy, alkoxy, cycloalkyl, heterocyclyl, aryl and heteroaryl;
$R^7$, $R^8$, $R^{10}$ and $R^{11}$ are identical or different and are each independently selected from the group consisting of hydrogen, alkyl, cycloalkyl, heterocyclyl, aryl, heteroaryl, —$C(O)R^6$ and —$S(O)_rR^6$, wherein the alkyl, cycloalkyl, heterocyclyl, aryl and heteroaryl are each independently optionally substituted with one or more substituents selected from the group consisting of alkyl, halogen, hydroxy, alkoxy, cycloalkyl, heterocyclyl, aryl and heteroaryl;
m is 0, 1, 2, 3, 4, 5 or 6;
n is 0, 1, 2, 3, 4 or 5; and
r is 0, 1 or 2.
In some embodiments of the present disclosure, for the compound of general formula (IA) or the atropisomer, tautomer, mesomer, racemate, enantiomer, diastereomer thereof or the mixture thereof, or the pharmaceutically acceptable salt thereof according to the present disclosure, the pharmaceutically acceptable salt of the compound of general formula (IA) is hydrochloride.

In some embodiments of the present disclosure, the compound of general formula (IA) or the atropisomer, tautomer, mesomer, racemate, enantiomer, diastereomer thereof or the mixture thereof, or the pharmaceutically acceptable salt thereof according to the present disclosure is a compound of general formula (I-1A) or an atropisomer, tautomer, mesomer, racemate, enantiomer, diastereomer thereof or a mixture thereof, or a pharmaceutically acceptable salt thereof,

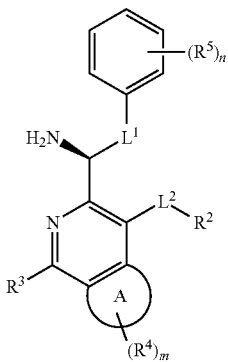

(I-1A)

wherein,
ring A, L$^1$, L$^2$, R$^2$-R$^5$, m and n are as defined in general formula (IA).

In some embodiments of the present disclosure, the compound of general formula (IA) or the atropisomer, tautomer, mesomer, racemate, enantiomer, diastereomer thereof or the mixture thereof, or the pharmaceutically acceptable salt thereof according to the present disclosure is a compound of general formula (IIA) or general formula (II-1A) or an atropisomer, tautomer, mesomer, racemate, enantiomer, diastereomer thereof or a mixture thereof, or a pharmaceutically acceptable salt thereof,

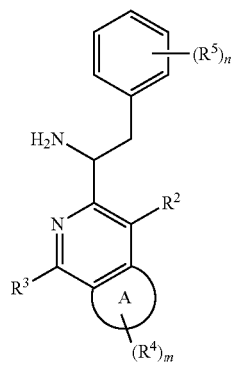

(IIA)

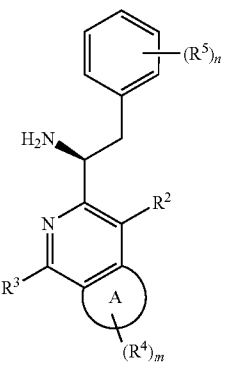

(II-1A)

wherein,
ring A, R$^2$-R$^5$, m and n are as defined in general formula (IA).

In some embodiments of the present disclosure, the compound of general formula (IA) or the atropisomer, tautomer, mesomer, racemate, enantiomer, diastereomer thereof or the mixture thereof, or the pharmaceutically acceptable salt thereof according to the present disclosure is a compound of general formula (IIIA) or general formula (III-1A) or an atropisomer, tautomer, mesomer, racemate, enantiomer, diastereomer thereof or a mixture thereof, or a pharmaceutically acceptable salt thereof,

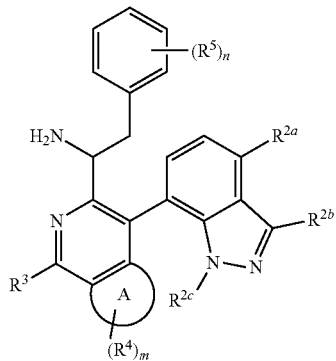

(IIIA)

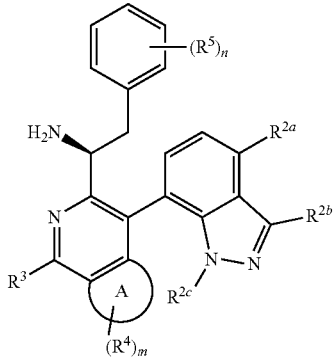

(III-1A)

wherein,
R$^{2a}$, R$^{2b}$ and R$^{2c}$ are identical or different and are each independently selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR$^6$, —OC(O)R$^6$, —OC (O)NR⁷R⁸, —NHS(O)ᵣR⁶, —NHS(O)₂OR⁶, —NHS(O)₂NR⁷R⁸, —C(O)R⁶, —C(O)OR⁶, —C(O)NR⁷R⁸, —S(O)ᵣR⁶, —S(O)ᵣNR⁷R⁸, —NR⁷R⁸, —NHC(O)R⁶, —NHC(O)OR⁶, —NHC(O)NR⁷R⁸ and —NHC(O)NHOR⁶; and ring A, R³-R⁵, m, n and r are as defined in general formula (IA); preferably, R²ᵃ is selected from the group consisting of hydrogen, halogen and C₁₋₆ alkyl; R²ᵇ is —NHS(O)₂R⁶ or —N(S(O)₂R⁶)₂, and R⁶ is C₁₋₆ alkyl or C₃₋₆ cycloalkyl; R²ᵉ is C₁₋₆ alkyl or halogenated C₁₋₆ alkyl.

In some embodiments of the present disclosure, the compound of general formula (IA) or the atropisomer, tautomer, mesomer, racemate, enantiomer, diastereomer thereof or the mixture thereof, or the pharmaceutically acceptable salt thereof according to the present disclosure is a compound of general formula (IVA) or general formula (IV-1A) or an atropisomer, tautomer, mesomer, racemate, enantiomer, diastereomer thereof or a mixture thereof, or a pharmaceutically acceptable salt thereof,

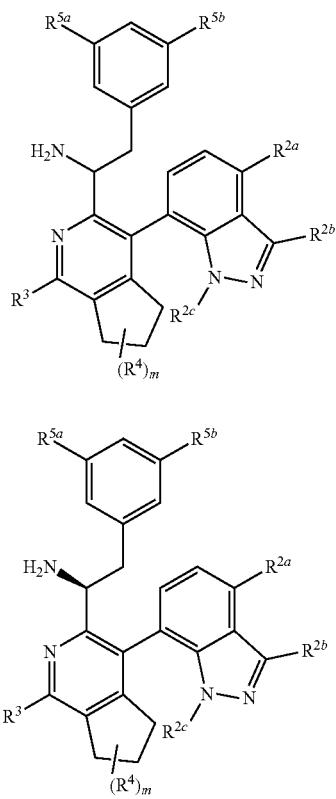

(IVA)

(IV-1A)

wherein,

R⁵ᵃ and R⁵ᵇ are identical or different and are each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl; and R²ᵃ, R²ᵇ, R²ᶜ, R³, R⁴ and m are as defined in general formula (IIIA).

In some embodiments of the present disclosure, the compound of general formula (IA) or the atropisomer, tautomer, mesomer, racemate, enantiomer, diastereomer thereof or the mixture thereof, or the pharmaceutically acceptable salt thereof according to the present disclosure is a compound of general formula (VA) or general formula (V-1A) or an atropisomer, tautomer, mesomer, racemate, enantiomer, diastereomer thereof or a mixture thereof, or a pharmaceutically acceptable salt thereof,

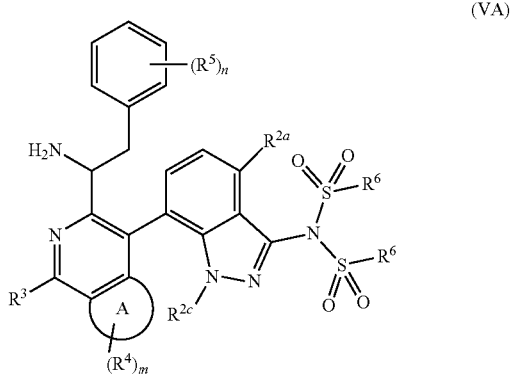

(VA)

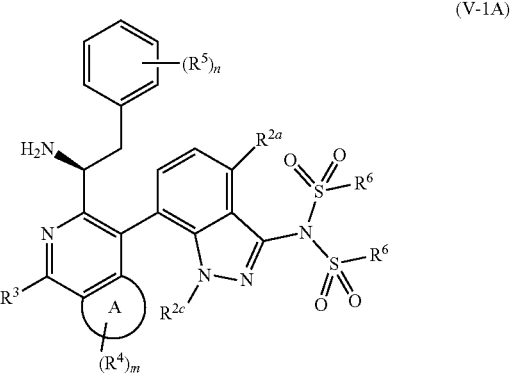

(V-1A)

wherein,

R⁶ is C₁₋₆ alkyl or C₃₋₆ cycloalkyl; preferably, R⁶ is C₁₋₆ alkyl;

R²ᵃ, R²ᶜ, R³-R⁵, m and n are as defined in general formula (IIIA).

In some embodiments of the present disclosure, the compound of general formula (IA) or the atropisomer, tautomer, mesomer, racemate, enantiomer, diastereomer thereof or the mixture thereof, or the pharmaceutically acceptable salt thereof according to the present disclosure is a compound of general formula (VIA) or general formula (VI-1A) or an atropisomer, tautomer, mesomer, racemate, enantiomer, diastereomer thereof or a mixture thereof, or a pharmaceutically acceptable salt thereof,

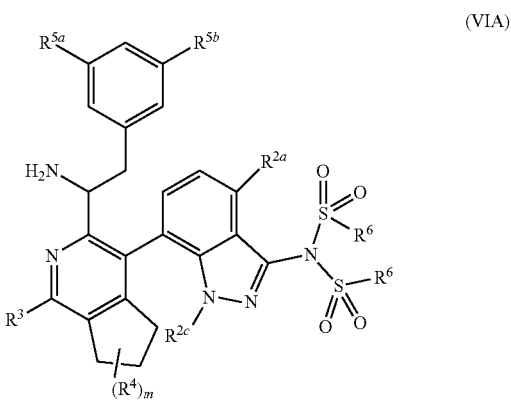

(VIA)

-continued

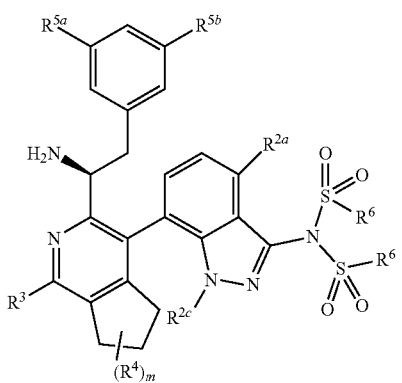

(VI-1A)

wherein, $R^{5a}$ and $R^{5b}$ are identical or different and are each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;

$R^6$ is $C_{1-6}$ alkyl or $C_{3-6}$ cycloalkyl; preferably, $R^6$ is $C_{1-6}$ alkyl;

$R^{2a}$, $R^{2c}$, $R^3$, $R^4$ and m are as defined in general formula (IIIA).

Typical compounds of general formula (IA) of the present disclosure include, but are not limited to:

| Example | Structure and name of compound |
|---|---|
| | N-(7-(-3-(1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride |
| | N-(7-(-3-(1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide |

| Example | Structure and name of compound |
|---|---|
| | 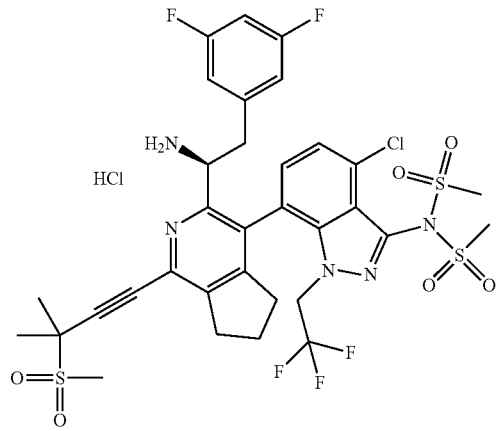 [SMILES: CC(C)(C#Cc1nc([C@@H](N)Cc2cc(F)cc(F)c2)c(-c2ccc(Cl)c3c(N(S(C)(=O)=O)S(C)(=O)=O)nn(CC(F)(F)F)c23)c2c1CCC2)S(C)(=O)=O ; Cl]
N-(7-(-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride |
| | 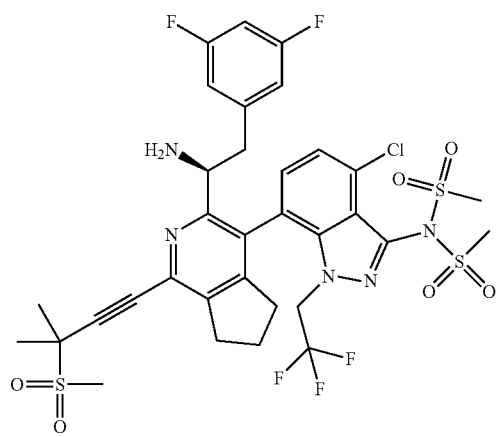 [SMILES: CC(C)(C#Cc1nc([C@@H](N)Cc2cc(F)cc(F)c2)c(-c2ccc(Cl)c3c(N(S(C)(=O)=O)S(C)(=O)=O)nn(CC(F)(F)F)c23)c2c1CCC2)S(C)(=O)=O]
N-(7-(-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide |
| 1n-1/1n-1a | 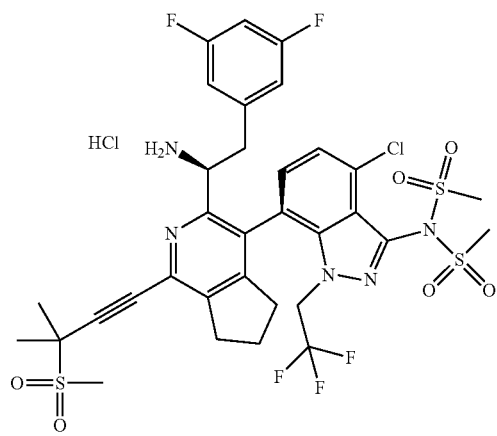
1n-1a N-(7-((R)-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4- |

| Example | Structure and name of compound |
|---|---|
| | chloro-1-(2,2,2-trifluoroethyl)-1H-indazol-3-yl)-N-(methylsulfonyl)<br>methanesulfonamide hydrochloride 1n-1/1n-1a<br>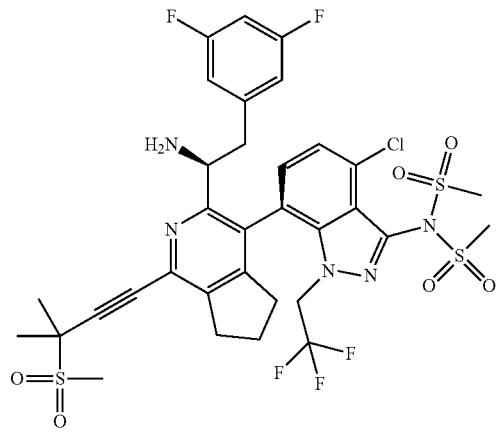<br>N-(7-((R)-3-((S)-1-amino-2-(3,5-difluorophenyl)ethyl)-1-(3-methyl-3-<br>(methylsulfonyl)but-1-yn-1-yl)-6,7-dihydro-5H-cyclopenta[c]pyridin-4-yl)-4-<br>chloro-1-(2,2,2-trifluoroethyl)-1H-indazol-3-yl)-N-(methylsulfonyl)<br>methanesulfonamide |
| 1n-1b | 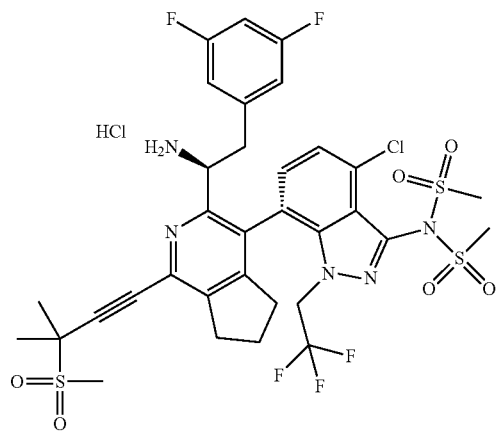<br>1n-1b<br>N-(7-((S)-3-((S)-1-amino-2-(3,5-difluorophenyl)ethyl)-1-(3-methyl-3-<br>(methylsulfonyl)but-1-yn-1-yl)-6,7-dihydro-5H-cyclopenta[c]pyridin-4-yl)-4-<br>chloro-1-(2,2,2-trifluoroethyl)-1H-indazol-3-yl)-N-(methylsulfonyl)<br>methanesulfonamide hydrochloride 1n-1b<br>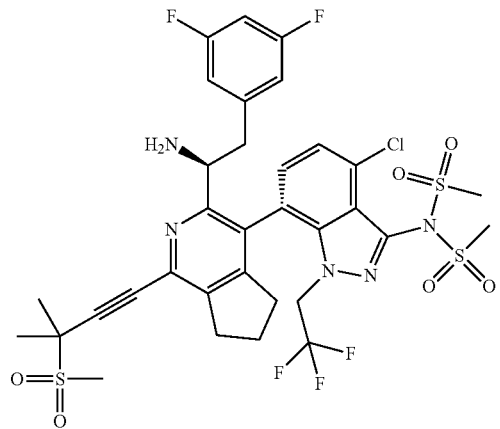 |

| Example | Structure and name of compound |
|---|---|
| | N-(7-((S)-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide 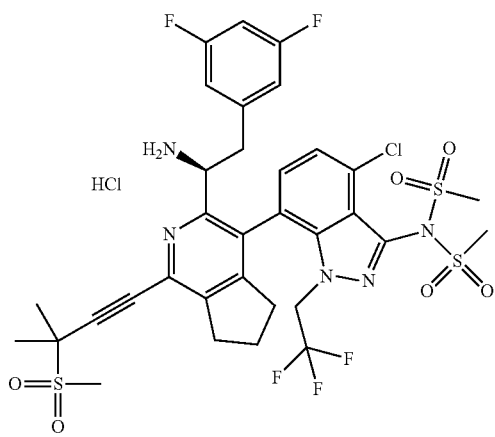 [SMILES: CC(C)(C#Cc1nc([C@@H](N)Cc2cc(F)cc(F)c2)c(-c2ccc(Cl)c3c(N(S(C)(=O)=O)S(C)(=O)=O)nn(CC(F)(F)F)c23)c2c1CCC2)S(C)(=O)=O ; Cl] N-(7-(-3-((R)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride 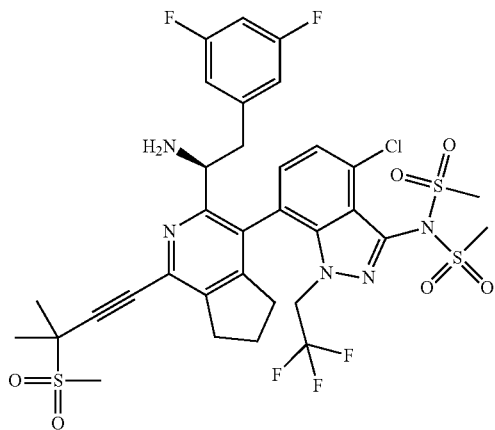 N-(7-(-3-((R)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide |

| Example | Structure and name of compound |
|---|---|
| 1n-2 | 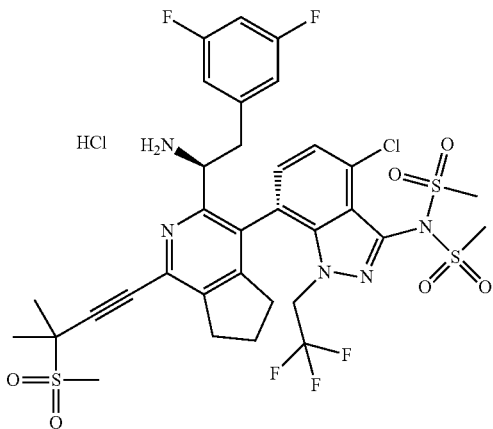

N-(7-((S)-3-((R)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride 1n-2

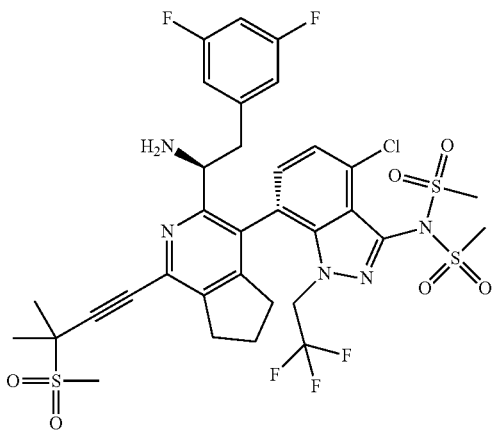

N-(7-((S)-3-((R)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide

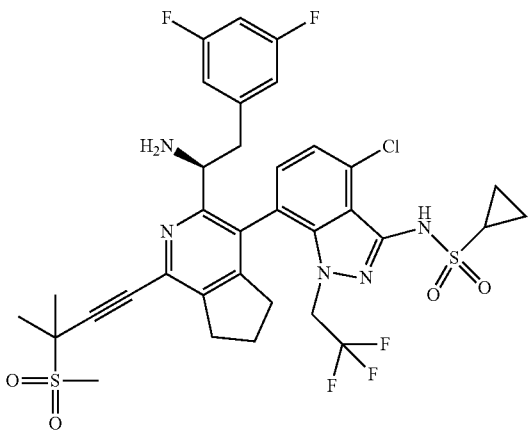 [SMILES: CC(C)(C#Cc1nc([C@@H](N)Cc2cc(F)cc(F)c2)c(-c2ccc(Cl)c3c(NS(=O)(=O)C4CC4)nn(CC(F)(F)F)c23)c2c1CCC2)S(C)(=O)=O] |

| Example | Structure and name of compound |
|---|---|
| | N-(7-(-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-cyclopropanesulfonamide |
| 2c | N-(7-((R)-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-cyclopropanesulfonamide 2c |
| | N-(7-((S)-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-cyclopropanesulfonamide |
| | N-(7-(-3-((S)-1-amino-2-(3,5-difluorophenyl)ethyl)-1-(3-(cyclopropylsulfonyl)-3-methyl-but-1-yn-1-yl)-6,7-dihydro-5H-cyclopenta[c]pyridin-4-yl)-4- |

| Example | Structure and name of compound |
|---|---|
| | chloro-1-(2,2,2-trifluoroethyl)-1H-indazol-3-yl)-N-(methylsulfonyl)methanesulfonamide |
| 3e | 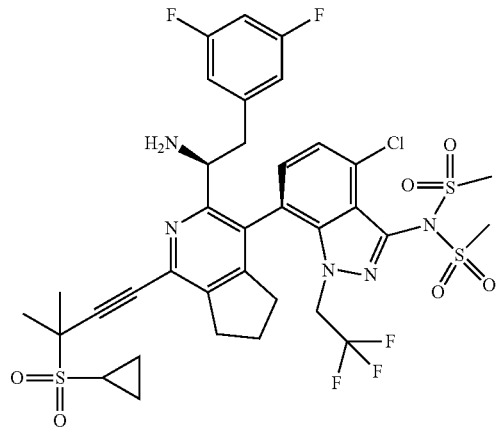<br>N-(7-((R)-3-((S)-1-amino-2-(3,5-difluorophenyl)ethyl)-1-(3-(cyclopropylsulfonyl)-3-methyl-but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide 3e |
| | 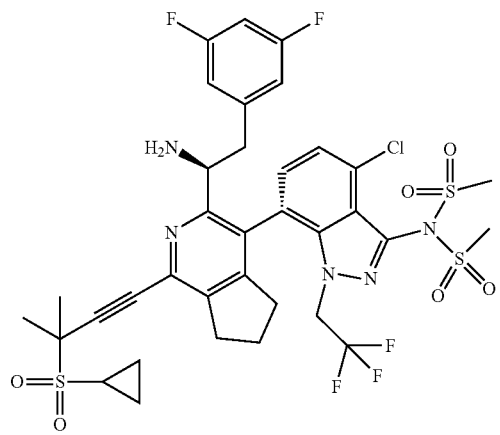<br>N-(7-((S)-3-((S)-1-amino-2-(3,5-difluorophenyl)ethyl)-1-(3-(cyclopropylsulfonyl)-3-methyl-but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide |
| | 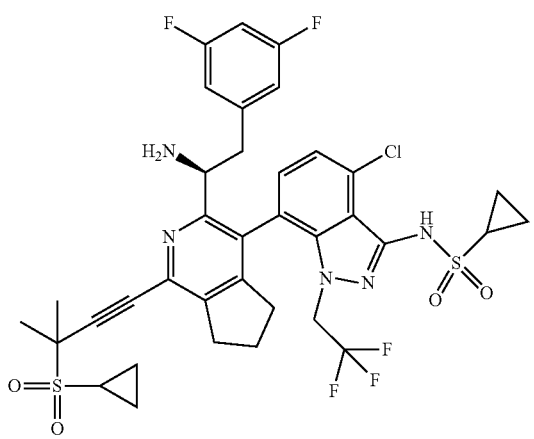 [SMILES: CC(C)(C#Cc1nc([C@@H](N)Cc2cc(F)cc(F)c2)c(-c2ccc(Cl)c3c(NS(=O)(=O)C4CC4)nn(CC(F)(F)F)c23)c2c1CCC2)S(=O)(=O)C1CC1] |

| Example | Structure and name of compound |
|---|---|
| | N-(7-(-3-((S)-1-amino-2-(3,5-difluorophenyl)ethyl)-1-(3-(cyclopropylsulfonyl)-3-methyl-but-1-yn-1-yl)-6,7-dihydro-5H-cyclopenta[c]pyridin-4-yl)-4-chloro-1-(2,2,2-trifluoroethyl)-1H-indazol-3-yl)-cyclopropanesulfonamide |
| 4b | |

N-(7-((R)-3-((S)-1-amino-2-(3,5-difluorophenyl)ethyl)-1-(3-(cyclopropylsulfonyl)-3-methyl-but-1-yn-1-yl)-6,7-dihydro-5H-cyclopenta[c]pyridin-4-yl)-4-chloro-1-(2,2,2-trifluoroethyl)-1H-indazol-3-yl)-cyclopropanesulfonamide 4b N-(7-((S)-3-((S)-1-amino-2-(3,5-difluorophenyl)ethyl)-1-(3-(cyclopropylsulfonyl)-3-methyl-but-1-yn-1-yl)-6,7-dihydro-5H-cyclopenta[c]pyridin-4-yl)-4-chloro-1-(2,2,2-trifluoroethyl)-1H-indazol-3-yl)-cyclopropanesulfonamide 5m 5m

| Example | Structure and name of compound |
|---|---|
| | N-(7-(-3-((S)-1-amino-2-(3,5-difluorophenyl)ethyl)-1-(3-methyl-3-(methylsulfonyl)but-1-yn-1-yl)-5,6,7,8-tetrahydroisoquinolin-4-yl)-4-chloro-1-(2,2,2-trifluoroethyl)-1H-indazol-3-yl)-N-(methylsulfonyl)methanesulfonamide hydrochloride 5m 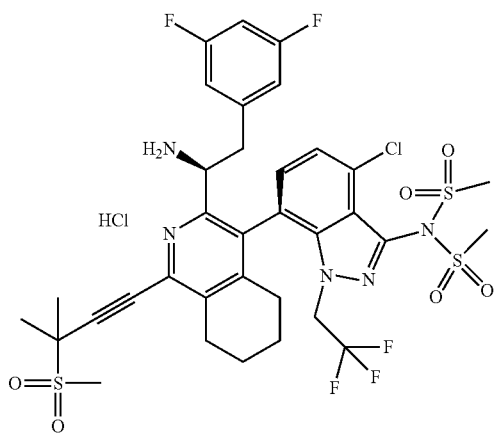 |
| | N-(7-((R)-3-((S)-1-amino-2-(3,5-difluorophenyl)ethyl)-1-(3-methyl-3-(methylsulfonyl)but-1-yn-1-yl)-5,6,7,8-tetrahydroisoquinolin-4-yl)-4-chloro-1-(2,2,2-trifluoroethyl)-1H-indazol-3-yl)-N-(methylsulfonyl)methanesulfonamide hydrochloride 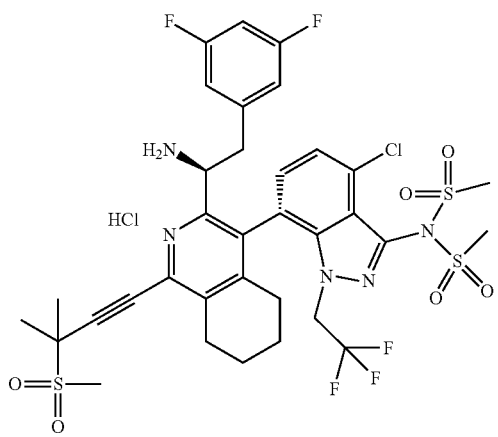 |
| | N-(7-((S)-3-((S)-1-amino-2-(3,5-difluorophenyl)ethyl)-1-(3-methyl-3-(methylsulfonyl)but-1-yn-1-yl)-5,6,7,8-tetrahydroisoquinolin-4-yl)-4-chloro-1-(2,2,2-trifluoroethyl)-1H-indazol-3-yl)-N-(methylsulfonyl)methanesulfonamide hydrochloride 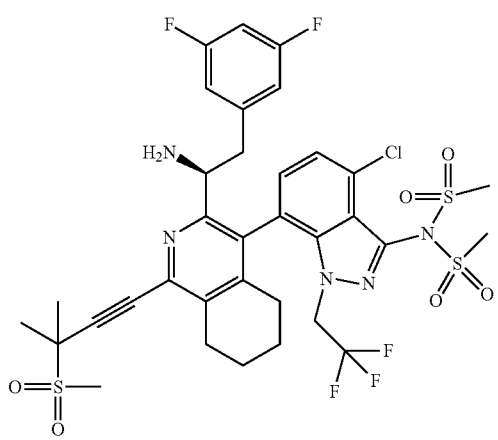 [SMILES: CC(C)(C#Cc1nc([C@@H](N)Cc2cc(F)cc(F)c2)c(-c2ccc(Cl)c3c(N(S(C)(=O)=O)S(C)(=O)=O)nn(CC(F)(F)F)c23)c2c1CCCC2)S(C)(=O)=O] |

| Example | Structure and name of compound |
|---|---|
| | N-(7-(-3-((S)-1-amino-2-(3,5-difluorophenyl)ethyl)1l-(3-methyl-3-(methylsulfonyl)but-1-yn-1-yl)-5,6,7,8-tetrahydroisoquinolin-4-yl)-4-chloro-1-(2,2,2-trifluoroethyl)-1H-indazol-3-yl)-N-(methylsulfonyl)methanesulfonamide 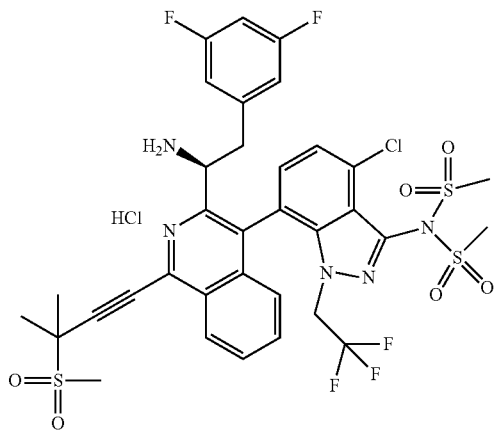 [SMILES: CC(C)(C#Cc1nc([C@@H](N)Cc2cc(F)cc(F)c2)c(-c2ccc(Cl)c3c(N(S(C)(=O)=O)S(C)(=O)=O)nn(CC(F)(F)F)c23)c2ccccc12)S(C)(=O)=O ; Cl] |
| | N-(7-(-3-((S)-1-amino-2-(3,5-difluorophenyl)ethyl)-1-(3-methyl-3-(methylsulfonyl)but-1-yn-1-yl)isoquinolin-4-yl)-4-chloro-1-(2,2,2-trifluoroethyl)-1H-indazol-3-yl)-N-(methylsulfonyl)methanesulfonamide hydrochloride |
| 6n | 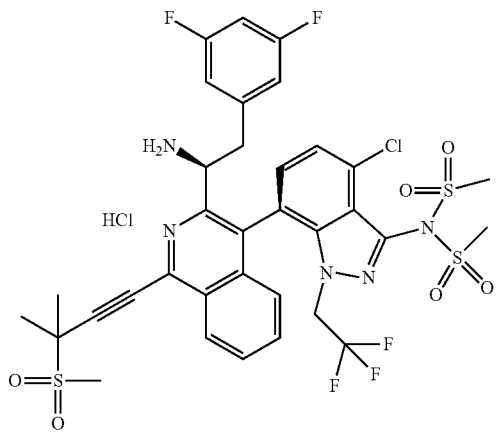 N-(7-((R)-3-((S)-1-amino-2-(3,5-difluorophenyl)ethyl)-1-(3-methyl-3-(methylsulfonyl)but-1-yn-1-yl)isoquinolin-4-yl)-4-chloro-1-(2,2,2-trifluoroethyl)-1H-indazol-3-yl)-N-(methylsulfonyl)methanesulfonamide hydrochloride 6n 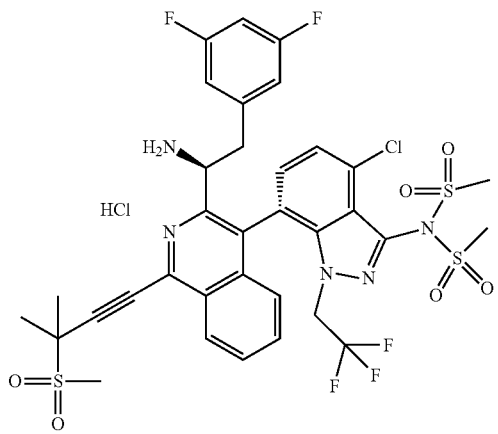 |

| Example | Structure and name of compound |
|---------|-------------------------------|

N-(7-((S)-3-((S)-1-amino-2-(3,5-difluorophenyl)ethyl)-1-(3-methyl-3-(methylsulfonyl)but-1-yn-1-yl)isoquinolin-4-yl)-4-chloro-1-(2,2,2-trifluoroethyl)-1H-indazol-3-yl)-N-(methylsulfonyl)methanesulfonamide hydrochloride

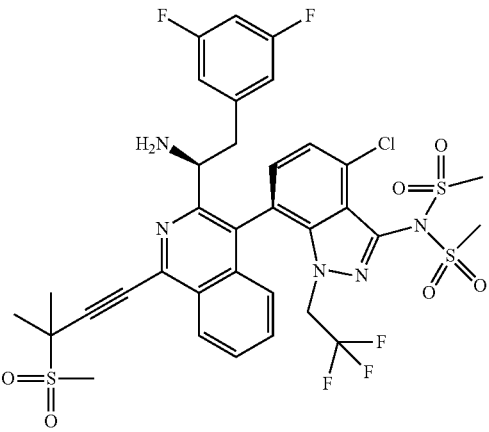

N-(7-((R)-3-((S)-1-amino-2-(3,5-difluorophenyl)ethyl)-1-(3-methyl-3-(methylsulfonyl)but-1-yn-1-yl)isoquinolin-4-yl)-4-chloro-1-(2,2,2-trifluoroethyl)-1H-indazol-3-yl)-N-(methylsulfonyl)methanesulfonamide

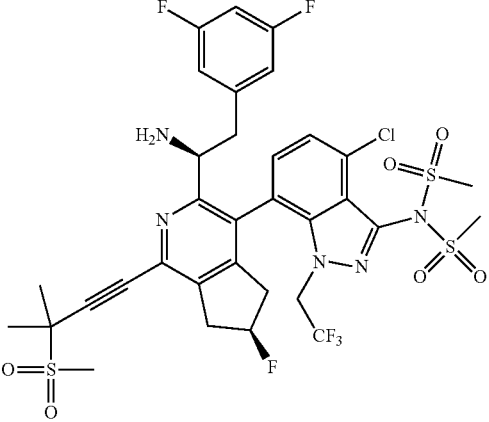 [SMILES: CC(C)(C#Cc1nc([C@@H](N)Cc2cc(F)cc(F)c2)c(-c2ccc(Cl)c3c(N(S(C)(=O)=O)S(C)(=O)=O)nn(CC(F)(F)F)c23)c2c1C[C@H](F)C2)S(C)(=O)=O]

N-(7-((4R or 4S,6R)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide

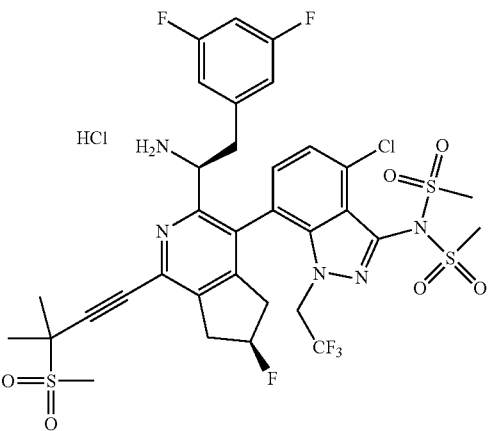 [SMILES: CC(C)(C#Cc1nc([C@@H](N)Cc2cc(F)cc(F)c2)c(-c2ccc(Cl)c3c(N(S(C)(=O)=O)S(C)(=O)=O)nn(CC(F)(F)F)c23)c2c1C[C@H](F)C2)S(C)(=O)=O ; Cl]

| Example | Structure and name of compound |
|---|---|
| | N-(7-((6R)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride |
| 7n-1 | 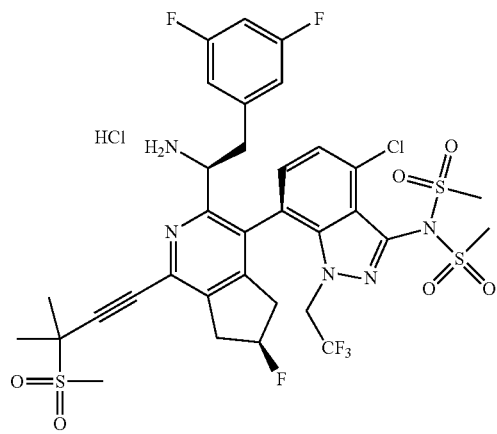<br>N-(7-((4R,6R)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride 7n-1 |
| | 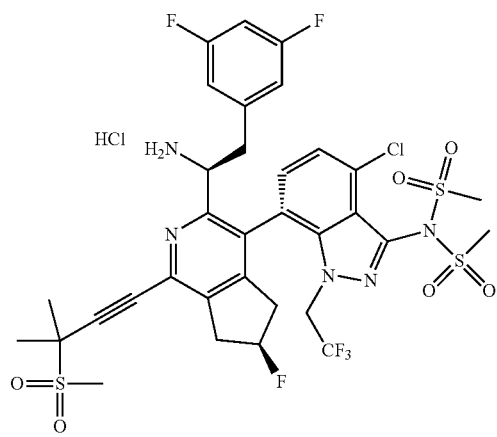<br>N-(7-((4S,6R)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride |

-continued

| Example | Structure and name of compound |
|---|---|
| | 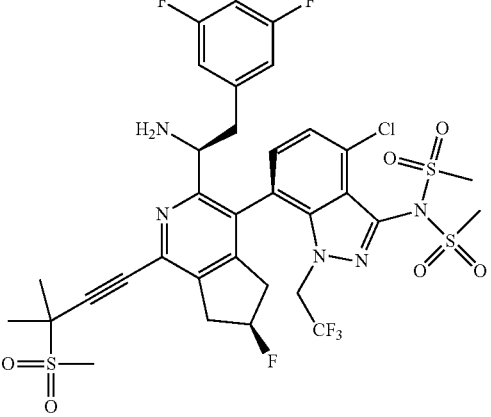
N-(7-((4R,6S)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide |
| | 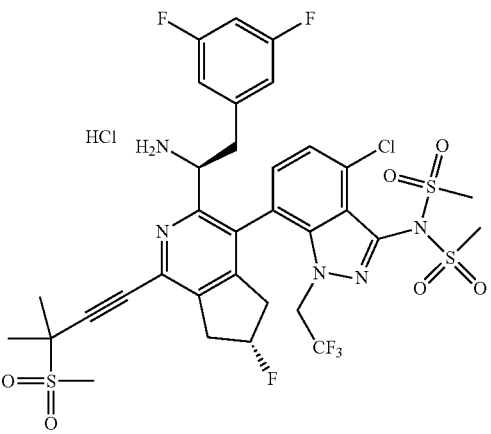 [SMILES: CC(C)(C#Cc1nc([C@@H](N)Cc2cc(F)cc(F)c2)c(-c2ccc(Cl)c3c(N(S(C)(=O)=O)S(C)(=O)=O)nn(CC(F)(F)F)c23)c2c1C[C@@H](F)C2)S(C)(=O)=O ; Cl]
N-(7-((6S)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride |
| 7n-2 | 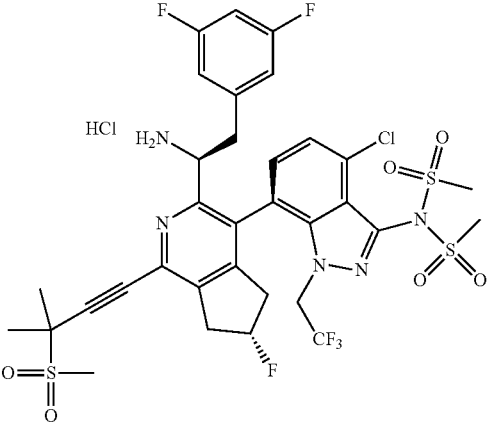
N-(7-((4R,6S)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride 7n-2 |

| Example | Structure and name of compound |
|---|---|
| | 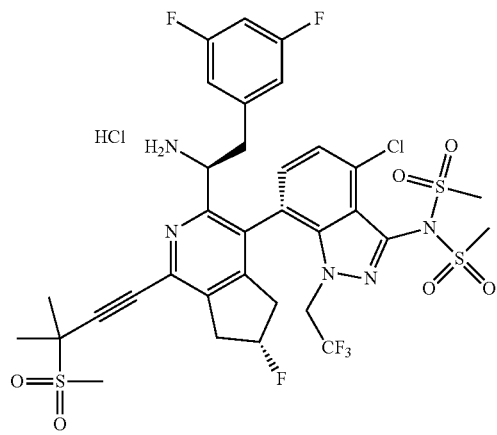
N-(7-((4S,6S)-3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride |
| | 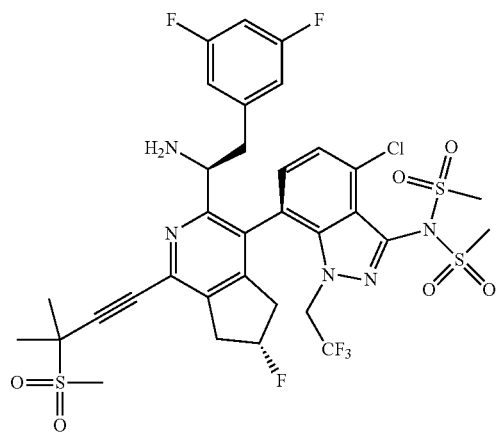
N-(7-((4R,6S)-3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide |

Another aspect of the present disclosure relates to a method for preparing the compound of general formula (I) or the atropisomer, tautomer, mesomer, racemate, enantiomer, diastereomer thereof or the mixture thereof, or the pharmaceutically acceptable salt thereof according to the present disclosure, which comprises the following steps:

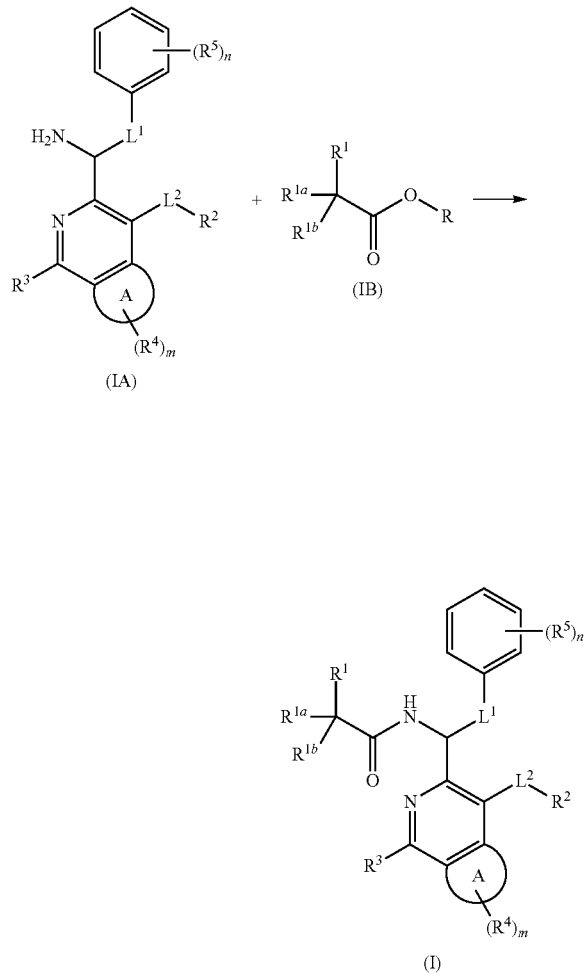

reacting a compound of general formula (IA) or a pharmaceutically acceptable salt thereof with a compound of general formula (IB) to give the compound of general formula (I) or the atropisomer, tautomer, mesomer, racemate, enantiomer, diastereomer thereof or the mixture thereof, or the pharmaceutically acceptable salt thereof, wherein, the pharmaceutically acceptable salt of the compound of general formula (IA) is preferably hydrochloride;

R is hydrogen or alkyl, and preferably hydrogen; and ring A, $L^1$, $L^2$, $R^1$-$R^5$, $R^{1a}$, $R^{1b}$, m and n are as defined in general formula (I).

Another aspect of the present disclosure relates to a method for preparing the compound of general formula (I-1) or the atropisomer, tautomer, mesomer, racemate, enantiomer, diastereomer thereof or the mixture thereof, or the pharmaceutically acceptable salt thereof according to the present disclosure, which comprises the following steps:

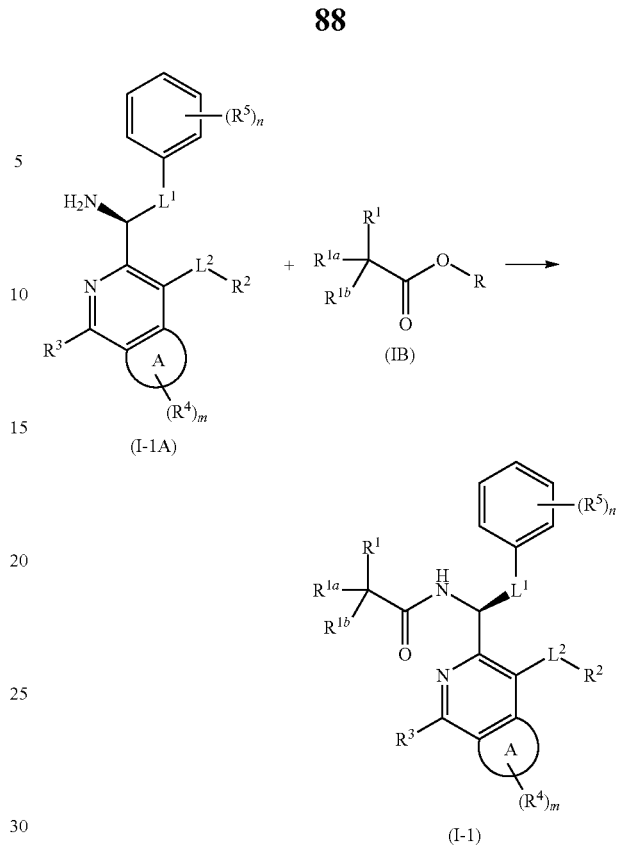

reacting a compound of general formula (I-1A) or a pharmaceutically acceptable salt thereof with a compound of general formula (IB) to give a compound of general formula (I-1) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (I-IA) is preferably hydrochloride;

R is hydrogen or alkyl, and preferably hydrogen; and ring A, $L^1$, $L^2$, $R^1$-$R^5$, $R^{1a}$, $R^{1b}$, m and n are as defined in general formula (I).

Another aspect of the present disclosure relates to a method for preparing the compound of general formula (II) or the atropisomer, tautomer, mesomer, racemate, enantiomer, diastereomer thereof or the mixture thereof, or the pharmaceutically acceptable salt thereof, which comprises the following steps:

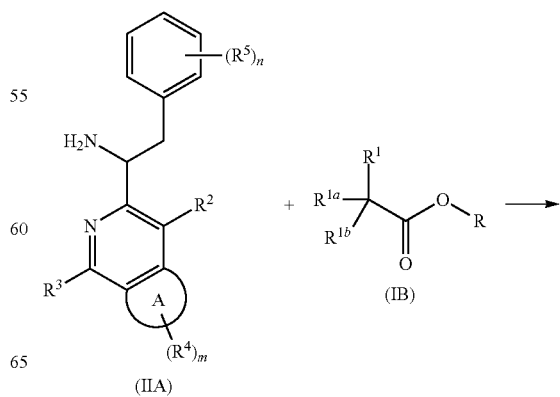

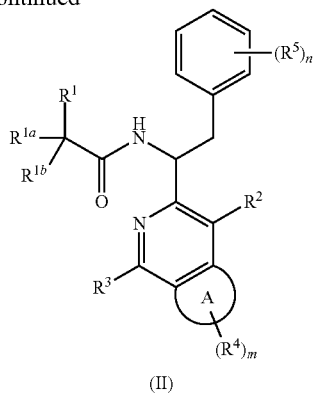

(II)

subjecting a compound of general formula (IIA) or a pharmaceutically acceptable salt thereof and a compound of general formula (IB) to a condensation reaction to give a compound of general formula (II) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (IIA) is preferably hydrochloride;

R is hydrogen or alkyl, and preferably hydrogen; and ring A, $R^1$-$R^5$, $R^{1a}$, $R^{1b}$, m and n are as defined in general formula (II).

Another aspect of the present disclosure relates to a method for preparing the compound of general formula (II-1) or the atropisomer, tautomer, mesomer, racemate, enantiomer, diastereomer thereof or the mixture thereof, or the pharmaceutically acceptable salt thereof, which comprises the following steps:

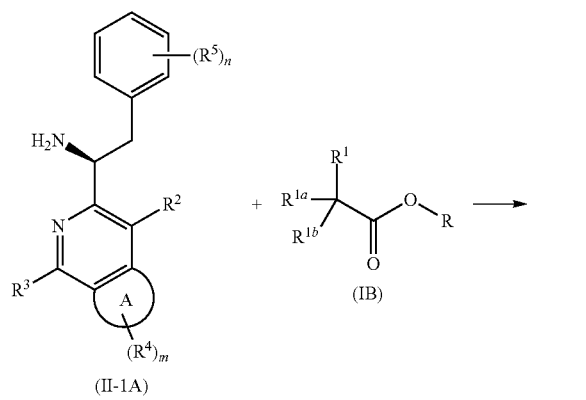

(II-1A)   (IB)

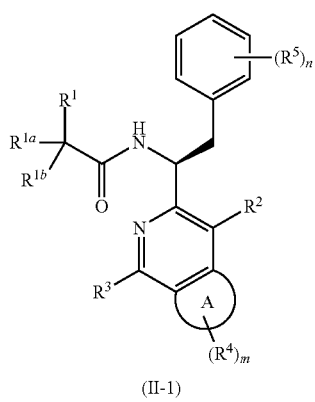

(II-1)

subjecting a compound of general formula (II-1A) or a pharmaceutically acceptable salt thereof and a compound of general formula (IB) to a condensation reaction to give a compound of general formula (II-1) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (II-1A) is preferably hydrochloride;

R is hydrogen or alkyl, and preferably hydrogen; and ring A, $R^1$-$R^5$, $R^{1a}$, $R^{1b}$, m and n are as defined in general formula (II).

Another aspect of the present disclosure relates to a method for preparing the compound of general formula (III) or the atropisomer, tautomer, mesomer, racemate, enantiomer, diastereomer thereof or the mixture thereof, or the pharmaceutically acceptable salt thereof, which comprises the following steps:

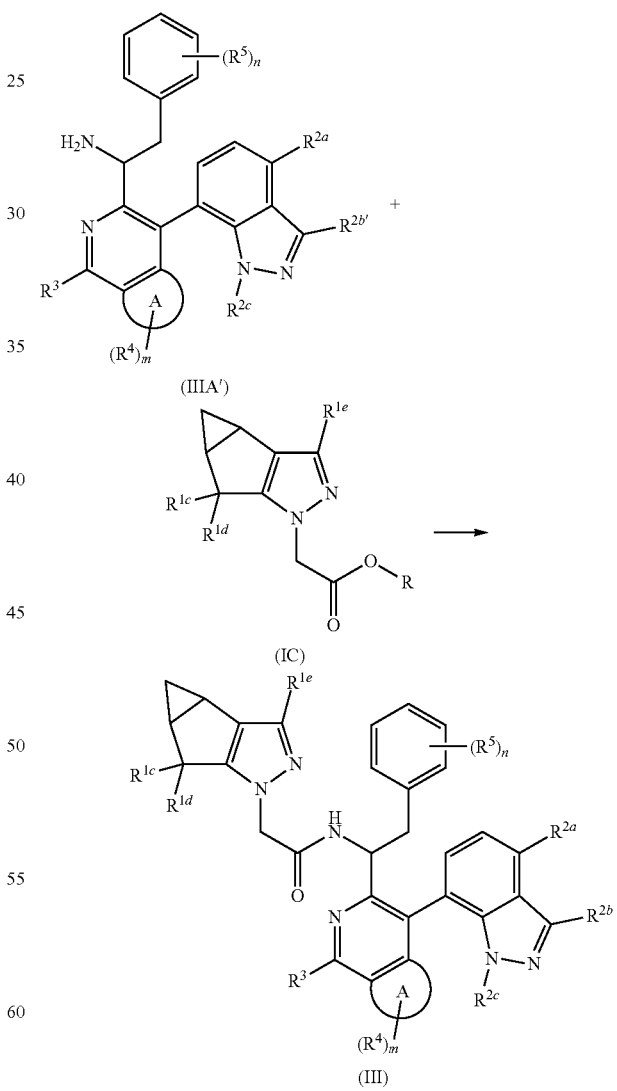

(IIIA')

(IC)

(III)

when $R^{2b'}$ in general formula (IIIA') and $R^{2b}$ in the final product are identical, subjecting a compound of general formula (IIIA') or a pharmaceutically acceptable salt thereof and a compound of general formula (IC) to a condensation reaction to give a compound of general formula (III) or an atropisomer, tautomer, mesomer, racemate, enantiomer, diastereomer thereof or a mixture thereof, or a pharmaceutically acceptable salt thereof, wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O)R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$;

when $R^{2b'}$ in general formula (IIIA') is

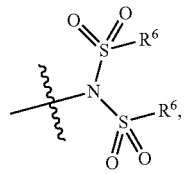

subjecting a compound of general formula (IIIA') or a pharmaceutically acceptable salt thereof and a compound of general formula (IC) to a condensation reaction, and meanwhile removing one —$S(O)_2R^6$ group to give a compound of general formula (III) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (IIIA) is preferably hydrochloride;

R is hydrogen or alkyl, and preferably hydrogen;

$R^{1c}$, $R^{1d}$, $R^{1e}$, $R^{2a}$, $R^{2b}$, $R^{2c}$, $R^3$-$R^5$, m and n are as defined in general formula (III).

Another aspect of the present disclosure relates to a method for preparing the compound of general formula (III-1) or the atropisomer, tautomer, mesomer, racemate, enantiomer, diastereomer thereof or the mixture thereof, or the pharmaceutically acceptable salt thereof, which comprises the following steps:

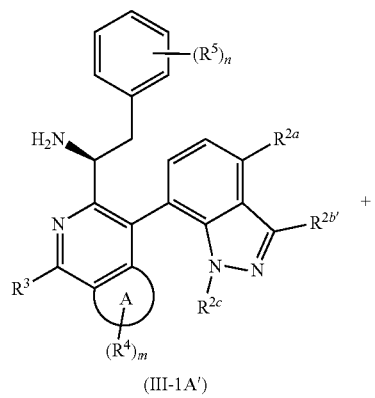

(III-1A')

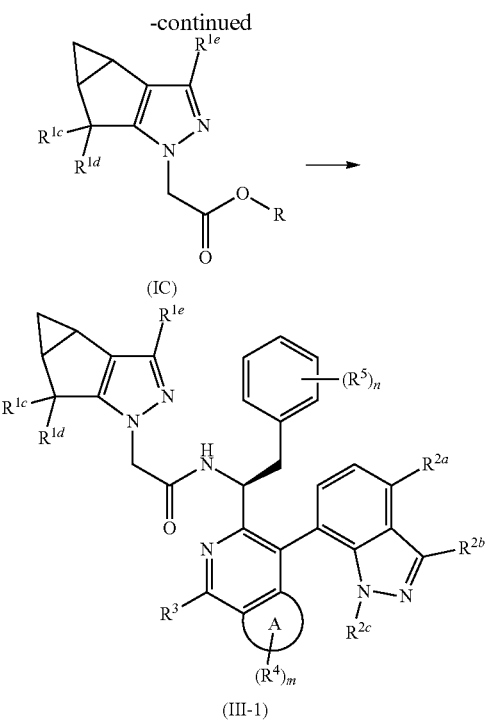

when $R^{2b'}$ in general formula (III-1A') and $R^{2b}$ in the final product are identical, subjecting a compound of general formula (III-1A') or a pharmaceutically acceptable salt thereof and a compound of general formula (IC) to a condensation reaction to give a compound of general formula (III-1) or an atropisomer, tautomer, mesomer, racemate, enantiomer, diastereomer thereof or a mixture thereof, or a pharmaceutically acceptable salt thereof;

when $R^{2b'}$ in general formula (III-1A') is

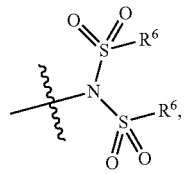

subjecting a compound of general formula (III-1A') or a pharmaceutically acceptable salt thereof and a compound of general formula (IC) to a condensation reaction, and meanwhile removing one —$S(O)_2R^6$ group to give a compound of general formula (III-1) or an atropisomer, tautomer, mesomer, racemate, enantiomer, diastereomer thereof or a mixture thereof, or a pharmaceutically acceptable salt thereof, wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O)R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$;

wherein, the pharmaceutically acceptable salt of the compound of general formula (III-1A') is preferably hydrochloride;

R is hydrogen or alkyl, and preferably hydrogen;
ring A, $R^{1c}$, $R^{1d}$, $R^{1e}$, $R^{2a}$, $R^{2b}$, $R^{2c}$, $R^3$-$R^5$, m and n are as defined in general formula (III).

Another aspect of the present disclosure relates to a method for preparing the compound of general formula (III) or the atropisomer, tautomer, mesomer, racemate, enantiomer, diastereomer thereof or the mixture thereof, or the pharmaceutically acceptable salt thereof, which comprises the following steps:

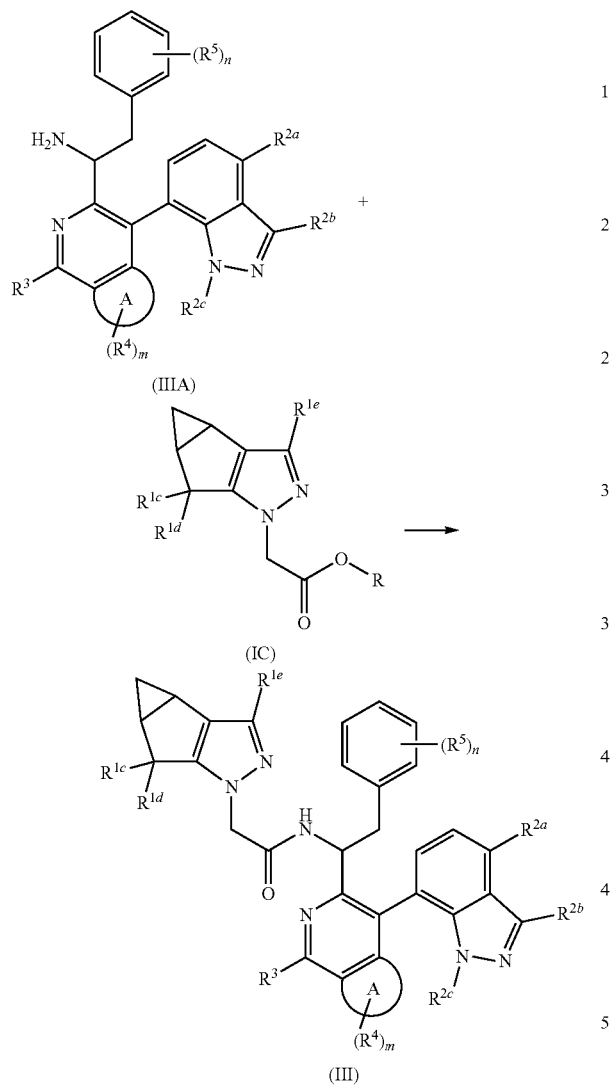

subjecting a compound of general formula (IIIA) or a pharmaceutically acceptable salt thereof and a compound of general formula (IC) to a condensation reaction to give a compound of general formula (III) or an atropisomer, tautomer, mesomer, racemate, enantiomer, diastereomer thereof or a mixture thereof, or a pharmaceutically acceptable salt thereof, wherein,
the pharmaceutically acceptable salt of the compound of general formula (IIIA) is preferably hydrochloride;
R is hydrogen or alkyl, and preferably hydrogen;
ring A, $R^{1c}$, $R^{1d}$, $R^{1e}$, $R^{2a}$, $R^{2b}$, $R^{2c}$, $R^3$-$R^5$, m and n are as defined in general formula (III).

Another aspect of the present disclosure relates to a method for preparing the compound of general formula (III-1) or the atropisomer, tautomer, mesomer, racemate, enantiomer, diastereomer thereof or the mixture thereof, or the pharmaceutically acceptable salt thereof, which comprises the following steps:

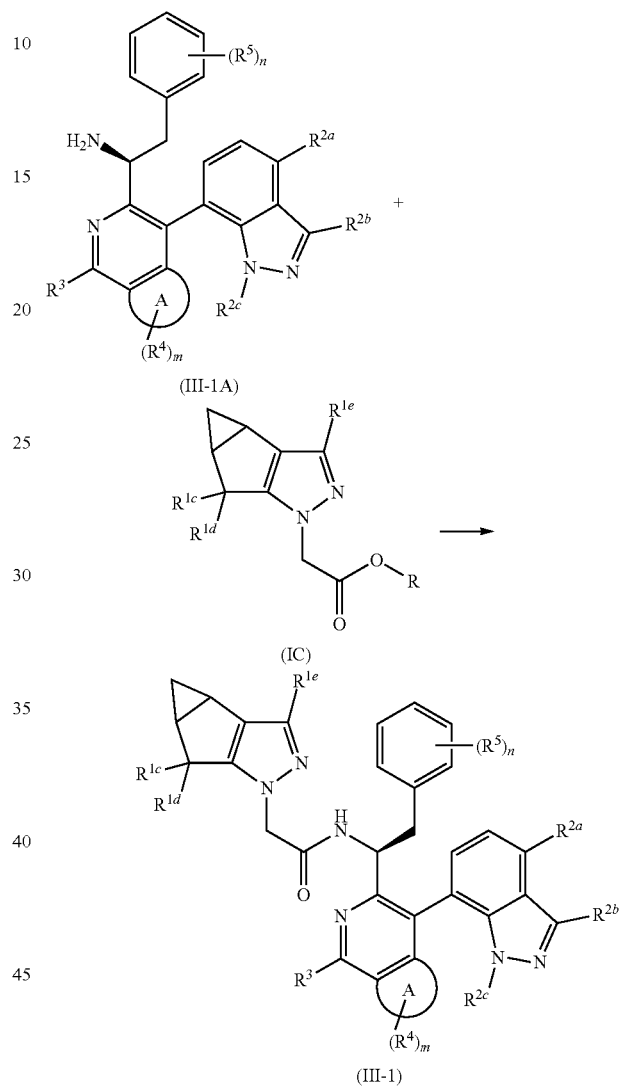

subjecting a compound of general formula (III-1A) or a pharmaceutically acceptable salt thereof and a compound of general formula (IC) to a condensation reaction to give a compound of general formula (III-1) or an atropisomer, tautomer, mesomer, racemate, enantiomer, diastereomer thereof or a mixture thereof, or a pharmaceutically acceptable salt thereof, wherein,
the pharmaceutically acceptable salt of the compound of general formula (III-1A) is preferably hydrochloride;
R is hydrogen or alkyl, and preferably hydrogen;
ring A, $R^{1c}$, $R^{1d}$, $R^{1e}$, $R^{2a}$, $R^{2b}$, $R^{2c}$, $R^3$-$R^5$, m and n are as defined in general formula (III).

Another aspect of the present disclosure relates to a method for preparing the compound of general formula (III-1a) or the atropisomer, tautomer, mesomer, racemate, enantiomer, diastereomer thereof or the mixture thereof, or the pharmaceutically acceptable salt thereof, which comprises the following steps:

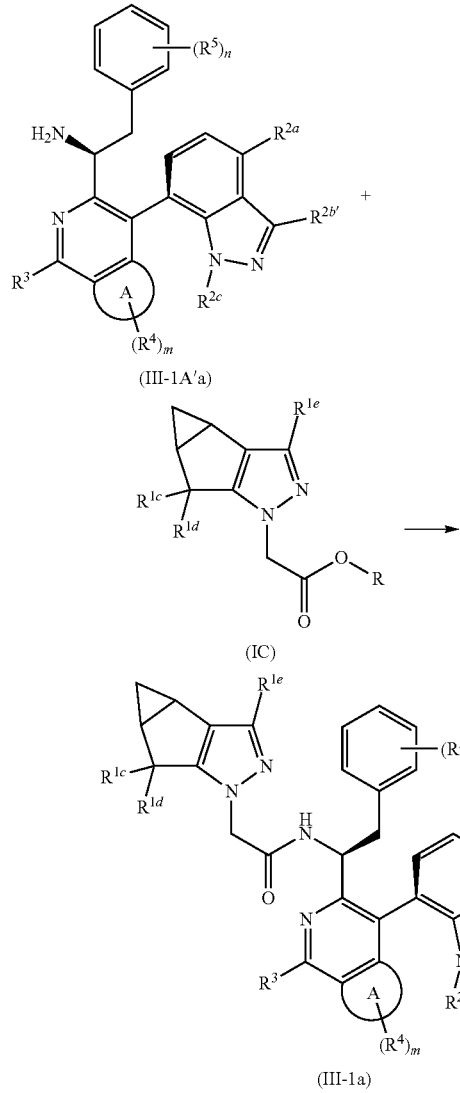

when $R^{2b'}$ in general formula (III-1A'a) and $R^{2b}$ in the final product are identical, subjecting a compound of general formula (III-1A'a) or a pharmaceutically acceptable salt thereof and a compound of general formula (IC) to a condensation reaction to give the compound of general formula (III-1a) or the atropisomer, tautomer, mesomer, racemate, enantiomer, diastereomer thereof or the mixture thereof, or the pharmaceutically acceptable salt thereof, wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR⁶, —OC(O)R⁶, —OC(O)NR⁷R⁸, —NHS(O)ᵣR⁶, —NHS(O)ᵣOR⁶, —NHS(O)₂NR⁷R⁸, —C(O)R⁶, —C(O)OR⁶, —C(O)NR⁷R⁸, —S(O)ᵣR⁶, —S(O)ᵣNR⁷R⁸, —NR⁷R⁸, —NHC(O)R⁶, —NHC(O)OR⁶, —NHC(O)NR⁷R⁸ and —NHC(O)NHOR⁶;

when $R^{2b'}$ in general formula (III-1A'a) is

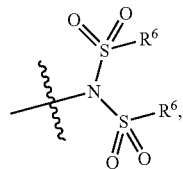

subjecting a compound of general formula (III-1A'a) or a pharmaceutically acceptable salt thereof and a compound of general formula (IC) to a condensation reaction, and meanwhile removing one —S(O)₂R⁶ group to give the compound of general formula (III-1a) or the atropisomer, tautomer, mesomer, racemate, enantiomer, diastereomer thereof or the mixture thereof, or the pharmaceutically acceptable salt thereof, wherein, the pharmaceutically acceptable salt of the compound of general formula (III-1A'a) is preferably hydrochloride;

R is hydrogen or alkyl, and preferably hydrogen; and ring A, $R^{1c}$, $R^{1d}$, $R^{1e}$, $R^{2a}$, $R^{2b}$, $R^{2c}$, $R^3$, $R^4$, $R^5$, n and m are as defined in general formula (III-1a).

Another aspect of the present disclosure relates to a method for preparing the compound of general formula (IV) or the atropisomer, tautomer, mesomer, racemate, enantiomer, diastereomer thereof or the mixture thereof, or the pharmaceutically acceptable salt thereof which comprises the following steps.

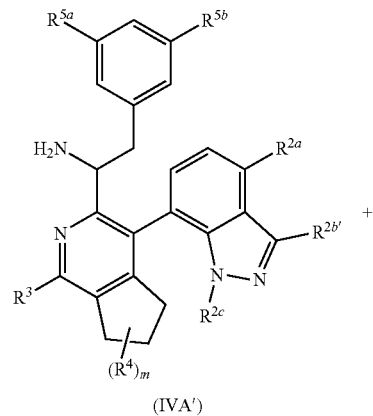

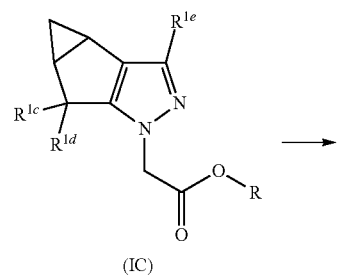

-continued

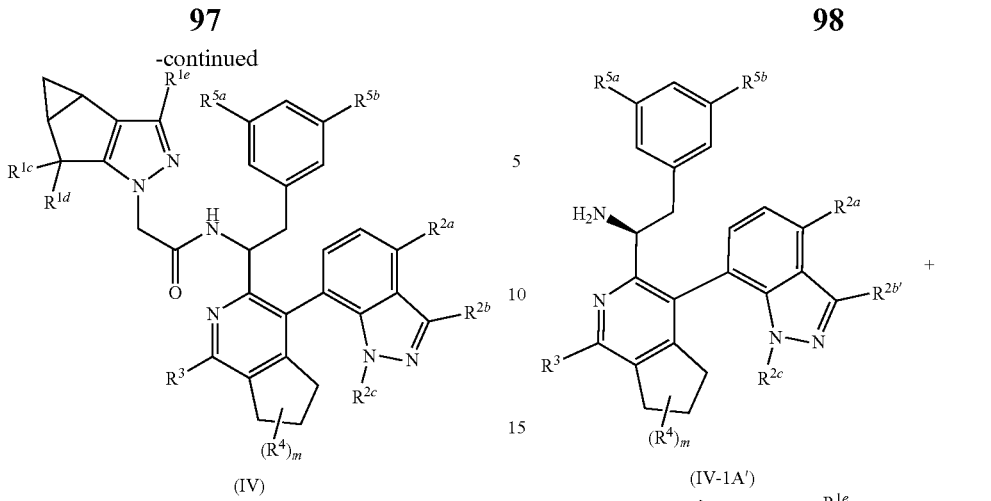

(IV)

when $R^{2b'}$ in general formula (IVA') and $R^{2b}$ in the final product are identical, subjecting a compound of general formula (IVA') or a pharmaceutically acceptable salt thereof and a compound of general formula (IC) to a condensation reaction to give a compound of general formula (IV), wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR$^6$, —OC(O)R$^6$, —OC(O)NR$^7$R$^8$, —NHS(O)$_r$R$^6$, —NHS(O)$_2$OR$^6$, —NHS(O)$_2$NR$^7$R$^8$, —C(O)R$^6$, —C(O)OR$^6$, —C(O)NR$^7$R$^8$, —S(O)$_r$R$^6$, —S(O)$_r$NR$^7$R$^8$, —NR$^7$R$^8$, —NHC(O)R$^6$, —NHC(O)OR$^6$, —NHC(O)NR$^7$R$^8$ and —NHC(O)NHOR$^6$;

when $R^{2b'}$ in general formula (IVA') is

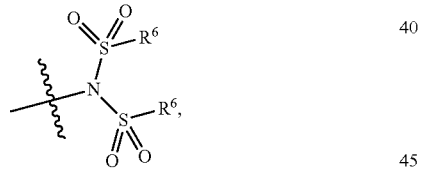

subjecting a compound of general formula (IVA') or a pharmaceutically acceptable salt thereof and a compound of formula (IC) to a condensation reaction, and meanwhile removing one —S(O)$_2$R$^6$ group to give a compound of general formula (IV), wherein, the pharmaceutically acceptable salt of the compound of general formula (IVA) is preferably hydrochloride;

R is hydrogen or alkyl, and preferably hydrogen; and $R^{1c}$, $R^{1d}$, $R^{1e}$, $R^{2a}$, $R^{2b}$, $R^{2c}$, $R^{5a}$, $R^{5b}$, $R^3$, $R^4$ and m are as defined in general formula (IV).

Another aspect of the present disclosure relates to a method for preparing a compound of general formula (IV-1) or an atropisomer, tautomer, mesomer, racemate, enantiomer, diastereomer thereof or a mixture thereof, or a pharmaceutically acceptable salt thereof, which comprises the following steps:

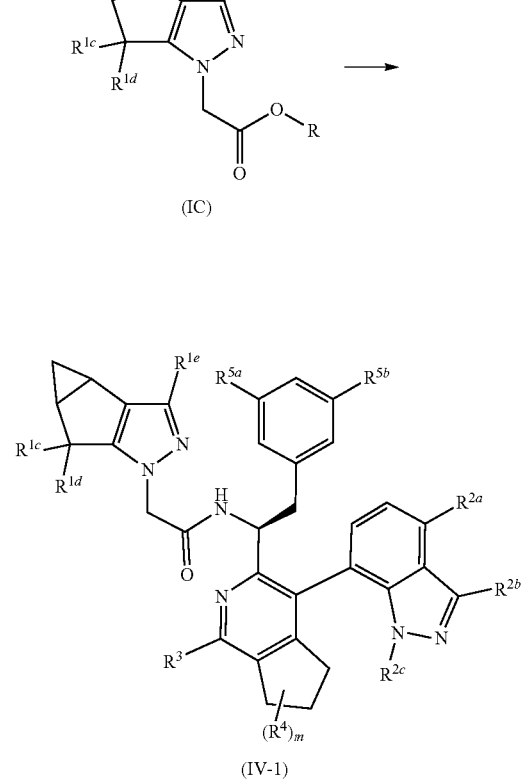

(IV-1A')

(IC)

(IV-1)

when $R^{2b'}$ in general formula (IV-1A') and $R^{2b}$ in the final product are identical, subjecting a compound of general formula (IV-1A') or a pharmaceutically acceptable salt thereof and a compound of general formula (IC) to a condensation reaction to give a compound of general formula (IV-1) or an atropisomer, tautomer, mesomer, racemate, enantiomer, diastereomer thereof or a mixture thereof, or a pharmaceutically acceptable salt thereof, wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR$^6$, —OC(O)R$^6$, —OC(O)NR$^7$R$^8$, —NHS(O)$_r$R$^6$, —NHS(O)$_2$OR$^6$, —NHS(O)$_2$NR$^7$R$^8$, —C(O)R$^6$, —C(O)OR$^6$, —C(O)NR$^7$R$^8$, —S(O)$_r$R$^6$, —S(O)$_r$NR$^7$R$^8$, —NR$^7$R$^8$, —NHC(O)R$^6$, —NHC(O)OR$^6$, —NHC(O)NR$^7$R$^8$ and —NHC(O)NHOR$^6$;

when R²ᵇ' in general formula (IV-1A') is

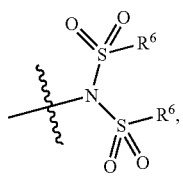

subjecting a compound of general formula (IV-1A') or a pharmaceutically acceptable salt thereof and a compound of general formula (IC) to a condensation reaction, and meanwhile removing one —S(O)₂R⁶ group to give a compound of general formula (IV-1) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (IV-1A) is preferably hydrochloride;

R is hydrogen or alkyl, and preferably hydrogen; and

R¹ᶜ, R¹ᵈ, R¹ᵉ, R²ᵃ, R²ᵇ, R²ᶜ, R⁵ᵃ, R⁵ᵇ, R³, R⁴ and m are as defined in general formula (IV).

Another aspect of the present disclosure relates to a method for preparing the compound of general formula (IV) or the atropisomer, tautomer, mesomer, racemate, enantiomer, diastereomer thereof or the mixture thereof, or the pharmaceutically acceptable salt thereof, which comprises the following steps:

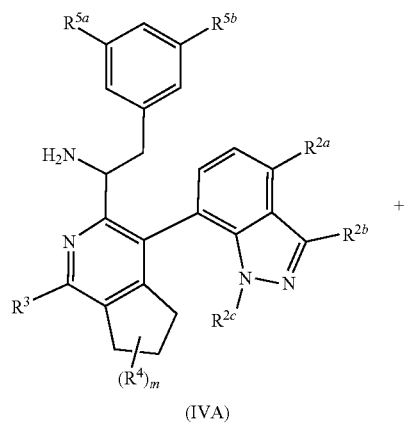
(IVA)

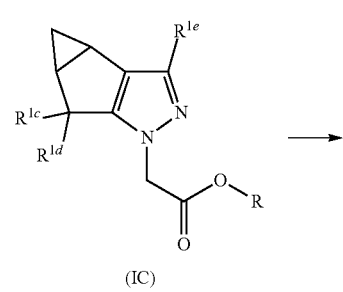
(IC)

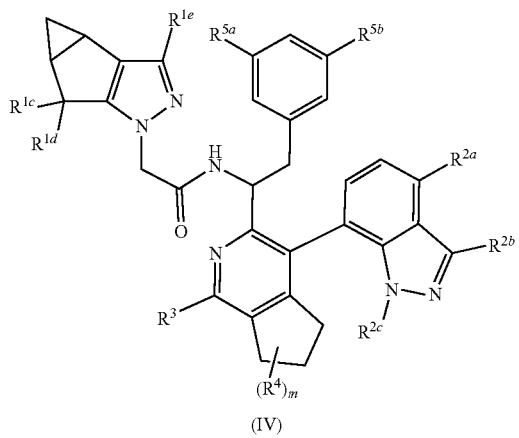
(IV)

subjecting a compound of general formula (IVA) or a pharmaceutically acceptable salt thereof and a compound of general formula (IC) to a condensation reaction to give a compound of general formula (IV), wherein, the pharmaceutically acceptable salt of the compound of general formula (IVA) is preferably hydrochloride;

R is hydrogen or alkyl, and preferably hydrogen; and

R¹ᶜ, R¹ᵈ, R¹ᵉ, R²ᵃ, R²ᵇ, R²ᶜ, R⁵ᵃ, R⁵ᵇ, R³, R⁴ and m are as defined in general formula (IV).

Another aspect of the present disclosure relates to a method for preparing a compound of general formula (IV-1) or an atropisomer, tautomer, mesomer, racemate, enantiomer, diastereomer thereof or a mixture thereof, or a pharmaceutically acceptable salt thereof, which comprises the following steps:

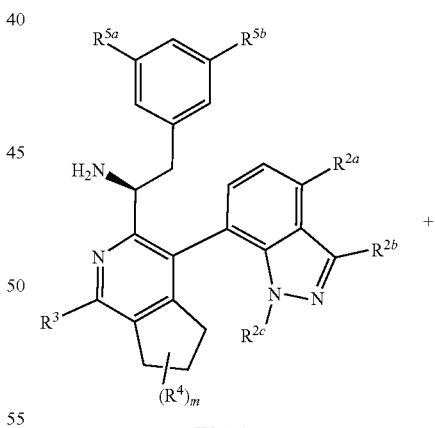
(IV-1A)

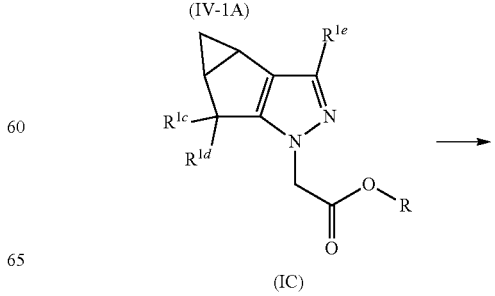
(IC)

-continued

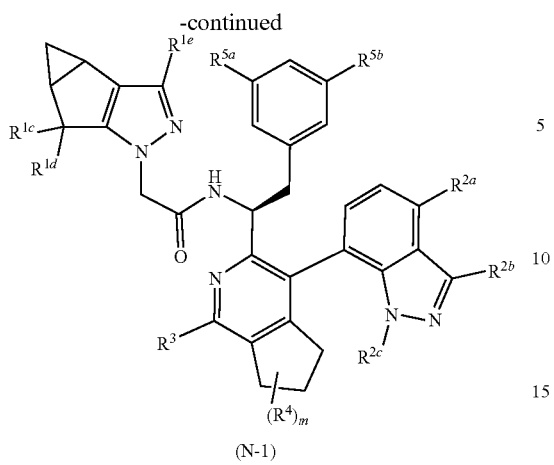

(N-1)

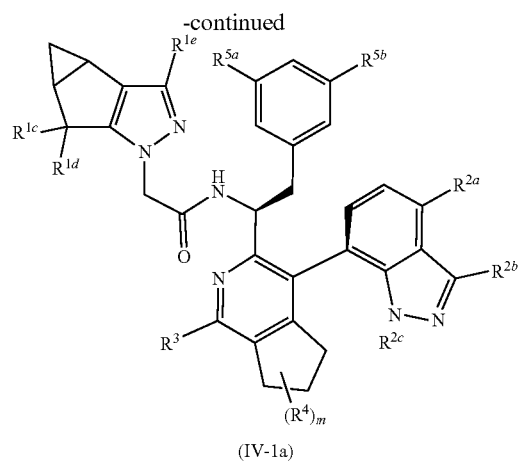

(IV-1a)

subjecting a compound of general formula (IV-1A) or a pharmaceutically acceptable salt thereof and a compound of general formula (IC) to a condensation reaction to give a compound of general formula (IV-1) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (IV-1A) is preferably hydrochloride;

R is hydrogen or alkyl, and preferably hydrogen; and $R^{1c}$, $R^{1d}$, $R^{1e}$, $R^{2a}$, $R^{2b}$, $R^{2c}$, $R^{5a}$, $R^{5b}$, $R^3$, $R^4$ and m are as defined in general formula (IV).

Another aspect of the present disclosure relates to a method for preparing a compound of general formula (IV-1a) or an atropisomer, tautomer, mesomer, racemate, enantiomer, diastereomer thereof or a mixture thereof, or a pharmaceutically acceptable salt thereof, which comprises the following steps:

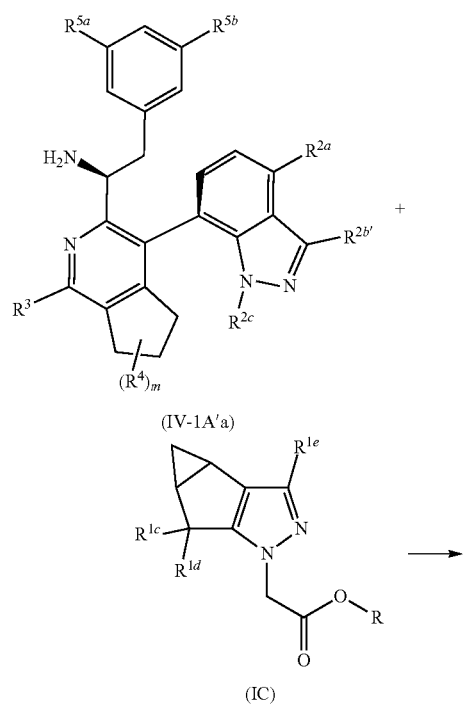

(IV-1A'a)

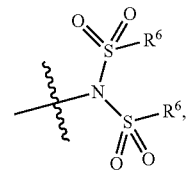

(IC)

when $R^{2b'}$ in general formula (IV-1A'a) and $R^{2b}$ in the final product are identical, subjecting a compound of general formula (IV-1A'a) or a pharmaceutically acceptable salt thereof and a compound of general formula (IC) to a condensation reaction to give a compound of general formula (IV-1a) or an atropisomer, tautomer, mesomer, racemate, enantiomer, diastereomer thereof or a mixture thereof, or a pharmaceutically acceptable salt thereof, wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O)R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$;

when $R^{2b'}$ in general formula (IV-1A'a) is $$\begin{array}{c} \text{O} \quad \text{O} \\ \diagdown \!\! \diagup \\ \text{S}\text{—}R^6 \\ | \\ \xi\text{—}N \\ | \\ \text{S}\text{—}R^6, \\ \diagup \!\! \diagdown \\ \text{O} \quad \text{O} \end{array}$$

subjecting a compound of general formula (IV-1A'a) or a pharmaceutically acceptable salt thereof and a compound of general formula (IC) to a condensation reaction, and meanwhile removing one —$S(O)_2R^6$ group to give a compound of general formula (IV-1a) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (IV-1A'a) is preferably hydrochloride;

R is hydrogen or alkyl, and preferably hydrogen; and $R^{1c}$, $R^{1d}$, $R^{1e}$, $R^{2a}$, $R^{2b}$, $R^{2c}$, $R^{5a}$, $R^{5b}$, $R^3$, $R^4$ and m are as defined in general formula (IV-1 a).

Another aspect of the present disclosure relates to a method for preparing a compound of general formula (V) or an atropisomer, tautomer, mesomer, racemate, enantiomer, diastereomer thereof or a mixture thereof, or a pharmaceutically acceptable salt thereof, which comprises the following steps:

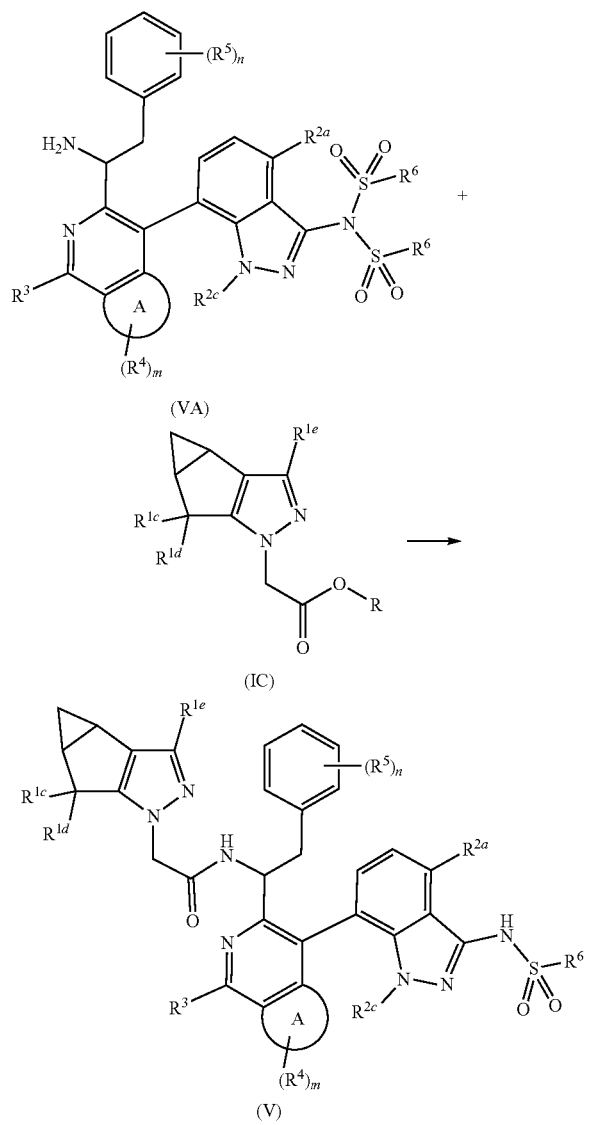

(VA)

(IC)

(V)

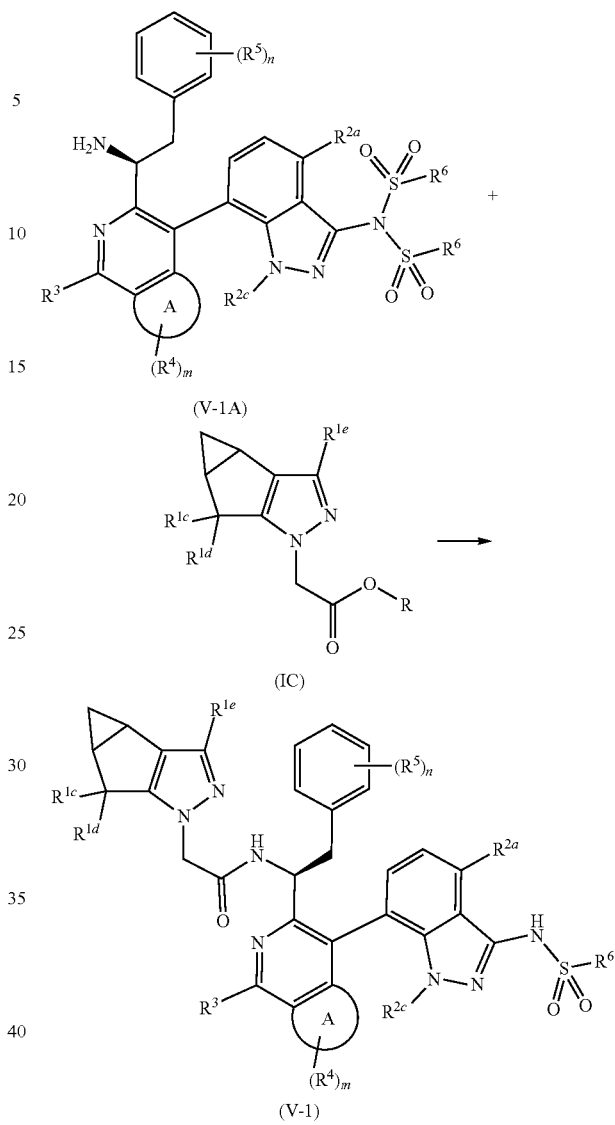

(V-1A)

(IC)

(V-1)

subjecting a compound of general formula (VA) or a pharmaceutically acceptable salt thereof and a compound of general formula (IC) to a condensation reaction, and meanwhile removing one —S(O)$_2$R$^6$ group to give a compound of general formula (V) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (VA) is preferably hydrochloride;

R is hydrogen or alkyl, and preferably hydrogen; and ring A, R$^{1c}$, R$^{1d}$, R$^{1e}$, R$^{2a}$, R$^{2c}$, R$^3$-R$^6$, m and n are as defined in general formula (V).

Another aspect of the present disclosure relates to a method for preparing a compound of general formula (V-1) or an atropisomer, tautomer, mesomer, racemate, enantiomer, diastereomer thereof or a mixture thereof, or a pharmaceutically acceptable salt thereof, which comprises the following steps:

subjecting a compound of general formula (V-1A) or a pharmaceutically acceptable salt thereof and a compound of general formula (IC) to a condensation reaction, and meanwhile removing one —S(O)$_2$R$^6$ group to give a compound of general formula (V-1) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (V-1A) is preferably hydrochloride;

R is hydrogen or alkyl, and preferably hydrogen; and ring A, R$^1$, R$^{1d}$, R$^{1e}$, R$^{2a}$, R$^{2c}$, R$^3$-R$^6$, m and n are as defined in general formula (V).

Another aspect of the present disclosure relates to a method for preparing a compound of general formula (VI) or an atropisomer, tautomer, mesomer, racemate, enantiomer, diastereomer thereof or a mixture thereof, or a pharmaceutically acceptable salt thereof, which comprises the following steps:

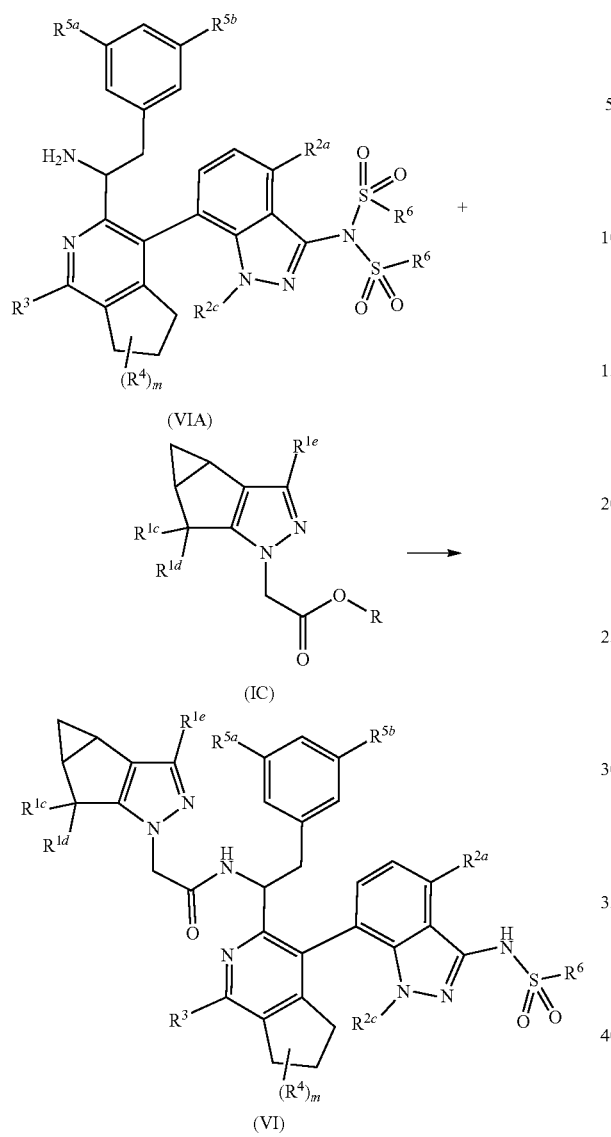

(VIA)

(IC)

(VI)

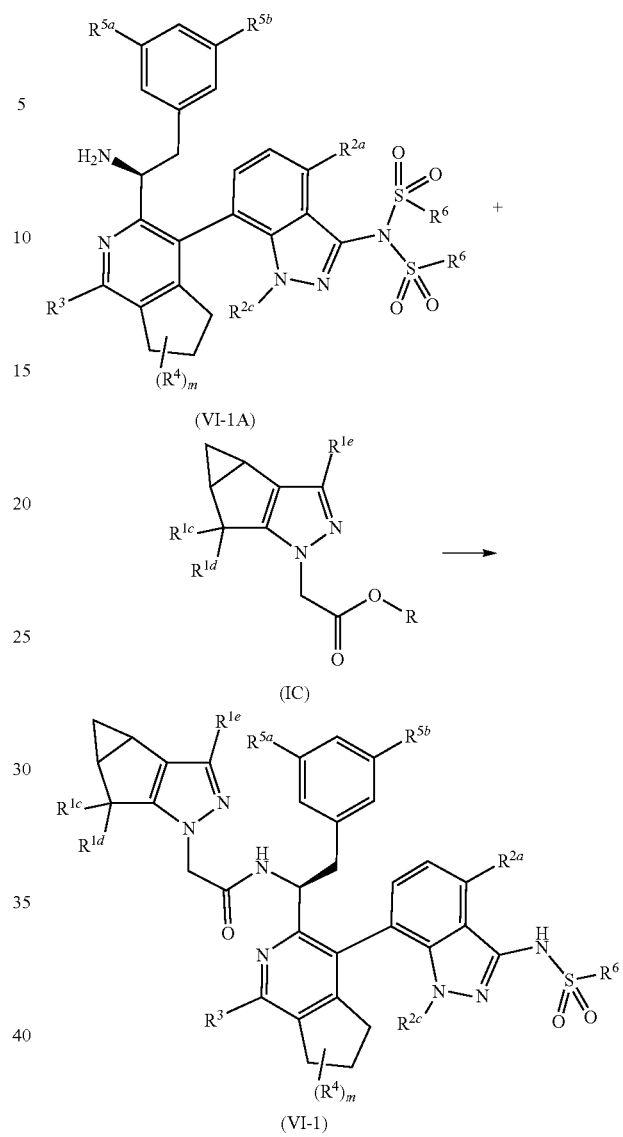

(VI-1A)

(IC)

(VI-1)

subjecting a compound of general formula (VIA) or a pharmaceutically acceptable salt thereof and a compound of general formula (IC) to a condensation reaction, and meanwhile removing one —S(O)$_2$R$^6$ group to give a compound of general formula (VI) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (VIA) is preferably hydrochloride;

R is hydrogen or alkyl, and preferably hydrogen; and

R$^{1c}$, R$^{1d}$, R$^{1e}$, R$^{2a}$, R$^{2c}$, R$^5$, R$^{5b}$, R$^3$, R$^4$, R$^6$ and m are as defined in general formula (VI).

Another aspect of the present disclosure relates to a method for preparing a compound of general formula (VI-1) or an atropisomer, tautomer, mesomer, racemate, enantiomer, diastereomer thereof or a mixture thereof, or a pharmaceutically acceptable salt thereof, which comprises the following steps:

subjecting a compound of general formula (VI-1A) or a pharmaceutically acceptable salt thereof and a compound of general formula (IC) to a condensation reaction, and meanwhile removing one —S(O)$_2$R$^6$ group to give a compound of general formula (VI-1) or an atropisomer, tautomer, mesomer, racemate, enantiomer, diastereomer thereof or a mixture thereof, or a pharmaceutically acceptable salt thereof, wherein, the pharmaceutically acceptable salt of the compound of general formula (VI-1A) is preferably hydrochloride;

R is hydrogen or alkyl, and preferably hydrogen; and

R$^{1c}$, R$^{1d}$, R$^{1e}$, R$^{2a}$, R$^{2c}$, R$^{5a}$, R$^{5b}$, R$^3$, R$^4$, R$^6$ and m are as defined in general formula (VI).

Another aspect of the present disclosure relates to a pharmaceutical composition comprising the compound of general formula (I) or the atropisomer, tautomer, mesomer, racemate, enantiomer, diastereomer thereof or the mixture thereof, or the pharmaceutically acceptable salt thereof according to the present disclosure, and one or more pharmaceutically acceptable carriers, diluents or excipients.

The present disclosure further relates to use of the compound of general formula (I) or the atropisomer, tautomer, mesomer, racemate, enantiomer, diastereomer thereof or the mixture thereof, or the pharmaceutically acceptable salt thereof according to the present disclosure, or the pharmaceutical composition comprising the same in the preparation of an HIV capsid protein inhibitor.

The present disclosure further relates to use of the compound of general formula (I) or the atropisomer, tautomer, mesomer, racemate, enantiomer, diastereomer thereof or the mixture thereof, or the pharmaceutically acceptable salt thereof according to the present disclosure, or the pharmaceutical composition comprising the same in the preparation of a medicament for the prevention and/or treatment of a viral infection disease which may be an HIV infection (e.g., HIV-1 and/or HIV-2).

The present disclosure also relates to a method for inhibiting an HIV capsid protein, which comprises administering to a patient in need thereof a therapeutically effective amount of the compound of general formula (I) or the atropisomer, tautomer, mesomer, racemate, enantiomer, diastereomer thereof or the mixture thereof, or the pharmaceutically acceptable salt thereof according to the present disclosure, or the pharmaceutical composition comprising the same.

The present disclosure also relates to a method for preventing and/or treating a viral infection disease which may be an HIV infection (e.g., HIV-1 and/or HIV-2), which comprises administering to a patient in need thereof a therapeutically effective amount of the compound of general formula (I) or the atropisomer, tautomer, mesomer, racemate, enantiomer, diastereomer thereof or the mixture thereof, or the pharmaceutically acceptable salt thereof according to the present disclosure, or the pharmaceutical composition comprising the same.

The present disclosure further relates to the compound of general formula (I) or the atropisomer, tautomer, mesomer, racemate, enantiomer, diastereomer thereof or the mixture thereof, or the pharmaceutically acceptable salt thereof according to the present disclosure, or the pharmaceutical composition comprising the same for use as a medicament.

The present disclosure also relates to the compound of general formula (I) or the atropisomer, tautomer, mesomer, racemate, enantiomer, diastereomer thereof or the mixture thereof, or the pharmaceutically acceptable salt thereof according to the present disclosure, or the pharmaceutical composition comprising the same for use as an HIV capsid protein inhibitor.

The present disclosure also relates to the compound of general formula (I) or the atropisomer, tautomer, mesomer, racemate, enantiomer, diastereomer thereof or the mixture thereof, or the pharmaceutically acceptable salt thereof according to the present disclosure, or the pharmaceutical composition comprising the same for use as a medicament for the prevention and/or treatment of a viral infection disease which may be an HIV infection (e.g., HIV-1 and/or HIV-2).

The active compound may be formulated into a form suitable for administration by any suitable route, preferably in a form of a unit dose, or in a form of a single dose that can be self-administered by a patient. The unit dose of the compound or composition disclosed herein may be in a tablet, a capsule, a cachet, a vial, a powder, a granule, a lozenge, a suppository, a powder for reconstitution or a liquid formulation.

The dosage of the compound or composition used in the treatment method disclosed herein will generally vary with the severity of the disease, the weight of the patient, and the relative efficacy of the compound. However, as a general guide, a suitable unit dose may be 0.1 mg to 1000 mg.

The pharmaceutical composition disclosed herein may comprise, in addition to the active compound, one or more excipients selected from the group consisting of a filler (diluent), a binder, a wetting agent, a disintegrant, an excipient, and the like. Depending on the method of administration, the compositions may comprise 0.1 to 99 wt. % of active compound.

The pharmaceutical compositions comprising the active ingredient may be in a form suitable for oral administration, for example, a tablet, a dragee, a lozenge, an aqueous or oil suspension, a dispersible powder or granule, an emulsion, a hard or soft capsule, or a syrup or elixir. Oral compositions can be prepared according to any method known in the art for preparing pharmaceutical compositions and may comprise one or more ingredients selected from the group consisting of a sweetener, a corrigent, a colorant and a preservative, so as to provide a pleasant-to-eye and palatable pharmaceutical formulation. A tablet comprises an active ingredient and a non-toxic pharmaceutically acceptable excipient which is used for mixing and is suitable for the preparation of the tablet. Such an excipient may be an inert excipient, a granulating agent, a disintegrating agent, a binder and a lubricant. Such a tablet may be uncoated or may be coated by known techniques for masking the taste of the drug or delaying the disintegration and absorption of the drug in the gastrointestinal tract and thus enabling sustained release of the drug over a longer period.

An oral formulation in a soft gelatin capsule where the active ingredient is mixed with an inert solid diluent or with a water-soluble carrier or oil vehicle may also be provided.

An aqueous suspension comprises an active substance and an excipient which is used for mixing and suitable for the preparation of the aqueous suspension. Such an excipient is a suspending agent, a dispersant or a wetting agent. The aqueous suspension may also comprise one or more preservatives, one or more colorants, one or more corrigents and one or more sweeteners.

An oil suspension may be formulated by suspending the active ingredient in a vegetable oil, or in a mineral oil. The oil suspension may comprise a thickening agent. The sweeteners and corrigents described above may be added to provide a palatable formulation. Antioxidants may also be added to preserve the compositions.

Dispersible powders and granules suitable for the preparation of an aqueous suspension may be allowed to provide an active ingredient, and a dispersant or a wetting agent, a suspending agent or one or more preservatives for mixing, by adding water. The description above can be exemplified by suitable dispersants or wetting agents and suspending agents. Other excipients, such as sweeteners, corrigents and colorants, may also be added. Antioxidants such as ascorbic acid are added to preserve these compositions.

The pharmaceutical composition disclosed herein may also be in a form of an oil-in-water emulsion. The oil phase may be a vegetable oil or a mineral oil, or a mixture thereof. Suitable emulsifiers may be naturally occurring phospholipids, and the emulsion may also comprise a sweetener, a corrigent, a preservative and an antioxidant. Such a formulation may also comprise a palliative, a preservative, a colorant and an antioxidant.

The pharmaceutical composition disclosed herein may be in a form of a sterile injectable aqueous solution. Available and acceptable vehicles or solvents include water, Ringer's solution and isotonic sodium chloride solution. A sterile injectable formulation may be a sterile injectable oil-inwater microemulsion in which an active ingredient is dissolved in an oil phase. The injection or microemulsion can be locally injected into the bloodstream of a patient in large quantities. Alternatively, it may be desirable to administer solutions and microemulsions in such a way as to maintain a constant circulating concentration of the compound disclosed herein. To maintain such a constant concentration, a continuous intravenous delivery device may be used. An example of such a device is a Deltec CADD-PLUS™ 5400 intravenous injection pump.

The pharmaceutical composition disclosed herein may be in a form of a sterile injectable aqueous or oil suspension for intramuscular and subcutaneous administration. The suspension can be prepared according to the prior art using those suitable dispersants or wetting agents and suspending agents mentioned above. The sterile injectable formulation may also be a sterile injection or suspension prepared in a parenterally acceptable non-toxic diluent or solvent. In addition, a sterile fixed oil may be conventionally used as a solvent or a suspending medium. For this purpose, any blend fixed oil may be employed. In addition, fatty acids may also be used to prepare injections.

The compound disclosed herein may be administered in a form of a suppository for rectal administration. Such a pharmaceutical composition can be prepared by mixing a drug with a suitable non-irritating excipient which is a solid at an ambient temperature but a liquid in the rectum and therefore will melt in the rectum to release the drug.

As is well known to those skilled in the art, the dosage of the drug administered depends on a variety of factors, including but not limited to, the activity of the particular compound employed, the age of the patient, the weight of the patient, the health condition of the patient, the behavior of the patient, the diet of the patient, the time of administration, the route of administration, the rate of excretion, the combination of drugs, and the like. In addition, the optimal treatment regimen, such as the mode of administration, the daily dose of the compound of formula (I) or the type of pharmaceutically acceptable salts, can be verified according to conventional treatment regimens.

Definition of Terms

Unless otherwise stated, the terms used in the specification and claims have the following meanings.

The term "alkyl" refers to a saturated aliphatic hydrocarbon group which is a linear or branched group containing 1 to 20 carbon atoms, preferably an alkyl containing 1 to 12 (e.g., 1, 2, 3, 4, 5, 6, 7, 8, 9, 10, 11 and 12) carbon atoms, and more preferably an alkyl containing 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various side-chain isomers thereof, etc. More preferred is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —S(O)$_x$R$^6$ and —NHS(O)$_x$R$^6$.

The term "alkylene" refers to a saturated linear or branched aliphatic hydrocarbon group having 2 residues derived from the parent alkane by removal of two hydrogen atoms from the same carbon atom or two different carbon atoms, which is a linear or branched group containing 1 to 20 carbon atoms, preferably an alkylene group containing 1 to 12 (e.g., 1, 2, 3, 4, 5, 6, 7, 8, 9, 10, 11 and 12) carbon atoms, and more preferably an alkylene group containing 1 to 6 carbon atoms. Non-limiting examples of alkylene include, but are not limited to, methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—) and the like. The alkylene may be substituted or unsubstituted. When substituted, the substituent may be substituted at any available connection site with one or more substituents preferably independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkenyl" refers to an alkyl compound containing at least one carbon-carbon double bond in the molecule, wherein the alkyl is as defined above. The alkenyl may be substituted or unsubstituted. When substituted, the substituent may be substituted with one or more substituents preferably independently selected from the group consisting of hydrogen, alkyl, alkoxy, halogen, haloalkyl, hydroxy, hydroxyalkyl, cyano, amino, nitro, cycloalkyl, heterocyclyl, aryl, heteroaryl, —S(O)$_x$R$^6$ and —NHS(O)$_x$R$^6$.

The term "alkynyl" refers to a linear or branched hydrocarbon having at least one carbon-carbon triple bond. It is a linear or branched group containing 2 to 20 carbon atoms, preferably containing 2 to 12 carbon atoms, and more preferably 2 to 6 carbon atoms. Non-limiting examples of alkynyl include, but are not limited to, —C≡CH, —CH$_2$C≡CH, —CH$_2$C≡CCH$_3$, —C≡CCH$_2$CH$_3$, —CH$_2$C≡CCH$_2$CH$_3$, —C≡CCH(CH$_3$)$_2$, —C(CH$_3$)$_2$C≡CH, —C(CH$_3$)$_2$C≡CCH$_3$, and the like. The alkynyl may be substituted or unsubstituted. When substituted, the substituent may be substituted with one or more substituents preferably independently selected from the group consisting of hydrogen, alkyl, alkoxy, halogen, haloalkyl, hydroxy, hydroxyalkyl, cyano, amino, nitro, cycloalkyl, heterocyclyl, aryl, heteroaryl, —S(O)$_x$R$^6$ and —NHS(O)$_x$R$^6$.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms, more preferably 3 to 8 carbon atoms, and most preferably 3 to 6 carbon atoms.

Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term "spiro cycloalkyl" refers to a 5- to 20-membered polycyclic group in which monocyclic rings share one carbon atom (referred to as the spiro atom), wherein the spiro cycloalkyl may contain one or more double bonds. Preferably, the spiro cycloalkyl is 6- to 14-membered, and more preferably 7- to 10-membered (e.g., 7-membered, 8-membered, 9-membered or 10-membered). According to the number of the spiro atoms shared among the rings, the spiro cycloalkyl may be monospiro cycloalkyl, bispiro cycloalkyl or polyspiro cycloalkyl, preferably monospiro cycloalkyl and bispiro cycloalkyl, more preferably 4-membered/4-membered, 4-membered/5-membered, 4-membered/6-membered, 5-membered/5-membered or 5-membered/6-membered monospiro cycloalkyl. Non-limiting examples of spiro cycloalkyl include:

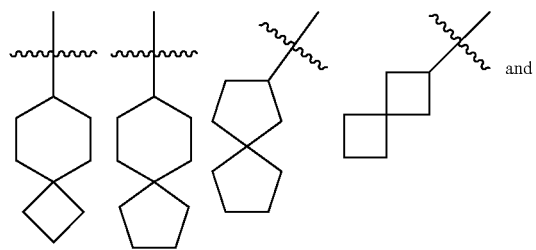

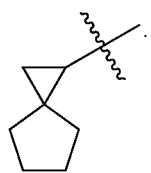

The term "fused cycloalkyl" refers to a 5- to 20-membered carbon polycyclic group in which each ring shares a pair of adjacent carbon atoms with the other rings in the system, wherein one or more of the rings may contain one or more double bonds. Preferably, the fused cycloalkyl is 6- to 14-membered, and more preferably 7- to 10-membered. According to the number of the formed rings, the fused cycloalkyl may be bicyclic, tricyclic, tetracyclic or polycyclic cycloalkyl, preferably bicyclic or tricyclic cycloalkyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic cycloalkyl. Non-limiting examples of fused cycloalkyl include:

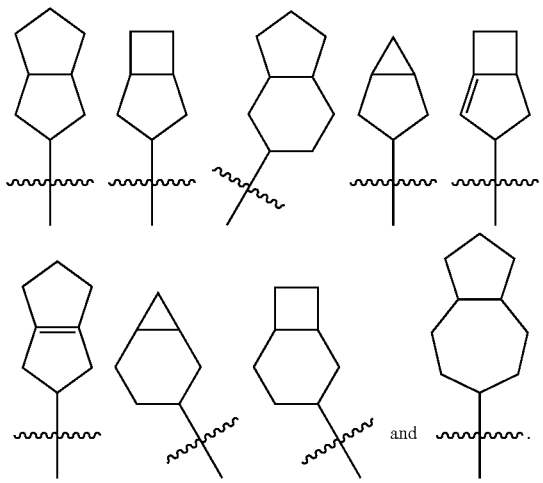

The term "bridged cycloalkyl" refers to a 5- to 20-membered carbon polycyclic group in which any two rings share two carbon atoms that are not directly connected to each other, wherein the bridged cycloalkyl may contain one or more double bonds. Preferably, the bridged cycloalkyl is 6- to 14-membered, and more preferably 7- to 10-membered. According to the number of the formed rings, the bridged cycloalkyl may be bicyclic, tricyclic, tetracyclic or polycyclic, preferably bicyclic, tricyclic or tetracyclic, and more preferably bicyclic or tricyclic. Non-limiting examples of bridged cycloalkyl include:

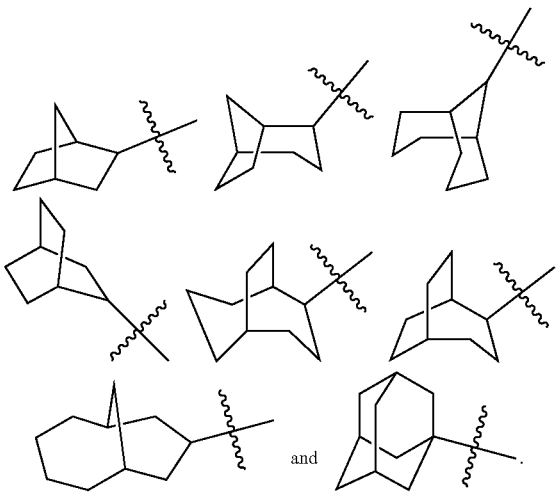

The cycloalkyl ring includes those in which the cycloalkyl described above (including monocyclic, spiro, fused and bridged rings) is fused to an aryl, heteroaryl or heterocycloalkyl ring, wherein the ring connected to the parent structure is cycloalkyl. Non-limiting examples include indanyl, tetrahydronaphthyl, benzocycloheptanyl, and the like, and preferably indanyl and tetrahydronaphthyl.

The cycloalkyl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —S(O)$_r$R$^6$ and —NHS(O)$_r$R$^6$.

The term "alkoxy" refers to —O-(alkyl) and —O-(unsubstituted cycloalkyl), wherein the alkyl is as defined above. Non-limiting examples of alkoxy include methoxy, ethoxy, propoxy, butoxy, cyclopropyloxy, cyclobutoxy, cyclopentyloxy, and cyclohexyloxy. The alkoxy may be optionally substituted or unsubstituted. When substituted, the substituent is preferably one or more groups independently selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —S(O)$_r$R$^6$ and —NHS(O)$_r$R$^6$.

The term "heterocyclyl" refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen, sulfur, S(O) and S(O)$_2$, excluding a cyclic portion of —O—O—, —O—S— or —S—S—, and the remaining ring atoms are carbon atoms. The heterocyclyl preferably contains 3 to 12 (e.g., 3, 4, 5, 6, 7, 8, 9, 10, 11 and 12) ring atoms, of which 1 to 4 (e.g., 1, 2, 3 and 4) are heteroatoms; more preferably 3 to 8 ring atoms, of which 1 to 3 are heteroatoms; more preferably 3 to 6 ring atoms, of which 1 to 3 are heteroatoms; most preferably 5 or 6 ring atoms, of which 1 to 3 are heteroatoms. Non-limiting examples of monocyclic heterocyclyl include pyrrolidinyl, tetrahydropyranyl, 1,3-dioxolane, 1,2,3,6-tetrahydropyridinyl, piperidinyl, piperazinyl, morpholinyl, thiomorpholinyl, homopiperazinyl, and the like. Polycyclic heterocyclyl includes spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more ring atoms are heteroatoms selected from the group consisting of nitrogen, oxygen, sulfur, S(O) and S(O)$_2$, and the remaining ring atoms are carbon atoms. The spiro heterocyclyl may contain one or more double bonds. Preferably, the spiro heterocyclyl is 6- to 14-membered, and more preferably 7- to 10-membered. According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 4-membered/4-membered, 4-membered/5-membered, 4-membered/6-membered, 5-membered/5-membered or 5-membered/6-membered monospiro heterocyclyl. Non-limiting examples of spiro heterocyclyl include:

The term "fused heterocyclyl" refers to a 5- to 20-membered polycyclic heterocyclyl group in which each ring shares a pair of adjacent atoms with the other rings in the system, wherein one or more of the rings may contain one or more double bonds. In the fused heterocyclyl, one or more of the ring atoms are heteroatoms selected from the group consisting of nitrogen, oxygen, sulfur, S(O) and S(O)$_2$, and the remaining ring atoms are carbon atoms. Preferably, the fused heterocyclyl is 6- to 14-membered, and more preferably 7- to 10-membered. According to the number of the formed rings, the fused heterocyclyl may be bicyclic, tricyclic, tetracyclic or polycyclic fused heterocyclyl, preferably bicyclic or tricyclic fused heterocyclyl, and more preferably 3-membered/4-membered, 3-membered/5-membered, 3-membered/6-membered, 4-membered/4-membered, 4-membered/5-membered, 4-membered/6-membered, 5-membered/4-membered, 5-membered/5-membered, 5-membered/6-membered, 6-membered/3-membered, 6-membered/4-membered, 6-membered/5-membered and 6-membered/6-membered bicyclic fused heterocyclyl. Non-limiting examples of fused heterocyclyl include:

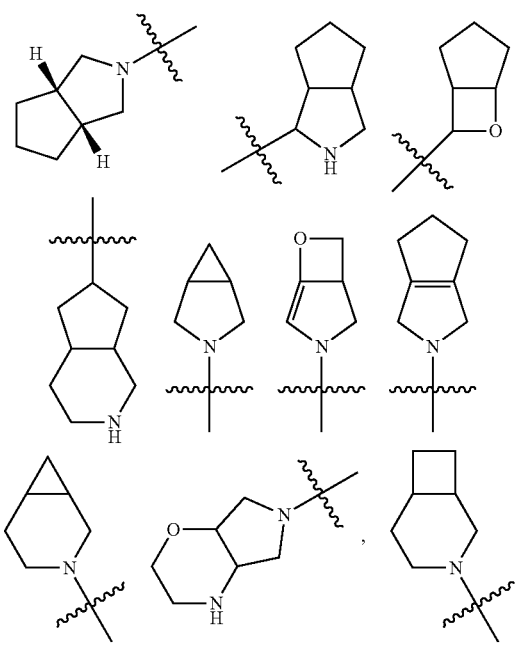

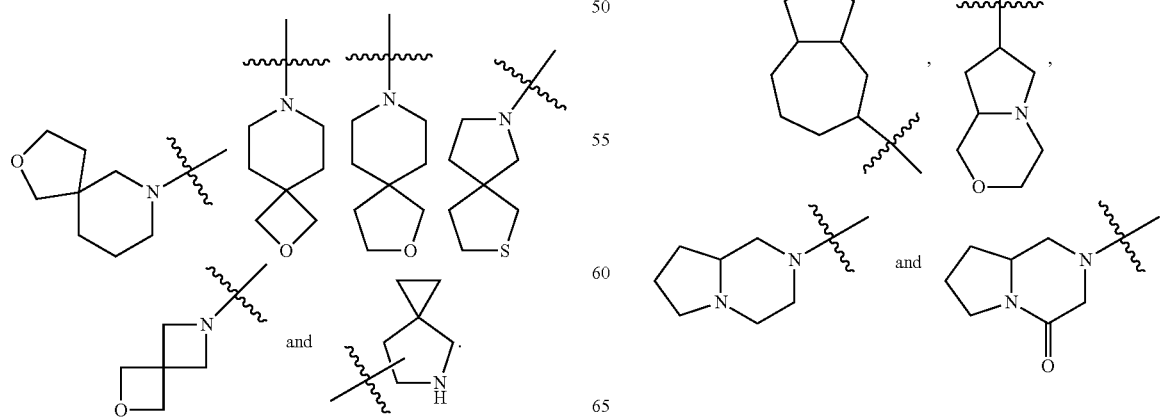

The term "bridged heterocyclyl" refers to a 5- to 14-membered polycyclic heterocyclyl group in which any two rings share two carbon atoms that are not directly connected to each other, wherein the bridged heterocyclyl may contain one or more double bonds. In the bridged heterocyclyl, one or more of the ring atoms are heteroatoms selected from the group consisting of nitrogen, oxygen, sulfur, S(O) and S(O)$_2$, and the remaining ring atoms are carbon atoms. Preferably, the bridged heterocyclyl is 6- to 14-membered, and more preferably 7- to 10-membered. According to the number of the formed rings, the bridged heterocyclyl may be bicyclic, tricyclic, tetracyclic or polycyclic, preferably bicyclic, tricyclic or tetracyclic, and more preferably bicyclic or tricyclic. Non-limiting examples of bridged heterocyclyl include:

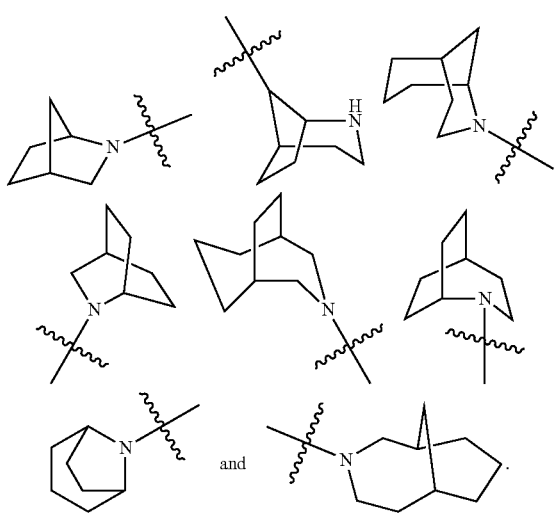

The heterocyclyl ring includes those in which the heterocyclyl described above (including monocyclic, spiro heterocyclic, fused heterocyclic and bridged heterocyclic rings) is fused to an aryl, heteroaryl or cycloalkyl ring, wherein the ring connected to the parent structure is heterocyclyl. Non-limiting examples include:

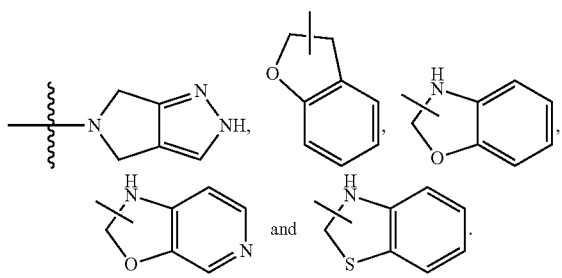

The heterocyclyl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —S(O)$_r$R$^6$ and —NHS(O)$_r$R$^6$.

The term "aryl" refers to a 6- to 14-membered, preferably 6- to 10-membered carbon monocyclic or fused polycyclic (fused polycyclic rings are those sharing a pair of adjacent carbon atoms) group having a conjugated π-electron system such as phenyl and naphthyl. The aryl ring includes those in which the aryl ring described above is fused to a heteroaryl, heterocyclyl or cycloalkyl ring, wherein the ring connected to the parent structure is an aryl ring. Non-limiting examples include:

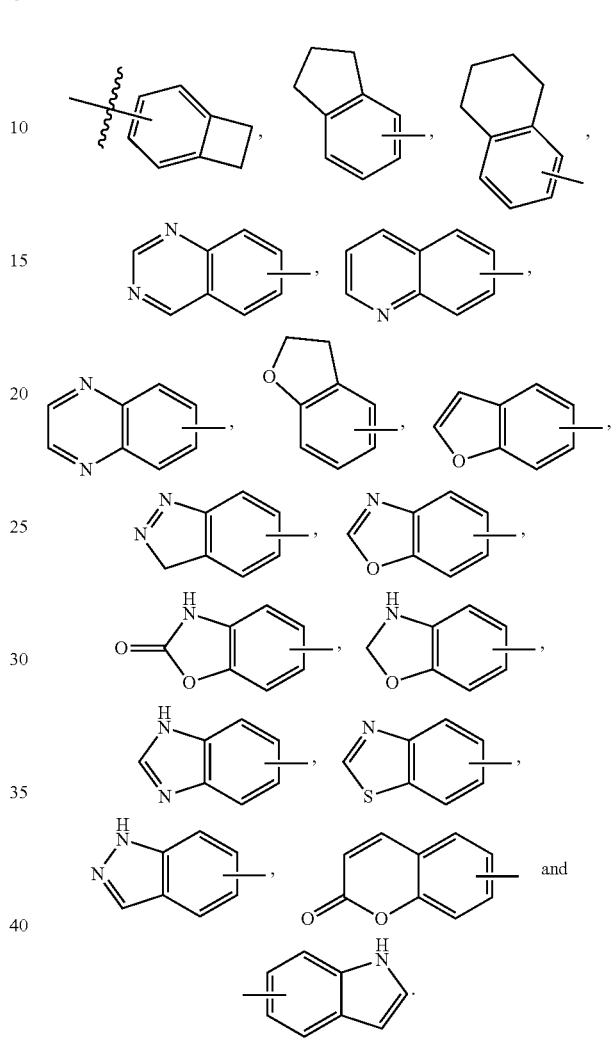

The aryl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —S(O)$_r$R$^6$ and —NHS(O)$_r$R$^6$.

The term "heteroaryl" refers to a heteroaromatic system containing 1 to 4 (e.g., 1, 2, 3 and 4) heteroatoms and 5 to 14 ring atoms, wherein the heteroatoms are selected from the group consisting of oxygen, sulfur and nitrogen. The heteroaryl is preferably 5- to 10-membered (e.g., 5, 6, 7, 8, 9 or 10) and more preferably 5- or 6-membered, e.g., furanyl, thienyl, pyridinyl, pyrrolyl, N-alkylpyrrolyl, pyrimidinyl, pyrazinyl, pyridazinyl, imidazolyl, pyrazolyl, triazolyl, and tetrazolyl. The heteroaryl ring includes those in which the heteroaryl ring described above is fused to an aryl, heterocyclyl or cycloalkyl ring, wherein the ring connected to the parent structure is a heteroaryl ring. Non-limiting examples include:

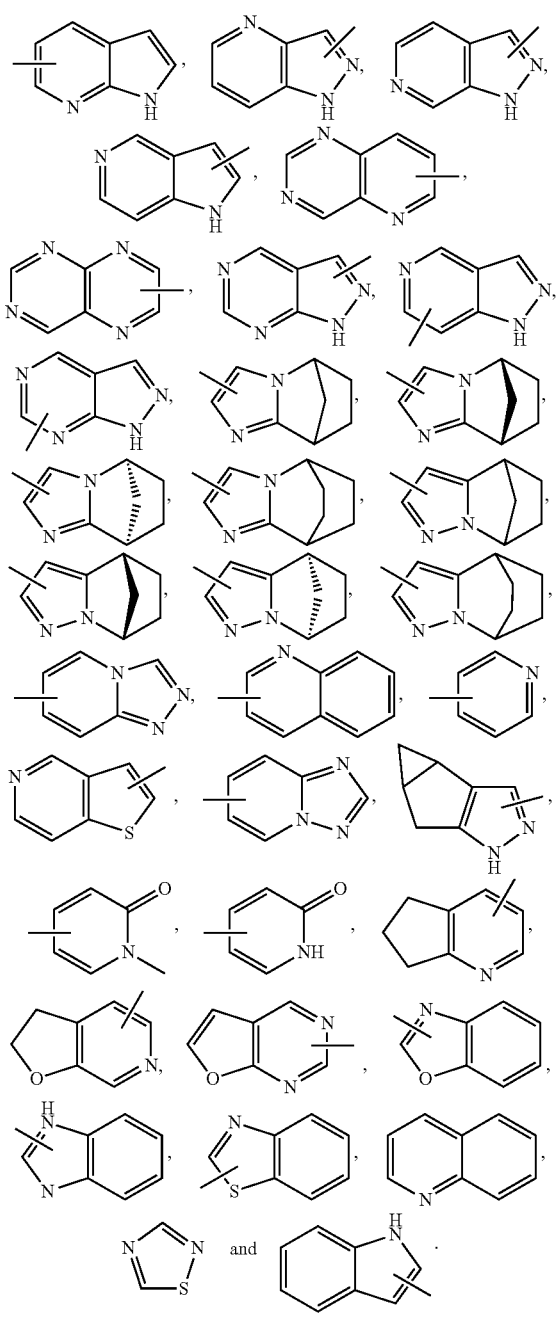

The heteroaryl may be substituted or unsubstituted. When substituted, the substituent may be substituted at any available connection site with one or more substituents preferably independently optionally selected from the group consisting of hydrogen, halogen, alkyl, alkoxy, haloalkyl, hydroxy, hydroxyalkyl, cyano, amino, nitro, cycloalkyl, heterocyclyl, aryl, heteroaryl, —S(O)$_r$R$^6$ and —NHS(O)$_r$R$^6$.

The cycloalkyl, heterocyclyl, aryl and heteroaryl described above have 1 residue derived from the parent ring by removal of one hydrogen atom from a ring atom, or 2 residues derived from the parent ring by removal of two hydrogen atoms from the same ring atom or two different ring atoms, i.e., "divalent cycloalkyl", "divalent heterocyclyl", "arylene", or "heteroarylene".

The term "amino protecting group" refers to a group that can be easily removed and is intended to protect an amino group from being changed when a reaction is conducted elsewhere in the molecule. Non-limiting examples include tetrahydropyranyl, tert-butoxycarbonyl, acetyl, benzyl, allyl, p-methoxybenzyl, and the like. These groups may be optionally substituted with 1 to 3 substituents selected from the group consisting of halogen, alkoxy and nitro. The amino protecting group is preferably tetrahydropyranyl.

The term "cycloalkyloxy" refers to cycloalkyl-O—, wherein the cycloalkyl is as defined above.

The term "haloalkyl" refers to an alkyl group substituted with one or more halogens, wherein the alkyl group is as defined above.

The term "haloalkoxy" refers to an alkoxy group substituted with one or more halogens, wherein the alkoxy group is as defined above.

The term "deuterated alkyl" refers to an alkyl group substituted with one or more deuterium atoms, wherein the alkyl group is as defined above.

The term "hydroxy" refers to —OH group.

The term "hydroxyalkyl" refers to an alkyl group substituted with hydroxy, wherein the alkyl group is as defined above.

The term "halogen" refers to fluorine, chlorine, bromine or iodine.

The term "amino" refers to —NH$_2$.

The term "cyano" refers to —CN.

The term "nitro" refers to —NO$_2$.

The term "oxo" refers to =O.

R$^6$ and r are as defined in general formula (I).

In the chemical structure of the compound disclosed herein, a bond " ⌀ " represents an unspecified configuration, namely if chiral isomers exist in the chemical structure, the bond " ⌀ " may be " ⌀ " or " ⌀ ", or contains both the configurations of " ⌀ " and " ⌀ " simultaneously.

The term "optional" or "optionally" means that the event or circumstance subsequently described may, but not necessarily, occur, and that the description includes instances where the event or circumstance occurs or does not occur. For example, "a heterocyclyl group optionally substituted with alkyl" means that alkyl may be, but not necessarily, present, and that the description includes instances where the heterocyclyl group is or is not substituted with alkyl.

The term "substituted" means that one or more, preferably up to 5, more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue efforts. For example, it may be unstable when an amino or hydroxy group having a free hydrogen is bound to a carbon atom having an unsaturated (e.g., olefinic) bond.

The term "pharmaceutical composition" refers to a mixture containing one or more of the compound disclosed herein or a physiologically/pharmaceutically acceptable salt or pro-drug thereof, and other chemical components, and other components for example physiologically/pharmaceutically acceptable carriers and excipients. The purpose of the pharmaceutical composition is to promote the administration to an organism, which facilitates the absorption of the active ingredient, thereby exerting biological activity.

The "pharmaceutically acceptable salt" refers to a salt of the compound disclosed herein, which may be selected from the group consisting of inorganic and organic salts.

The salts are safe and effective for use in the body of a mammal and possess the requisite biological activity. The salts may be prepared separately during the final separation and purification of the compound, or by reacting an appropriate group with an appropriate base or acid. Bases commonly used to form pharmaceutically acceptable salts include inorganic bases such as sodium hydroxide and potassium hydroxide, and organic bases such as ammonia. Acids commonly used to form pharmaceutically acceptable salts include inorganic acids and organic acids.

The compound disclosed herein may also include an isotopic derivative thereof. The term "isotopic derivative" refers to compounds that differ in structure only by having one or more enriched isotopic atoms. For example, compounds having the structure disclosed herein having "deuterium" or "tritium" in place of hydrogen, or $^{18}$F-fluorine labeling ($^{18}$F isotope) in place of fluorine, or $^{11}$C-, $^{13}$C- or $^{14}$C-enriched carbon ($^{11}$C-, $^{13}$C- or $^{14}$C-carbon labeling; $^{11}$C-, $^{13}$C- or $^{14}$C-isotope) in place of a carbon atom are within the scope of the present disclosure. Such a compound can be used as an analytical tool or a probe in, for example, a biological assay, or may be used as a tracer for in vivo diagnostic imaging of disease, or as a tracer in a pharmacodynamic, pharmacokinetic or receptor study. Deuterations can generally retain comparable activity to non-deuterated compounds and can achieve better metabolic stability when deuterated at certain specific sites, thereby achieving certain therapeutic advantages (e.g., increased in vivo half-life or reduced dosage requirements). The various deuterated forms of the compound of formula (I) of the present disclosure mean that each available hydrogen atom connected to a carbon atom may be independently replaced with a deuterium atom. Those skilled in the art are able to synthesize the compound of formula (I) in deuterated form with reference to the relevant literature. Commercially available deuterated starting materials can be used in preparing the deuterated forms of the compound of formula (I), or they can be synthesized using conventional techniques with deuterated reagents including, but not limited to, deuterated borane, tri-deuterated borane in tetrahydrofuran, deuterated lithium aluminum hydride, deuterated iodoethane, deuterated iodomethane, and the like. Unless otherwise stated, when a position is specifically designated as deuterium (D), that position shall be understood to be deuterium having an abundance that is at least 1000 times greater than the natural abundance of deuterium (which is 0.015%) (i.e., at least 10% deuterium incorporation). The compounds of examples comprise deuterium having an abundance that is greater than at least 1000 times the natural abundance, at least 2000 times the natural abundance, at least 3000 times the natural abundance, at least 4000 times the natural abundance, at least 5000 times the natural abundance, at least 6000 times the natural abundance, or higher times the natural abundance.

For drugs and pharmacological active agents, the term "therapeutically effective amount" refers to an amount of a medicament or an agent that is sufficient to provide the desired effect but is non-toxic. The determination of the effective amount varies from person to person. It depends on the age and general condition of a subject, as well as the particular active substance used. The appropriate effective amount in a case may be determined by those skilled in the art in the light of routine tests.

The compound disclosed herein may contain all manner of rotamers and conformationally constrained states thereof. Also included is an atropisomer. The term "atropisomer" is a stereoisomer resulting from hindered rotation about a single bond, wherein the energy difference due to steric strain or other contributing factors forms a sufficiently high rotational barrier to allow separation of the individual conformers. For example, certain compounds disclosed herein may exist in a form of a mixture of atropisomers or a purified atropisomer or an enriched atropisomer. Non-limiting examples of compounds that exist in an atropisomeric form include the following compounds:

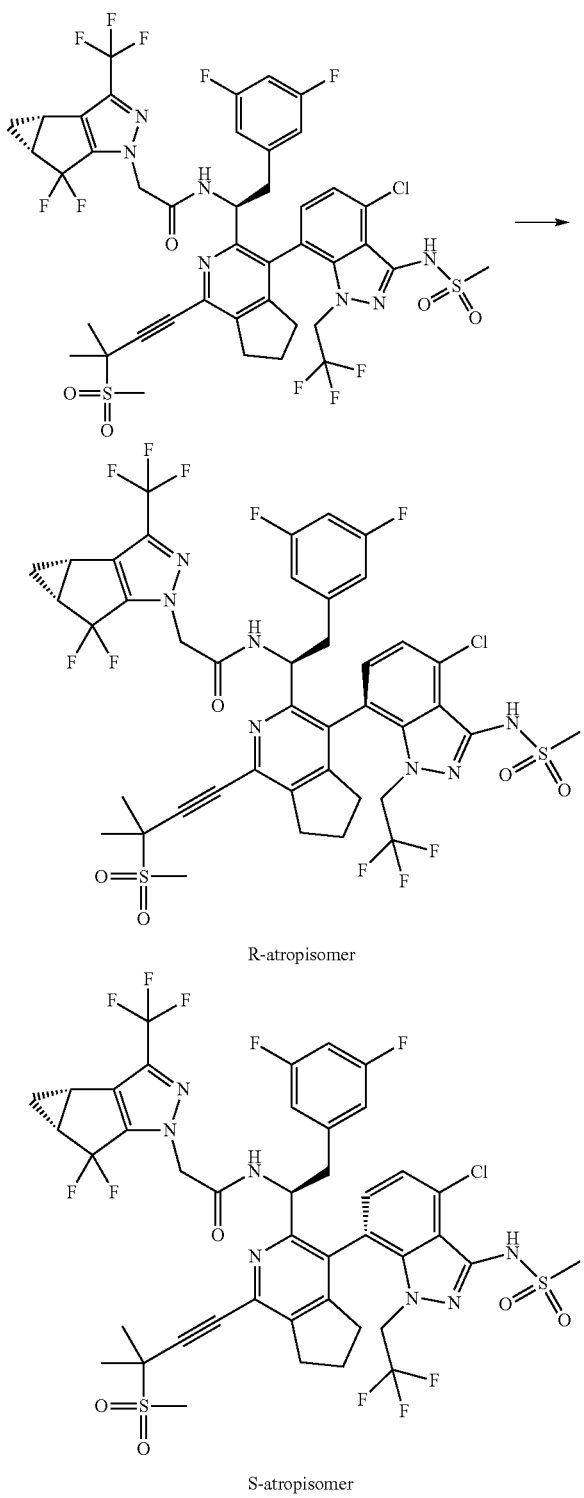

R-atropisomer

S-atropisomer

Unlike compound 1 disclosed in prior art WO2019035904, in which two axial chiral isomers are interconverted (in a ratio of 1:5 to 1:8 at different temperatures and pH, and a half-life of about 1-2 hours), the atropisomers disclosed herein have been subjected to stability testing, and are both stable single-configuration compounds at different temperatures, preferably from room temperature to 120° C., and the two atropisomers are not interconverted, specifically see Test Example 1 and FIGS. 2 and 3.

Compared with the positive control example 1 (Compound 24 in the prior art WO2018035359), the compound disclosed herein has lower clearance rate and longer half life in the large animal pharmacokinetic study, and is suitable for long-acting formulations, and the specific data are shown in Test Example 2, Test Example 3 and FIG. 1.

Synthesis Method of Compounds Disclosed Herein

In order to achieve the purpose of the present disclosure, the following technical schemes are adopted in the present disclosure:

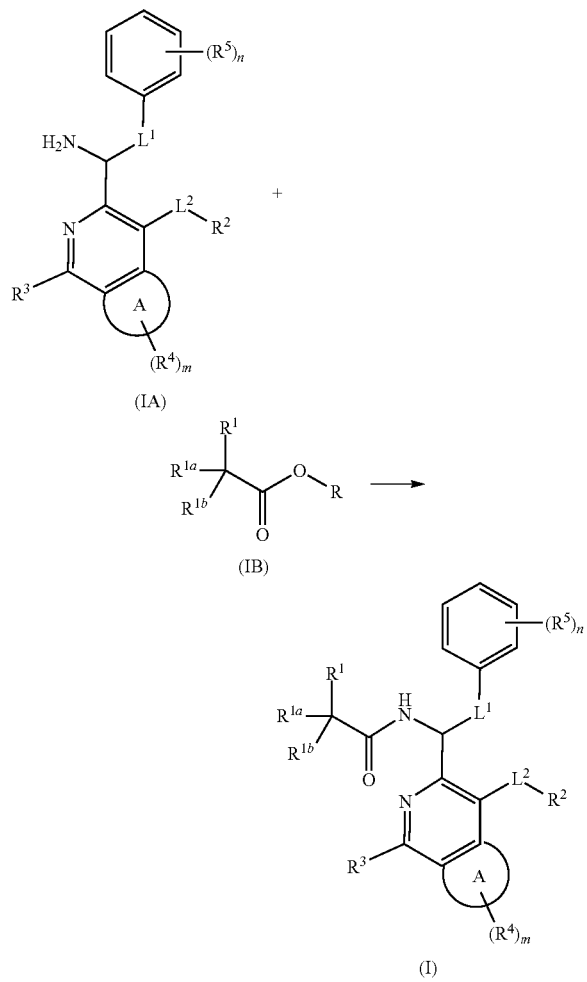

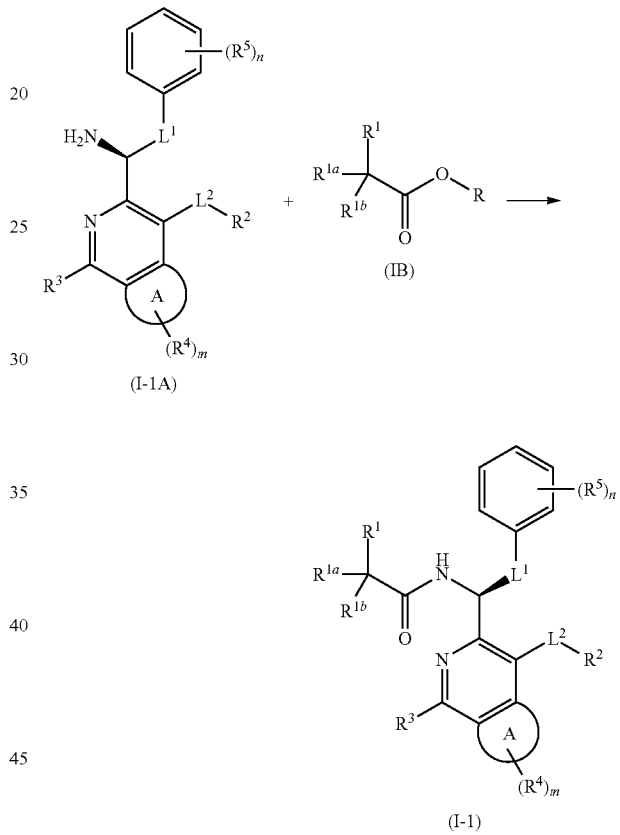

Provided is a method for preparing a compound of general formula (I) or an atropisomer, tautomer, mesomer, racemate, enantiomer, diastereomer thereof or a mixture thereof, or a pharmaceutically acceptable salt thereof, which comprises the following steps:

reacting a compound of general formula (IA) or a pharmaceutically acceptable salt thereof with a compound of general formula (IB) in the presence of a condensing agent in an alkaline condition to give a compound of general formula (I), wherein, the pharmaceutically acceptable salt of the compound of general formula (IA) is preferably hydrochloride;

R is hydrogen or alkyl, and preferably hydrogen; and ring A, $L^1$, $L^2$, $R^1$-$R^5$, $R^{1a}$, $R^{1b}$, m and n are as defined in general formula (I).

Provided is a method for preparing a compound of general formula (I-1) or an atropisomer, tautomer, mesomer, racemate, enantiomer, diastereomer thereof or a mixture thereof, or a pharmaceutically acceptable salt thereof, which comprises the following steps:

reacting a compound of general formula (I-1A) or a pharmaceutically acceptable salt thereof with a compound of general formula (IB) in the presence of a condensing agent in an alkaline condition to give a compound of general formula (I-1), wherein, the pharmaceutically acceptable salt of the compound of general formula (I-1A) is preferably hydrochloride;

R is hydrogen or alkyl, and preferably hydrogen; and ring A, $L^1$, $L^2$, $R^1$-$R^5$, $R^{1a}$, $R^{1b}$, m and n are as defined in general formula (I).

Scheme 3

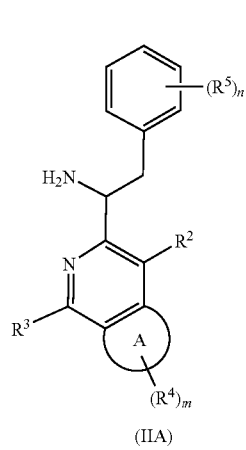

Scheme 4

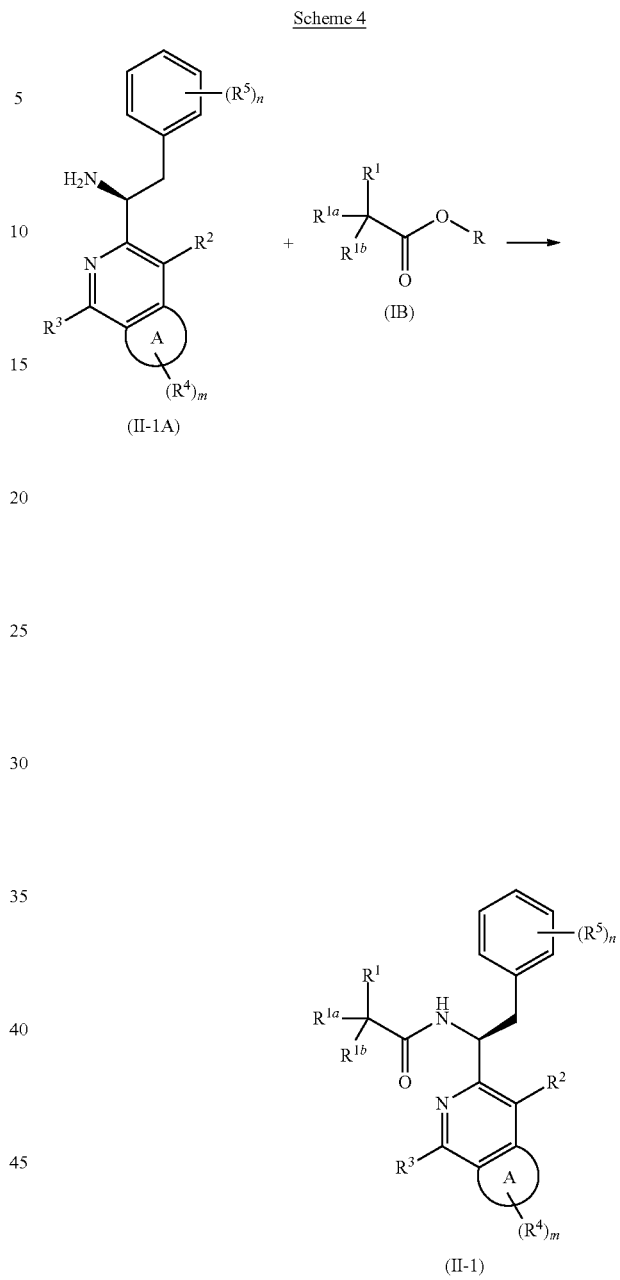

Provided is a method for preparing a compound of general formula (II) or an atropisomer, tautomer, mesomer, racemate, enantiomer, diastereomer thereof or a mixture thereof, or a pharmaceutically acceptable salt thereof, which comprises the following steps:

reacting a compound of general formula (IIA) or a pharmaceutically acceptable salt thereof with a compound of general formula (IB) in the presence of a condensing agent in an alkaline condition to give a compound of general formula (II), wherein, the pharmaceutically acceptable salt of the compound of general formula (IIA) is preferably hydrochloride;

R is hydrogen or alkyl, and preferably hydrogen; and ring A, $R^1$-$R^5$, $R^{1a}$, $R^{1b}$, m and n are as defined in general formula (II).

Provided is a method for preparing a compound of general formula (II-1) or an atropisomer, tautomer, mesomer, racemate, enantiomer, diastereomer thereof or a mixture thereof, or a pharmaceutically acceptable salt thereof, which comprises the following steps:

reacting a compound of general formula (II-1A) or a pharmaceutically acceptable salt thereof with a compound of general formula (IB) in the presence of a condensing agent in an alkaline condition to give a compound of general formula (II-1), wherein, the pharmaceutically acceptable salt of the compound of general formula (II-1A) is preferably hydrochloride;

R is hydrogen or alkyl, and preferably hydrogen; and ring A, $R^1$-$R^5$, $R^{1a}$, $R^{1b}$, m and n are as defined in general formula (II).

Scheme 5

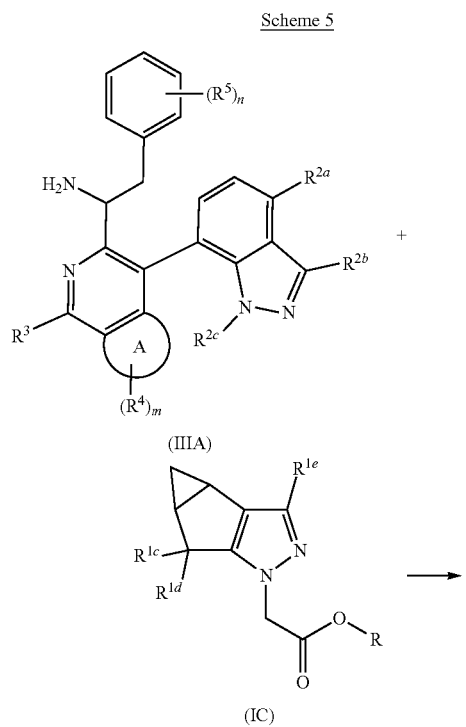

(IIIA)

(IC)

(III)

Scheme 6

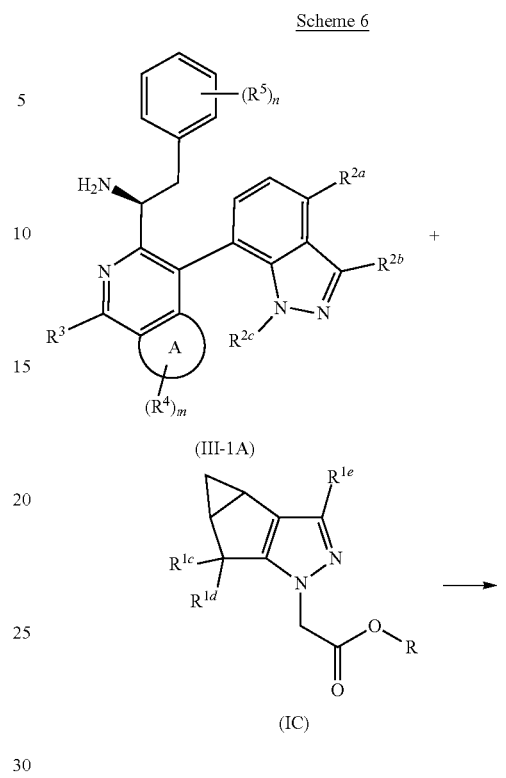

(III-1A)

(IC)

(III-1)

Provided is a method for preparing a compound of general formula (III) or an atropisomer, tautomer, mesomer, racemate, enantiomer, diastereomer thereof or a mixture thereof, or a pharmaceutically acceptable salt thereof, which comprises the following steps:

reacting a compound of general formula (IIIA) or a pharmaceutically acceptable salt thereof with a compound of general formula (IC) in the presence of a condensing agent in an alkaline condition to give a compound of general formula (III), wherein, the pharmaceutically acceptable salt of the compound of general formula (IIIA) is preferably hydrochloride;

R is hydrogen or alkyl, and preferably hydrogen; and ring A, $R^{1c}$, $R^{1d}$, $R^{1e}$, $R^{2a}$, $R^{2b}$, $R^{2c}$, $R^3$-$R^5$, m and n are as defined in general formula (III).

Provided is a method for preparing a compound of general formula (III-1) or an atropisomer, tautomer, mesomer, racemate, enantiomer, diastereomer thereof or a mixture thereof, or a pharmaceutically acceptable salt thereof, which comprises the following steps:

reacting a compound of general formula (III-1A) or a pharmaceutically acceptable salt thereof with a compound of general formula (IC) in the presence of a condensing agent in an alkaline condition to give a compound of general formula (III-1), wherein, the pharmaceutically acceptable salt of the compound of general formula (III-1A) is preferably hydrochloride;

R is hydrogen or alkyl, and preferably hydrogen; and ring A, $R^{1c}$, $R^{1d}$, $R^{1e}$, $R^{2a}$, $R^{2b}$, $R^{2c}$, $R^3$-$R^5$, m and n are as defined in general formula (III).

Scheme 7

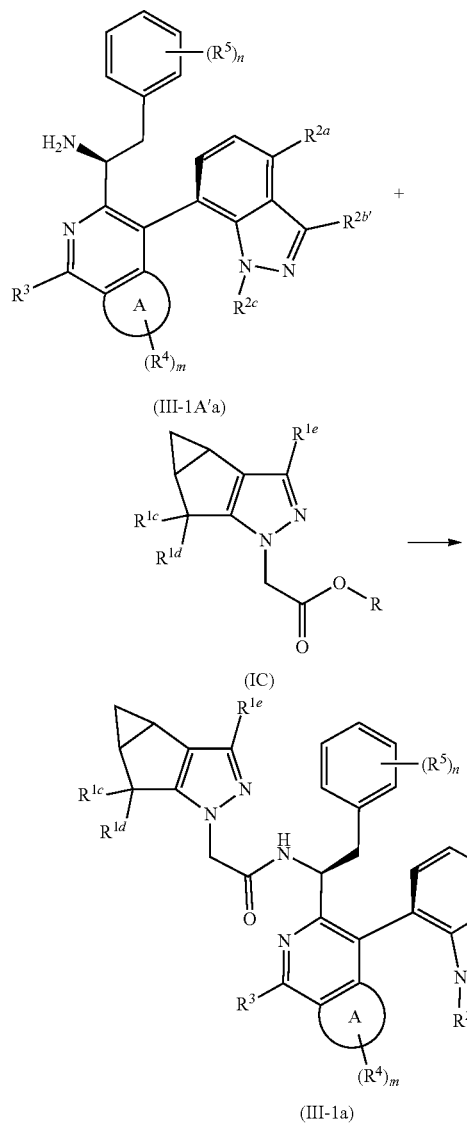

(III-1A'a)

(IC)

(III-1a)

Another aspect of the present disclosure relates to a method for preparing the compound of general formula (III-1a) or the atropisomer, tautomer, mesomer, racemate, enantiomer, diastereomer thereof or the mixture thereof, or the pharmaceutically acceptable salt thereof, which comprises the following steps:

when $R^{2b'}$ in general formula (III-1A'a) and $R^{2b}$ in the final product are identical, subjecting a compound of general formula (III-1A'a) or a pharmaceutically acceptable salt thereof and a compound of general formula (IC) to a condensation reaction to give the compound of general formula (III-1a) or the atropisomer, tautomer, mesomer, racemate, enantiomer, diastereomer thereof or the mixture thereof, or the pharmaceutically acceptable salt thereof, wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR$^6$, —OC(O)R$^6$, —OC(O)NR$^7$R$^8$, —NHS(O)$_r$R$^6$, —NHS(O)$_2$OR$^6$, —NHS(O)$_2$NR$^7$R$^8$, —C(O)R$^6$, —C(O)OR$^6$, —C(O)NR$^7$R$^8$, —S(O)$_r$R$^6$, —S(O)$_r$NR$^7$R$^8$, —NR$^7$R$^8$, —NHC(O)R$^6$, —NHC(O)OR$^6$, —NHC(O)NR$^7$R$^8$ and —NHC(O)NHOR$^6$;

when $R^{2b'}$ in general formula (III-1A'a) is

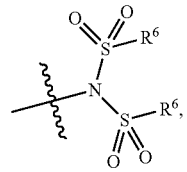

subjecting a compound of general formula (III-1A'a) or a pharmaceutically acceptable salt thereof and a compound of general formula (IC) to a condensation reaction, and meanwhile removing one —S(O)$_2$R$^6$ group to give the compound of general formula (III-1a) or the atropisomer, tautomer, mesomer, racemate, enantiomer, diastereomer thereof or the mixture thereof, or the pharmaceutically acceptable salt thereof, wherein, the pharmaceutically acceptable salt of the compound of general formula (III-1A'a) is preferably hydrochloride;

R is hydrogen or alkyl, and preferably hydrogen; and ring A, $R^{1c}$, $R^{1d}$, $R^{1e}$, $R^{2a}$, $R^{2b}$, $R^{2c}$, $R^3$, $R^4$, $R^5$, n and m are as defined in general formula (III-1a).

Scheme 8

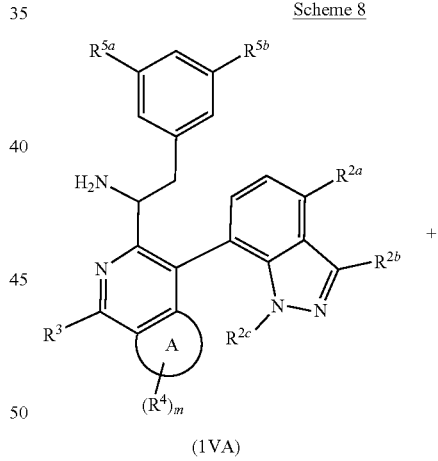

(IVA)

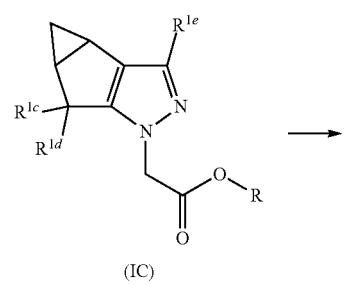

(IC)

-continued

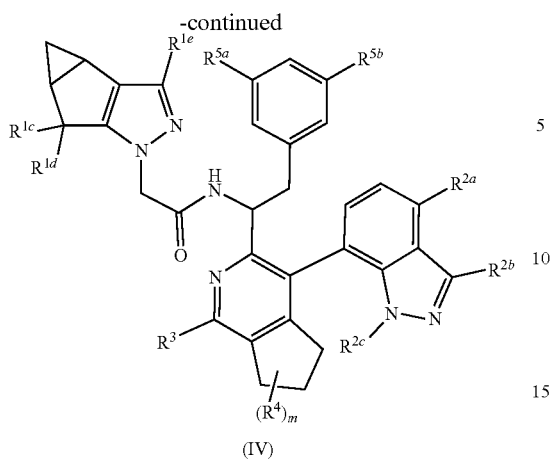

(IV)

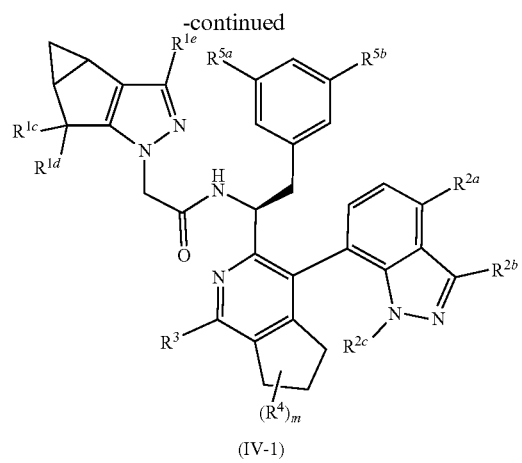

(IV-1)

Provided is a method for preparing a compound of general formula (IV) or an atropisomer, tautomer, mesomer, racemate, enantiomer, diastereomer thereof or a mixture thereof, or a pharmaceutically acceptable salt thereof, which comprises the following steps:

reacting a compound of general formula (IVA) or a pharmaceutically acceptable salt thereof with a compound of general formula (IC) in the presence of a condensing agent in an alkaline condition to give a compound of general formula (IV), wherein, the pharmaceutically acceptable salt of the compound of general formula (IVA) is preferably hydrochloride;

R is hydrogen or alkyl, and preferably hydrogen; and $R^{1c}$, $R^{1d}$, $R^{1e}$, $R^{2a}$, $R^{2b}$, $R^{2c}$, $R^{5a}$, $R^{5b}$, $R^3$, $R^4$ and m are as defined in general formula (IV).

Provided is a method for preparing a compound of general formula (IV-1) or an atropisomer, tautomer, mesomer, racemate, enantiomer, diastereomer thereof or a mixture thereof, or a pharmaceutically acceptable salt thereof, which comprises the following steps:

reacting a compound of general formula (IV-1A) or a pharmaceutically acceptable salt thereof with a compound of general formula (IC) in the presence of a condensing agent in an alkaline condition to give a compound of general formula (IV-1), wherein, the pharmaceutically acceptable salt of the compound of general formula (IV-1A) is preferably hydrochloride;

R is hydrogen or alkyl, and preferably hydrogen; and $R^{1c}$, $R^{1d}$, $R^{1e}$, $R^{2a}$, $R^{2b}$, $R^{2c}$, $R^{5a}$, $R^{5b}$, $R^3$, $R^4$ and m are as defined in general formula (IV).

Scheme 9

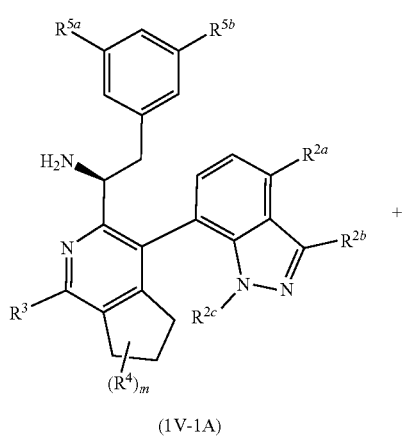

(IV-1A)

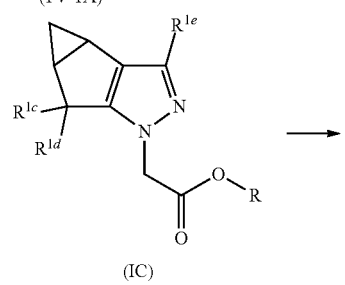

(IC)

Scheme 10

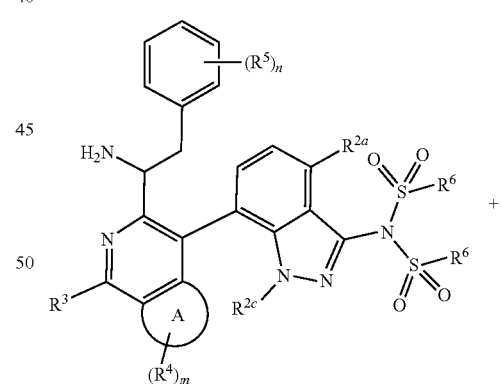

(VA)

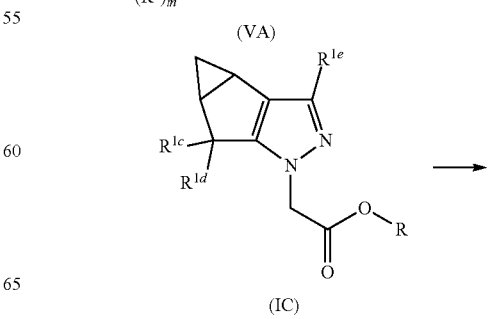

(IC)

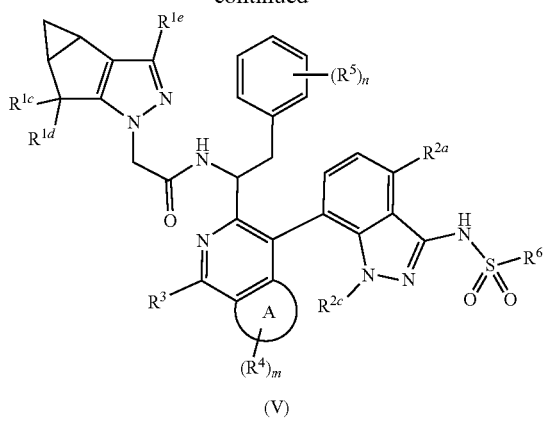

(V)

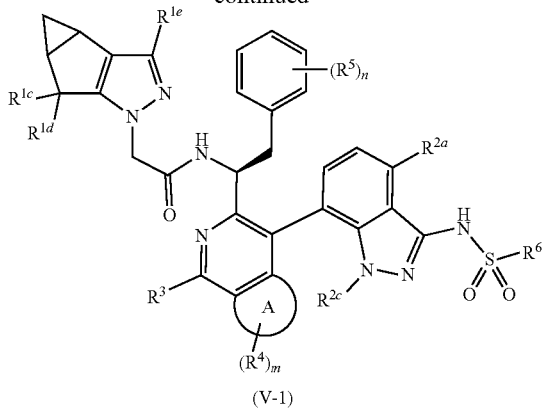

(V-1)

Provided is a method for preparing a compound of general formula (V) or an atropisomer, tautomer, mesomer, racemate, enantiomer, diastereomer thereof or a mixture thereof, or a pharmaceutically acceptable salt thereof, which comprises the following steps:

reacting a compound of general formula (VA) or a pharmaceutically acceptable salt thereof with a compound of general formula (IC) in the presence of a condensing agent in an alkaline condition to give a compound of general formula (V), wherein, the pharmaceutically acceptable salt of the compound of general formula (VA) is preferably hydrochloride;

R is hydrogen or alkyl, and preferably hydrogen; and ring A, $R^{1c}$, $R^{1d}$, $R^{1e}$, $R^{2a}$, $R^{2c}$, $R^3$-$R^6$, m and n are as defined in general formula (V).

Provided is a method for preparing a compound of general formula (V-1) or an atropisomer, tautomer, mesomer, racemate, enantiomer, diastereomer thereof or a mixture thereof, or a pharmaceutically acceptable salt thereof, which comprises the following steps:

reacting a compound of general formula (V-1A) or a pharmaceutically acceptable salt thereof with a compound of general formula (IC) in the presence of a condensing agent in an alkaline condition to give a compound of general formula (V-1), wherein, the pharmaceutically acceptable salt of the compound of general formula (V-1A) is preferably hydrochloride;

R is hydrogen or alkyl, and preferably hydrogen; and ring A, $R^{1c}$, $R^{1d}$, $R^{1e}$, $R^{2a}$, $R^{2c}$, $R^3$-$R^6$, m and n are as defined in general formula (V).

Scheme 11

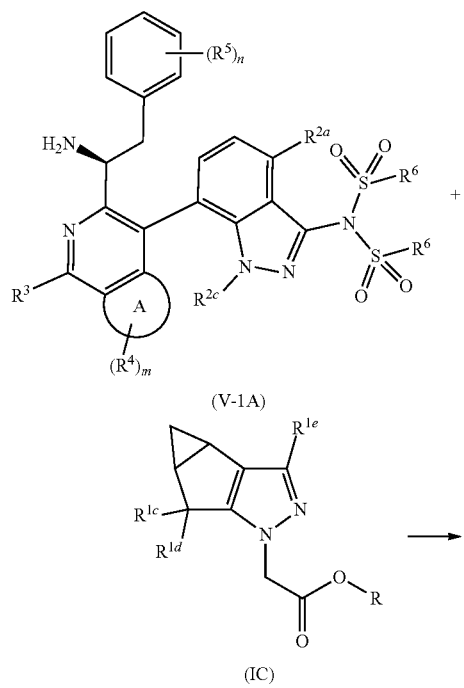

Scheme 12

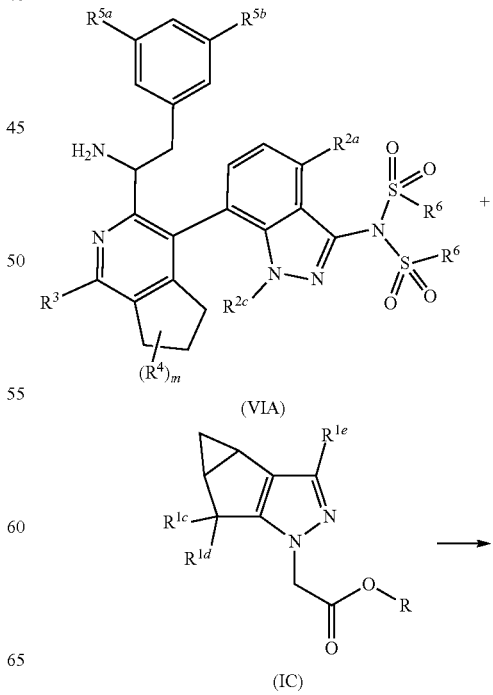

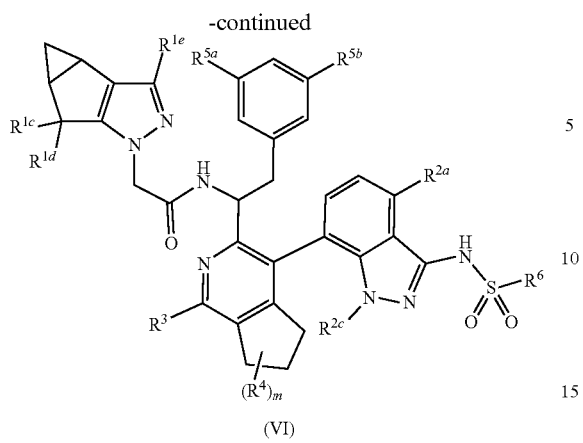

(VI)

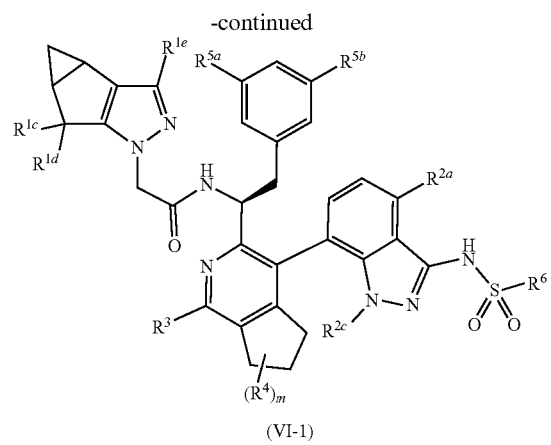

(VI-1)

Provided is a method for preparing a compound of general formula (VI) or an atropisomer, tautomer, mesomer, racemate, enantiomer, diastereomer thereof or a mixture thereof, or a pharmaceutically acceptable salt thereof, which comprises the following steps:

reacting a compound of general formula (VIA) or a pharmaceutically acceptable salt thereof with a compound of general formula (IC) in the presence of a condensing agent in an alkaline condition to give a compound of general formula (VI), wherein, the pharmaceutically acceptable salt of the compound of general formula (VIA) is preferably hydrochloride;

R is hydrogen or alkyl, and preferably hydrogen; and $R^{1c}$, $R^{1d}$, $R^{1e}$, $R^{2a}$, $R^{2c}$, $R^{5a}$, $R^{5b}$, $R^3$, $R^4$, $R^6$ and m are as defined in general formula (VI).

Provided is a method for preparing a compound of general formula (VI-1) or an atropisomer, tautomer, mesomer, racemate, enantiomer, diastereomer thereof or a mixture thereof, or a pharmaceutically acceptable salt thereof, which comprises the following steps:

reacting a compound of general formula (VI-1A) or a pharmaceutically acceptable salt thereof with a compound of general formula (IC) in the presence of a condensing agent in an alkaline condition to give a compound of general formula (VI-1), wherein, the pharmaceutically acceptable salt of the compound of general formula (VI-1A) is preferably hydrochloride;

R is hydrogen or alkyl, and preferably hydrogen; and $R^{1c}$, $R^{1d}$, $R^{1e}$, $R^{2a}$, $R^{2c}$, $R^{5a}$, $R^{5b}$, $R^3$, $R^4$, $R^6$ and m are as defined in general formula (VI).

Scheme 13

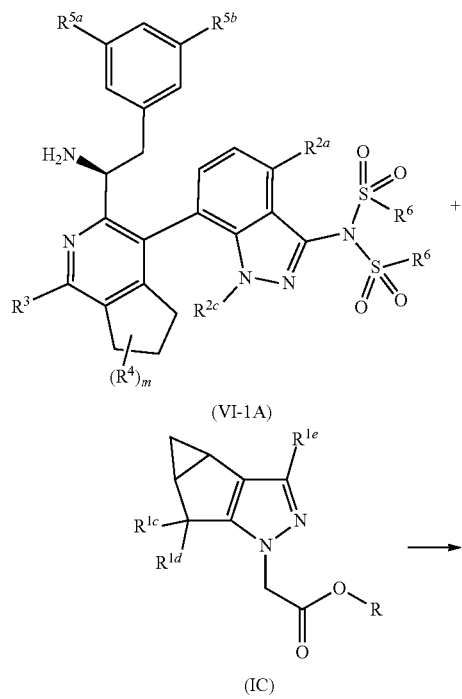

Scheme 14

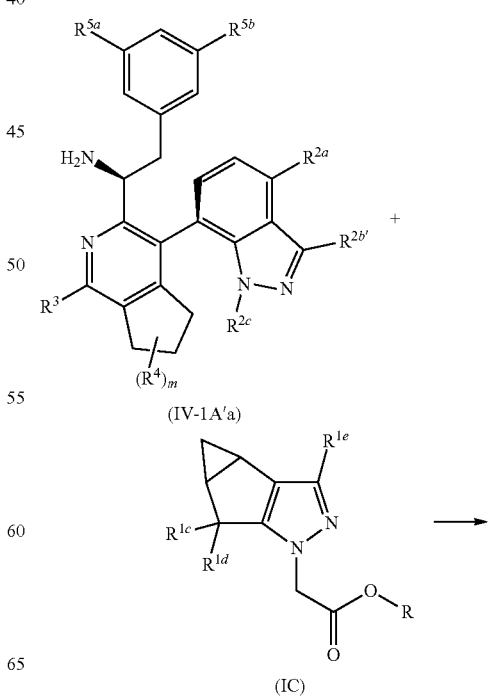

-continued

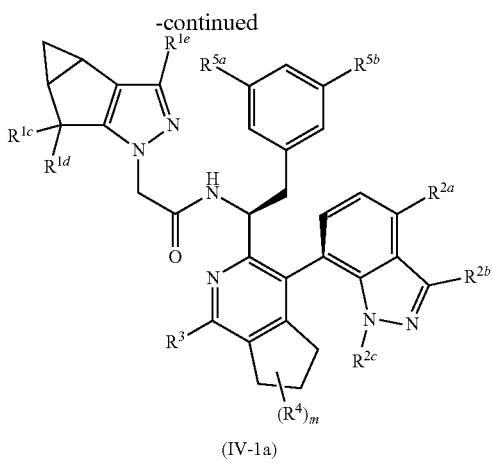

(IV-1a)

Another aspect of the present disclosure relates to a method for preparing a compound of general formula (IV-1a) or an atropisomer, tautomer, mesomer, racemate, enantiomer, diastereomer thereof or a mixture thereof, or a pharmaceutically acceptable salt thereof, which comprises the following steps:

when $R^{2b'}$ in general formula (IV-1A'a) and $R^{2b}$ in the final product are identical, subjecting a compound of general formula (IV-1A'a) or a pharmaceutically acceptable salt thereof and a compound of general formula (IC) to a condensation reaction to give a compound of general formula (IV-1a) or an atropisomer, tautomer, mesomer, racemate, enantiomer, diastereomer thereof or a mixture thereof, or a pharmaceutically acceptable salt thereof;

when $R^{2b'}$ in general formula (IV-1A'a) is

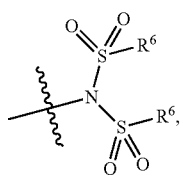

subjecting a compound of general formula (IV-1A'a) or a pharmaceutically acceptable salt thereof and a compound of general formula (IC) to a condensation reaction, and meanwhile removing one —S(O)₂R⁶ group to give a compound of general formula (IV-1a) or an atropisomer, tautomer, mesomer, racemate, enantiomer, diastereomer thereof or a mixture thereof, or a pharmaceutically acceptable salt thereof, wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR⁶, —OC(O)R⁶, —OC(O)NR⁷R⁸, —NHS(O)ᵣR⁶, —NHS(O)₂OR⁶, —NHS(O)₂NR⁷R⁸, —C(O)R⁶, —C(O)OR⁶, —C(O)NR⁷R⁸, —S(O)ᵣR⁶, —S(O)ᵣNR⁷R⁸, —NR⁷R⁸, —NHC(O)R⁶, —NHC(O)OR⁶, —NHC(O)NR⁷R⁸ and —NHC(O)NHOR⁶;

wherein,
the pharmaceutically acceptable salt of the compound of general formula (IV-1A'a) is preferably hydrochloride;
R is hydrogen or alkyl, and preferably hydrogen; and $R^{1c}$, $R^{1d}$, $R^{1e}$, $R^{2a}$, $R^{2b}$, $R^{2c}$, $R^{5a}$, $R^{5b}$, $R^3$, $R^4$ and m are as defined in general formula (IV-1 a).

In the above schemes 1 to 14, the reagent providing an alkaline condition comprises an organic base and an inorganic base, wherein the organic base includes, but is not limited to, triethylamine, N,N-diisopropylethylamine, n-butyllithium, lithium diisopropylamide, lithium bis(trimethylsilyl)amide, potassium acetate, sodium tert-butoxide, potassium tert-butoxide and sodium n-butoxide, and the inorganic base includes, but is not limited to, sodium bicarbonate, potassium bicarbonate, sodium hydride, potassium phosphate, sodium carbonate, potassium acetate, cesium carbonate, sodium hydroxide and lithium hydroxide and hydrates thereof; preferably N,N-diisopropylethylamine; In the above schemes 1 to 14, the condensing agent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazol-N,N,N',N'-tetramethyluronium tetrafluoroborate, 1-hydroxybenzotriazole, 1-hydroxybenzotriazole and N-methylmorpholine, 1-hydroxy-7-azobenzotriazol, O-benzotriazol-N,N,N',N'-tetramethyluronium hexafluorophosphate, 2-(7-benzotriazole oxide)-N,N,N',N'-tetramethylurea hexafluorophosphate O-(7-Azabenzotriazol-1-yl)-N,N,N',N'-tetramethyluronium hexafluorophosphate, (benzotriazollyloxy)tris(dimethylamino)phosphonium hexafluophosphate or benzotriazol-1-yl-oxytripyrrolidino-phosphonium hexafluorophosphate, and preferably 2-(7-benzotriazole oxide)-N,N,N',N'-tetramethyluronium hexafluorophosphate or 1-hydroxybenzotriazole and N-methylmorpholine.

The reactions of the above schemes 1 to 14 are preferably carried out in solvents including, but not limited to: acetic acid, methanol, ethanol, n-butanol, tert-butanol, toluene, tetrahydrofuran, dichloromethane, petroleum ether, ethyl acetate, n-hexane, dimethyl sulfoxide, 1,4-dioxane, ethylene glycol dimethyl ether, water or N,N-dimethylformamide, and mixtures thereof.

DETAILED DESCRIPTION

Figure 1:
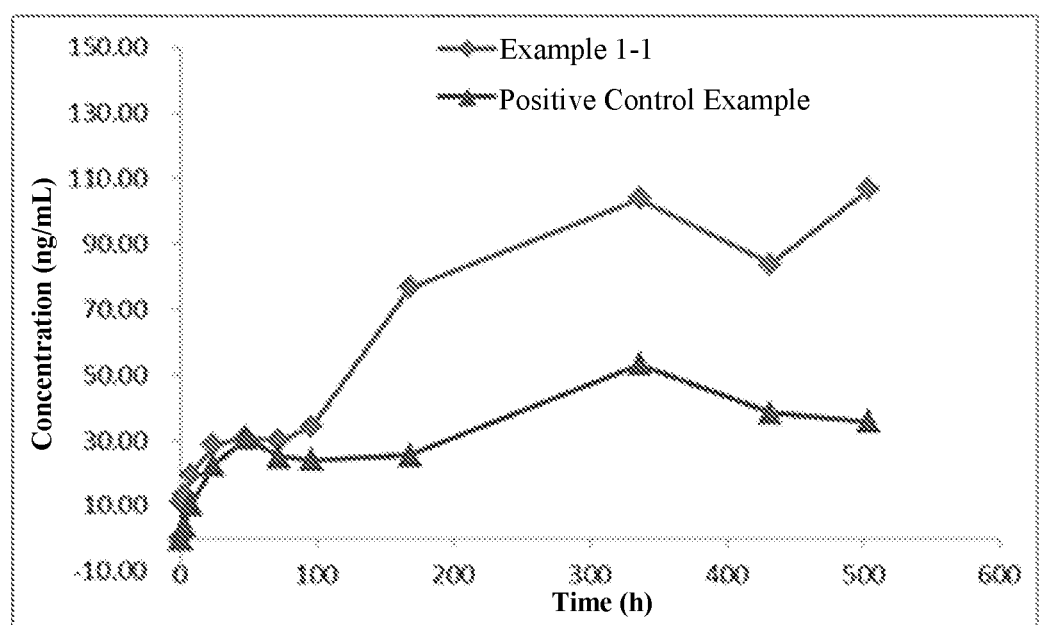
FIG. 1 is a graph of the concentration of the compound of Example 1-1 versus time following subcutaneous administration at 6 mg/kg in dogs.

The following examples further illustrate the present disclosure, but the present disclosure is not limited thereto.

EXAMPLES

The structure of the compound was determined by nuclear magnetic resonance (NMR) spectroscopy and/or mass spectrometry (MS). NMR shift (δ) is given in a unit of 10⁻⁶ (ppm). NMR spectra were measured using a Bruker AVANCE-400 nuclear magnetic resonance instrument or Bruker AVANCE NEO 500M, with deuterated dimethyl sulfoxide (DMSO-d$_6$), deuterated chloroform (CDCl$_3$) and deuterated methanol (CD$_3$OD) as determination solvents, with tetramethylsilane (TMS) as internal standard.

Mass spectra were measured using Agilent 1200/1290 DAD-6110/6120 Quadrupole MS liquid chromatography-mass spectrometry system (manufacturer: Agilent; MS model: 6110/6120 Quadrupole MS), Waters ACQuity UPLC-QD/SQD (manufacturer: Waters, MS model: Waters ACQuity Qda Detector/waters SQ Detector) and THERMO Ultimate 3000-Q Exactive (manufacturer: THERMO, MS model: THERMO Q Exactive).

High performance liquid chromatography (HPLC) was performed using Agilent HPLC 1200DAD, Agilent HPLC 1200VWD and Waters HPLC e2695-2489 high pressure liquid chromatography.

Chiral HPLC was performed on Agilent 1260 DAD HPLC.

HPLC preparation was performed using Waters 2767, Waters 2767-SQ Detecor2, Shimadzu LC-20AP and Gilson-281 preparative chromatographs.

Chiral preparation was performed on a Shimadzu LC-20AP preparative chromatograph.

A CombiFlash Rf200 (TELEDYNE ISCO) system was used for rapid preparation.

Huanghai HSGF254 or Qingdao GF254 silica gel plates of specifications 0.15 mm to 0.2 mm were adopted for thin layer chromatography (TLC) analysis and 0.4 mm to 0.5 mm for TLC separation and purification.

The silica gel column chromatography generally used 200 to 300-mesh silica gel (Huanghai, Yantai) as the carrier.

The mean inhibition of kinase and the IC$_{50}$ value were measured using a NovoStar microplate reader (BMG, Germany).

Known starting materials disclosed herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions can be performed in an argon atmosphere or a nitrogen atmosphere unless otherwise specified.

An argon atmosphere or a nitrogen atmosphere means that the reaction flask is connected to a balloon containing about 1 L of argon or nitrogen.

A hydrogen atmosphere means that the reaction flask is connected to a balloon containing about 1 L of hydrogen.

Parr 3916EKX hydrogenator, Qinglan QL-500 hydrogenator or HC2-SS hydrogenator was used for pressurized hydrogenation reactions.

The hydrogenation reaction usually involved 3 cycles of vacuumization and hydrogen purge.

A CEM Discover-S 908860 microwave reactor was used for the microwave reaction.

In the examples, a solution refers to an aqueous solution unless otherwise specified.

In the examples, the reaction temperature was room temperature, i.e., 20° C. to 30° C., unless otherwise specified.

The monitoring of the reaction progress in the examples was conducted by thin layer chromatography (TLC). The developing solvent for reactions, the eluent system for column chromatography purification and the developing solvent system for thin layer chromatography included: A: n-hexane/ethyl acetate system, and B: dichloromethane/methanol system. The volume ratio of the solvents was adjusted according to the polarity of the compound, or by adding a small amount of basic or acidic reagents such as triethylamine and acetic acid.

In the following examples, compound 1m-1 is structurally identical to compound 1m-1a; compound 1n-1 is structurally identical to compound 1n-1a; compound 1-1 is structurally identical to compound 1-1a.

Example 1-1

N—((S)-1-((R)-4-(4-chloro-3-(methanesulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4, 4a,5-tetrahydro-1H-cyclopropa[3,4]cyclopenta[1,2-c]pyrazol-1-yl)acetamide 1-1

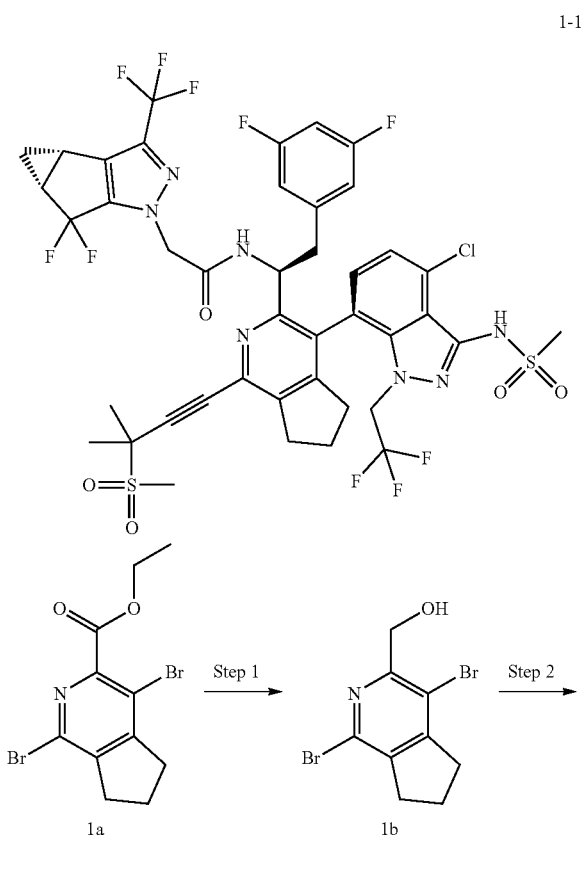

-continued
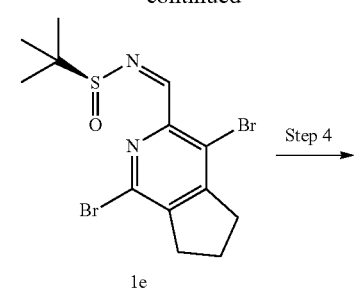
1e
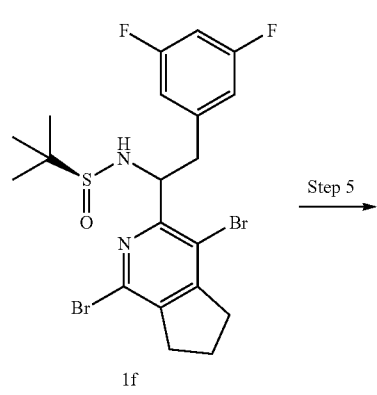
1f
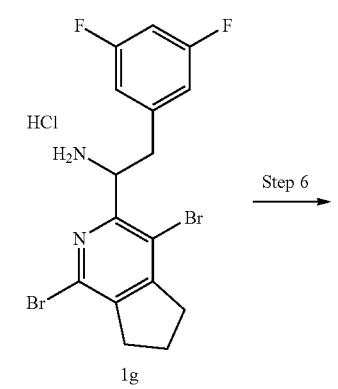
1g
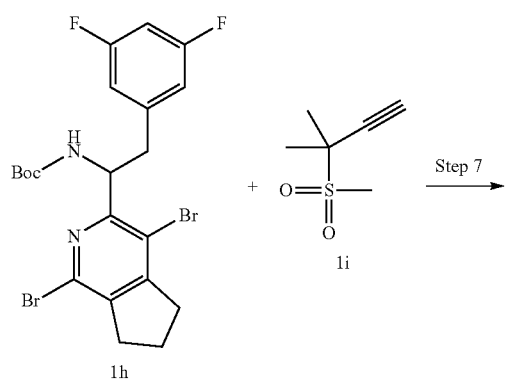
1h
-continued
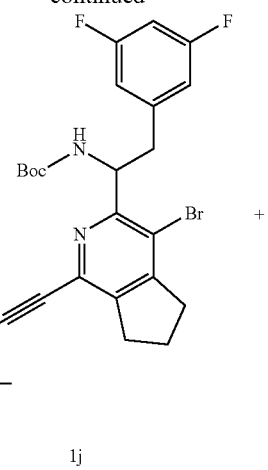
1j
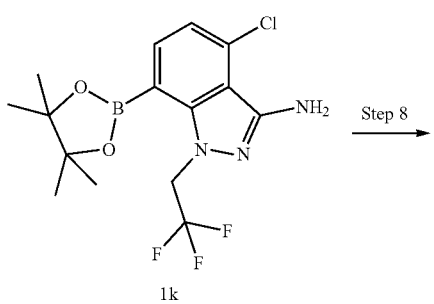
1k
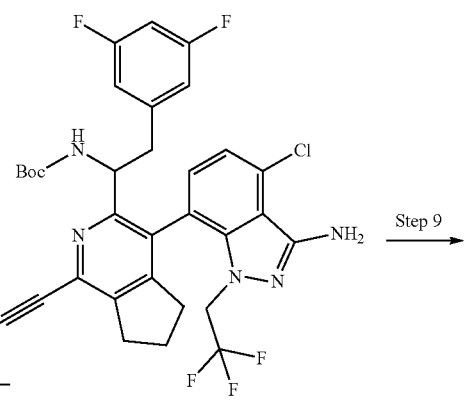
1l
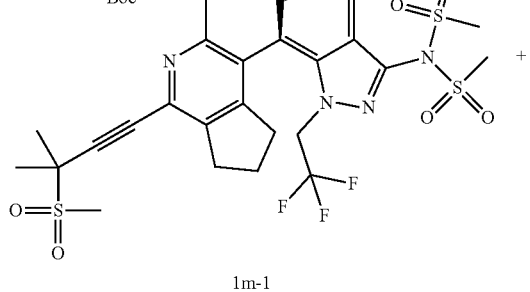
1m-1

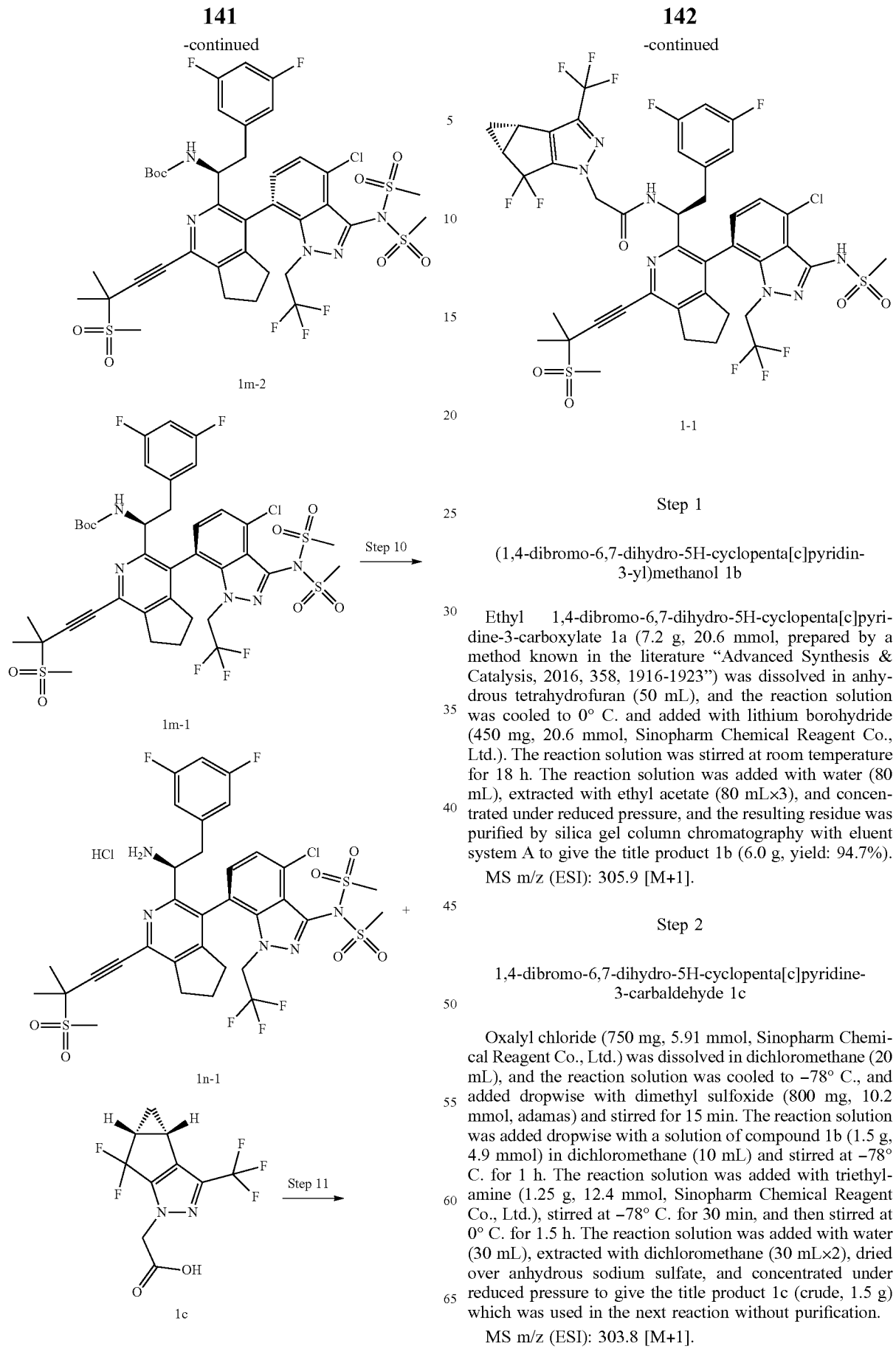

Step 1

(1,4-dibromo-6,7-dihydro-5H-cyclopenta[c]pyridin-3-yl)methanol 1b

Ethyl 1,4-dibromo-6,7-dihydro-5H-cyclopenta[c]pyridine-3-carboxylate 1a (7.2 g, 20.6 mmol, prepared by a method known in the literature "Advanced Synthesis & Catalysis, 2016, 358, 1916-1923") was dissolved in anhydrous tetrahydrofuran (50 mL), and the reaction solution was cooled to 0° C. and added with lithium borohydride (450 mg, 20.6 mmol, Sinopharm Chemical Reagent Co., Ltd.). The reaction solution was stirred at room temperature for 18 h. The reaction solution was added with water (80 mL), extracted with ethyl acetate (80 mL×3), and concentrated under reduced pressure, and the resulting residue was purified by silica gel column chromatography with eluent system A to give the title product 1b (6.0 g, yield: 94.7%).

MS m/z (ESI): 305.9 [M+1].

Step 2

1,4-dibromo-6,7-dihydro-5H-cyclopenta[c]pyridine-3-carbaldehyde 1c

Oxalyl chloride (750 mg, 5.91 mmol, Sinopharm Chemical Reagent Co., Ltd.) was dissolved in dichloromethane (20 mL), and the reaction solution was cooled to −78° C., and added dropwise with dimethyl sulfoxide (800 mg, 10.2 mmol, adamas) and stirred for 15 min. The reaction solution was added dropwise with a solution of compound 1b (1.5 g, 4.9 mmol) in dichloromethane (10 mL) and stirred at −78° C. for 1 h. The reaction solution was added with triethylamine (1.25 g, 12.4 mmol, Sinopharm Chemical Reagent Co., Ltd.), stirred at −78° C. for 30 min, and then stirred at 0° C. for 1.5 h. The reaction solution was added with water (30 mL), extracted with dichloromethane (30 mL×2), dried over anhydrous sodium sulfate, and concentrated under reduced pressure to give the title product 1c (crude, 1.5 g) which was used in the next reaction without purification.

MS m/z (ESI): 303.8 [M+1].

Step 3

(S,Z)—N-((1,4-dibromo-6,7-dihydro-5H-cyclopenta[c]pyridin-3-yl)methylene)-2-methylpropane-2-sulfinamide 1e Compound 1c (5.0 g, 16.4 mmol) and (S)-2-methylpropane-2-sulfinamide 1d (1.99 g, 16.4 mmol, Bide Pharmatech Ltd.) were dissolved in dichloromethane (50 mL), and the reaction solution was added with cesium carbonate (6.4 g, 19.6 mmol, Bide Pharmatech Ltd.), stirred at room temperature for 2 h, then added with water (50 mL), extracted with dichloromethane (50 mL×3), and concentrated under reduced pressure. The resulting residue was purified by silica gel column chromatography with eluent system A to give the title product 1e (4.5 g, yield: 67%).

MS m/z (ESI): 406.9 [M+1].

Step 4

(S)—N-(1-(1,4-dibromo-6,7-dihydro-5H-cyclopenta[c]pyridin-3-yl)-2-(3,5-difluorophenyl)ethyl)-2-methylpropane-2-sulfinamide 1f To a suspension of zinc powder (1.3 g, 20.0 mmol, Sinopharm Chemical Reagent Co., Ltd.) in anhydrous tetrahydrofuran (15 mL) was added one drop of 1,2-dibromoethane. Under the state of heating at reflux, two drops of trimethylchlorosilane were added, and the reaction solution was vigorously stirred and refluxed for 15 min. The reaction solution was cooled to 0° C., added with 1-(bromomethyl)-3,5-difluorobenzene (2.1 g, 10.0 mmol, Bide Pharmatech Ltd.), and stirred at room temperature for 4 h. Compound 1e (2.7 g, 6.6 mmol) was dissolved in anhydrous N,N-dimethylformamide (13 mL), and the reaction solution was added dropwise with the prepared zinc reagent at 0° C., stirred at room temperature for 16 h, added with water (50 mL), extracted with ethyl acetate (50 mL×3), and concentrated under reduced pressure. The resulting residue was purified by silica gel column chromatography with eluent system A to give the title product if (2.6 g, yield: 75%).

MS m/z (ESI): 534.7 [M+1].

Step 5

1-(1,4-dibromo-6,7-dihydro-5H-cyclopenta[c]pyridin-3-yl)-2-(3,5-difluorophenyl)ethan-1-amine hydrochloride 1g Compound 1f (2.6 g, 6.6 mmol) was dissolved in dichloromethane (20 mL), and the reaction solution was added with 4 M hydrogen chloride solution in dioxane (40 mL), stirred at room temperature for 1 h, and concentrated under reduced pressure to give the title product 1g (2.3 g, yield: 100%).

MS m/z (ESI): 430.8 [M−35].

Step 6

Tert-butyl (1-(1,4-dibromo-6,7-dihydro-5H-cyclopenta[c]pyridin-3-yl)-2-(3,5-difluorophenyl)ethyl)carbamate 1h To a suspension of compound 1g (2.3 g, 5.3 mmol) in dichloromethane (30 mL) were added triethylamine (3.3 g, 32.7 mmol, Shanghai Hushi Chemical Co., Ltd.) and di-tert-butyl dicarbonate (2.4 g, 11.0 mmol, Accela ChemBio Co., Ltd.). The reaction solution was stirred at room temperature for 3 h, added with water (30 mL), extracted with dichloromethane (30 mL×3), and concentrated under reduced pressure. The resulting residue was purified by silica gel column chromatography with eluent system A to give the title product 1h (2.1 g, yield: 74%).

MS m/z (ESI): 530.8 [M+1].

Step 7

Tert-butyl (1-(4-bromo-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 1j Compound 1h (500.0 mg, 0.9 mmol) and compound 1i (207.0 mg, 1.4 mmol, prepared by the method disclosed in the patent application "WO2018035359A1, intermediate im-14 on page 83") were dissolved in N,N-dimethylformamide (8 mL). Bis(triphenylphosphine)palladium dichloride (80.0 mg, 0.1 mmol, Accela ChemBio Co., Ltd.), cuprous iodide (108.0 mg, 0.6 mmol, Sinopharm Chemical Reagent Co., Ltd.) and triethylamine (286.0 mg, 2.8 mmol, Shanghai Hushi Chemical Co., Ltd.) were added. The reaction solution was purged with nitrogen three times, stirred at room temperature for 4 h, added with water (20 mL), extracted with ethyl acetate (20 mL×3), and concentrated under reduced pressure. The resulting residue was purified by silica gel column chromatography with eluent system A to give the title product 1j (500 mg, yield: 89%).

MS m/z (ESI): 596.8 [M+1].

Step 8

Tert-butyl (1-4-(3-amino-4-chloro-1-(2,2,2-trifluoroethyl)-1H-indazol-7-yl)-1-(3-methyl-3-(methanesulfonyl)but-1-yn-1-yl)-6,7-dihydro-5H-cyclopenta[c]pyridin-3-yl)-2-(3,5-difluorophenyl)ethyl)carbamate 1l Compound 1j (400.0 mg, 0.7 mmol) and compound 1k (378.0 mg, 1 mmol, prepared by the method disclosed in the patent application "WO2018035359A1, intermediate im-12 on page 82") were dissolved in dioxane (12 mL) and water (2 mL). Di-tert-butyl-(4-dimethylaminophenyl)phosphine palladium dichloride (15.0 mg, 0.02 mmol, Accela ChemBio Co., Ltd.) and potassium phosphate (426.0 mg, 2.0 mmol, J&K Chemical) were added. The reaction solution was purged with nitrogen three times, stirred at 90° C. for 16 h, added with water (20 mL), extracted with ethyl acetate (20 mL×3), and concentrated under reduced pressure. The resulting residue was purified by silica gel column chromatography with eluent system A to give the title product 1l (160.0 mg, yield: 31%).

MS m/z (ESI): 765.8 [M+1].

Step 9

Tert-butyl ((5)-1-((R)-4-(4-chloro-3-(N-(methyl-sulfonyl)methanesulfonamide)-1-(2,2,2-trifluoro-ethyl)-1H-indazol-7-yl)-1-(3-methyl-3-(methylsulfo-nyl)but-1-yn-1-yl)-6,7-dihydro-5H-cyclopenta[c]pyridin-3-yl)-2-(3,5-difluorophenyl)ethyl)carbamate 1m-1

Tert-butyl ((R)-1-((S)-4-(4-chloro-3-(N-(methyl-sulfonyl)methanesulfonamide)-1-(2,2,2-trifluoro-ethyl)-1H-indazol-7-yl)-1-(3-methyl-3-(methylsulfo-nyl)but-1-yn-1-yl)-6,7-dihydro-5H-cyclopenta[c]pyridin-3-yl)-2-(3,5-difluorophenyl)ethyl)carbamate 1m-2

Compound 1l (160.0 mg, 0.2 mmol) and triethylamine (127.0 mg, 1.3 mmol, Shanghai Hushi Chemical Co., Ltd.) were dissolved in dichloromethane (3 mL), and methane-sulfonyl chloride (72.0 mg, 0.6 mmol, Sinopharm Chemical Reagent Co., Ltd.) was added. The reaction solution was stirred at room temperature for 1 h, added with water (20 mL), extracted with dichloromethane (20 mL×3), and concentrated under reduced pressure. The resulting residue was purified by silica gel column chromatography with eluent system A to give a racemate. The racemate (170 mg, 0.18 mmol) was subjected to chiral preparation (separation conditions: CHIRALPAK OD chiral preparation column, 5.0 cm I.D.×25 cmL, 10 μm; mobile phase: n-hexane/isopropanol=70/30 (V/V), flow rate: 60 mL/min), and the corresponding fractions were collected and concentrated under reduced pressure to give the title products 1m-1 (92 mg, yield: 48%) and 1m-2 (66 mg, yield: 34%).

Single-Configuration Compound (Shorter Retention Time) 1m-1:

MS m/z (ESI): 921.8 [M+1].

Chiral HPLC analysis: retention time: 4.471 min, chiral purity: 100% (column: CHIRALPAK OD 0.46 cm I.D.×25 cmL, 10 μm; mobile phase: n-hexane/ethanol/dichloromethane/diethylamine=60/30/10/0.1 (V/V/V/V)).

Single-Configuration Compound (Longer Retention Time) 1m-2:

MS m/z (ESI): 921.8 [M+1].

Chiral HPLC analysis: retention time: 6.579 min, chiral purity: 100% (column: CHIRALPAK OD 0.46 cm I.D.×25 cmL, 10 μm; mobile phase: n-hexane/ethanol/dichloromethane/diethylamine=60/30/10/0.1 (V/V/V/V)).

Step 10

N-(7-((R)-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride in-1

Compound 1m-1 (92.0 mg, 0.1 mmol) was dissolved in dichloromethane (0.5 mL), and the reaction solution was added with 4 M hydrogen chloride solution in dioxane (3 mL), stirred at room temperature for 1 h, and concentrated under reduced pressure to give the title product in-1 (86 mg, yield: 100%).

MS m/z (ESI): 821.8 [M−35].

Step 11

N—((S)-1-((R)-4-(4-chloro-3-(methanesulfona-mide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4, 4a,5-tetrahydro-1H-cyclopropa[3,4]cyclopenta[1,2-c]pyrazol-1-yl) acetamide 1-1

Compound 1n-1 (86.0 mg, 0.1 mmol), compound 1o (29.0 mg, 0.1 mmol, prepared by the method disclosed in the patent application "WO2018035359A1, intermediate im-8a on page 80") and 2-(7-benzotriazole oxide)-N,N,N',N'-tetramethylurea hexafluorophosphate (50.0 mg, 0.13 mmol, Sinopharm Chemical Reagent Co., Ltd.) were dissolved in N,N-dimethylformamide (2 mL), and N,N-diisopropylethylamine (65.0 mg, 0.5 mmol, adamas) was added. The reaction solution was stirred at room temperature for 1 h, added with 2 N sodium hydroxide (0.3 mL), stirred at room temperature for 1 h, then added with water (10 mL), extracted with ethyl acetate (10 mL×3), and concentrated under reduced pressure. The resulting residue was purified by high performance liquid chromatography (Sharpsil-T C18, 150×30 mm, 5 μm, eluent system: H$_2$O (0.1% trifluoroacetic acid), acetonitrile) to give the title product 1-1 (33 mg, yield: 30%).

MS m/z (ESI): 1007.5 [M+1].

$^1$H NMR (400 MHz, CD$_3$OD) δ 7.20 (d, 1H), 6.76 (t, 1H), 6.49 (d, 1H), 6.26 (d, 2H), 4.92-4.75 (m, 3H), 4.66-4.59 (m, 1H), 4.01-3.95 (m, 1H), 3.24 (s, 3H), 3.23 (s, 3H), 3.17-3.13 (m, 2H), 3.05-3.00 (m, 1H), 2.91-2.86 (m, 1H), 2.82-2.74 (m, 1H), 2.57-2.41 (m, 3H), 2.18-2.15 (m, 1H), 2.07-1.99 (m, 1H), 1.83 (s, 6H), 1.45-1.40 (m, 1H), 1.09 (s, 1H).

Example 1-2

N—((R)-1-((S)-4-(4-chloro-3-(methanesulfona-mide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4, 4a,5-tetrahydro-1H-cyclopropa[3,4]cyclopenta[1,2-c]pyrazol-1-yl) acetamide 1-2

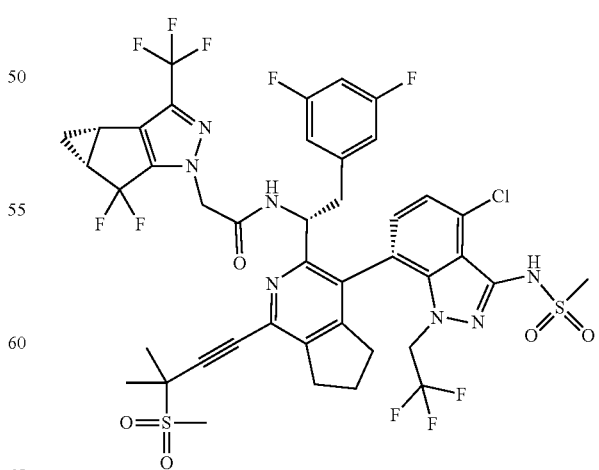

1-2

-continued

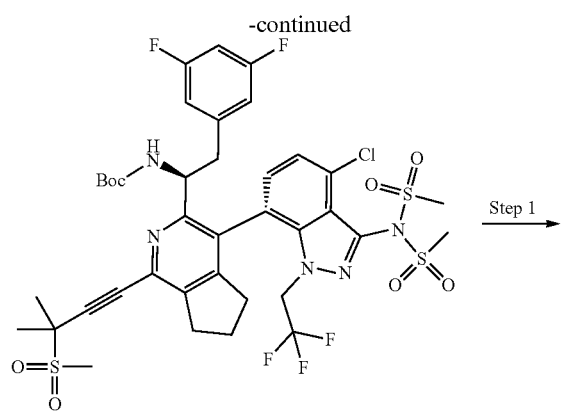

1m-2

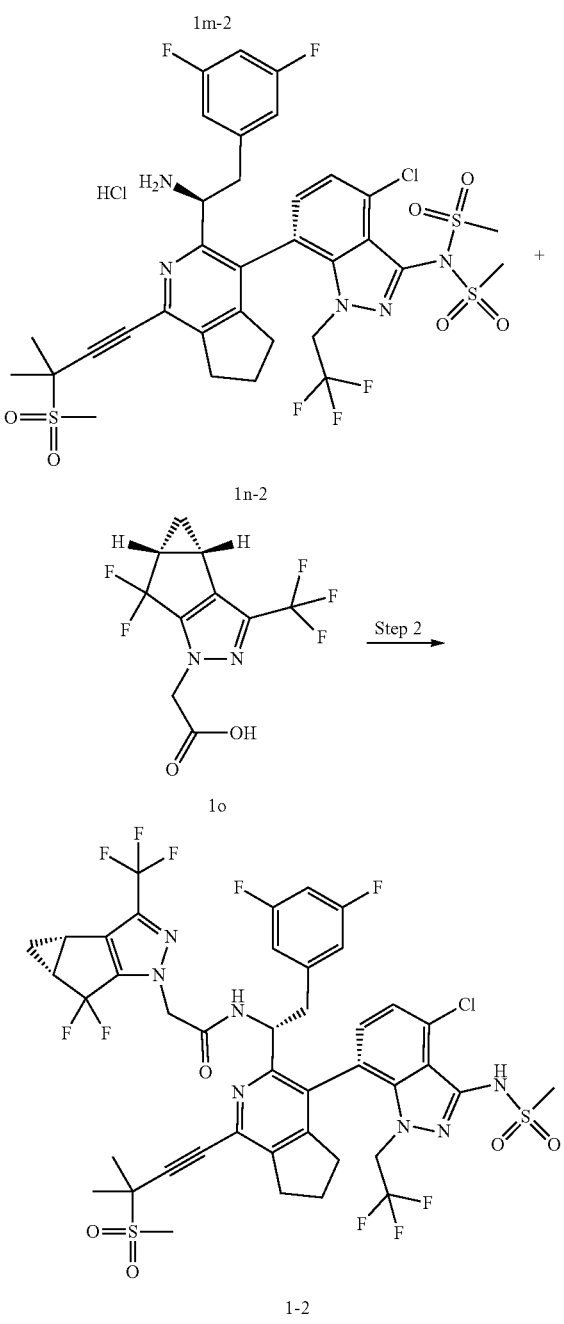

1n-2

1o 1-2

Step 1

Step 2

Step 1

N-(7-((S)-3-((R)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride 1n-2

Compound 1m-2 (66.0 mg, 0.07 mmol) was dissolved in dichloromethane (0.5 mL), and the reaction solution was added with 4 M hydrogen chloride solution in dioxane (2 mL), stirred at room temperature for 1 h, and concentrated under reduced pressure to give the title compound 1n-2 (62 mg, yield: 100%).

MS m/z (ESI): 821.8 [M−35].

Step 2

N—((R)-1-((S)-4-(4-chloro-3-(methanesulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4, 4a,5-tetrahydro-7H-cyclopropa[3,4]cyclopenta[1,2-c]pyrazol-1-yl)acetamide 1-2

Compound 1n-2 (62.0 mg, 0.07 mmol), compound 1o (21.0 mg, 0.07 mmol, prepared by the method disclosed in the patent application "WO2018035359A1, intermediate im-8a on page 80") and 2-(7-benzotriazole oxide)-N,N,N',N'-tetramethylurea hexafluorophosphate (38.0 mg, 0.1 mmol, Sinopharm Chemical Reagent Co., Ltd.) were dissolved in N,N-dimethylformamide (1.5 mL), and N,N-diisopropylethylamine (45.0 mg, 0.4 mmol, adamas) was added. The reaction solution was stirred at room temperature for 1 h, added with 2 N sodium hydroxide (0.3 mL), and stirred at room temperature for 1 h, then added with water (10 mL), extracted with ethyl acetate (10 mL×3), and concentrated under reduced pressure. The resulting residue was purified by high performance liquid chromatography (Sharpsil-T C18, 150×30 mm, 5 μm, eluent system: H$_2$O (0.1% trifluoroacetic acid), acetonitrile) to give the title product 1-2 (27 mg, yield: 34%).

MS m/z (ESI): 1007.5 [M+1].

$^1$H NMR (400 MHz, CD$_3$OD) δ 7.21 (d, 1H), 6.76 (t, 1H), 6.52 (d, 1H), 6.26 (d, 2H), 4.91-4.76 (m, 3H), 4.63-4.57 (m, 1H), 4.04-3.96 (m, 1H), 3.26 (s, 3H), 3.23 (s, 3H), 3.17-3.13 (m, 2H), 3.04-2.99 (m, 1H), 2.90-2.85 (m, 1H), 2.82-2.73 (m, 1H), 2.54-2.41 (m, 3H), 2.18-2.15 (m, 1H), 2.07-1.99 (m, 1H), 1.83 (s, 6H), 1.44-1.39 (m, 1H), 1.14 (s, 1H).

149

Examples 1-1a, 1-1b

N—((S)-1-((R)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b, 4,4a,5-tetrahydro-1H-cyclopropa[3,4]cyclopenta[1,2-c]pyrazol-1-yl)acetamide 1-1a N—((S)-1-((S)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-6,7-dihydro-5H-cyclopenta[c]pyrid in-3-yl)-2-(3,5-difluorophenyl)ethyl)-2-((3bS,4aR)-5,5-difluoro-3-(trifluoromethyl)-3b,4,4a, 5-tetrahydro-1H-cyclopropa[3,4]cyclopenta[1,2-c]pyrazol-1-yl)acetamide 1-1b

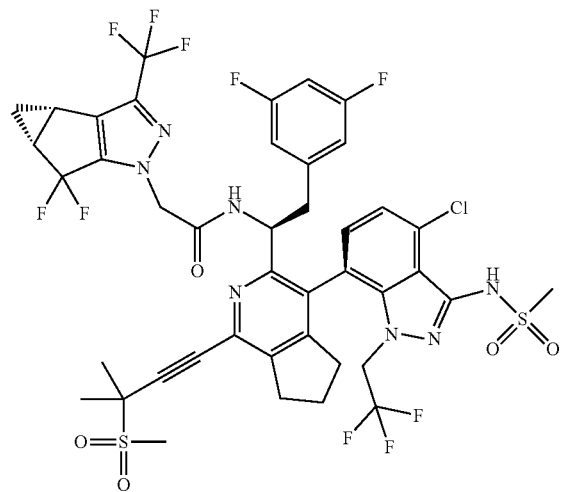

1-1a 1-1b

150

-continued

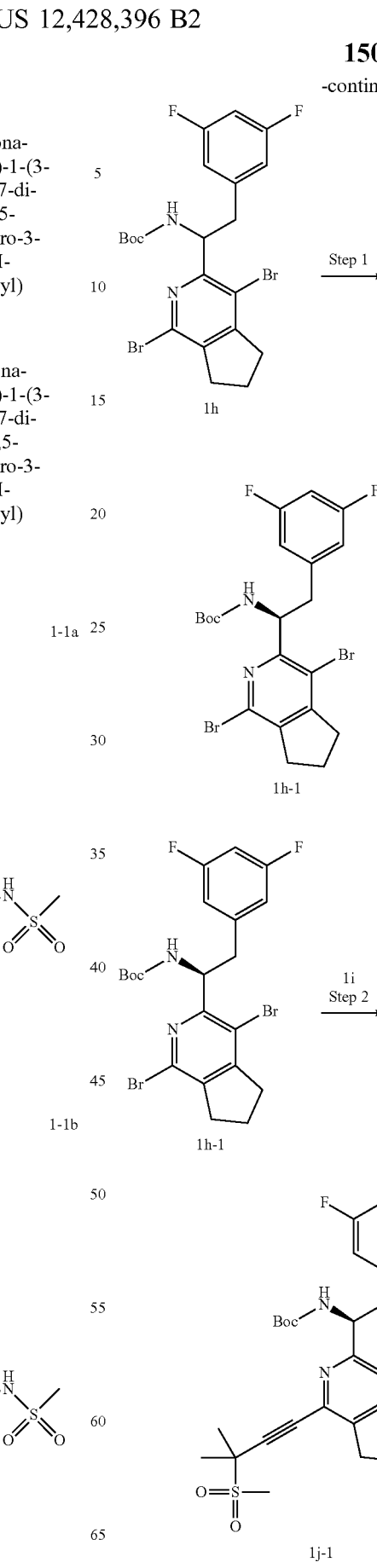

151
-continued
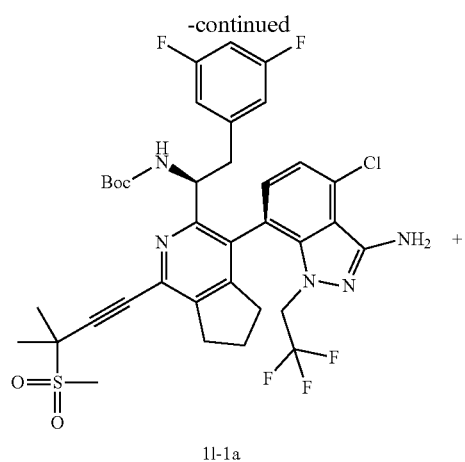
1l-1a
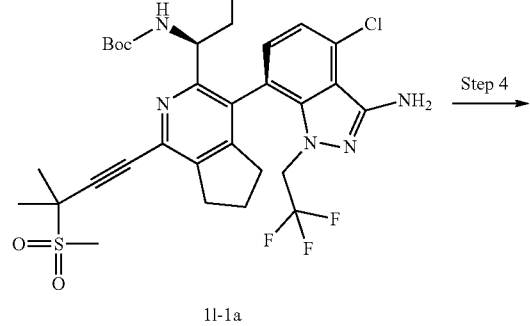
1l-1b
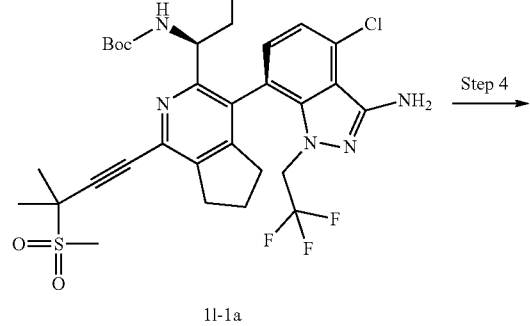
1l-1a
Step 4 →
152
-continued
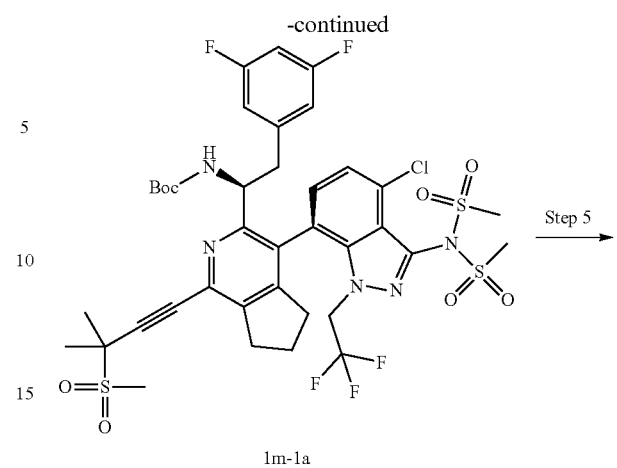
1m-1a
Step 5 →
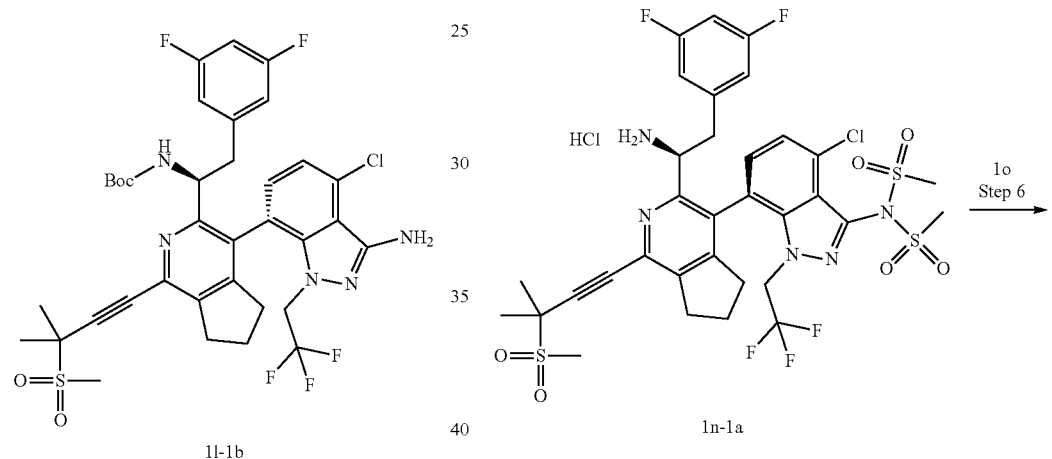
1n-1a
1o
Step 6 →
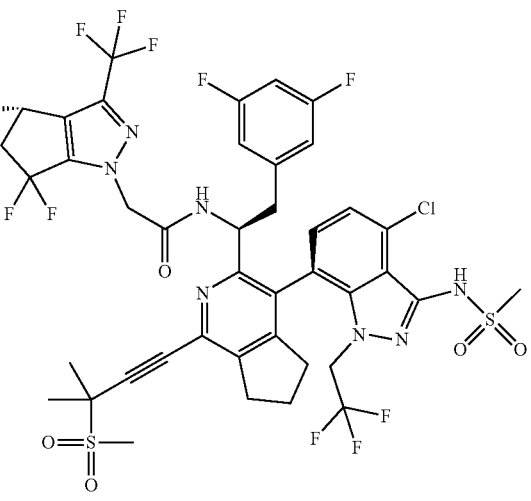
1-1a

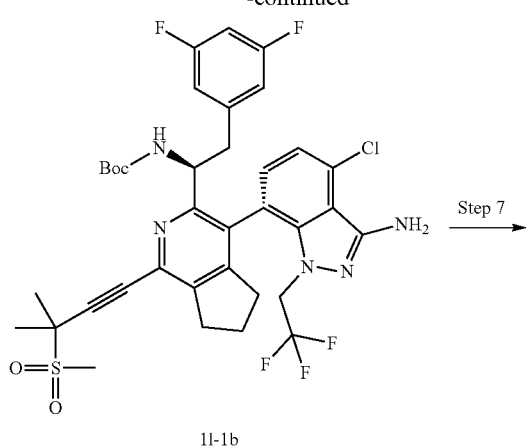

1l-1b

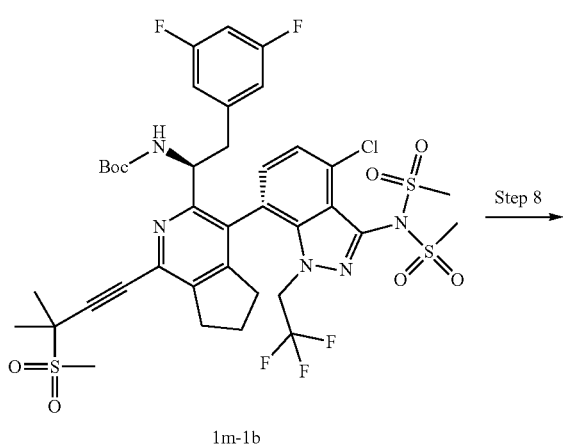

1m-1b

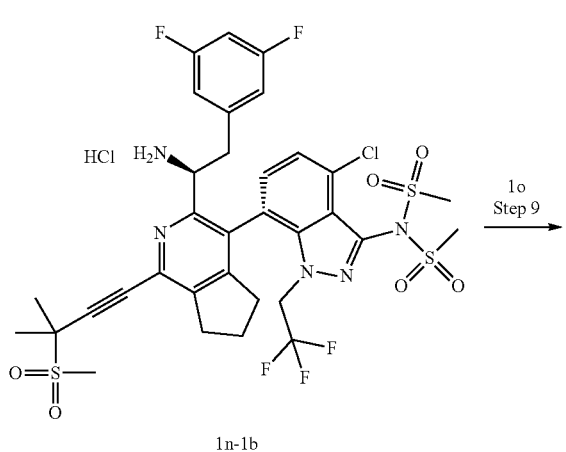

1n-1b

Step 7 →

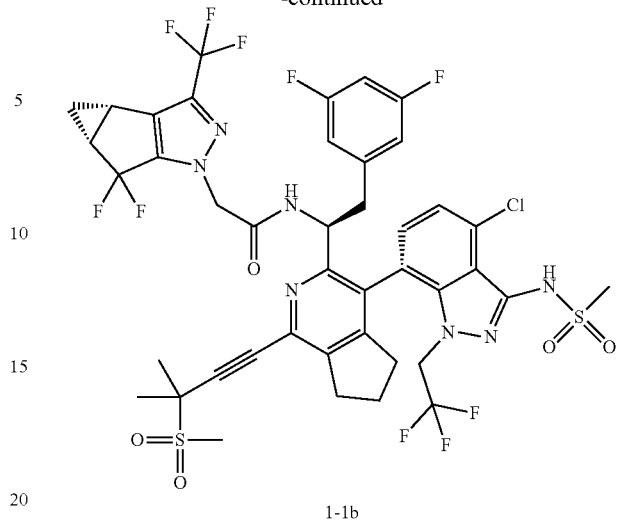

1-1b

Step 8 →

1o
Step 9 →

Step 1

(S)-tert-butyl (1-(1,4-dibromo-6,7-dihydro-5H-cyclopenta[c]pyridin-3-yl)-2-(3,5-difluorophenyl)ethyl)carbamate 1h-1

(R)-tert-butyl (1-(1,4-dibromo-6,7-dihydro-5H-cyclopenta[c]pyridin-3-yl)-2-(3,5-difluorophenyl)ethyl)carbamate 1h-2

The racemate 1h (2.1 g, 3.96 mmol) was subjected to chiral preparation (separation conditions: CHIRALPAK IG chiral preparation column, 2.5 cm I.D.×25 cmL, 10 μm; mobile phase: methanol=100%, flow rate: 60 mL/min), and the corresponding fractions were collected and concentrated under reduced pressure to give the title products 1h-1 (1.23 g, yield: 48%) and 1h-2 (620 mg, yield: 24%).

Single-Configuration Compound 1h-1:
MS m/z (ESI): 530.8 [M+1].
Chiral HPLC analysis: retention time: 7.144 min, chiral purity: 100% (column: CHIRALPAK IG-3(IG30CD-WE016) 0.46 cm I.D.×15 cmL, 10 μm; mobile phase: methanol=100%).

Single-Configuration Compound 1h-2:
MS m/z (ESI): 530.8 [M+1].
Chiral HPLC analysis: retention time: 3.739 min, chiral purity: 100% (column: CHIRALPAK IG-3(IG30CD-WE016) 0.46 cm I.D.×15 cmL, 10 μm; mobile phase: methanol=100%).

Step 2

Tert-butyl (S)-(1-(4-bromo-1-(3-methyl-3-(methanesulfonyl)but-1-yn-1-yl)-6,7-dihydro-5H-cyclopenta[c]pyridin-3-yl)-2-(3,5-difluorophenyl)ethyl)carbamate 1j-1

Compound 1h-1 (620.0 mg, 1.16 mmol) and compound 1i (255.5 mg, 1.75 mmol) were dissolved in N,N-dimethylformamide (10 mL). Bis(triphenylphosphine)palladium dichloride (98.0 mg, 0.14 mmol, Accela ChemBio Co., Ltd.), cuprous iodide (133.2 mg, 0.7 mmol, Sinopharm Chemical Reagent Co., Ltd.) and triethylamine (353.7 mg, 3.5 mmol, Shanghai Hushi Chemical Co., Ltd.) were added. The reaction solution was purged with nitrogen three times, stirred at room temperature for 4 h, added with water (20 mL), extracted with ethyl acetate (20 mL×3), and concentrated under reduced pressure. The resulting residue was purified by silica gel column chromatography with eluent system A to give the title product 1j-1 (670.0 mg, yield: 96%).

MS m/z (ESI): 596.8 [M+1].

Step 3

Tert-butyl ((S)-1-((R)-4-(3-amino-4-chloro-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 1l-1a Tert-butyl ((S)-1-((S)-4-(3-amino-4-chloro-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 1l-1b Compound 1j-1 (320.0 mg, 0.54 mmol) and compound 1k (301.8 mg, 0.8 mmol) were dissolved in dioxane (10 mL) and water (1.5 mL). Di-tert-butyl-(4-dimethylaminophenyl)phosphonium dichloropalladium (75.9 mg, 0.11 mmol, Accela ChemBio Co., Ltd.) and potassium phosphate (340.7 mg, 1.6 mmol, J&K Chemical) were added. The reaction solution was purged with nitrogen three times, stirred at 90° C. for 16 h, added with water (20 mL), extracted with ethyl acetate (20 mL×3), and concentrated under reduced pressure. The resulting residue was purified by silica gel column chromatography with eluent system A to give the title products 1l-1a (140 mg, yield: 34%) and 1l-1b (60.0 mg, yield: 14.6%).

Single-Configuration Compound (Longer Retention Time) 1l-1a:
MS m/z (ESI): 765.8 [M+1].
LCMS analysis: retention time: 3.146 min. Column: HD 2.1×50 mm 1.8-Micron; mobile phase: water (0.1% formic acid):acetonitrile (0.1% formic acid).

Single-Configuration Compound (Shorter Retention Time) 1l-1b:
MS m/z (ESI): 765.8 [M+1].
LCMS analysis: retention time: 3.019 min. Column: HD 2.1×50 mm 1.8-Micron; mobile phase: water (0.1% formic acid):acetonitrile (0.1% formic acid).

Step 4 and Step 7

Tert-butyl ((S)-1-((R)-4-(4-chloro-3-(N-(methylsulfonyl)methanesulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 1m-1a Tert-butyl ((S)-1-((S)-4-(4-chloro-3-(N-(methylsulfonyl)methanesulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 1m-1b Compound 1l-11a/1l-1b (140.0 mg/60 mg, 0.18 mmol/0.08 mmol) and triethylamine (110.8 mg/47.5 mg, 1.1 mmol/0.47 mmol, Shanghai Hushi Chemical Co., Ltd.) were dissolved in dichloromethane (2 mL/1.5 mL), and the reaction solution was added with methanesulfonyl chloride (62.5 mg/26.8 mg, 0.55 mmol/0.24 mmol, Sinopharm Chemical Reagent Co., Ltd.), stirred at room temperature for 1 h, added with water (20 mL), extracted with dichloromethane (20 mL×3), and concentration under reduced pressure. The resulting residue was purified by silica gel column chromatography with eluent system A to give the title products 1m-1a (140.0 mg, yield: 83%) and 1m-1b (70.0 mg, yield: 97%).

Single-Configuration Compound 1m-1a:
MS m/z (ESI): 921.8 [M+1].
Single-Configuration Compound 1m-1b:
MS m/z (ESI): 921.8 [M+1].

Step 5 and Step 8

N-(7-((R)-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride 1n-1a N-(7-((S)-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide hydrochloride 1n-1b Compound 1m-1a/1m-1b (140.0 mg/70 mg, 0.15 mmol/0.08 mmol) was dissolved in dichloromethane (1 mL/0.5 mL), and the reaction solution was added with 4 M hydrogen chloride solution in dioxane (4 mL/2 mL), stirred at room temperature for 1 h, and concentrated under reduced pressure to give the title products 1n-1a (130.0 mg, yield: 104%) and 1n-1b (60.0 mg, yield: 96%).

Single-Configuration Compound 1n-1a
MS m/z (ESI): 821.8 [M−35].
Single-Configuration Compound 1n-1b
MS m/z (ESI): 821.8 [M−35].

Step 6 and Step 9

N—((S)-1-((R)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 1-1a N—((S)-1-((S)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-6,7-dihydro-5H-cyclopenta[c]pyrid in-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 1-1b Compound 1n-1a/1n-1b (130.0 mg/60.0 mg, 0.15 mmol/0.07 mmol), compound to (43.0 mg/20 mg, 0.15 mmol/0.07 mmol) and 2-(7-benzotriazole oxide)-N,N,N',N'-tetramethylurea hexafluorophosphate (75.0 mg/35 mg, 0.2 mmol/0.09 mmol, Sinopharm Chemical Reagent Co., Ltd.) were dissolved in N,N-dimethylformamide (3 mL/3 mL), and the reaction solution was added with N,N-diisopropylethylamine (98.0 mg/46.0 mg, 0.8 mmol/0.36 mmol, adamas), stirred at room temperature for 1 h, added with 2 N sodium hydroxide (0.7 mL/0.4 mL), stirred at room temperature for 1 h, then added with water (10 mL), extracted with ethyl acetate (10 mL×3), and concentrated under reduced pressure. The resulting residue was purified by high performance liquid chromatography (Sharpsil-T C18, 150×30 mm, 5 µm, eluent system: H₂O (0.1% trifluoroacetic acid), acetonitrile) to give the title products 1-1a (46.0 mg, yield: 30%) and 1-1b (20.0 mg, yield: 28%).

Single-Configuration Compound 1-1a

MS m/z (ESI): 1007.5 [M+1].

¹H NMR (400 MHz, CD₃OD) δ 7.19 (d, 1H), 6.76 (t, 1H), 6.48 (d, 1H), 6.26 (d, 2H), 4.88-4.75 (m, 3H), 4.68-4.58 (m, 1H), 4.02-3.92 (m, 1H), 3.24 (s, 3H), 3.23 (s, 3H), 3.19-3.13 (m, 2H), 3.05-3.00 (m, 1H), 2.91-2.86 (m, 1H), 2.82-2.74 (m, 1H), 2.55-2.40 (m, 3H), 2.18-2.15 (m, 1H), 2.06-1.99 (m, 1H), 1.83 (s, 6H), 1.45-1.40 (m, 1H), 1.09 (s, 1H).

Single-Configuration Compound 1-1b

MS m/z (ESI): 1007.5 [M+1].

¹H NMR (400 MHz, CD₃OD) δ 7.25 (d, 1H), 7.16 (d, 1H), 6.73 (t, 1H), 6.64 (d, 2H), 4.92-4.88 (m, 1H), 4.66-4.55 (m, 2H), 4.13-4.05 (m, 1H), 3.99-3.89 (m, 1H), 3.30-3.26 (m, 3H), 3.23 (s, 4H), 3.17-3.09 (m, 3H), 2.71-2.63 (m, 1H), 2.53-2.48 (m, 3H), 2.16-2.04 (m, 2H), 1.82 (s, 6H), 1.44-1.39 (m, 1H), 1.09 (s, 1H).

Example 2

N—((S)-1-((R)-4-(4-chloro-3-(cyclopropylsulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3 b,4,4a,5-tetrahydro-1H-cyclopropa[3,4]cyclopenta[1,2-c]pyrazol-1-yl)acetamide 2

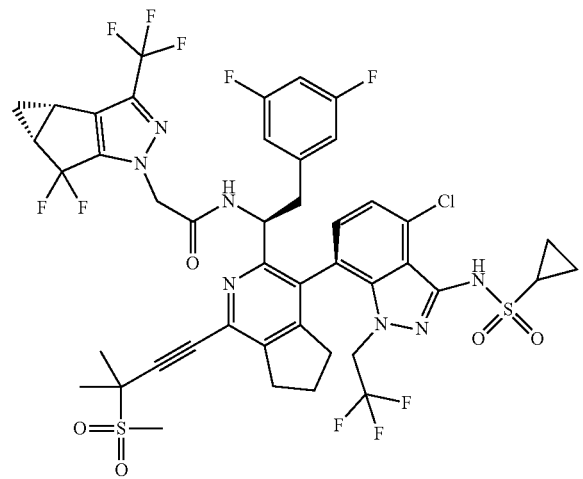

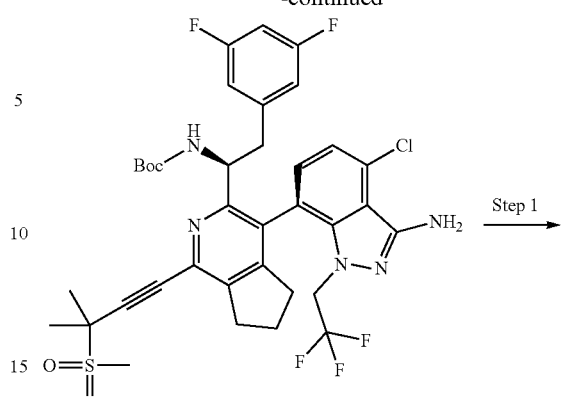

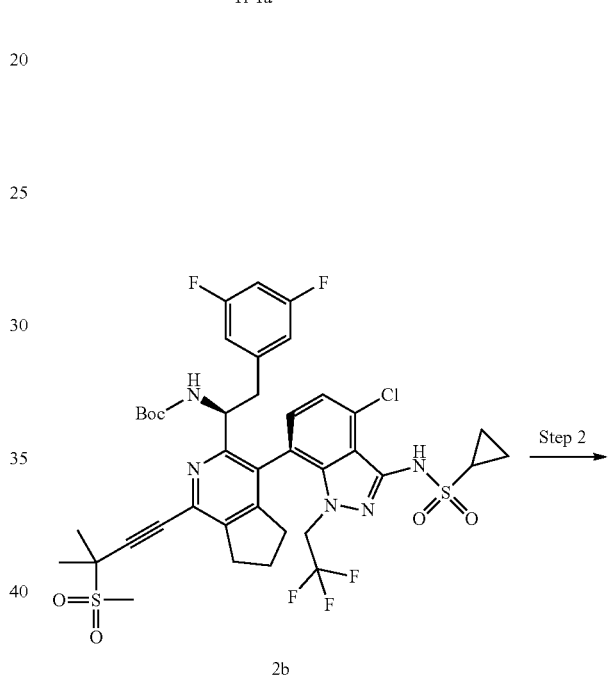

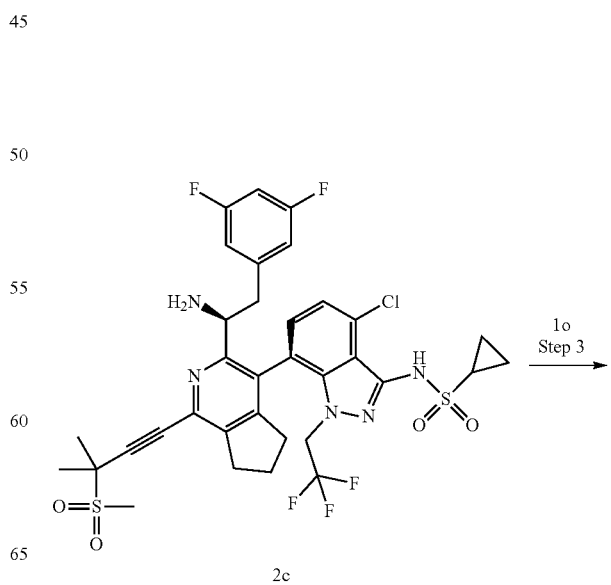

-continued

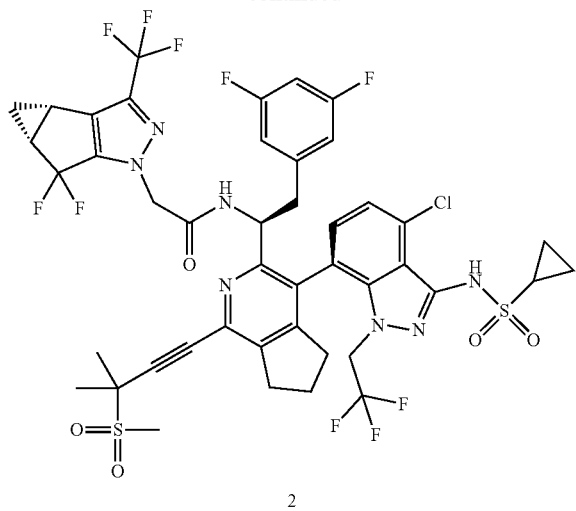

2

Step 1

Tert-butyl ((1S)-1-((R)-4-(4-chloro-3-(cyclopropylsulfonamido)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 2b Compound 1l-1a (90.0 mg, 0.12 mmol) and 4-dimethylaminopyridine (14.5 mg, 0.12 mmol, adamas) were dissolved in pyridine (1 mL), and the reaction solution was added with cyclopropanesulfonyl chloride (199.0 mg, 1.42 mmol, Bide Pharmatech Ltd.), stirred at 80° C. for 16 h, added with water (10 mL), extracted with ethyl acetate (20 mL×3), and concentrated under reduced pressure. The resulting residue was purified by silica gel column chromatography with eluent system A to give the title product 2b (100.0 mg, yield: 98%).

MS m/z (ESI): 869.7 [M+1].

Step 2

N-(7-((R)-3-((S)-1-amino-2-(3,5-difluorophenyl)ethyl)-1-(3-methyl-3-(methylsulfonyl)but-1-yn-1-yl)-6,7-dihydro-5H-cyclopenta[c]pyridin-4-yl)-4-chloro-1-(2,2,2-trifluoroethyl)-1H-indazol-3-yl)-cyclopropanesulfonamide 2c Compound 2b (100.0 mg, 0.12 mmol) was dissolved in dichloromethane (3 mL), and the reaction solution was added with trifluoroacetic acid (1 mL), stirred at room temperature for 1 h, and concentrated under reduced pressure. The resulting residue was neutralized with aqueous sodium hydrogencarbonate, then extracted with ethyl acetate (20 mL×3), and concentrated under reduced pressure to give the title product 2c (88.0 mg, yield: 99%).

MS m/z (ESI): 769.7 [M+1].

Step 3

N—((S)-1-((R)-4-(4-chloro-3-(cyclopropylsulfonamide)-1-(2,2,2-trifluoroethyl)-1H-indazol-7-yl)-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3 b,4,4a,5-tetrahydro-1H-cyclopropyl[3,4]cyclopenta[1,2-c]pyrazol-1-yl)acetamide 2

Compound 2c (88.0 mg, 0.11 mmol), compound to (32.3 mg, 0.11 mmol), 1-(3-dimethylaminopropyl)-3-ethylcarbodiimide hydrochloride (32.8 mg, 0.17 mmol, Accela ChemBio Co., Ltd.)) and 1-hydroxybenzotriazole (23.2 mg, 0.17 mmol, Sinopharm Chemical Reagent Co., Ltd.) were dissolved in N,N-dimethylformamide (1 mL), and the reaction solution was added with N-methylmorpholine (34.7 mg, 0.34 mmol, Shanghai Hushi Chemical Co., Ltd.), stirred at room temperature for 16 h, added with water (10 mL), extracted with ethyl acetate (20 mL×3), and concentrated under reduced pressure. The resulting residue was purified by high performance liquid chromatography (Sharpsil-T C18, 150×30 mm, 5 μm, eluent system: H$_2$O (0.1% trifluoroacetic acid), acetonitrile) to give the title product 2 (20.0 mg, yield: 15%).

MS m/z (ESI): 1034.0 [M+1].

$^1$H NMR (400 MHz, CD$_3$OD) δ7.20 (d, 1H), 6.76 (t, 1H), 6.49 (d, 1H), 6.25 (d, 2H), 4.87-4.75 (m, 3H), 4.63-4.57 (m, 1H), 4.02-3.96 (m, 1H), 3.23 (s, 3H), 3.15 (t, 2H), 3.00-2.98 (m, 1H), 2.92-2.85 (m, 2H), 2.82-2.74 (m, 1H), 2.53-2.42 (m, 3H), 2.18-2.15 (m, 1H), 2.07-1.99 (m, 1H), 1.83 (s, 6H), 1.45-1.40 (m, 1H), 1.13-1.09 (m, 3H), 1.03-0.96 (m, 2H).

Example 3

N—((S)-1-((R)-4-(4-chloro-3-(methanesulfonamido)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 3

3

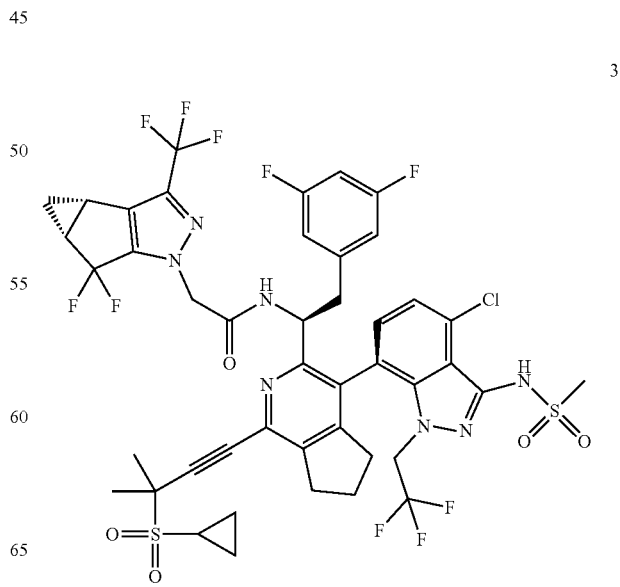

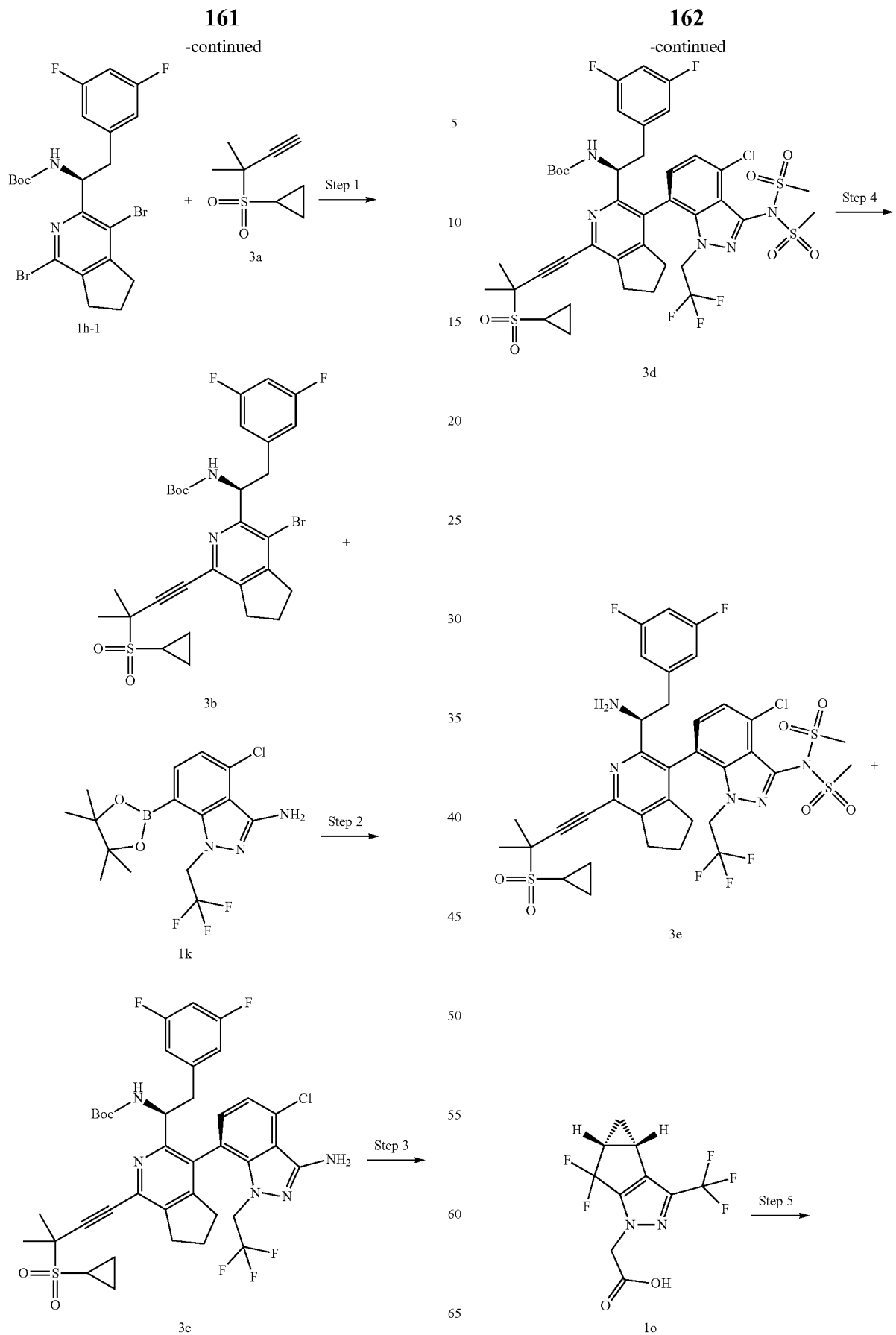

163
-continued

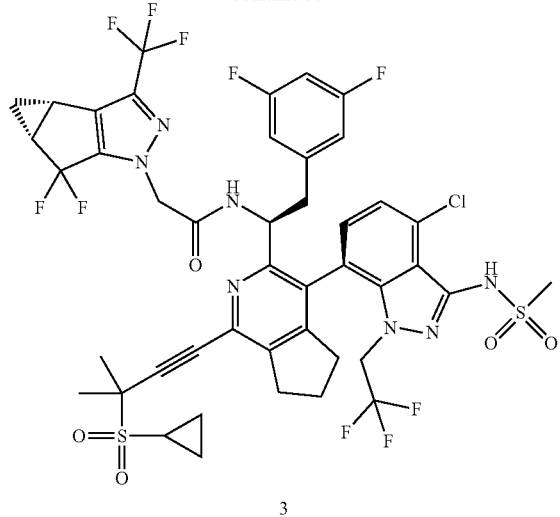

3

Step 1

Tert-butyl (S)-(1-(4-bromo-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)carbamate 3b Compound 1h-1 (300.0 mg, 0.56 mmol) and compound 3a (146.0 mg, 0.85 mmol, prepared by the method disclosed in the patent application "WO2019/161017 A1, intermediate 1E on page 80") were dissolved in N,N-dimethylformamide (5 mL). Bis(triphenylphosphine)palladium dichloride (38.0 mg, 0.07 mmol, Accela ChemBio Co., Ltd.), cuprous iodide (65.0 mg, 0.34 mmol, Sinopharm Chemical Reagent Co., Ltd.) and triethylamine (172.0 mg, 1.7 mmol, Shanghai Hushi Chemical Co., Ltd.) were added. The reaction solution was purged with nitrogen three times, stirred at room temperature for 4 h, added with water (20 mL), extracted with ethyl acetate (20 mL×3), and concentrated under reduced pressure. The resulting residue was purified by silica gel column chromatography with eluent system A to give the title product 3b (310.0 mg, yield: 88%).
MS m/z (ESI): 622.8 [M+1].

Step 2

Tert-butyl ((1S)-1-((R)-4-(3-amino-4-chloro-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)carbamate 3c Compound 3b (310.0 mg, 0.5 mmol) and compound 1k (281.0 mg, 0.75 mmol) were dissolved in dioxane (10 mL) and water (1.5 mL). Di-tert-butyl-(4-dimethylaminophenyl)phosphonium dichloropalladium (71.0 mg, 0.1 mmol, Accela ChemBio Co., Ltd.) and potassium phosphate (317.0 mg, 1.5 mmol, J&K Chemical) were added. The reaction solution was purged with nitrogen three times, stirred at 90° C. for 16 h, added with water (20 mL), extracted with ethyl acetate (20 mL×3), and concentrated under reduced pressure. The resulting residue was purified by silica gel column chromatography with eluent system A to give the title product 3c (170.0 mg, yield: 43%).
MS m/z (ESI): 791.8 [M+1].

Step 3

Tert-butyl ((1S)-1-((R)-4-(4-chloro-3-(N-(methylsulfonyl)methanesulfonamido)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)carbamate 3d Compound 3c (110.0 mg, 0.14 mmol) and triethylamine (85.0 mg, 0.84 mmol, Shanghai Hushi Chemical Co., Ltd.) were dissolved in dichloromethane (2 mL), and the reaction solution was added with methanesulfonyl chloride (48.0 mg, 0.42 mmol, Sinopharm Chemical Reagent Co., Ltd.), stirred at room temperature for 1 h, added with water (10 mL), extracted with dichloromethane (20 mL×3), and concentrated under reduced pressure. The resulting residue was purified by silica gel column chromatography with eluent system A to give the title product 3d (130.0 mg, yield: 99%).
MS m/z (ESI): 947.5 [M+1].

Step 4

N-(7-((R)-3-((S)-1-amino-2-(3,5-difluorophenyl)ethyl)-1-(3-(cyclopropylsulfonyl)-3-methyl-but-1-yn-1-yl)-6,7-dihydro-5H-cyclopenta[c]pyridin-4-yl)-4-chloro-1-(2,2,2-trifluoroethyl)-1H-indazol-3-yl)-N-(methylsulfonyl)methanesulfonamide 3e Compound 3d (100.0 mg, 0.12 mmol) was dissolved in dichloromethane (3 mL), and the reaction solution was added with trifluoroacetic acid (1 mL), stirred at room temperature for 1 h, and concentrated under reduced pressure. The resulting residue was neutralized with aqueous sodium hydrogencarbonate, then extracted with ethyl acetate (20 mL×3), and concentrated under reduced pressure to give the title product 3e (89.0 g, yield: 99%).
MS m/z (ESI): 847.6 [M+1].

Step 5

N—((S)-1-((R)-4-(4-chloro-3-(methanesulfonamido)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 3

Compound 3e (90.0 mg, 0.11 mmol), compound to (33.0 mg, 0.12 mmol) and 2-(7-benzotriazole oxide)-N,N,N',N'-tetramethyluronium hexafluorophosphate (33.0 mg, 0.14 mmol, Sinopharm Chemical Reagent Co., Ltd.) were dissolved in N,N-dimethylformamide (1.5 mL), and the reaction solution was added with N,N-diisopropylethylamine (42.0 mg, 0.32 mmol, adamas), stirred at room temperature for 0.5 h, added with 2 N sodium hydroxide (0.3 mL), and stirred at room temperature for 1 h, then added with water (10 mL), extracted with ethyl acetate (10 mL×3), and concentrated under reduced pressure. The resulting residue was purified by high performance liquid chromatography (Sharpsil-T C18, 150×30 mm, 5 μm, eluent system: $H_2O$ (0.1% trifluoroacetic acid), acetonitrile) to give the title product 3 (43 mg, yield: 35%).
MS m/z (ESI): 1033.6 [M+1].

¹H NMR (400 MHz, CD₃OD) δ 7.19 (d, 1H), 6.76 (t, 1H), 6.47 (d, 1H), 6.26 (d, 2H), 4.87-4.75 (m, 3H), 4.68-4.58 (m, 1H), 4.02-3.92 (m, 1H), 3.24 (s, 3H), 3.15 (t, 2H), 3.06-3.01 (m, 1H), 2.99-2.95 (m, 1H), 2.91-2.86 (m, 1H), 2.82-2.73 (m, 1H), 2.54-2.40 (m, 3H), 2.19-2.16 (m, 1H), 2.08-1.99 (m, 1H), 1.85 (s, 6H), 1.45-1.38 (m, 1H), 1.29-1.23 (m, 4H), 1.09-1.08 (m, 1H).
Example 4
N—((S)-1-((R)-4-(4-chloro-3-(cyclopropylsulfonamide)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta [c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-1) acetamide 4
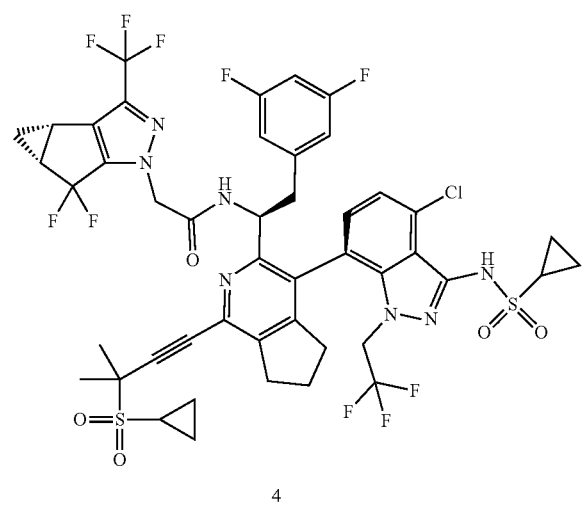
4
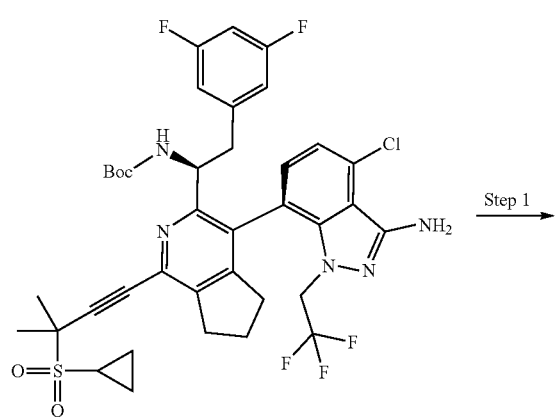
3c
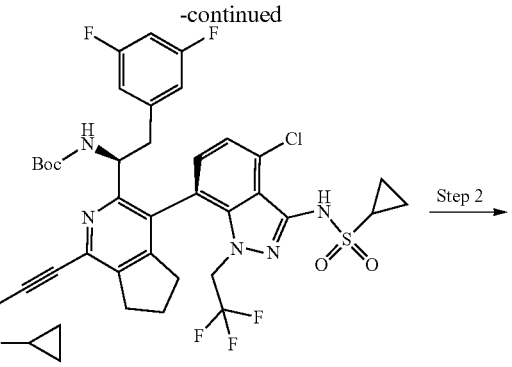
4a
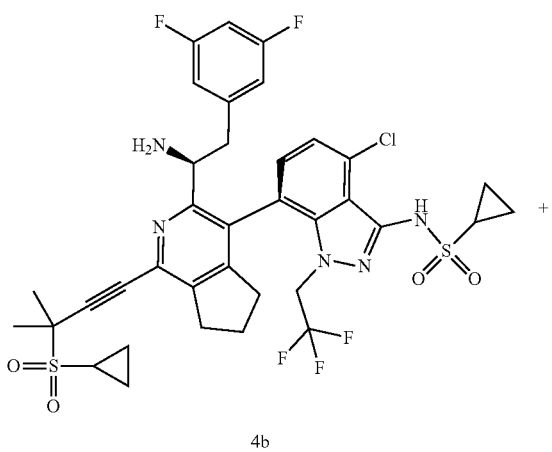
4b
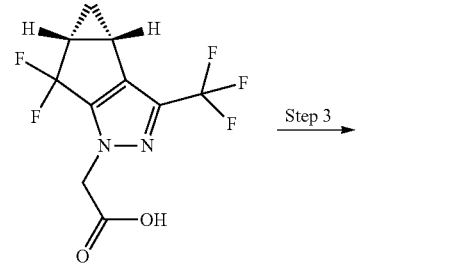
1o
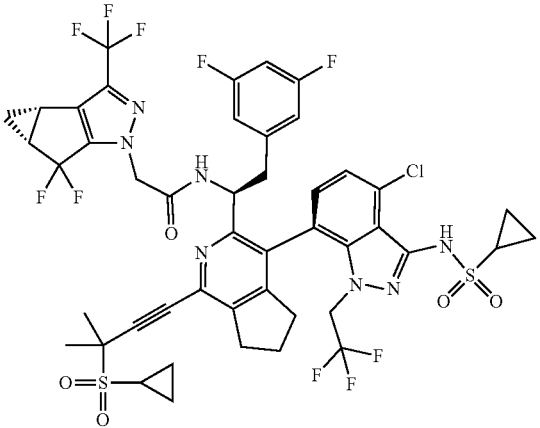
4

Step 1

Tert-butyl ((1S)-1-((R)-4-(4-chloro-3-(cyclopropylsulfonamide)-1-(2,2,2-trifluoroethyl)-1H-indazol-7-yl)-1-(3-methyl-3-(cyclopropylsulfonyl)but-1-yn-1-yl)-6,7-dihydro-5H-cyclopenta[c]pyridin-3-yl)-2-(3,5-difluorophenyl)ethyl)carbamate 4a Compound 3c (110.0 mg, 0.14 mmol) and 4-dimethylaminopyridine (34.3 mg, 0.28 mmol, adamas) were dissolved in pyridine (1.5 mL). The reaction solution was added with cyclopropanesulfonyl chloride (293.0 mg, 2.08 mmol, Bide Pharmatech Ltd.), stirred at 80° C. for 16 h, added with water (10 mL), extracted with ethyl acetate (20 mL×3), and concentrated under reduced pressure. The resulting residue was purified by silica gel column chromatography with eluent system A to give the title product 4a (90.0 mg, yield: 72%).

MS m/z (ESI): 895.7 [M+1].

Step 2

N-(7-((R)-3-((S)-1-amino-2-(3,5-difluorophenyl)ethyl)-1-(3-(cyclopropylsulfonyl)-3-methyl-but-1-yn-1-yl)-6,7-dihydro-5H-cyclopenta[c]pyridin-4-yl)-4-chloro-1-(2,2,2-trifluoroethyl)-1H-indazol-3-yl)-cyclopropanesulfonamide 4b Compound 4a (100.0 mg, 0.1 mmol) was dissolved in dichloromethane (3 mL), and the reaction solution was added with trifluoroacetic acid (1 mL), stirred at room temperature for 1 h, and concentrated under reduced pressure. The resulting residue was neutralized with aqueous sodium hydrogencarbonate, then extracted with ethyl acetate (20 mL×3), and concentrated under reduced pressure to give the title product 4b (80.0 mg, yield: 100%).

MS m/z (ESI): 795.8 [M+1].

Step 3

N—((S)-1-((R)-4-(4-chloro-3-(cyclopropylsulfonamide)-1-(2,2,2-trifluoroethyl)-1H-indazol-7-yl)-1-(3-(cyclopropylsulfonyl)-3-methyl-but-1-yn-1-yl)-6,7-dihydro-5H-cyclopenta [c]pyridin-3-yl)-2-((3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 4

Compound 4b (80.0 mg, 0.1 mmol), compound to (32.0 mg, 0.11 mmol), 1-(3-dimethylaminopropyl)-3-ethylcarbodiimide hydrochloride (29.0 mg, 0.15 mmol, Accela ChemBio Co., Ltd.)) and 1-hydroxybenzotriazole (21.0 mg, 0.16 mmol, Sinopharm Chemical Reagent Co., Ltd.) were dissolved in N,N-dimethylformamide (1 mL), and the reaction solution was added with N-methylmorpholine (31.0 mg, 0.31 mmol, Shanghai Hushi Chemical Co., Ltd.), stirred at room temperature for 16 h, added with water (10 mL), extracted with ethyl acetate (20 mL×3), and concentrated under reduced pressure. The resulting residue was purified by high performance liquid chromatography (Sharpsil-T C18, 150×30 mm, 5 μm, eluent system: H$_2$O (0.1% trifluoroacetic acid), acetonitrile) to give the title product 4 (22.0 mg, yield: 19%).

MS m/z (ESI): 1059.6 [M+1].

$^1$H NMR (400 MHz, CD$_3$OD) δ 7.20 (d, 1H), 6.76 (t, 1H), 6.48 (d, 1H), 6.26 (d, 2H), 4.87-4.75 (m, 3H), 4.63-4.57 (m, 1H), 4.01-3.95 (m, 1H), 3.17-3.13 (m, 2H), 3.04-2.95 (m, 2H), 2.91-2.86 (m, 2H), 2.82-2.73 (m, 1H), 2.53-2.42 (m, 3H), 2.21-2.14 (m, 1H), 2.06-1.99 (m, 1H), 1.85 (s, 6H), 1.45-1.40 (m, 1H), 1.29-1.21 (m, 4H), 1.11-1.09 (m, 3H), 1.00-0.96 (m, 2H).

Examples 5-1, 5-2

N—((S)-1-((R)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-5,6,7,8-tetrahydroisoquinolin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 5-1

N—((S)-1-((S)-4-(4-chloro-3-(methanesulfonamido)-1-(2,2,2-trifluoroethyl)-1H-indazol-7-yl)-1-(3-methyl-3-(methanesulfonyl)but-1-yn-1-yl)-5,6,7,8-tetrahydroisoquinolin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 5-2

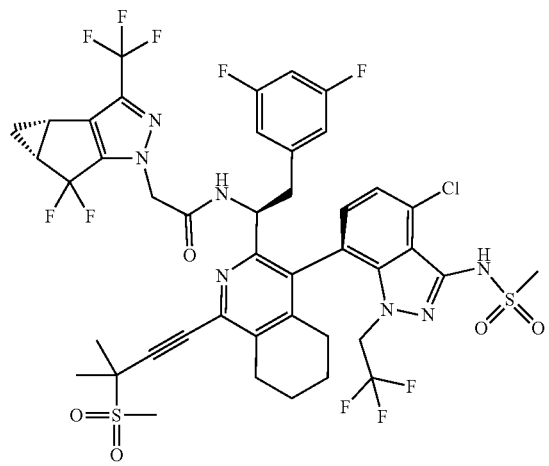

5-1

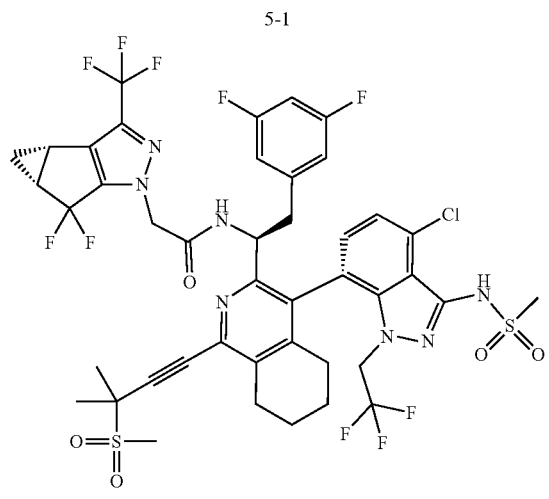

5-2

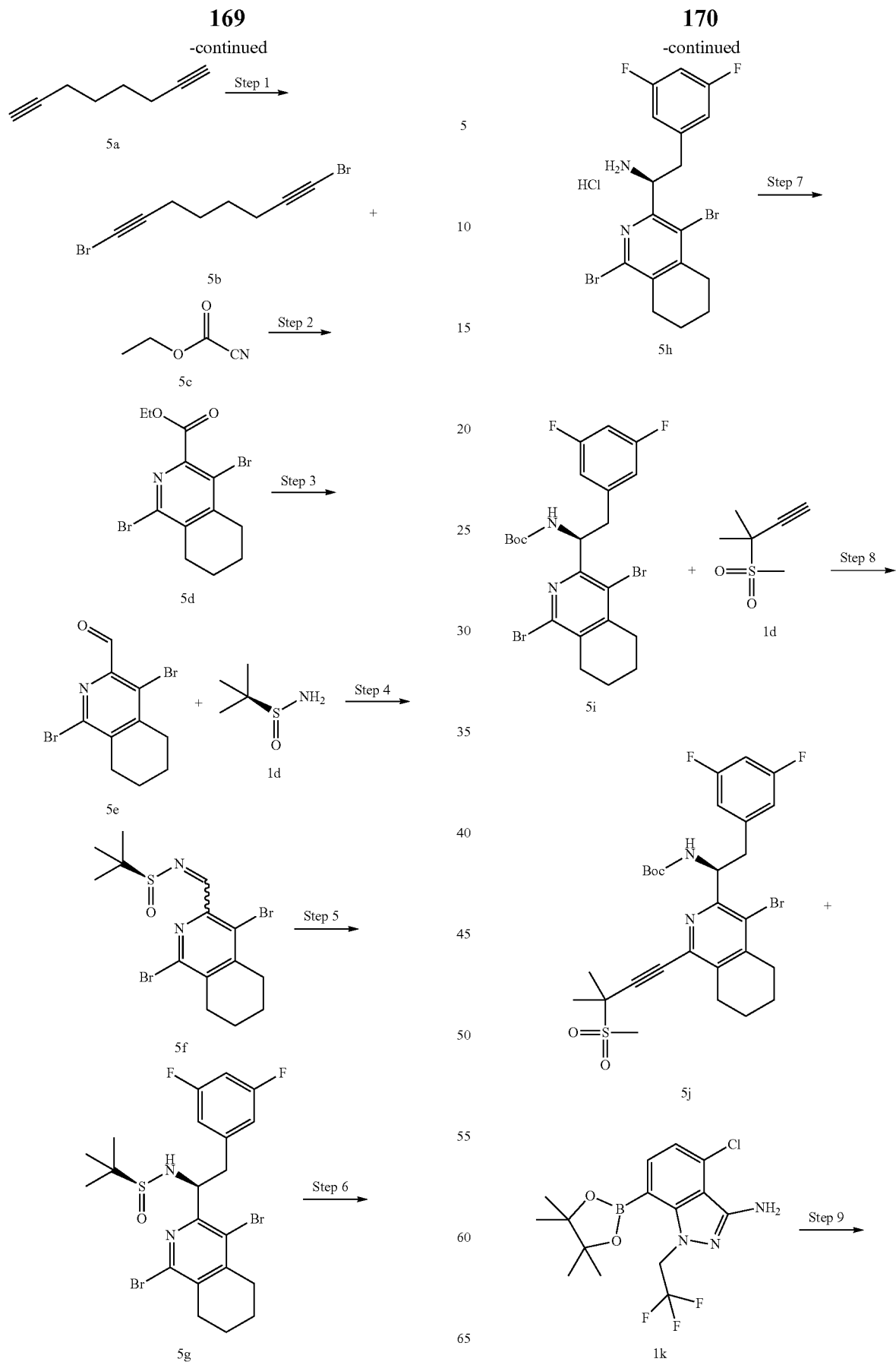

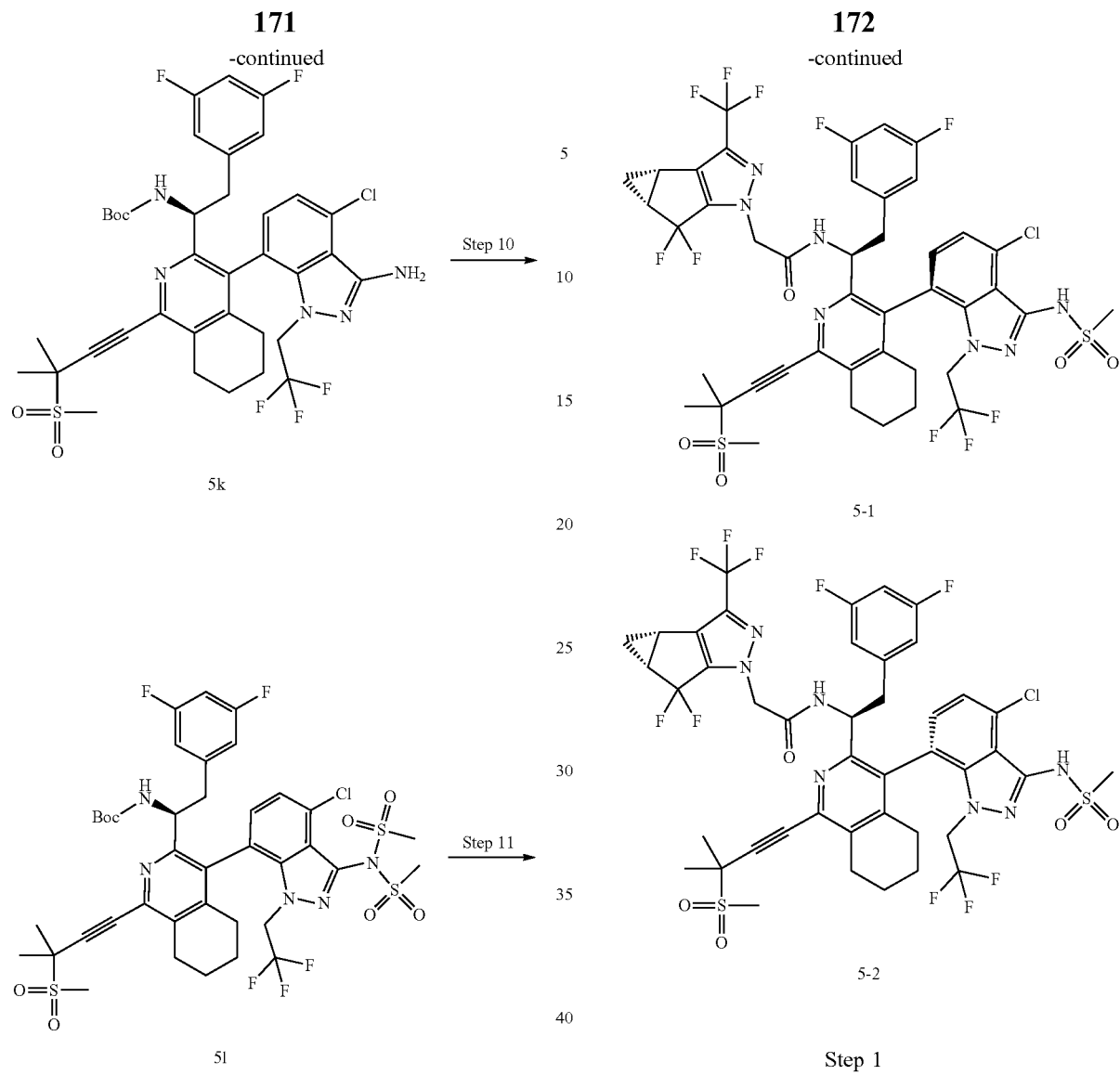

Step 1

1,8-dibromooctyl-1,7-diyne 5b 1,7-octadiyne 5a (5.0 g, 47.1 mmol, TCI), N-bromosuccinimide (17.5 g, 98.3 mmol, adamas) and silver nitrate (800 mg, 4.71 mmol, Sinopharm Chemical Reagent Co., Ltd.) were dissolved in acetone (100 mL), and the reaction solution was reacted at room temperature under nitrogen atmosphere in the dark for 2 h, added with water (200 mL), extracted with n-hexane (100 mL×3), and concentrated under reduced pressure. The resulting residue was purified by silica gel column chromatography with eluent system A to give the title product 5b (12.0 g, yield: 96.5%).

$^1$H NMR (400 MHz, CDCl$_3$) δ 2.25-2.23 (m, 4H), 1.64-1.60 (m, 4H).

Step 2

Ethyl 1,4-dibromo-5,6,7,8-tetrahydroisoquinoline-3-carboxylate 5d

Bis(diphenylphosphino)-1,1'-binaphthyl (1.54 g, 2.47 mmol, Accela ChemBio Co., Ltd.) and bis(1,5-cyclooctadiene)rhodium(I)tetrafluoroborate (1.0 g, 2.46 mmol, adamas) were dissolved in anhydrous dichloromethane (50 mL), and the reaction solution was stirred at room temperature for 10 min, then purged with hydrogen, and stirred at room temperature for 1 h. The dichloromethane was removed by rotary evaporation, and the residue was dissolved in 1,2-dichloroethane (150 mL). The reaction solution was added with compound 5b (11.5 g, 5.91 mmol) and ethyl cyanoformate 5c (8.7 g, 87.8 mmol, InnoChem), purged with nitrogen three times, stirred at 80° C. for 18 h, added with water (80 mL), extracted with dichloromethane (100 mL×2), and concentrated under reduced pressure. The resulting residue was purified by silica gel column chromatography with eluent system A to give the title product 5d (3.6 g, yield: 22.7%).

MS m/z (ESI): 361.9 [M+1].

Step 3

1,4-dibromo-5,6,7,8-tetrahydroisoquinoline-3-formaldehyde 5e

Compound 5d (3.6 g, 9.92 mmol) was dissolved in tetrahydrofuran (50 mL), diisobutylaluminum hydride (1.0 M, 11.0 mL, 11.0 mmol) was added dropwise at −78° C., and after the addition was completed, the reaction solution was stirred at −78° C. for 3 h, added with saturated aqueous ammonium chloride (200 mL) to quench the reaction, extracted with dichloromethane (150 mL×3), dried and concentrated under reduced pressure to give the title product 5e (crude, 3.2 g, yield: 101.2%).

MS m/z (ESI): 317.9 [M+1].

Step 4

(S)—N-((1,4-dibromo-5,6,7,8-tetrahydroisoquinolin-3-yl)methylene)-2-methylpropane-2-sulfinamide 5f Compound 5e (3.2 g, 10.0 mmol) and (S)-2-methylpropane-2-sulfinamide 1d (1.46 g, 12.0 mmol, Bide Pharmatech Ltd.) were dissolved in dichloromethane (40 mL), and the reaction solution was added with cesium carbonate (4.0 g, 12.4 mmol, Bide Pharmatech Ltd.), stirred at room temperature for 16 h, added with water (50 mL), extracted with dichloromethane (50 mL×3), and concentrated under reduced pressure. The resulting residue was purified by silica gel column chromatography with eluent system A to give the title product 5f (3.4 g, yield: 80.3%).

MS m/z (ESI): 422.8 [M+1].

Step 5

(S)—N—((S)1-(1,4-dibromo-5,6,7,8-tetrahydroisoquinolin-3-yl)-2-(3,5-difluorophenyl)ethyl)-2-methylpropane-2-sulfinamide 5g Two drops of 1,2-dibromoethane were added to a suspension of zinc powder (2.0 g, 30.8 mmol, Sinopharm Chemical Reagent Co., Ltd.) in anhydrous tetrahydrofuran (20 mL). Under the state of heating at reflux, three drops of trimethylchlorosilane were added, and the reaction solution was vigorously stirred and refluxed for 15 min. The reaction solution was cooled to 0° C., added with 1-(bromomethyl)-3,5-difluorobenzene (3.2 g, 15.5 mmol, Bide Pharmatech Ltd.), and stirred at room temperature for 4 h. Compound 5f (3.2 g, 7.58 mmol) was dissolved in anhydrous N,N-dimethylformamide (10 mL), and the reaction solution was added dropwise with the prepared zinc reagent at 0° C., stirred at room temperature for 16 h, added with saturated aqueous ammonium chloride (50 mL), extracted with ethyl acetate (50 mL×3), and concentrated under reduced pressure. The resulting residue was purified by high performance liquid chromatography (Sharpsil-T C18, 150×30 mm, 5 μm; eluent system: H₂O (0.1% trifluoroacetic acid), acetonitrile) to give the title product 5g (1.44 g, yield: 34.5%).

MS m/z (ESI): 550.8 [M+1].

Step 6

(S)-1-(1,4-dibromo-5,6,7,8-tetrahydroisoquinolin-3-yl)-2-(3,5-difluorophenyl)ethylamine hydrochloride 5h Compound 5g (1.44 g, 2.62 mmol) was dissolved in dichloromethane (10 mL), and the reaction solution was added with 4 M hydrogen chloride solution in dioxane (10 mL), stirred at room temperature for 2 h, and concentrated under reduced pressure to give the title product 5h (1.26 g, yield: 99.8%).

MS m/z (ESI): 446.8 [M−35].

Step 7

Tert-butyl (S)-(1-(1,4-dibromo-5,6,7,8-tetrahydroisoquinolin-3-yl)-2-(3,5-difluorophenyl)ethyl)carbamate 5i To a suspension of compound 5h (1.26 g, 2.61 mmol) in dichloromethane (20 mL) were added triethylamine (800 mg, 7.91 mmol, Shanghai Hushi Chemical Co., Ltd.) and di-tert-butyl dicarbonate (800 mg, 3.67 mmol, Accela ChemBio Co., Ltd.). The reaction solution was stirred at room temperature for 16 h, added with water (20 mL), extracted with dichloromethane (20 mL×2), and concentrated under reduced pressure. The resulting residue was purified by silica gel column chromatography with eluent system A to give the title product 5i (1.2 g, yield: 84.1%).

MS m/z (ESI): 546.7 [M+1].

Step 8

Tert-butyl (S)-(1-(4-bromo-1-(3-methyl-3-(methylsulfonyl)but-1-yn-1-yl)-5,6,7,8-tetrahydroisoquinolin-3-yl)-2-(3,5-difluorophenyl)ethyl)carbamate 5j Compound 5i (1.2 g, 2.20 mmol) and compound 1i (480 mg, 3.28 mmol) were dissolved in N,N-dimethylformamide (10 mL). Bis(triphenylphosphine)palladium dichloride (200 mg, 0.285 mmol, J&K Chemical), cuprous iodide (250 mg, 1.31 mmol, Alfa) and triethylamine (670 mg, 6.62 mmol, Shanghai Hushi Chemical Co., Ltd.) were added. The reaction solution was purged with nitrogen three times, stirred at room temperature for 4 h, added with water (20 mL), extracted with ethyl acetate (20 mL×4), and concentrated under reduced pressure. The resulting residue was purified by silica gel column chromatography with eluent system A to give the title product 5j (1.1 g, yield: 81.9%).

MS m/z (ESI): 610.8 [M+1].

Step 9

Tert-butyl ((1S)-1-(−4-(3-amino-4-chloro-1-(2,2,2-trifluoroethyl)-1H-indazol-7-yl)-1-(3-methyl-3-(methylsulfonyl)but-1-yn-1-yl)-5,6,7,8-tetrahydroisoquinolin-3-yl)-2-(3,5-difluorophenyl)ethyl)carbamate 5k Compound 5j (400 mg, 0.654 mmol) and compound 1k (370 mg, 0.985 mmol) were dissolved in dioxane (6 mL) and water (2 mL). Di-tert-butyl-(4-dimethylaminophenyl)phosphine palladium dichloride (90 mg, 0.127 mmol, Accela ChemBio Co., Ltd.) and potassium phosphate (420 mg, 1.28 mmol, J&K Chemical) were added. The reaction solution was purged with nitrogen three times, stirred at 80° C. in microwave reactor for 3 h, added with water (10 mL), extracted with ethyl acetate (20 mL×3), and concentrated under reduced pressure. The resulting residue was purified by silica gel column chromatography with eluent system A to give the title product 5k (120 mg, yield: 23.5%).

MS m/z (ESI): 779.8 [M+1].

Step 10

Tert-butyl ((1S)-1-(-4-(4-chloro-3-(N-(methylsulfonyl)methanesulfonamido)-1-(2,2,2-trifluoroethyl)-1H-indazol-7-yl)-1-(3-methyl-3-(methylsulfonyl)but-1-yn-1-yl)-5,6,7,8-tetrahydroisoquinolin-3-yl)-2-(3,5-difluorophenyl)ethyl)carbamate 5l Compound 5k (120 mg, 0.154 mmol) and triethylamine (90.0 mg, 0.891 mmol, Shanghai Hushi Chemical Co., Ltd.) were dissolved in dichloromethane (3 mL), and methanesulfonyl chloride (50.0 mg, 0.439 mmol, Sinopharm Chemical Reagent Co., Ltd.) was added. The reaction solution was stirred at room temperature for 0.5 h, added with water (20 mL), extracted with dichloromethane (20 mL×3), and concentrated under reduced pressure. The resulting residue was purified by silica gel column chromatography with eluent system A to give the title product 5l (120 mg, yield: 83.3%).

MS m/z (ESI): 935.6 [M+1].

Step 11

N-(7-(-3-((S)-1-amino-2-(3,5-difluorophenyl)ethyl)-1-(3-methyl-3-(methylsulfonyl)but-1-yn-1-yl)-5,6,7,8-tetrahydroisoquinolin-4-yl)-4-chloro-1-(2,2,2-trifluoroethyl)-1H-indazol-3-yl)-N-(methylsulfonyl)methanesulfonamide hydrochloride 5m Compound 5l (120 mg, 0.128 mmol) was dissolved in dichloromethane (3.0 mL), and the reaction solution was added with 4 M hydrogen chloride solution in dioxane (1 mL), stirred at room temperature for 1 h, and concentrated under reduced pressure to give the title product 5m (110 mg, yield: 98.4%).

MS m/z (ESI): 835.6 [M−35].

Step 12

N—((S)-1-((R)-4-(4-chloro-3-(methanesulfonamido)-1-(2,2,2-trifluoroethyl)-1H-indazol-7-yl)-1-(3-methyl-3-(methylsulfonyl)but-1-yn-1-yl)-5,6,7,8-tetrahydroisoquinolin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 5-1

N—((S)-1-((S)-4-(4-chloro-3-(methanesulfonamido)-1-(2,2,2-trifluoroethyl)-1H-indazol-7-yl)-1-(3-methyl-3-(methylsulfonyl)but-1-yn-1-yl)-5,6,7,8-tetrahydroisoquinolin-3-yl)-2-(3,5-difluorophenyl)ethyl)-2-((3bS,4aR)-5,5-difluoro-3-(trifluoromethyl)-3b,4,4a,5-tetrahydro-TH-cyclopropa[3,4]cyclopenta[1, 2-c]pyrazol-1-yl)acetamide 5-2

Compound 5m (110 mg, 0.126 mmol), compound to (40.0 mg, 0.142 mmol) and 2-(7-benzotriazole oxide)-N,N,N',N'-tetramethylurea hexafluorophosphate (40.0 mg, 0.170 mmol, Sinopharm Chemical Reagent Co., Ltd.) were dissolved in N,N-dimethylformamide (2.0 mL), and the reaction solution was added with N,N-diisopropylethylamine (50.0 mg, 0.387 mmol, adamas), stirred at room temperature for 1 h, added with 2 N sodium hydroxide (0.3 mL), stirred at room temperature for 1 h, then added with water (10 mL), extracted with ethyl acetate (10 mL×3), and concentrated under reduced pressure. The resulting residue was purified by high performance liquid chromatography (Sharpsil-T C18, 150×30 mm, 5 μm, eluent system: H₂O (0.1% trifluoroacetic acid), acetonitrile) to give the title products 5-1 (30 mg, yield: 23%) and 5-2 (5.0 mg, yield: 3.9%).

Single-Configuration Compound (Longer Retention Time) 5-1:

MS m/z (ESI): 1021.6 [M+1].

LCMS analysis: retention time: 3.123 min. Column: HD 2.1×50 mm 1.8-Micron; mobile phase: water (0.1% formic acid):acetonitrile (0.1% formic acid).

¹H NMR (400 MHz, CD₃OD) δ 7.23 (d, 1H), 6.78 (t, 1H), 6.49 (d, 1H), 6.33 (d, 2H), 4.84-4.72 (m, 3H), 4.60-4.54 (m, 1H), 3.93-3.87 (m, 1H), 3.25 (s, 3H), 3.24 (s, 3H), 3.10-3.05 (m, 2H), 2.93-2.88 (m, 2H), 2.55-2.50 (m, 2H), 2.46-2.38 (m, 1H), 2.14-2.09 (m, 1H), 1.94-1.90 (m, 1H), 1.85 (s, 6H), 1.76-1.70 (m, 2H), 1.58-1.46 (m, 1H), 1.44-1.42 (m, 1H), 1.11-1.08 (m, 1H).

Single-Configuration Compound (Shorter Retention Time) 5-2:

MS m/z (ESI): 1021.6 [M+1].

LCMS analysis: retention time: 3.018 min. Column: HD 2.1×50 mm 1.8-Micron; mobile phase: water (0.1% formic acid):acetonitrile (0.1% formic acid).

¹H NMR (400 MHz, CD₃OD) δ 7.18-7.16 (m, 1H), 7.08-7.03 (m, 1H), 6.65-6.61 (m, 1H), 6.51-6.49 (m, 2H), 4.69-4.66 (m, 1H), 4.65-4.55 (m, 2H), 3.91-3.87 (m, 1H), 3.71-3.67 (m, 1H), 3.24 (s, 3H), 3.14 (s, 3H), 2.99-2.90 (m, 4H), 2.40-2.38 (m, 2H), 2.29-2.23 (m, 1H), 2.08-2.03 (m, 1H), 1.92-1.88 (m, 1H), 1.75 (s, 6H), 1.66-1.63 (m, 2H), 1.55-1.50 (m, 1H), 1.32-1.30 (m, 1H), 1.06-1.03 (m, 1H).

Example 6

N—((S)-1-((R)-4-(4-chloro-3-(methanesulfonamido)-1-(2,2,2-trifluoroethyl)-1H-indazol-7-yl)-1-(3-methyl-3-(methanesulfonyl)but-1-yn-1-yl)isoquinolin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 6

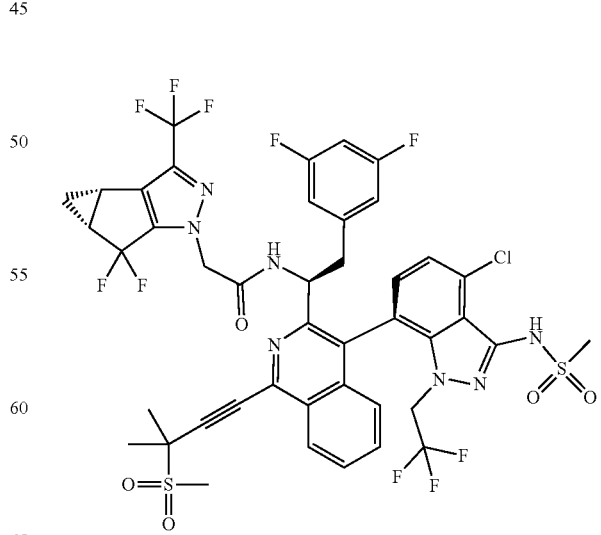

6

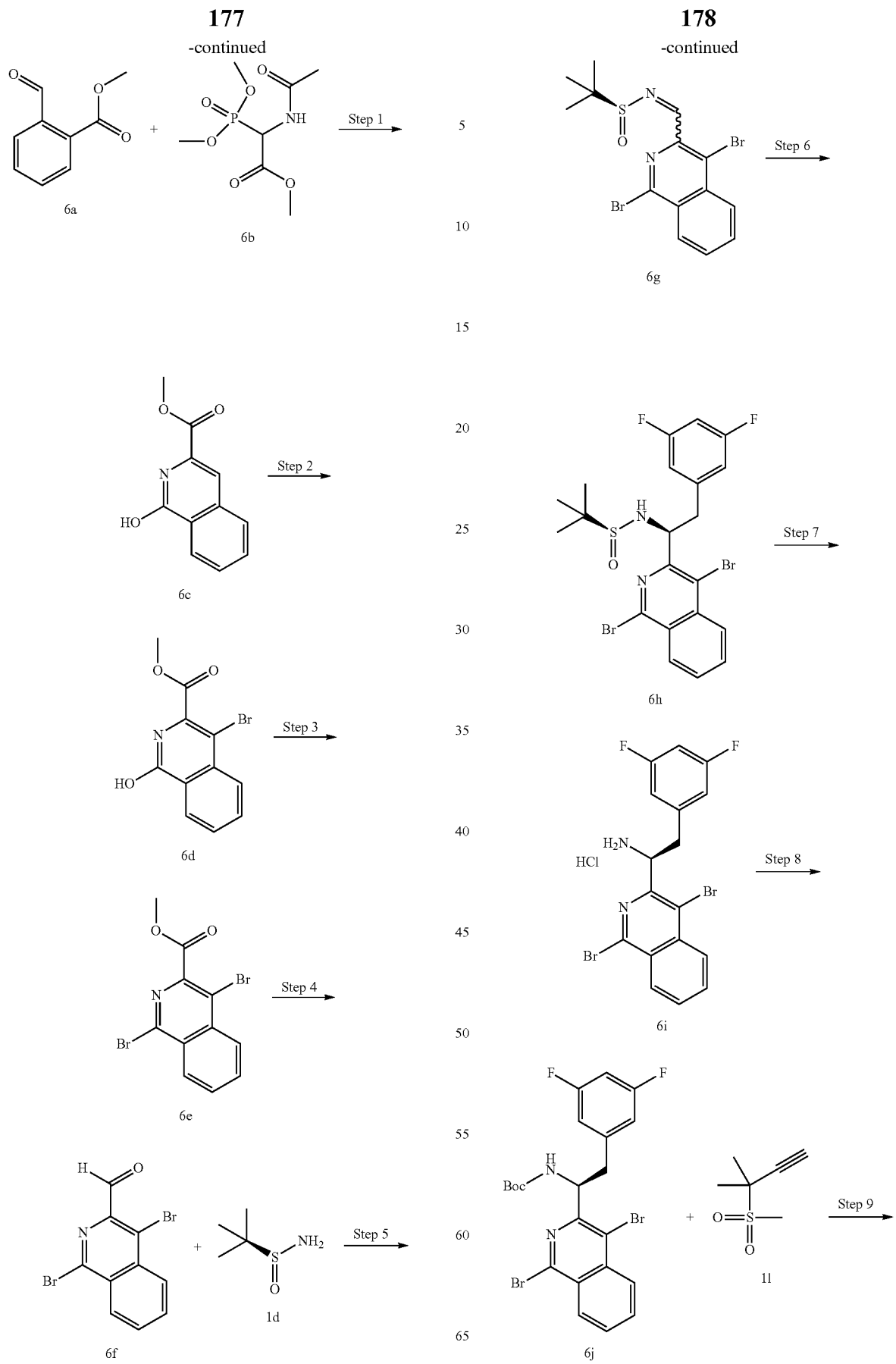

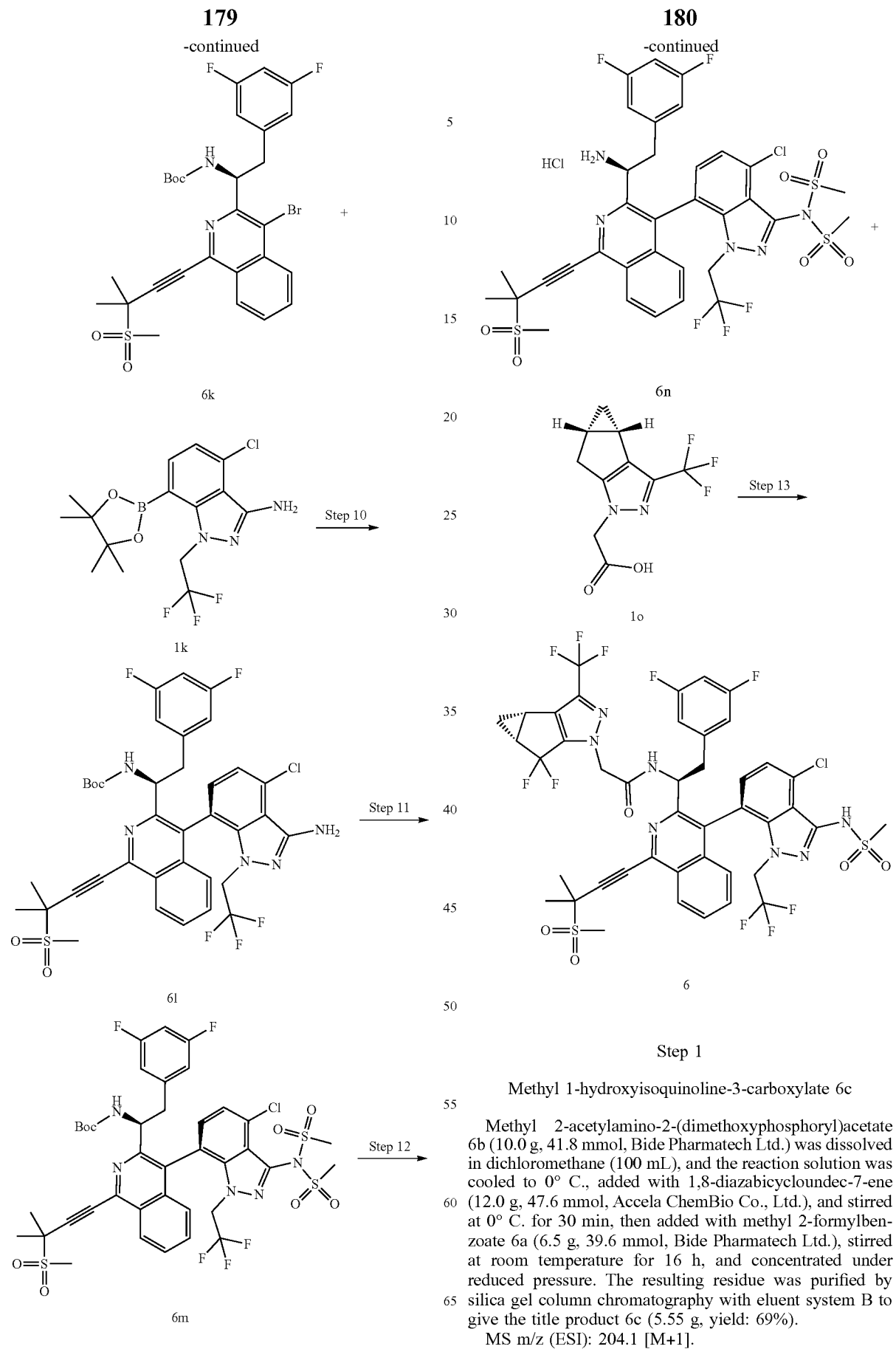

Step 1

Methyl 1-hydroxyisoquinoline-3-carboxylate 6c

Methyl 2-acetylamino-2-(dimethoxyphosphoryl)acetate 6b (10.0 g, 41.8 mmol, Bide Pharmatech Ltd.) was dissolved in dichloromethane (100 mL), and the reaction solution was cooled to 0° C., added with 1,8-diazabicycloundec-7-ene (12.0 g, 47.6 mmol, Accela ChemBio Co., Ltd.), and stirred at 0° C. for 30 min, then added with methyl 2-formylbenzoate 6a (6.5 g, 39.6 mmol, Bide Pharmatech Ltd.), stirred at room temperature for 16 h, and concentrated under reduced pressure. The resulting residue was purified by silica gel column chromatography with eluent system B to give the title product 6c (5.55 g, yield: 69%).

MS m/z (ESI): 204.1 [M+1].

Step 2

Methyl 4-bromo-1-hydroxyisoquinoline-3-carboxylate 6d

Compound 6c (5.55 g, 27.3 mmol) and N-bromosuccinimide (6.0 g, 33.7 mmol, adamas) were dissolved in N,N-dimethylformamide (60 mL), and the reaction solution was stirred at room temperature for 2 h, and added with water (100 mL) to precipitate the solid which was filtered under reduced pressure, and the filter cake was washed with water and dried to give the title product 6d (7.38 g, yield: 95.8%).
MS m/z (ESI): 281.9 [M+1].

Step 3

Methyl 1,4-dibromo-isoquinoline-3-carboxylate 6e

Compound 6d (7.38 g, 26.2 mmol) and tribromooxyphosphorus (22.0 g, 77.5 mmol, adamas) were dissolved in toluene (100 mL), and the reaction solution was stirred at 100° C. for 16 h, added with saturated aqueous sodium bicarbonate (100 mL), extracted with ethyl acetate (50 mL×3), and concentrated under reduced pressure. The resulting residue was purified by silica gel column chromatography with eluent system A to give the title product 6e (6.35 g, yield: 70.4%).
MS m/z (ESI): 345.9 [M+1].

Step 4

1,4-dibromo-isoquinoline-3-carbaldehyde 6f

Compound 6e (6.35 g, 18.4 mmol) was dissolved in tetrahydrofuran (100 mL), diisobutylaluminum hydride (1.0 M, 12.0 mL, 12.0 mmol) was added dropwise at −78° C., and after the dropwise addition was completed, the reaction solution was reacted at −78° C. for 3 h, added with saturated aqueous ammonium chloride (200 mL) to quench the reaction, extracted with dichloromethane (150 mL×3), dried and concentrated under reduced pressure to give the title product 6f (crude, 5.79 g, yield: 99.9%).
MS m/z (ESI): 315.8 [M+1].

Step 5

(S)—N-((1,4-dibromo-isoquinolin-3-yl)methylene)-2-methylpropane-2-sulfinamide 6g Compound 6f (5.79 g, 18.4 mmol) and (S)-2-methylpropane-2-sulfinamide 1d (2.5 g, 20.6 mmol, Bide Pharmatech Ltd.) were dissolved in dichloromethane (100 mL), and the reaction solution was added with cesium carbonate (7.0 g, 21.5 mmol, Bide Pharmatech Ltd.), stirred at room temperature for 16 h, added with water (50 mL), extracted with dichloromethane (50 mL×3), and concentrated under reduced pressure. The resulting residue was purified by silica gel column chromatography with eluent system A to give the title product 6g (5.8 g, yield: 75.5%).
MS m/z (ESI): 418.9 [M+1].

Step 6

(S)—N—((S)1-(1,4-dibromo-isoquinolin-3-yl)-2-(3,5-difluorophenyl)ethyl)-2-methylpropane-2-sulfinamide 6h Two drops of 1,2-dibromoethane were added to a suspension of zinc powder (1.0 g, 15.3 mmol, Sinopharm Chemical Reagent Co., Ltd.) in anhydrous tetrahydrofuran (20 mL). Under the state of heating at reflux, three drops of trimethylchlorosilane were added, and the reaction solution was vigorously stirred and refluxed for 20 min, cooled to 0° C., added with 1-(bromomethyl)-3,5-difluorobenzene (1.5 g, 7.25 mmol, Bide Pharmatech Ltd.), and stirred at room temperature for 3 h. Compound 6g (1.5 g, 3.59 mmol) was dissolved in anhydrous N,N-dimethylformamide (10 mL), and the reaction solution was added dropwise with the prepared zinc reagent at 0° C., stirred at room temperature for 16 h, added with saturated aqueous ammonium chloride (50 mL), extracted with ethyl acetate (50 mL×3), and concentrated under reduced pressure. The resulting residue was purified by high performance liquid chromatography (Sharpsil-T C18, 150×30 mm, 5 μm, eluent system: H₂O (0.1% trifluoroacetic acid), acetonitrile) to give the title product 6h (620 mg, yield: 31.6%).
MS m/z (ESI): 546.9 [M+1].

Step 7

(S)-1-(1,4-dibromo-isoquinolin-3-yl)-2-(3,5-difluorophenyl)ethylamine hydrochloride 6i Compound 6h (620 mg, 1.14 mmol) was dissolved in dichloromethane (5.0 mL), and the reaction solution was added with 4 M hydrogen chloride solution in dioxane (5.0 mL), stirred at room temperature for 1 h, and concentrated under reduced pressure to give the title product 6i (543 mg, yield: 100%).
MS m/z (ESI): 442.3 [M−35].

Step 8

Tert-butyl (S)-(1-(1,4-dibromo-isoquinolin-3-yl)-2-(3,5-difluorophenyl)ethyl)carbamate 6j To a suspension of compound 6i (543 g, 21.13 mmol) in dichloromethane (20 mL) were added triethylamine (300 mg, 2.96 mmol, Shanghai Hushi Chemical Co., Ltd.) and di-tert-butyl dicarbonate (700 mg, 3.21 mmol, Accela ChemBio Co., Ltd.). The reaction solution was stirred at room temperature for 16 h, added with water (20 mL), extracted with dichloromethane (20 mL×2), and concentrated under reduced pressure. The resulting residue was purified by silica gel column chromatography with eluent system A to give the title product 6j (300 mg, yield: 48.8%).
MS m/z (ESI): 544.9 [M+1].

Step 9

Tert-butyl (S)-(1-(4-bromo-1-(3-methyl-3-(methylsulfonyl)but-1-yn-1-yl)isoquinolin-3-yl)-2-(3,5-difluorophenyl)ethyl)carbamate 6k Compound 6j (300 mg, 0.55 mmol) and compound 1i (100 mg, 0.68 mmol) were dissolved in N,N-dimethylformamide (5.0 mL). Bis(triphenylphosphine)palladium dichloride (40 mg, 0.06 mmol, J&K Chemical), cuprous iodide (60 mg, 0.32 mmol, Alfa) and triethylamine (170 mg, 1.68 mmol, Shanghai Hushi Chemical Co., Ltd.) were added. The reaction solution was purged with nitrogen three times, stirred at room temperature for 4 h, added with water (20 mL), extracted with ethyl acetate (20 mL×4), and concentrated under reduced pressure. The resulting residue was purified by silica gel column chromatography with eluent system A to give the title product 6k (280 mg, yield: 83.3%).
MS m/z (ESI): 608.9 [M+1].

Step 10

Tert-butyl ((1S)-1-((R)-4-(3-amino-4-chloro-1-(2,2,2-trifluoroethyl)-1H-indazol-7-yl)-1-(3-methyl-3-(methylsulfonyl)but-1-yn-1-yl)isoquinolin-3-yl)-2-(3,5-difluorophenyl)ethyl)carbamate 6l Compound 6k (240 mg, 0.40 mmol) and compound 1k (250 mg, 0.67 mmol) were dissolved in dioxane (6 mL) and water (2 mL). Di-tert-butyl-(4-dimethylaminophenyl)phosphine palladium dichloride (30 mg, 0.04 mmol, Accela ChemBio Co., Ltd.) and potassium phosphate (250 mg, 1.18 mmol, J&K Chemical) were added. The reaction solution was purged with nitrogen three times, stirred at 95° C. for 16 h, added with water (10 mL), extracted with ethyl acetate (10 mL×4), and concentrated under reduced pressure. The resulting residue was purified by silica gel column chromatography with eluent system A to give the title product 6l (90 mg, yield: 29.3%).

MS m/z (ESI): 776.0 [M+1].

Step 11

Tert-butyl ((1S)-1-((R)-4-(4-chloro-3-(N-(methylsulfonyl)methanesulfonamido)-1-(2,2,2-trifluoroethyl)-1H-indazol-7-yl)-1-(3-methyl-3-(methylsulfonyl)but-1-yn-1-yl)isoquinolin-3-yl)-2-(3,5-difluorophenyl)ethyl)carbamate 6m Compound 6l (90 mg, 0.116 mmol) and triethylamine (75.0 mg, 0.743 mmol, Shanghai Hushi Chemical Co., Ltd.) were dissolved in dichloromethane (3 mL), and methanesulfonyl chloride (40.0 mg, 0.351 mmol, Sinopharm Chemical Reagent Co., Ltd.) was added. The reaction solution was stirred at room temperature for 16 h, added with water (10 mL), extracted with dichloromethane (10 mL×3), and concentrated under reduced pressure. The resulting residue was purified by silica gel column chromatography with eluent system A to give the title product 6m (90 mg, yield: 83.2%).

MS m/z (ESI): 932.1 [M+1].

Step 12

N-(7-((R)-3-((S)-1-amino-2-(3,5-difluorophenyl)ethyl)-1-(3-methyl-3-(methylsulfonyl)but-1-yn-1-yl)isoquinolin-4-yl)-4-chloro-1-(2,2,2-trifluoroethyl)-1H-indazol-3-yl)-N-(methylsulfonyl)methanesulfonamide hydrochloride 6n Compound 6m (90 mg, 0.097 mmol) was dissolved in dichloromethane (1.0 mL), and the reaction solution was added with 4 M hydrogen chloride solution in dioxane (2.0 mL), stirred at room temperature for 1 h, and concentrated under reduced pressure to give the title product 6n (84 mg, yield: 100%).

MS m/z (ESI): 831.9 [M−35].

Step 13

N—((S)-1-((R)-4-(4-chloro-3-(methanesulfonamido)-1-(2,2,2-trifluoroethyl)-1H-indazol-7-yl)-1-(3-methyl-3-(methylsulfonyl)but-1-yn-1-yl)isoquinolin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 6

Compound 6n (84 mg, 0.97 mmol), compound to (35.0 mg, 0.124 mmol) and 2-(7-benzotriazole oxide)-N,N,N',N'-tetramethylurea hexafluorophosphate (29.0 mg, 0.123 mmol, Sinopharm Chemical Reagent Co., Ltd.) were dissolved in N,N-dimethylformamide (1.0 mL), and the reaction solution was added with N,N-diisopropylethylamine (38.0 mg, 0.294 mmol, adamas), and stirred at room temperature for 30 min, then added with 2 N sodium hydroxide (0.4 mL), stirred at room temperature for 30 min, added with water (10 mL), extracted with ethyl acetate (15 mL×3), and concentrated under reduced pressure. The resulting residue was purified by high performance liquid chromatography (Gilson-281, eluent system: 10 mmol/L ammonium bicarbonate, water, acetonitrile) to give the title product 6 (5.0 mg, yield: 5.08%).

MS m/z (ESI): 1019.0 [M+1].

$^1$H NMR (400 MHz, CD$_3$OD) δ 8.46 (d, 1H), 7.73 (t, 1H), 7.62 (t, 1H), 7.22 (d, 1H), 7.14 (d, 1H), 6.65 (m, 1H), 6.34 (d, 1H), 6.25-6.24 (d, 2H), 4.84 (d, 1H), 4.78 (d, 1H), 4.67 (d, 1H), 4.00 (m, 1H), 3.70 (m, 1H), 3.20 (s, 3H), 3.13 (s, 3H), 3.10 (m, 1H), 2.94 (m, 1H), 2.40 (m, 2H), 1.84 (s, 6H), 1.31 (m, 1H), 0.96 (m, 1H).

Examples 7-1, 7-2

N-((1S)-1-((4R,6R)-4-(4-chloro-3-(methanesulfonamido)-1-(2,2,2-trifluoroethyl)-1H-indazol-7-yl)-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 7-1

N-((1S)-1-((4R,6S)-4-(4-chloro-3-(methanesulfonamido)-1-(2,2,2-trifluoroethyl)-1H-indazol-7-yl)-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 7-2

7-1

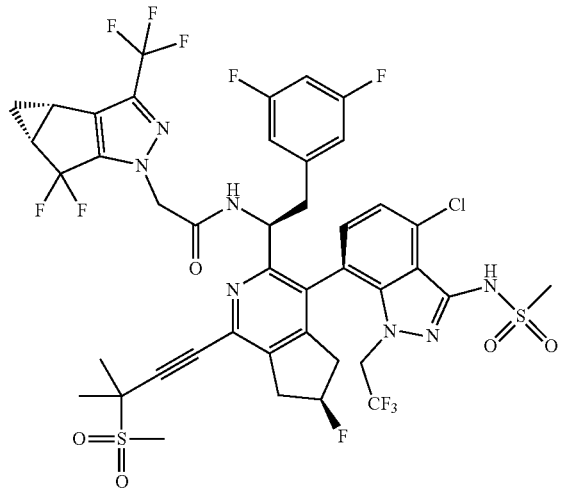

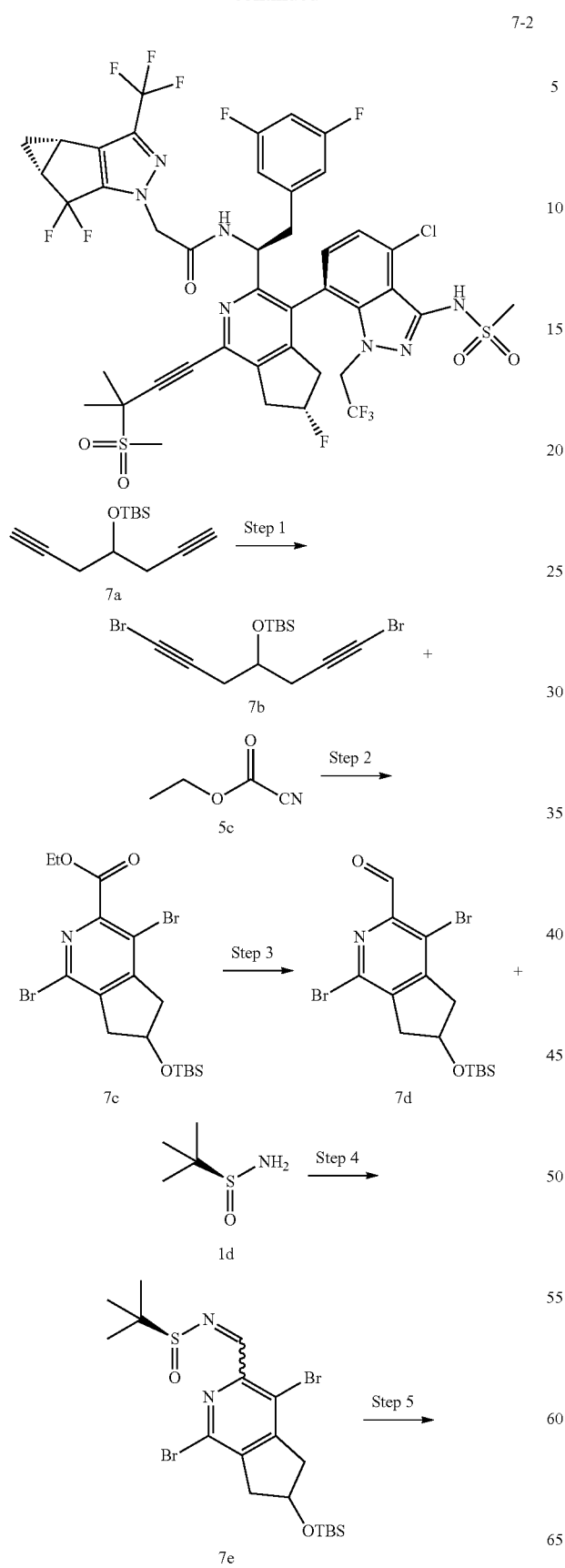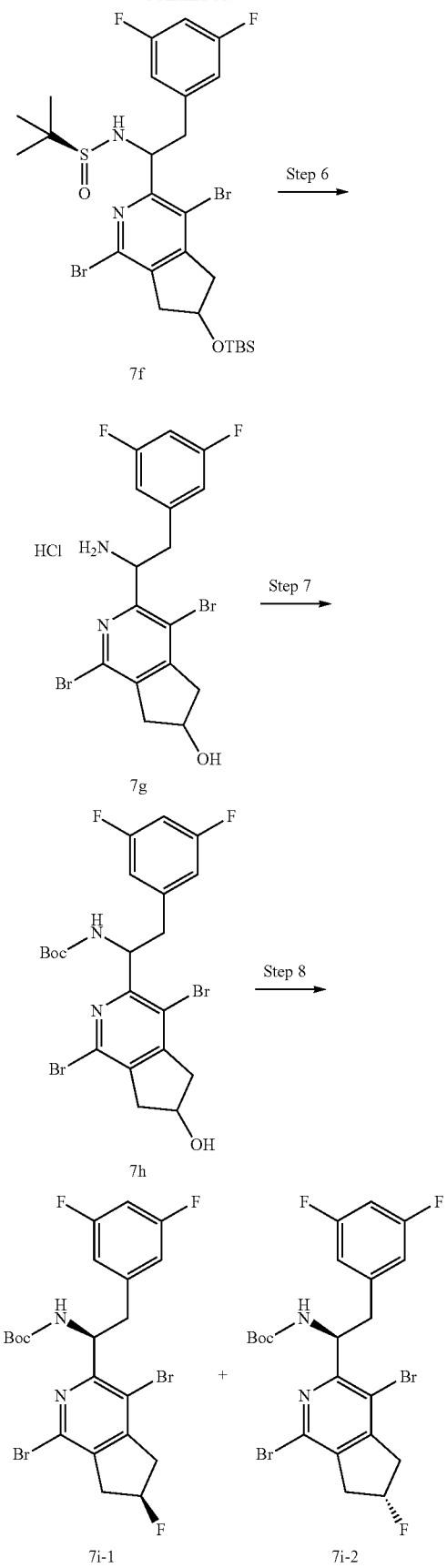

187
-continued
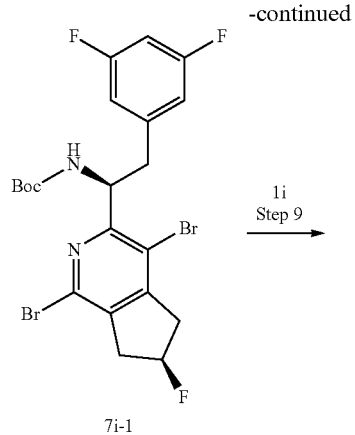
7i-1
1i
Step 9 →
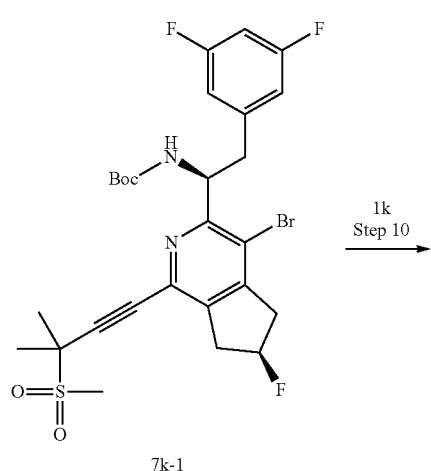
7k-1
1k
Step 10 →
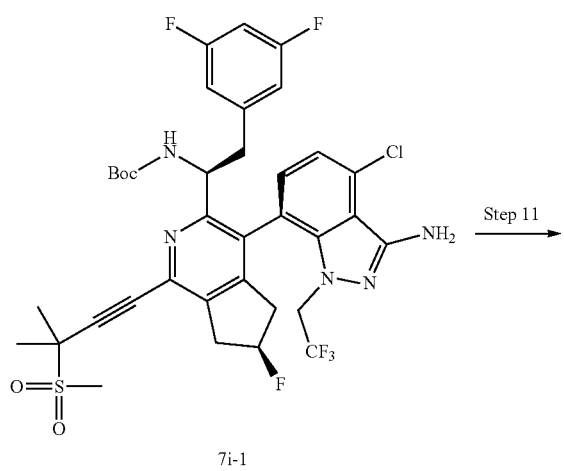
7i-1
Step 11 →
188
-continued
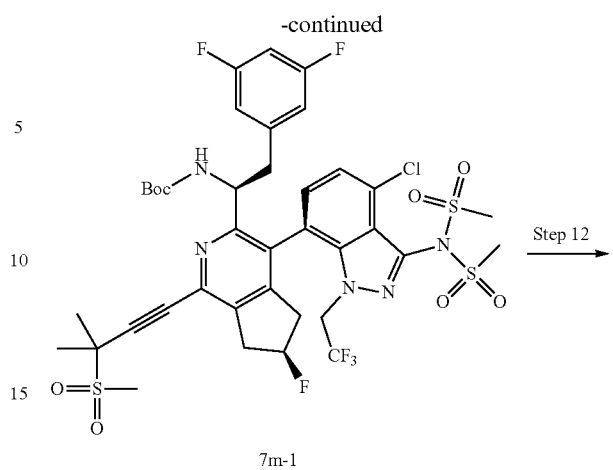
7m-1
Step 12 →
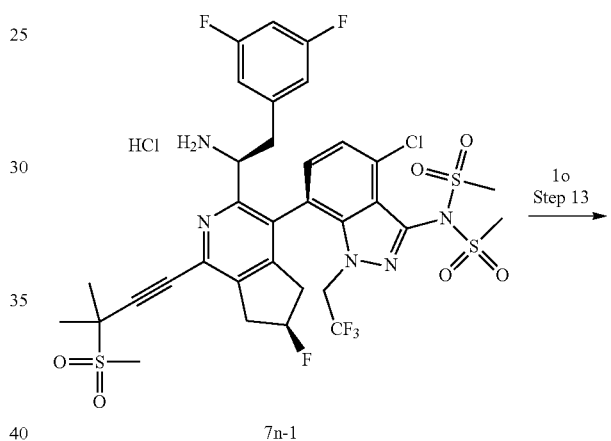
7n-1
1o
Step 13 →
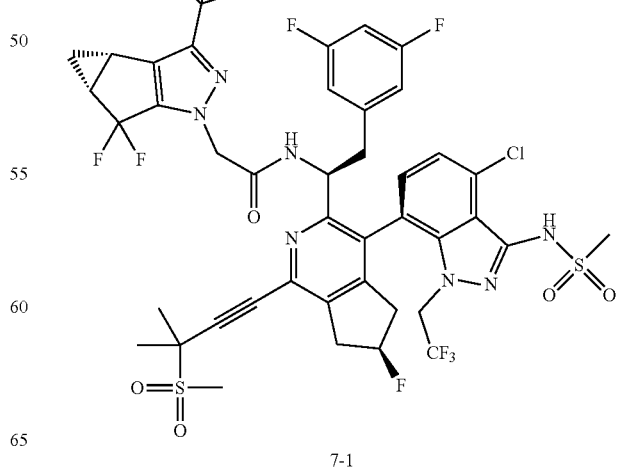
7-1

189
-continued
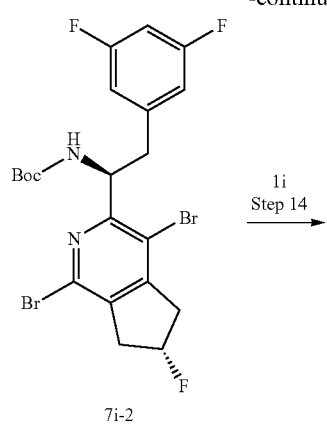
7i-2
1i
Step 14 →
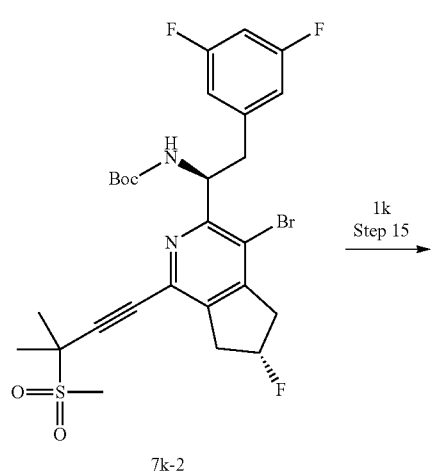
7k-2
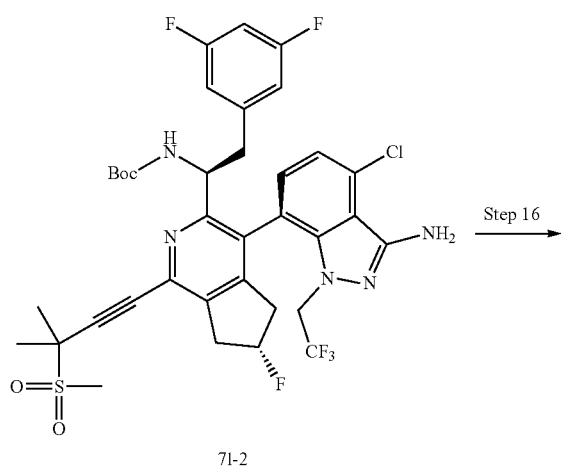
7l-2
Step 16 →
190
-continued
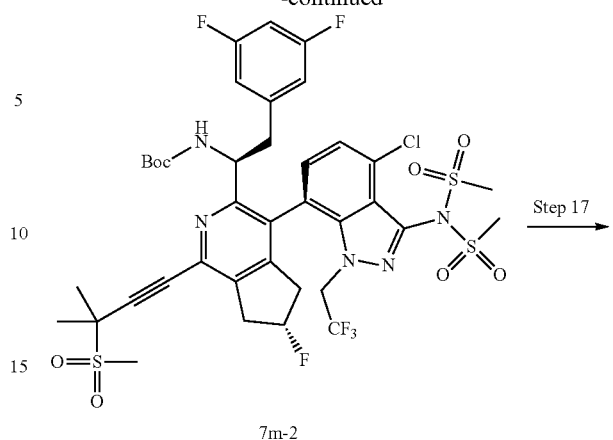
7m-2
Step 17 →
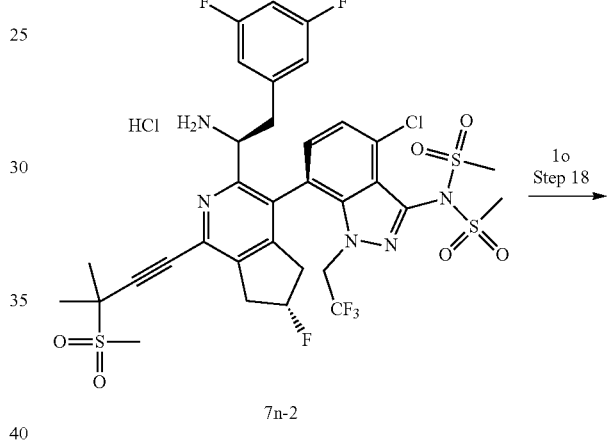
7n-2
1o
Step 18 →
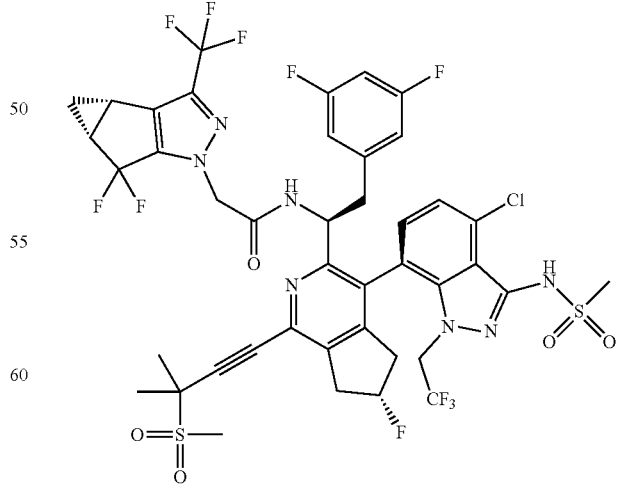
7-2

Step 1

Tert-butyl ((1,7-dibromohept-1,6-diyn-4-yl)oxy)dimethylsilane 7b

Tert-butyl (hept-1,6-diyn-4-yloxy)dimethylsilane 7a (6.5 g, 29.2 mmol, prepared by a method known in the literature Organic Letters, 14(9), 2406-2409, 2012), N-bromosuccinimide (11.5 g, 64.6 mmol, adamas) and silver nitrate (500 mg, 2.94 mmol, Shanghai pharmaceutical company chemical Co., Ltd.) were dissolved in acetone (100 mL), and the reaction solution was reacted at room temperature under nitrogen atmosphere in the dark for 2 h, added with water (200 mL), extracted with n-hexane (200 mL×3), and concentrated under reduced pressure. The resulting residue was purified by silica gel column chromatography with eluent system A to give the title product 7b (9.2 g, yield: 82.8%).

$^1$H NMR (400 MHz, CDCl$_3$) δ 3.83 (m, 1H), 2.40-2.28 (m, 4H), 0.79 (s, 9H), 0.10 (s, 6H).

Step 2

Ethyl 1,4-dibromo-6-((tert-butyldimethylsilyl)oxy)-6,7-dihydro-5H-cyclopenta[c]pyridine-3-carboxylate 7c Chloro(1,5-cyclooctadiene)(pentamethylcyclopentadienyl)ruthenium (II) (500 mg, 1.32 mmol, Jiangsu Aikon Biopharmaceutical R&D co., Ltd.) and ethyl cyanoformate 5c (2.73 g, 27.6 mmol, InnoChem) were dissolved in 1,2-dichloroethane (200 mL), and the reaction solution was purged with argon, stirred at room temperature for 10 min, added with compound 7b (5.0 g, 13.2 mmol), and stirred at room temperature for 18 h, then added with water (80 mL), extracted with dichloromethane (100 mL×2), and concentrated under reduced pressure. The resulting residue was purified by silica gel column chromatography with eluent system A to give the title product 7c (4.2 g, yield: 66.6%).

MS m/z (ESI): 477.9 [M+1].

Step 3

1,4-dibromo-6-((tert-butyldimethylsilyl)oxy)-6,7-dihydro-5H-cyclopenta[c]pyridine-3-carbaldehyde 7d Compound 7c (7.0 g, 14.6 mmol) was dissolved in tetrahydrofuran (100 mL), diisobutylaluminum hydride (1.0 M, 17.5 mL, 17.5 mmol) was added dropwise at −78° C., and after the addition was completed, the reaction solution was reacted at −78° C. for 2.5 h, added with aqueous potassium sodium tartrate (100 mL) to quench the reaction, extracted with ethyl acetate (100 mL×3), dried and concentrated under reduced pressure to give the title product 7d (crude, 6.35 g, yield: 99.9%).

MS m/z (ESI): 434.0 [M+1].

Step 4

(S)—N-((1,4-dibromo-6-((tert-butyldimethylsilyl)oxy)-6,7-dihydro-5H-cyclopenta[c]pyridin-3-yl)methylene)-2-methylpropane-2-sulfinamide 7e Compound 7d (6.35 g, 14.6 mmol) and compound 1d (2.12 g, 17.5 mmol, Bide Pharmatech Ltd.) were dissolved in dichloromethane (60 mL), and the reaction solution was added with cesium carbonate (9.5 g, 29.2 mmol, Bide Pharmatech Ltd.), stirred at room temperature for 16 h, added with water (150 mL), extracted with dichloromethane (80 mL×3), and concentrated under reduced pressure. The resulting residue was purified by silica gel column chromatography with eluent system A to give the title product 7e (5.4 g, yield: 68.7%).

MS m/z (ESI): 537.0 [M+1].

Step 5

(S)—N-(1-(1,4-dibromo-6-((tert-butyldimethylsilyl)oxy)-6,7-dihydro-5H-cyclopenta[c]pyridin-3-yl)-2-(3,5-difluorophenyl)ethyl)-2-methylpropane-2-sulfinamide 7f To a suspension of zinc powder (3.4 g, 60.7 mmol, Sinopharm Chemical Reagent Co., Ltd.) in anhydrous tetrahydrofuran (50 mL) was added 1,2-dibromoethane (0.1 mL). Under the state of heating at reflux, trimethylchlorosilane (0.2 mL) was added, and the reaction solution was vigorously stirred and refluxed for 15 min, cooled to 0° C., added with 1-(bromomethyl)-3,5-difluorobenzene (6.2 g, 30.1 mmol, Bide Pharmatech Ltd.), and stirred at room temperature for 4 h. Compound 7e (5.4 g, 10.1 mmol) was dissolved in anhydrous N,N-dimethylformamide (26 mL), and the reaction solution was added dropwise with the prepared zinc reagent at 0° C., stirred at room temperature for 16 h, added with saturated aqueous ammonium chloride (50 mL), extracted with ethyl acetate (50 mL×3), and concentrated under reduced pressure. The resulting residue was purified by silica gel column chromatography with eluent system A to give the title product 7f (6.7 g, yield: 100%).

MS m/z (ESI): 664.7 [M+1].

Step 6

3-(1-amino-2-(3,5-difluorophenyl)ethyl)-1,4-dibromo-6,7-dihydro-5H-cyclopenta[c]pyridin-6-ol hydrochloride 7g Compound 7f (1.44 g, 2.62 mmol) was dissolved in dichloromethane (10 mL), and the reaction solution was added with 4 M hydrogen chloride solution in dioxane (68 mL), stirred at room temperature for 1 h, and concentrated under reduced pressure to give the title product 7g (4.9 g, yield: 100%).

MS m/z (ESI): 446.8 [M−35].

Step 7

Tert-butyl (1-(1,4-dibromo-6-hydroxy-6,7-dihydro-5H-cyclopenta[c]pyridin-3-yl)-2-(3,5-difluorophenyl)ethyl)carbamate 7h To a suspension of compound 7g (4.9 g, 10.1 mmol) in dichloromethane (50 mL) were added triethylamine (6.2 g, 61.4 mmol, Shanghai Hushi Chemical Co., Ltd.) and di-tert-butyl dicarbonate (3.2 g, 15.1 mmol, Accela ChemBio Co., Ltd.). The reaction solution was stirred at room temperature for 16 h, added with water (30 mL), extracted with dichloromethane (30 mL×2), and concentrated under reduced pressure. The resulting residue was purified by silica gel column chromatography with eluent system A to give the title product 7h (4.2 g, yield: 72.2%).

MS m/z (ESI): 546.8 [M+1].

Step 8

Tert-butyl ((S)-1-((R)-(1,4-dibromo-6-fluoro-6,7-dihydro-5H-cyclopenta[c]pyridin-3-yl)-2-(3,5-difluorophenyl)ethyl)carbamate 7i-1

Tert-butyl ((S)-1-((S)-(1,4-dibromo-6-fluoro-6,7-dihydro-5H-cyclopenta[c]pyridin-3-yl)-2-(3,5-difluorophenyl)ethyl)carbamate 7i-2

Compound 7h (2.0 g, 3.7 mmol) was dissolved in dichloromethane (40 mL), and the reaction solution was added with diethylaminosulfur trifluoride (884.6 mg, 5.5 mmol, Bide Pharmatech Ltd.) at 0° C., stirred at 0° C. for 30 min, added with water (30 mL), extracted with dichloromethane (30 mL×2), and concentrated under reduced pressure. The resulting residue was purified by silica gel column chromatography with eluent system A to give fraction I and fraction II, wherein fraction I was subjected to chiral preparation (separation conditions: CHIRALPAK IH chiral preparation column, 5.0 cm I.D.×25 cmL, 10 μm; mobile phase: methanol=100 (V/V), flow rate: 60 mL/min), and concentrated under reduced pressure to give fraction A (332.8 mg, 2.348 min) and fraction B (588.5 mg, 2.869 min); fraction II was subjected to chiral preparation (CHIRALPAK IG chiral preparation column, 5.0 cm I.D.×25 cmL, 10 μm; mobile phase: methanol=100 (V/V), flow rate: 60 mL/min), and concentrated under reduced pressure to give fraction C (165.6 mg, 2.547 min) and fraction D (452.6 mg, 3.492 min).

Single-Configuration Compound (Retention Time: 2.869 Min)

MS m/z (ESI): 492.5 [M−56].

Chiral HPLC analysis: retention time: 2.869 min, chiral purity: 99.3% (column: CHIRALPAK IH 0.46 cm I.D.×15 cmL; flow rate: 1.0 mL/min; mobile phase: methanol=100 (V/V))

Single-Configuration Compound (Retention Time: 3.492 Min)

MS m/z (ESI): 492.5 [M−56].

Chiral HPLC analysis: retention time: 3.492 min, chiral purity: 100% (column: CHIRALPAK IG 0.46 cm I.D.×15 cmL; flow rate: 1.0 mL/min; mobile phase: methanol=100 (V/V)).

Step 9 and Step 14

Tert-butyl ((S)-1-((S)-(4-bromo-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 7k-1

Tert-butyl ((S)-1-((R)-(4-bromo 6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 7k-2

Compound fraction B/D (588.5 mg/450.0 mg, 1.1/0.8 mmol) and compound 1i (236.0 mg/179.8 mg, 1.6 mmol/1.2 mmol) were dissolved in N,N-dimethylformamide (9 mL/7 mL). Bis(triphenylphosphine)palladium dichloride (91.0 mg/69.1 mg, 0.13 mmol/0.1 mmol, Accela ChemBio Co., Ltd.), cuprous iodide (123.0 mg/93.6 mg, 0.7 mmol/0.5 mmol, Sinopharm Chemical Reagent Co., Ltd.) and triethylamine (326.0 mg/248.8 mg, 3.2 mmol/2.5 mmol, Shanghai Hushi Chemical Co., Ltd.) were added. The reaction solution was purged with nitrogen three times, stirred at room temperature for 4 h, added with water (20 mL), extracted with ethyl acetate (20 mL×3), and concentrated under reduced pressure. The resulting residue was purified by silica gel column chromatography with eluent system A to give the title product (590.0 mg, 427.0 mg).

Single-Configuration Compound (590.0 mg)

MS m/z (ESI): 614.5 [M+1].

Single-Configuration Compound (427.0 mg)

MS m/z (ESI): 614.5 [M+1].

Step 10 and Step 15

Tert-butyl ((1S)-1-((4R,6R)-4-(3-amino-4-chloro-1-(2,2,2-trifluoroethyl)-1H-indazol-7-yl)-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 7l-1

Tert-butyl ((1S)-1-((4R,6S)-4-(3-amino-4-chloro-1-(2,2,2-trifluoroethyl)-1H-indazol-7-yl)-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 7l-2

Compound 7k (200.0 mg/200 mg, 0.3 mmol/0.3 mmol) and compound 1k (183.1 mg/183.1 mg, 0.5 mmol/0.5 mmol) were dissolved in dioxane (7 mL/7 mL) and water (1.5 mL/1.5 mL). Di-tert-butyl-(4-dimethylaminophenyl)phosphonium dichloropalladium (46.1 mg/46.1 mg, 0.07 mmol/0.07 mmol, Accela ChemBio Co., Ltd.) and potassium phosphate (137.8 mg/137.8 mg, 0.7 mmol/0.7 mmol, J&K Scientific Ltd.) were added. The reaction solution was purged with nitrogen three times, stirred at 90° C. for 16 h, added with water (20 mL), extracted with ethyl acetate (20 mL×3), and concentrated under reduced pressure. The resulting residue was purified by silica gel column chromatography with eluent system A to give the title product (170.0 mg, 120.0 mg).

Single-Configuration Compound (170.0 mg)

MS m/z (ESI): 783.5 [M+1].

Single-Configuration Compound (120.0 mg)

MS m/z (ESI): 783.5 [M+1].

Step 11 and Step 16

Tert-butyl ((1S)-1-((4R,6R)-4-(4-chloro-3-(N-(methylsulfonyl)methanesulfonamide)-1-(2,2,2-trifluoroethyl)-1H-indazol-7-yl)-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 7m-1

((1S)-1-((4R,6S)-4-(4-chloro-3-(N-(methylsulfonyl)methanesulfonamide)-1-(2,2,2-trifluoroethyl)-1H-indazol-7-yl)-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)carbamate 7m-2

Compound 7l (170.0 mg/120 mg, 0.2 mmol/0.15 mmol) and triethylamine (134.1 mg/92.8 mg, 1.3 mmol/0.9 mmol, Shanghai Hushi Chemical Co., Ltd.) were dissolved in dichloromethane (3 mL/2 mL), and the reaction solution was added with methanesulfonyl chloride (74.2 mg/52.4 mg, 0.7 mmol/0.5 mmol, Sinopharm Chemical Reagent Co., Ltd.), stirred at room temperature for 1 h, added with water (20 mL), extracted with dichloromethane (20 mL×3), and concentrated under reduced pressure. The resulting residue was purified by silica gel column chromatography with eluent system A to give the title product (130.0 mg, 80.0 mg).
Single-Configuration Compound (130.0 mg)
MS m/z (ESI): 940.2 [M+1].
Single-Configuration Compound (80.0 mg)
MS m/z (ESI): 940.2 [M+1].

Step 12 and Step 17

N-(7-((4R,6R)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2, 2-trifluoroethyl)-1H-indazol-3-yl)-N-(methylsulfonyl)methanesulfonamide hydrochloride 7n-1

N-(7-((4R,6S)-(3-((S)-1-amino-2-(3,5-difluorophenyl)ethyl)-6-fluoro-1-(3-methyl-3-(methylsulfonyl)but-1-yn-1-yl)-6,7-dihydro-5H-cyclopenta[c]pyridin-4-yl)-4-chloro-1-(2,2, 2-trifluoroethyl)-1H-indazol-3-yl)-N-(methylsulfonyl)methanesulfonamide hydrochloride 7n-2

To compound 7m (130.0 mg/80 mg, 0.14 mmol/0.09 mmol) was added 4 M hydrogen chloride solution in dioxane (3 mL/3 mL), stirred at room temperature for 1 h, and concentrated under reduced pressure to give the title product (116.0 mg, 72.0 mg).
Single-Configuration Compound (116.0 mg)
MS m/z (ESI): 839.8 [M−35].
Single-Configuration Compound (72.0 mg)
MS m/z (ESI): 839.8 [M−35].

Step 13 and Step 18

N-((1S)-1-((4R,6R)-4-(4-chloro-3-(methanesulfonamido)-1-(2,2,2-trifluoroethyl)-1H-indazol-7-yl)-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 7-1

N-((1S)-1-((4R,6S)-4-(4-chloro-3-(methanesulfonamido)-1-(2,2,2-trifluoroethyl)-1H-indazol-7-yl)-6-fluoro-1-(3-methyl-3-(methylsulfonyl)but-1-yn-1-yl)-6,7-dihydro-5H-cyclopenta[c]pyridin-3-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide 7-2

Compound 7n (116.0 mg/72 mg, 0.14 mmol/0.09 mmol), compound to (51.4 mg/31.3 mg, 0.18 mmol/0.1 mmol) and 2-(7-oxybenzotriazole)-N,N,N',N'-tetramethylurea hexafluorophosphate (79.9 mg/48.6 mg, 0.21 mmol/0.13 mmol, Sinopharm Chemical Reagent Co., Ltd.) were dissolved in N,N-dimethylformamide (2 mL), and the reaction solution was added with N,N-diisopropylethylamine (905.2 mg/549.9 mg, 7 mmol/4.3 mmol, Shanghai Hushi Chemical Co., Ltd.), stirred at room temperature for 7 h, added with water (10 mL), extracted with ethyl acetate (10 mL×3), and concentrated under reduced pressure. The resulting residue was purified by high performance liquid chromatography (Sharpsil-T C18, 150×30 mm, 5 μm, eluent system: $H_2O$ (0.1% trifluoroacetic acid), acetonitrile) to give the title product (25.0 mg, 25.0 mg).
Single-Configuration Compound (25.0 mg)
MS m/z (ESI): 1025.7 [M+1].
$^1$H NMR (500 MHz, $CD_3OD$) δ 8.87 (d, 1H), 7.24 (d, 1H), 6.76 (t, 1H), 6.54 (d, 1H), 6.26 (d, 2H), 5.51 (s, 1H), 5.41 (s, 1H), 4.88 (d, 1H), 4.77 (d, 1H), 4.66-4.56 (m, 1H), 4.02-3.94 (m, 1H), 3.49-3.40 (m, 2H), 3.29 (s, 3H), 3.24 (s, 3H), 3.04-2.85 (m, 4H), 2.54-2.49 (m, 2H), 1.84 (s, 6H), 1.44-1.40 (m, 1H), 1.09-1.07 (m, 1H).
Single-Configuration Compound (25.0 mg)
MS m/z (ESI): 1025.7 [M+1].
$^1$H NMR (500 MHz, $CD_3OD$) δ 8.82 (d, 1H), 7.20 (d, 1H), 6.74 (t, 1H), 6.50 (d, 1H), 6.24 (d, 2H), 5.49 (t, 1H), 5.38 (t, 1H), 4.90 (d, 1H), 4.78 (d, 1H), 4.68-4.59 (m, 1H), 4.08-3.99 (m, 1H), 3.55-3.37 (m, 2H), 3.28-3.14 (m, 7H), 3.03-2.98 (m, 1H), 2.89-2.85 (m, 1H), 2.72-2.64 (m, 1H), 2.55-2.47 (m, 2H), 1.84 (s, 6H), 1.46-1.41 (m, 1H), 1.11-1.07 (m, 1H).

Positive Control Example 1

N—((S)-1-(3-(4-chloro-3-(methylsulfonamido)-1-(2, 2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide

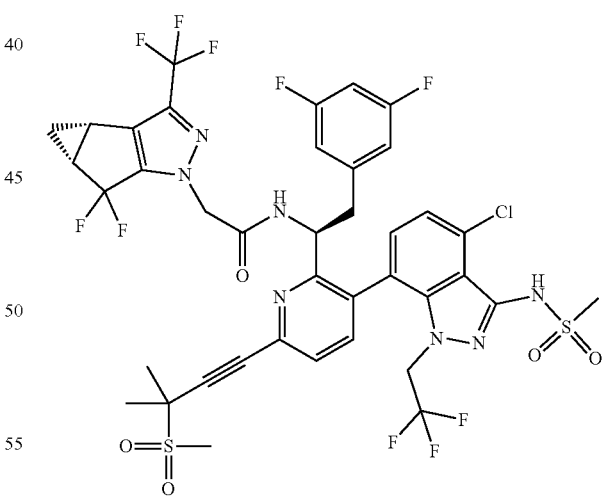

The title compound was prepared using the method disclosed in the patent application "WO2018035359".
MS m/z (ESI): 967.6 [M+1].
$^1$H NMR (400 MHz, $CD_3OD$) δ 7.68 (t, 2H), 7.19 (d, 1H), 6.77 (t, 1H), 6.48 (d, 1H), 6.30 (d, 2H), 4.88-4.74 (m, 3H), 4.67-4.57 (m, 1H), 3.97-3.93 (m, 1H) 3.23 (s, 6H), 3.13-3.06 (m, 1H), 2.96-2.91 (m, 1H), 2.53-2.49 (m, 2H), 1.82 (s, 6H), 1.46-1.39 (m, 1H), 1.07 (s, 1H).

Test Example 1. Thermodynamic Stability Test of Atropisomerism of Compounds of the Present Disclosure 1.1. Thermodynamic Stability Test of Atropisomerism of Compounds of Examples 1-1a, 1-1b 1.1.1. Experimental Instruments Agilent 1200 DAD model LC-MS; column: waters sunfire C18, 4.6×75 mm, 3.5 μm; mobile phase: water (0.1% trifluoroacetic acid):acetonitrile (0.1% trifluoroacetic acid).

1.1.2. Test Samples

Compounds of Examples 1-1a, 1-1b (also referred to as Compounds 1-1a, 1-1b)

1.1.3. Experimental Procedures

The compounds of Examples 1-1a, 1-1b were atropisomers of each other and had different retention times in the LC-MS spectra, and the tautomerism of the atropisomers could be detected by LC-MS.

Compound 1-1a (1.5 mg) was dissolved in acetonitrile (1.0 mL), and the reaction solution was heated at 40° C. for 1.0 h, and the change in purity of compound 1-1a was detected by LC-MS. Compound 1-1a (1.5 mg) was dissolved in dimethyl sulfoxide (1.0 mL), and the reaction solution was heated at 120° C. for 3.0 h, and the change in purity of compound 1-1a was detected by LC-MS.

The same procedure was used to test the change in purity of compound 1-1b at 40° C. and 120° C.

1.1.4. Experimental Results

Figure 2:
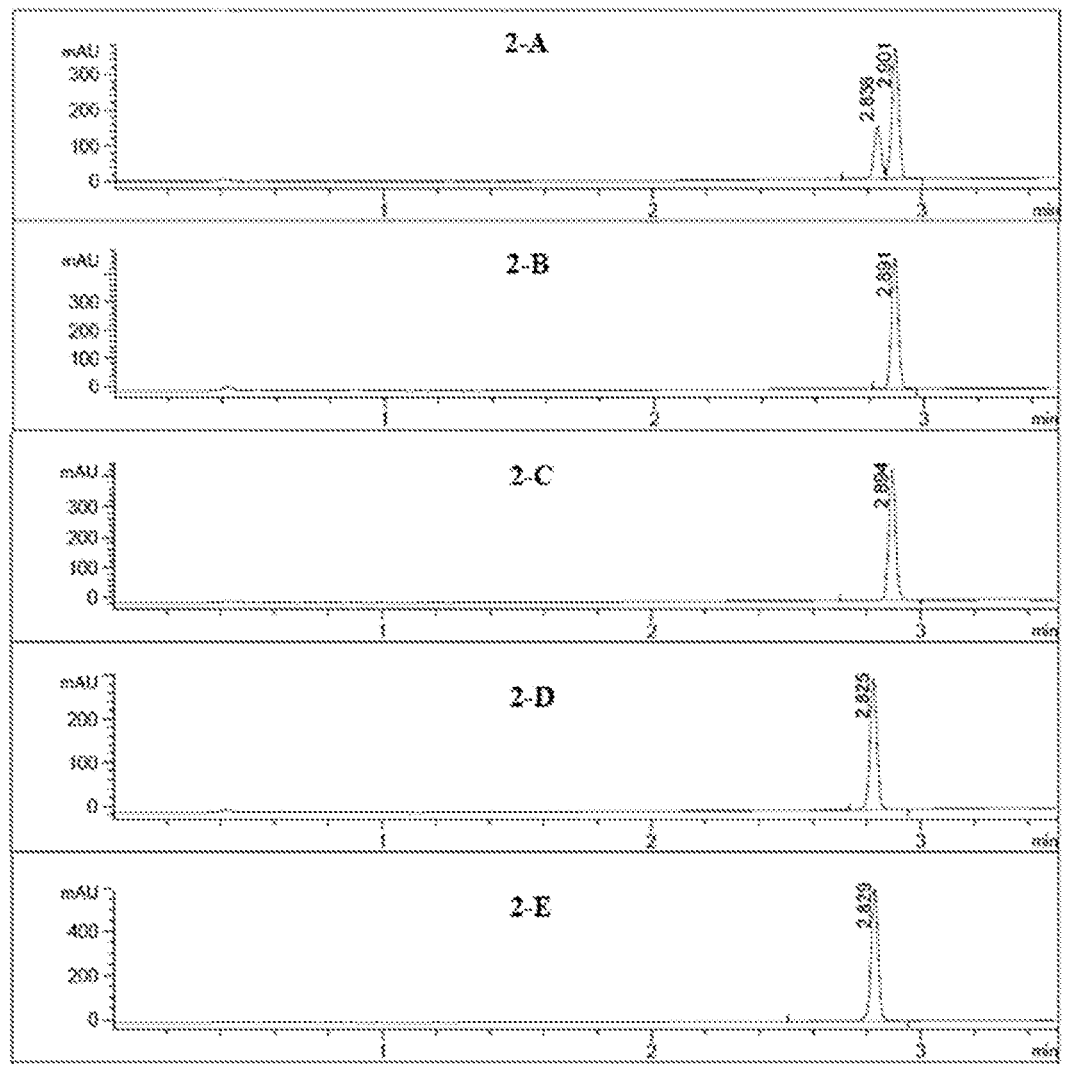
FIG. 2 is LC-MS spectra for the thermodynamic stability test of atropisomerism in Examples 1-1a and 1-1b, wherein 2-A shows the mixture of Examples 1-1a and 1-1b at 25° C.; 2-B shows the stability test of Example 1-1a at 40° C.; 2-C shows the stability test of Example 1-1a at 120° C.; 2-D shows the stability test of Example 1-1b at 40° C.; 2-E shows the stability test of Example 1-1b at 120° C.

The LC-MS test results showed that the compounds of Examples 1-1a, 1-1b were stable single-configuration compounds under the heating conditions of 40° C. and 120° C., and mutual transformation of atropisomers would not occur (see FIG. 2).

1.2. Thermodynamic Stability Test of Atropisomerism of Compound of Examples 5-1

1.2.1. Experimental Instruments

Agilent 1200 DAD model LC-MS; column: waters sunfire C18, 4.6×75 mm, 3.5 μm; mobile phase: water (0.1% trifluoroacetic acid):acetonitrile (0.1% trifluoroacetic acid).

1.2.2. Test Samples

Compound of Example 5-1 (also referred to as Compound 5-1)

1.2.3. Experimental Procedures

The compounds of Examples 5-1, 5-2 were atropisomers of each other and had different retention times in the LC-MS spectra, and the tautomerism of the atropisomers could be detected by LC-MS.

Compound 5-1 (1.0 mg) was dissolved in DMSO (1.0 mL), and the reaction solution was heated at 37° C. and 120° C. for 3.0 h, respectively, and the change in purity of compound 5-1 was detected by LC-MS.

1.2.4. Experimental Results

Figure 3:
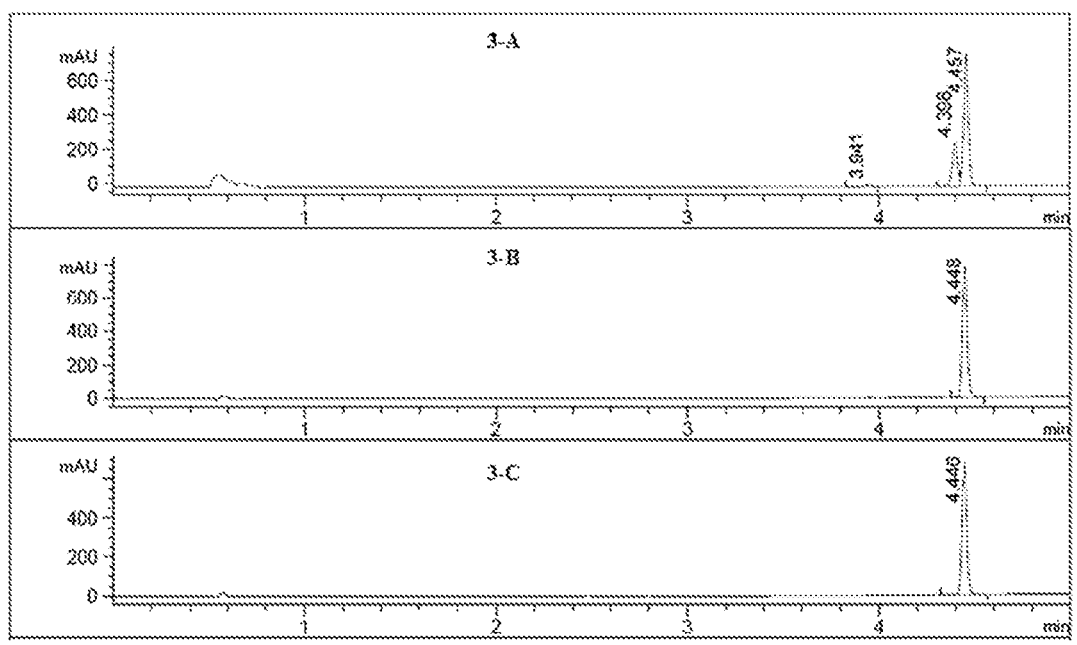
FIG. 3 is LC-MS spectra for the thermodynamic stability test of atropisomerism in Example 5-1, wherein 3-A shows the mixture of Examples 5-1 and 5-2 at 25° C.; 3-B shows the stability test of Example 5-1 at 37° C.; 3-C shows the stability test of Example 5-1 at 120° C.

The LC-MS test results showed that the compound of Example 5-1 was stable single-configuration compound under the heating conditions of 37° C. and 120° C., and mutual transformation of atropisomers would not occur (see FIG. 3).

Biological Evaluation

Test Example 2. Effect of Compounds of the Present Disclosure on In Vitro Polymerization of HIV-1 Capsid Protein I. Materials and Instruments 1. MAb Anti GST-Eu cryptate (Cisbio)
2. MAb Anti 6HIS-XL665 (Cisbio)
3. His tag HIV-1 capsid protein (hereinafter referred to as His-CA)
4. GST tag HIV-1 capsid protein (hereinafter referred to as GST-CA)
5. 384-well unbound surface microplate, white (Corning)
6. Microplate reader (BMG)

II. Procedures

The HIV-1 capsid proteins aggregate spontaneously in high-salt solutions. Capsid protein sequences derived from HIV-1 NL4-3 strains (GeneBank AF324493.2) were separately tagged with 6His tag and GST tag sequences at the C-terminus, cloned into pET30 vectors, and expressed and separately tagged for expression in *E. coli* system and purified. His-CA and GST-CA were mixed at high-salt concentrations, and the level of polymerization of capsid proteins was detected using GST antibody labeled with Eu3+-Cryptate (energy donor) and His antibody labeled with XL665 (energy acceptor). Since the excitation spectrum of Eu3+-Cryptate overlapped with the excitation spectrum of XL665, when the capsid proteins with these two tags formed a poly complex, the energy donor and the energy acceptor could be drawn to a sufficiently close distance, the energy donor released part of the captured energy under the excitation of an external light source (such as a xenon lamp or a laser), with the emission wavelength being 620 nM, part of the resonance was transferred to the energy acceptor to excite the energy acceptor, with the emission wavelength being 665 nM, and an optical signal was generated, the signal intensity of which was in direct proportion to the degree of polymerization of the tag proteins.

His-CA was diluted to 2 μM in a clean tube with protein diluent (50 mM Tris-HCl, pH 8.0, 50 mM NaCl, 0.4 mM $MgCl_2$, 0.05% Triton X-100, 2% glycerol) while MAb Anti 6HIS-XL665 at a final concentration of 260 nM was added; GST-CA was diluted to 20 nM with protein diluent in another clean tube while MAb Anti GST-Eu cryptate at a final concentration of 3.33 nM was added and incubated on ice for half an hour. Compounds were first formulated into a concentration of 20 mM with DMSO, then diluted to a first concentration of 2 mM with DMSO and serially 5-fold diluted to the $8^{th}$ concentration. Control wells were set and added with DMSO, and serially-diluted compounds were then 20-fold diluted with protein diluent to 10-fold working concentrations. Preparation of capsid protein polymerization liquid at 2-fold concentration: 50 mM Tris-HCl, pH 8.0, 1 M NaCl, 800 mM KF; to a pre-cooled white round-bottomed 384-well plate were added 4 uL of His-CA-His antibody mixture, 4 uL of GST-CA-GST antibody mixture, 2 uL of the compounds at 10-fold concentration and 10 uL of capsid protein polymerization reaction liquid at 2-fold concentration, the plate was sealed with a light-shielding sealing plate membrane after uniformly mixing, and the reaction plate was placed in a 37° C. incubator for incubation for 2 h. After incubation, the samples were excited with an excitation light at 337 nM, and signal values at 620 nM and 665 nM were collected for detection, wherein Ratio values=(665 nM/620 nM signal)×10000 was calculated according to the signal values. $IC_{50}$ values for compounds were calculated using Graphpad Prism software based on each concentration of the compounds and the corresponding Ratio values.

Table 1 showed the $IC_{50}$ values determined by polymerization inhibition of the compounds of the present disclosure against the HIV-1 capsid protein.

TABLE 1

$IC_{50}$ values of compounds of the present disclosure by polymerization inhibition of HIV-1 capsid proteins

| Example | $IC_{50}$ (nM) | Imax (%) |
|---|---|---|
| 1-1 | 9 | 100 |
| 2 | 19 | 100 |
| 3 | 24 | 98 |
| 4 | 68 | 91 |
| 5-1 | 37 | 108 |
| 6 | 107 | 75 |
| One of 7-1 and 7-2, which was synthesized by taking the compound with the retention time of 2.869 in 7i-1 and 7i-2 as a raw material | 12 | 103 |
| The other of 7-1 and 7-2, which was synthesized by taking the compound with the retention time of 3.492 in 7i-1 and 7i-2 as a raw material | 8 | 101 |

Conclusion: the compounds of the present disclosure had a significant inhibition effect on the polymerization of HIV-1 capsid proteins.

Pharmacokinetic Evaluation

Test Example 3. Beagle Pharmacokinetic Study of Compounds of the Present Disclosure 1. Introduction Taking beagles as test animals, and the drug concentrations in dog plasma at various times after intragastric administration (ig)/subcutaneous injection (sc)/intravenous injection (iv) administration of the compound of Example 1-1 and Positive Control Example 1 were measured by using LC/MS/MS method. The pharmacokinetic performance in beagles of the compounds of the present disclosure was studied and the pharmacokinetic profile thereof was evaluated.

2. Methodology 2.1. Test Compounds

Compounds of Example 1-1 and Positive Control Example 1 were included.

2.2. Test Animals 18 non-naïve beagles (999M-004, medicilon) with 7-12 kg, every 3 of which were in one group.

2.3. Pharmaceutical Formulation

The intragastric administration group: a certain amount of the compounds was weighed, ethanol with a volume of 5% of the final volume, 20% PG, 45% PEG300 and 30% deionized water were added (the pH was adjusted to be about 2 with 0.01 N HCl), and the reaction mixture was subjected to ultrasonic stirring for uniform mixing to give an administration solution at a concentration of 0.8 mg/mL.

The subcutaneous injection administration group: a certain amount of the compounds was weighed, 2% aqueous poloxamer 188 solution with a proper volume was added, and the reaction mixture was subjected to ultrasonic stirring for uniform mixing to give a suspension administration solution at a concentration of 200 mg/mL.

The intravenous administration group: a certain amount of the compounds was weighed, 5% volume of DMSO, 30% PG, 30% PEG400 and 35% volume of normal saline were added, and the reaction mixture was subjected to vortex ultrasonic stirring for uniform mixing to give an administration solution at a concentration of 0.5 mg/mL.

2.4. Administration

Beagles were intragastrically administered with the compounds after fasting overnight, at a dose of 4.0 mg/kg and a volume of 5.0 mL/kg.

Beagles were subcutaneously injected with the compounds after fasting overnight, at a dose of 6.0 mg/kg and a volume of 0.03 mL/kg.

Beagles were intravenously injected with the compounds after fasting overnight, at a dose of 1.0 mg/kg and a volume of 2 mL/kg.

3. Procedures

Beagles were intragastrically administered with the compound of Example 1-1/Positive Control Example 1, and 1 mL of blood was collected from the orbit before administration and at 0.25 h, 0.5 h, 1.0 h, 2.0 h, 4.0 h, 6.0 h, 8.0 h, 12.0 h, 24 h, 32 h, 48 h, 56 h and 72 h after administration, respectively, and placed in EDTA-K2 anticoagulant blood collection tubes, plasma was centrifuged (centrifugal force: 2200 g, centrifugation time: 10 min, 2-8° C.), and stored at −80° C., and food intake was resumed 3 h after administration.

The compound of Example 1-1/Positive Control Example 1 was subcutaneously injected to beagles, and 1 mL of blood was collected before administration and at 1.0 h, 3.0 h, 8.0 h, 24 h, 48 h, 72 h, 96 h, 168 h, 336 h, 432 h and 504 h after administration, respectively, and placed in EDTA-K2 anticoagulant blood collection tubes, plasma was centrifuged (centrifugal force: 2200 g, centrifugation time: 10 min, 2-8° C.), and stored at −80° C., and food intake was resumed 3 h after administration.

The content of the compound to be tested in the plasma of beagles was determined after the intragastric administration of the compounds at different concentrations: 20 μL of the plasma in beagles at each time after administration was taken, 200 μL of methanol containing internal standard (100 ng/mL) was added, the reaction mixture was subjected to vortex mixing for 1 min, and centrifuged for 7 min (centrifugal force: 18000 g), and 1 μL of the supernatant was taken from the plasma sample for LC/MS/MS analysis.

The compound of Example 1-1/Positive Control Example 1 was intravenously injected to beagles, and 1 mL of blood was collected from the orbit before administration and at 5 min, 0.25 h, 0.5 h, 1.0 h, 2.0 h, 4.0 h, 8.0 h, 12.0 h, 24 h, 32 h, 48 h, 56 h and 72 h after administration, respectively, and placed in EDTA-K2 anticoagulant blood collection tubes, plasma was centrifuged (centrifugal force: 2200 g, centrifugal time: 10 min, 2-8° C.), and stored at −80° C., and food intake was resumed 3 h after administration.

4. Pharmacokinetics

TABLE 2

Pharmacokinetics parameters of compounds of the present disclosure

| Route of administration | No. | Dosage (mg/kg) | Plasma concentration Cmax (ng/mL) | Area under curve $AUC_{0-72}$ (ng/mL * h) | Half life $T\frac{1}{2}$ (h) | Clearance CLz/F (ml/min/kg) | Apparent distribution Volume Vz/F (ml/kg) |
|---|---|---|---|---|---|---|---|
| Intragastric administration | Example 1-1 | 4 | 250.6 | 8232 | 44.3 | — | — |
| | Positive Control Example 1 | 4 | 414.5 | 11238 | 23.0 | — | — |
| Subcutaneous injection | Example 1-1 | 6 | 122.5 | 34826 | — | — | — |
| | Positive Control Example 1 | 6 | 54.6 | 17660 | — | — | — |
| Intravenous injection | Example 1-1 | 1 | 1316.0 | 16511 | 41.8 | 0.7 | 2628 |
| | Positive Control Example 1 | 1 | 1107.1 | 14746 | 13.7 | 1.1 | 1290 |

Note:
for subcutaneous administration, the software failed to provide $T\frac{1}{2}$ as the plasma concentration was still rising.

Conclusion: the compound of the present disclosure had good absorption profile in beagles, and particularly had a longer half-life period $T\frac{1}{2}$, large apparent distribution volume Vz and low clearance rate CL, and thus was more favorable for long-acting administration. The change in drug concentrations over time after subcutaneous injection is shown in FIG. 1. As shown in FIG. 1, in the pharmacokinetic experiment of the same dose and at the same time after administration, the plasma concentration of the compound disclosed herein was higher than that of the positive control example, and particularly, the difference between the compound of this example and the compound of the positive control example was increased along with the increase of the time, which indicates that the compound disclosed herein was more favorable for long-acting administration.

Test Example 4. Monkey Pharmacokinetic Study of Compounds of the Present Disclosure 1. Introduction
Taking cynomolgus monkeys as test animals and the drug concentrations in monkey plasma at various times after intravenous injection (iv) of the compounds of Example 1-1 and Positive Control Example 1 were measured by using LC/MS/MS method. The pharmacokinetic performance in cynomolgus monkeys of the compounds of the present disclosure was studied and the pharmacokinetic profile thereof was evaluated.
2. Methodology
2.1. Test Compounds
Compounds of Example 1-1 and Positive Control Example 1 were included.
2.2. Test Animals
6 non-naïve cynomolgus monkeys (999M-004, medicilon) with 2-5 kg, every 3 of which were in one group.
2.3. Pharmaceutical Formulation
A certain amount of the compounds was weighed, 5% volume of DMSO, 30% PG, 30% PEG400 and 35% volume of normal saline were added, and the reaction mixture was subjected to vortex ultrasonic stirring for uniform mixing to give a clean administration solution at a concentration of 0.5 mg/mL.

2.4. Administration
Monkeys were intravenously injected with the compounds after fasting overnight, at a dose of 1.0 mg/kg and a volume of 2 mL/kg.
3. Procedures
The compound of Example 1-1/Positive Control Example 1 was intravenously injected to monkeys, and 1 mL of blood was collected through femoral vein before administration and at 5 min, 0.25 h, 0.5 h, 1.0 h, 2.0 h, 4.0 h, 8.0 h, 12.0 h, 24 h, 32 h, 48 h, 56 h and 72 h after administration, respectively, and placed in EDTA-K2 anticoagulant blood collection tubes, plasma was centrifuged (centrifugal force: 2200 g, centrifugal time: 10 min, 2-8° C.), and stored at −80° C., and food intake was resumed 3 h after administration.
4. Pharmacokinetics

TABLE 3

Pharmacokinetics parameters of compounds of the present disclosure

| | Dosage (mg/kg) | Area under curve $AUC_{0-72}$ (ng/mL * h) | Clearance CLz/F (ml/min/kg) | Apparent volume of distribution Vz/F (ml/kg) |
|---|---|---|---|---|
| Example 1-1 | 1 | 8522 | 2.0 | 1507 |
| Positive Control Example 1 | 1 | 2132 | 7.8 | 6992 |

Conclusion: the compound of the present disclosure had low clearance rate in monkeys after intravenous injection, and the exposure AUC was significantly higher than that of the positive control example in the pharmacokinetic experiment of the same dose, and thus the compound disclosed herein was more favorable for being taken as a long-acting sustained release formulation.

The invention claimed is:
1. A compound of general formula (I) or an atropisomer, tautomer, mesomer, racemate, enantiomer, diastereomer thereof or a mixture thereof, or a pharmaceutically acceptable salt thereof,

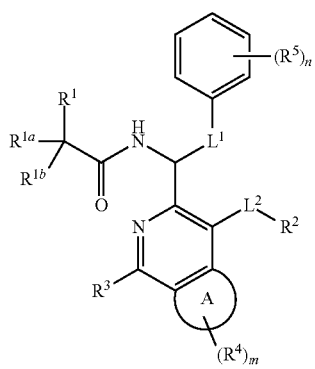

wherein, ring A is selected from the group consisting of cycloalkyl and aryl;

$L^1$ is alkylene;

$L^2$ is absent or selected from the group consisting of —CH$_2$—, —O—, —S— and —NR$^6$—;

$R^1$ is selected from the group consisting of cycloalkyl, heterocyclyl, aryl and heteroaryl, wherein the cycloalkyl, heterocyclyl, aryl and heteroaryl are each independently optionally substituted with one or more substituents selected from the group consisting of oxo, halogen, alkyl, haloalkyl, cyano, amino, nitro, hydroxy, hydroxyalkyl and cycloalkyl;

$R^{1a}$ and $R^{1b}$ are identical or different and are each independently selected from the group consisting of hydrogen, halogen, alkyl and haloalkyl;

$R^2$ is selected from the group consisting of cycloalkyl, heterocyclyl, aryl and heteroaryl, wherein the cycloalkyl, heterocyclyl, aryl and heteroaryl are each independently optionally substituted with one or more substituents selected from the group consisting of oxo, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR$^6$, —OC(O)R$^6$, —OC(O)NR$^7$R$^8$, —NHS(O)$_r$R$^6$, —NHS(O)$_2$OR$^6$, —NHS(O)$_2$NR$^7$R$^8$, —C(O)R$^6$, —C(O)OR$^6$, —C(O)NR$^7$R$^8$, —S(O)$_r$R$^6$, —S(O)$_r$NR$^7$R$^8$, —NR$^7$R$^8$, —NHC(O)R$^6$, —NHC(O)OR$^6$, —NHC(O)NR$^7$R$^8$ and —NHC(O)NHOR$^6$;

$R^3$ is C$_{2-12}$ alkynyl, the C$_{2-12}$ alkynyl being optionally substituted with one or more —S(O)$_2$R$^9$; R$^9$ is C$_{1-6}$ alkyl or C$_{3-6}$ cycloalkyl;

$R^4$ is identical or different and is each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;

$R^5$ is identical or different and is each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;

$R^6$ is selected from the group consisting of hydrogen, alkyl, cycloalkyl, heterocyclyl, aryl and heteroaryl, wherein the alkyl, cycloalkyl, heterocyclyl, aryl or heteroaryl is each independently optionally substituted with one or more substituents selected from the group consisting of alkyl, halogen, hydroxy, alkoxy, cycloalkyl, heterocyclyl, aryl and heteroaryl;

$R^7$ and $R^8$ are identical or different and are each independently selected from the group consisting of hydrogen, alkyl, cycloalkyl, heterocyclyl, aryl, heteroaryl, —C(O)R$^6$ and —S(O)$_r$R$^6$, wherein the alkyl, cycloalkyl, heterocyclyl, aryl and heteroaryl are each independently optionally substituted with one or more substituents selected from the group consisting of alkyl, halogen, hydroxy, alkoxy, cycloalkyl, heterocyclyl, aryl and heteroaryl;

m is 0, 1, 2, 3, 4, 5 or 6;

n is 0, 1, 2, 3, 4 or 5; and r is 0, 1 or 2.

2. The compound of general formula (I) or the atropisomer, tautomer, mesomer, racemate, enantiomer, diastereomer thereof or the mixture thereof, or the pharmaceutically acceptable salt thereof according to claim 1, wherein $L^1$ is methylene; and $L^2$ is absent.

3. The compound of general formula (I) or the atropisomer, tautomer, mesomer, racemate, enantiomer, diastereomer thereof or the mixture thereof, or the pharmaceutically acceptable salt thereof according to claim 1, wherein $R^1$ is

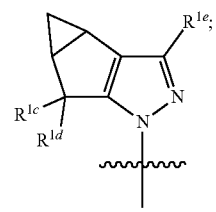

$R^{1c}$, $R^{1d}$ and $R^{1e}$ are identical or different and are each independently selected from the group consisting of hydrogen, halogen, alkyl, haloalkyl, cyano, amino, nitro, hydroxy, hydroxyalkyl and cycloalkyl.

4. The compound of general formula (I) or the atropisomer, tautomer, mesomer, racemate, enantiomer, diastereomer thereof or the mixture thereof, or the pharmaceutically acceptable salt thereof according to claim 1, wherein $R^2$ is

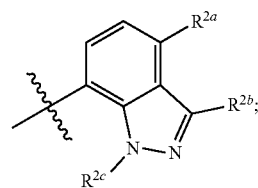

$R^{2a}$, $R^{2b}$ and $R^{2c}$ are identical or different and are each independently selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —OR$^6$, —OC(O) R$^6$, —OC(O)NR$^7$R$^8$, —NHS(O)$_r$R$^6$, —NHS(O)$_2$OR$^6$, —NHS(O)$_2$NR$^7$R$^8$, —C(O)R$^6$, —C(O)OR$^6$, —C(O)NR$^7$R$^8$, —S(O)$_r$R$^6$, —S(O)$_r$NR$^7$R$^8$, —NR$^7$R$^8$, —NHC(O)R$^6$, —NHC(O)OR$^6$, —NHC(O)NR$^7$R$^8$ and —NHC(O)NHOR$^6$; R$^6$-R$^8$ and r are as defined in claim 1.

5. The compound of general formula (I) or the atropisomer, tautomer, mesomer, racemate, enantiomer, diastereomer thereof or the mixture thereof, or the pharmaceutically acceptable salt thereof according to claim 1, wherein the compound of general formula (I) or the atropisomer, tautomer, mesomer, racemate, enantiomer, diastereomer thereof or the mixture thereof, or the pharmaceutically acceptable salt thereof is a compound of general formula (III) or general formula (III-1) or an atropisomer, tautomer, mesomer, racemate, enantiomer, diastereomer thereof or a mixture thereof, or a pharmaceutically acceptable salt thereof,

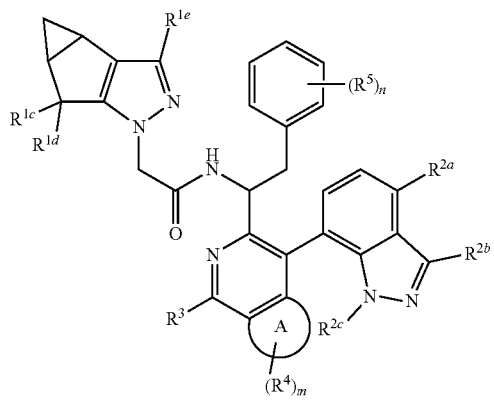

(III)

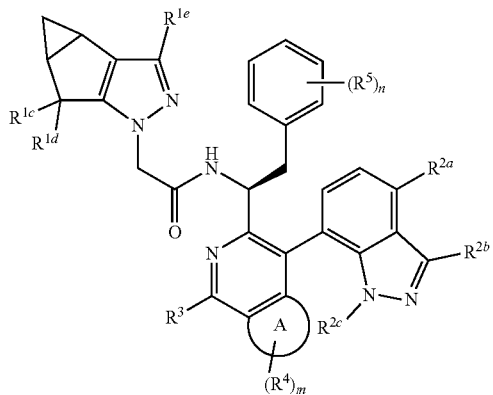

(III-1)

wherein,
$R^{1c}$, $R^{1d}$ and $R^{1e}$ are identical or different and are each independently selected from the group consisting of hydrogen, halogen, alkyl, haloalkyl, cyano, amino, nitro, hydroxy, hydroxyalkyl and cycloalkyl;
$R^{2a}$, $R^{2b}$ and $R^{2c}$ are identical or different and are each independently selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O)R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$; and
ring A, $R^3$-$R^8$, m, n and r are as defined in claim 1.

6. The compound of general formula (I) or the atropisomer, tautomer, mesomer, racemate, enantiomer, diastereomer thereof or the mixture thereof, or the pharmaceutically acceptable salt thereof according to claim 1, wherein the compound of general formula (I) or the atropisomer, tautomer, mesomer, racemate, enantiomer, diastereomer thereof or the mixture thereof, or the pharmaceutically acceptable salt thereof is a compound of general formula (III-1a) or an atropisomer, tautomer, mesomer, racemate, enantiomer, diastereomer thereof or a mixture thereof, or a pharmaceutically acceptable salt thereof,

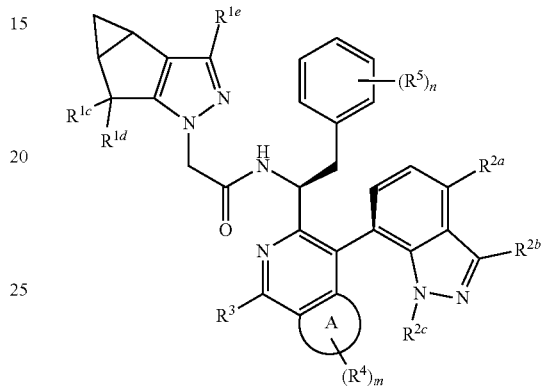

(III-1a)

wherein, ring A, $R^{1c}$, $R^{1d}$, $R^{1e}$, $R^{2a}$, $R^{2b}$, $R^{2c}$, $R^3$, $R^4$, $R^5$, n and m are as defined in claim 5.

7. The compound of general formula (I) or the atropisomer, tautomer, mesomer, racemate, enantiomer, diastereomer thereof or the mixture thereof, or the pharmaceutically acceptable salt thereof according to claim 1, wherein ring A is selected from the group consisting of $C_{3-6}$ cycloalkyl and phenyl.

8. The compound of general formula (I) or the atropisomer, tautomer, mesomer, racemate, enantiomer, diastereomer thereof or the mixture thereof, or the pharmaceutically acceptable salt thereof according to claim 3, wherein $R^{1c}$ and $R^{1d}$ are each independently halogen; $R^{1e}$ is haloalkyl.

9. The compound of general formula (I) or the atropisomer, tautomer, mesomer, racemate, enantiomer, diastereomer thereof or the mixture thereof, or the pharmaceutically acceptable salt thereof according to claim 4, wherein $R^{2a}$ is halogen; $R^{2b}$ is —$NHS(O)_2R^6$; $R^6$ is $C_{1-6}$ alkyl or $C_{3-6}$ cycloalkyl; and $R^{2c}$ is haloalkyl.

10. The compound of general formula (I) or the atropisomer, tautomer, mesomer, racemate, enantiomer, diastereomer thereof or the mixture thereof, or the pharmaceutically acceptable salt thereof according to claim 1, wherein $R^4$ is identical or different and is each independently hydrogen or halogen; and $R^5$ is identical or different and is each independently hydrogen or halogen.

11. A compound or an atropisomer, tautomer, mesomer, racemate, enantiomer, diastereomer thereof or a mixture thereof, or a pharmaceutically acceptable salt, wherein the compound is selected from the group consisting of:

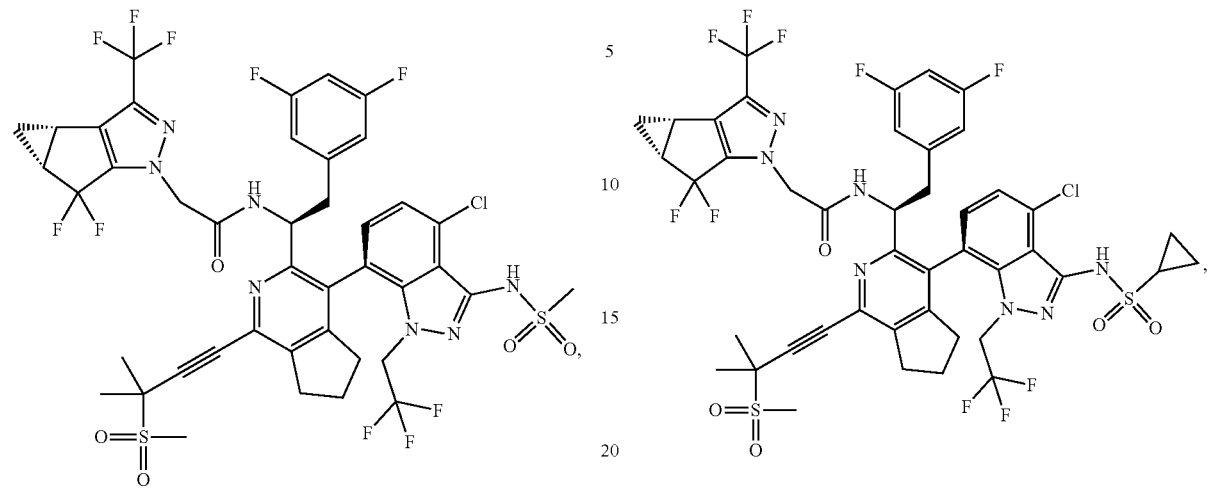
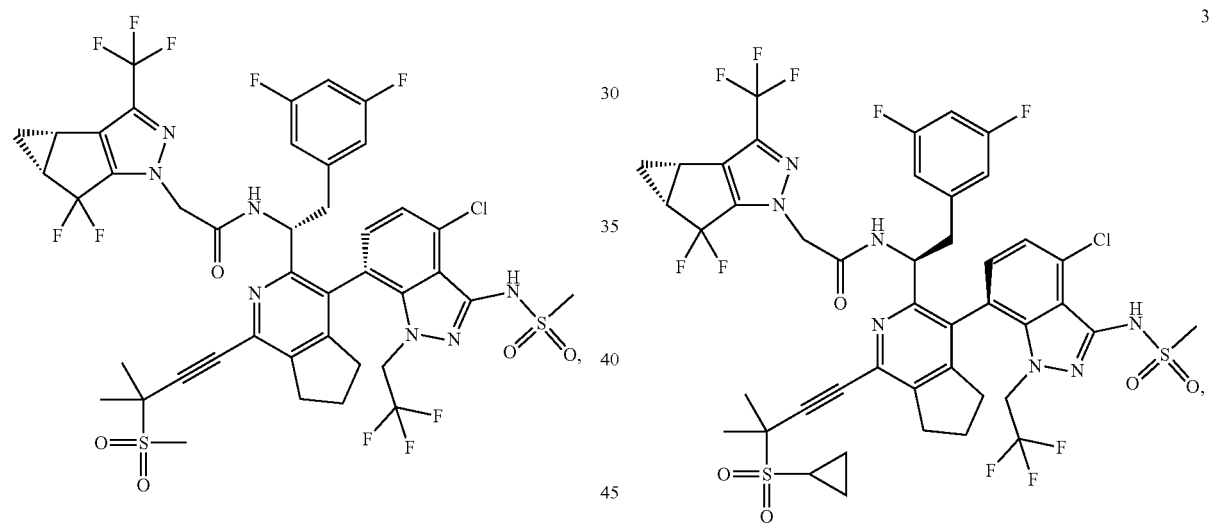
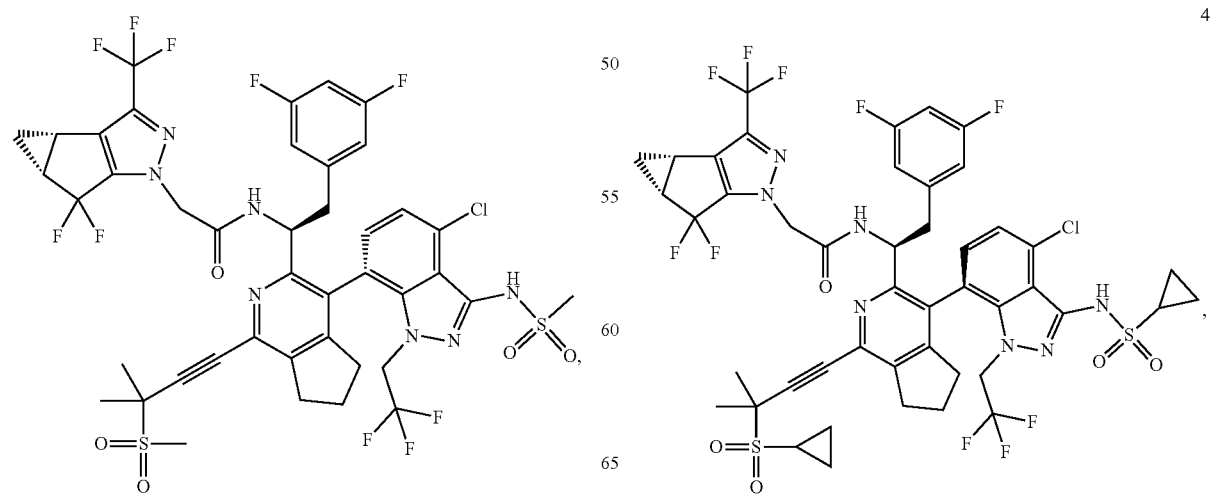

-continued
5-1
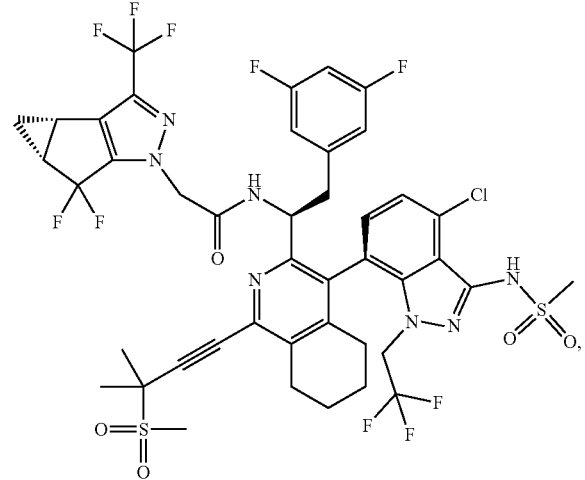
5-2
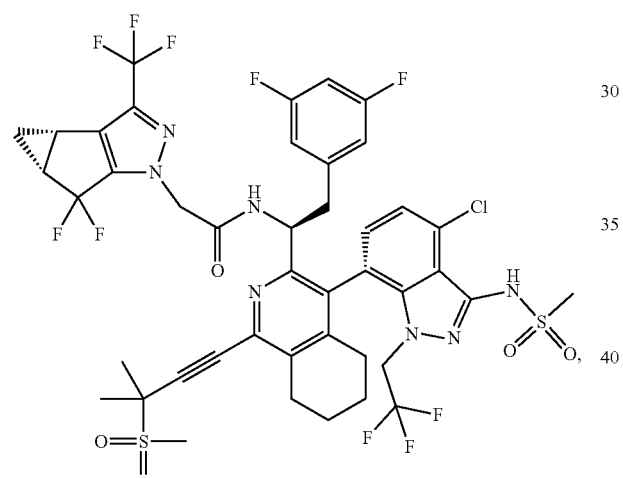
6
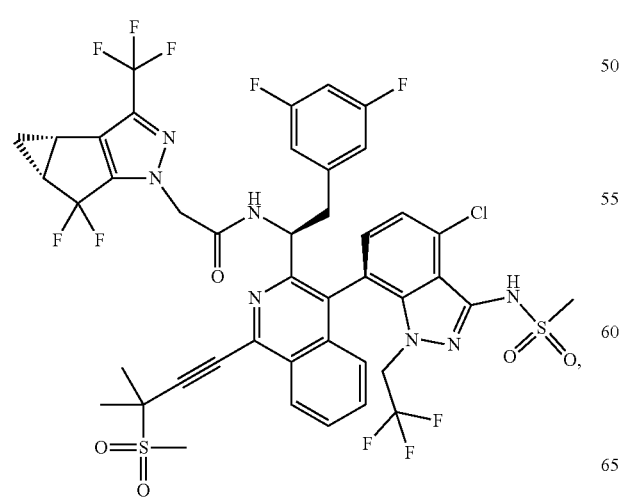
-continued
7-1
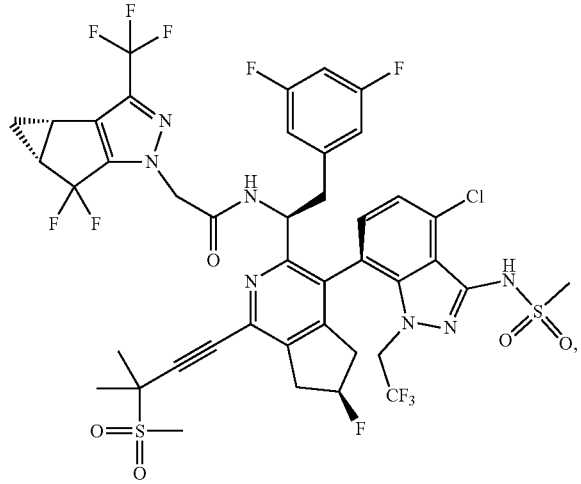
7-2
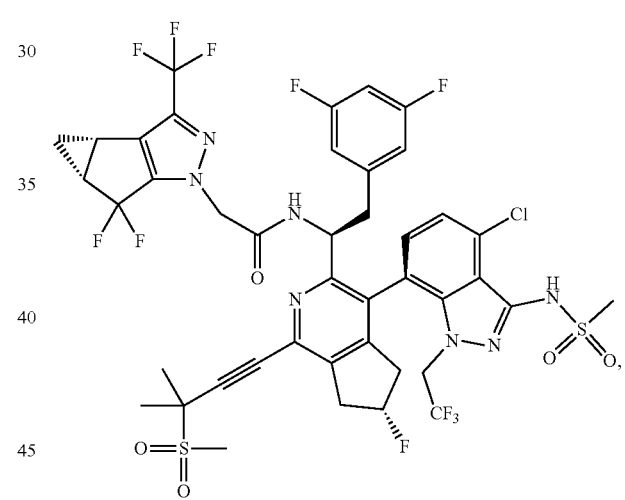
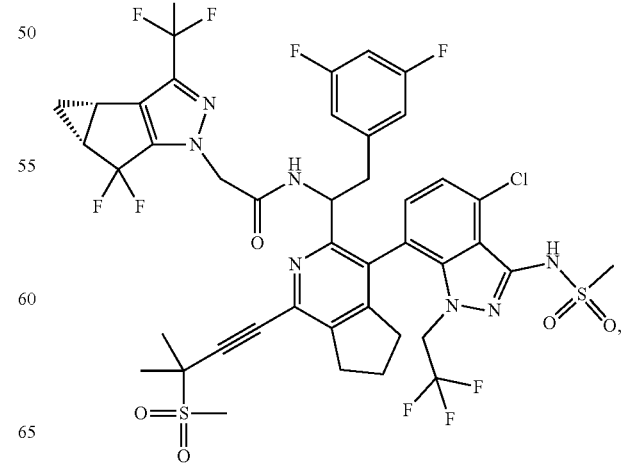

211
-continued
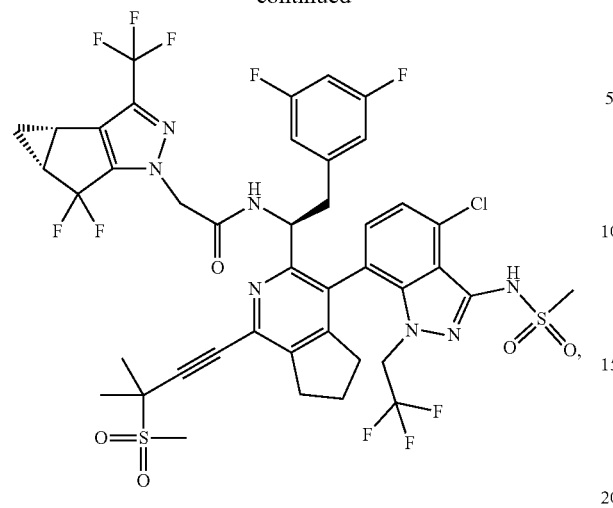
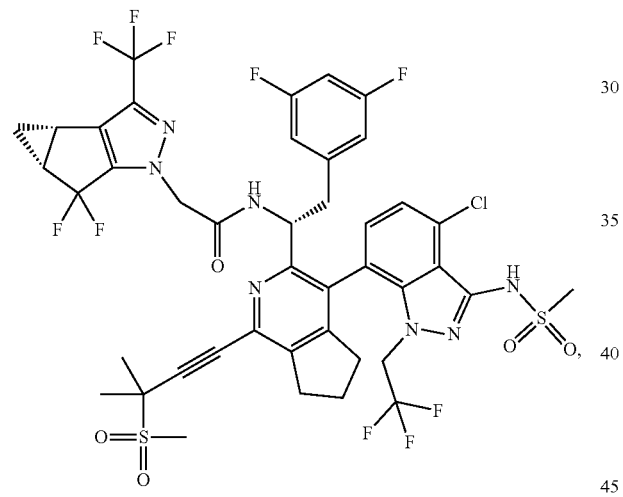
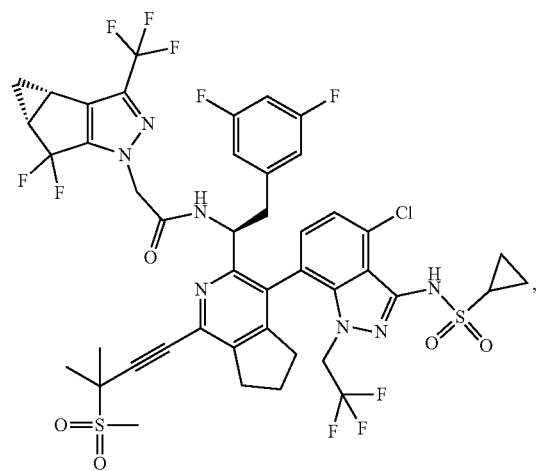
212
-continued
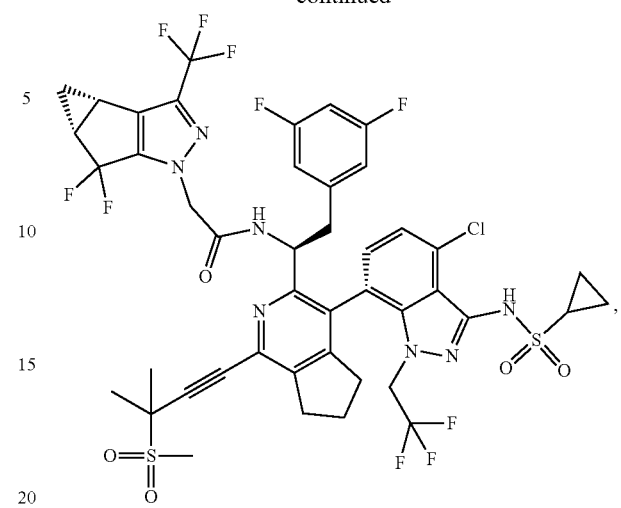
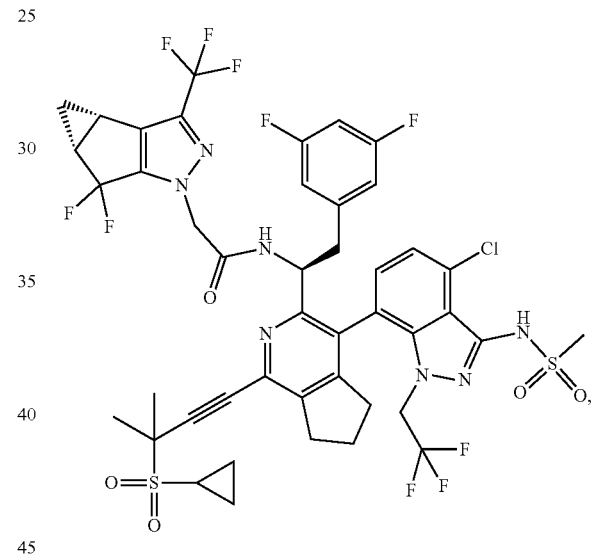
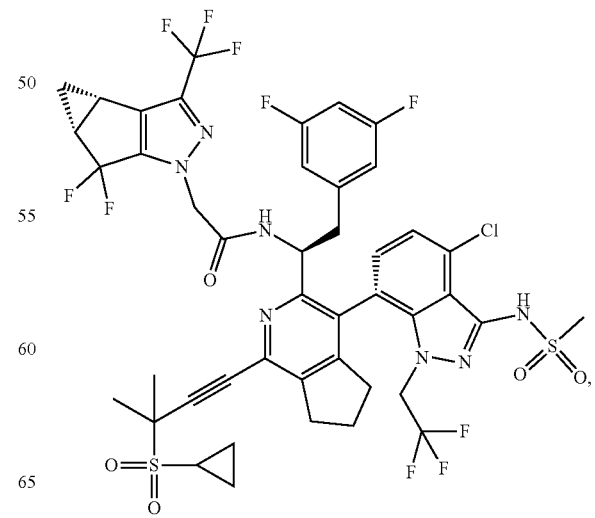

213
-continued
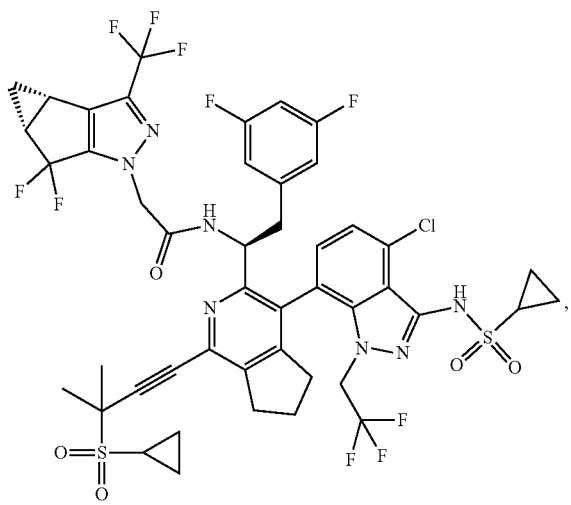
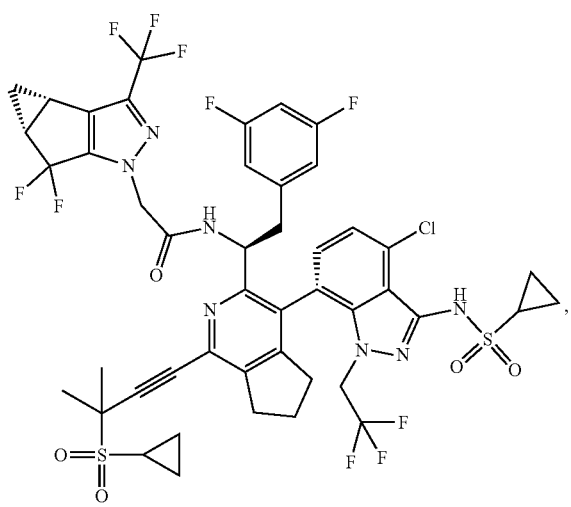
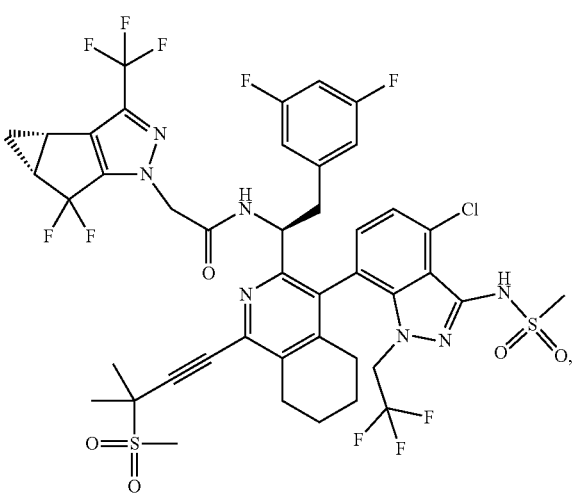
214
-continued
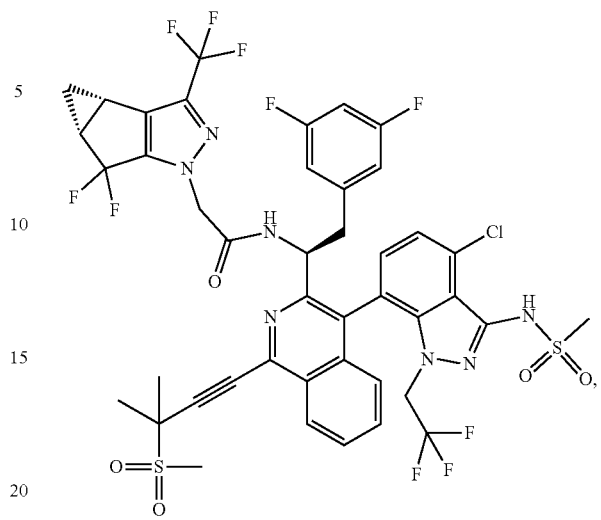
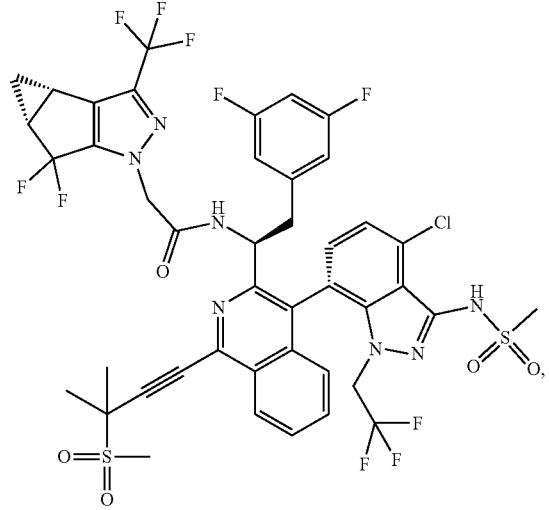
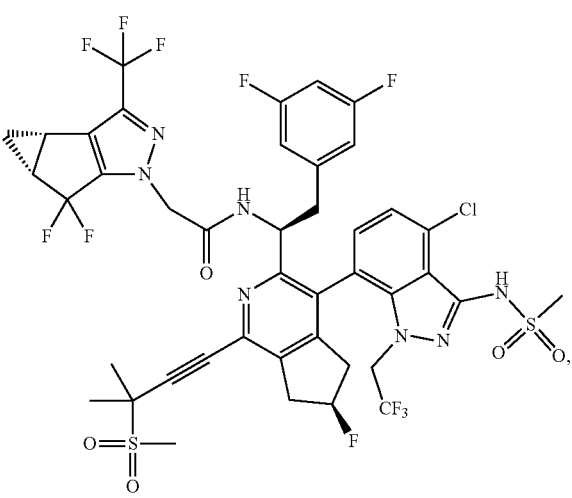

-continued

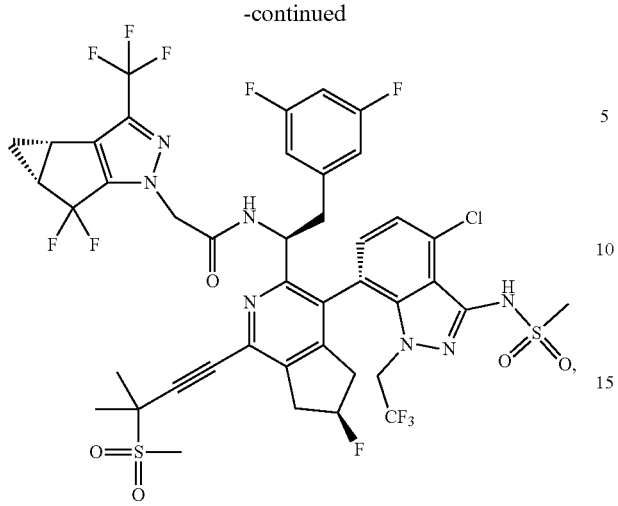

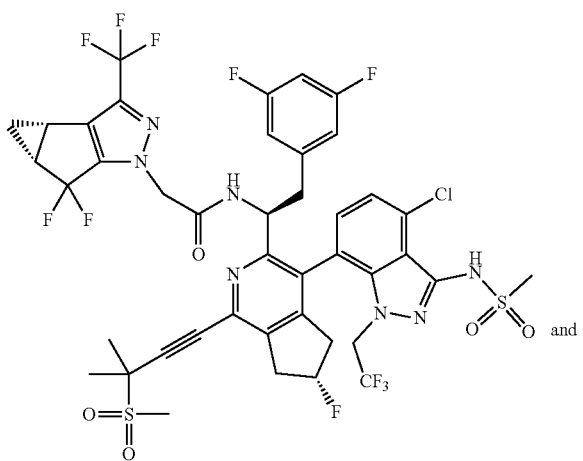

and

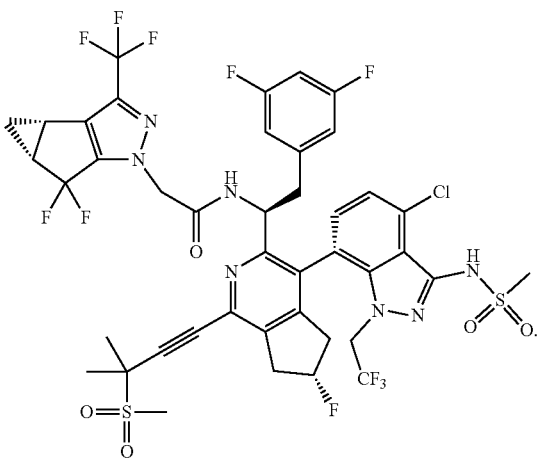

12. A compound of general formula (IA) or an atropisomer, tautomer, mesomer, racemate, enantiomer, diastereomer thereof or a mixture thereof, or a pharmaceutically acceptable salt thereof,

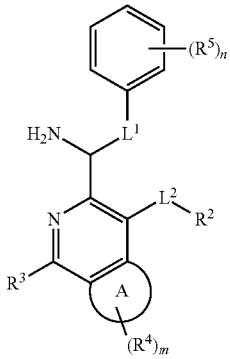

(IA)

wherein,
ring A is selected from the group consisting of cycloalkyl, and aryl;
$L^1$ is alkylene;
$L^2$ is absent or selected from the group consisting of —$CH_2$—, —O—, —S— and —$NR^6$—;
$R^2$ is selected from the group consisting of cycloalkyl, heterocyclyl, aryl and heteroaryl, wherein the cycloalkyl, heterocyclyl, aryl and heteroaryl are each independently optionally substituted with one or more substituents selected from the group consisting of oxo, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —OC(O) $R^6$, —OC(O)$NR^7R^8$, —NHS(O)$_r R^6$, —NHS(O)$_2 OR^6$, —NHS(O)$_2 NR^7 R^8$, —C(O)$R^6$, —C(O)$OR^6$, —C(O)$NR^7R^8$, —S(O)$_r R^6$, —S(O)$_r NR^7 R^8$, —$NR^7 R^8$, —NHC(O)$R^6$, —NHC(O)$OR^6$, —NHC(O)$NR^7R^8$ and —NHC(O)NHOR$^6$;
$R^3$ is $C_{2-12}$ alkynyl, the $C_{2-12}$ alkynyl being optionally substituted with one or more —S(O)$_2 R^9$; $R^9$ is $C_{1-6}$ alkyl or $C_{3-6}$ cycloalkyl;
$R^4$ is identical or different and is each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;
$R^5$ is identical or different and is each independently selected from the group consisting of hydrogen, halogen, alkyl, alkoxy, haloalkyl, cyano, amino, nitro, hydroxy, hydroxyalkyl, cycloalkyl, heterocyclyl, aryl and heteroaryl;
$R^6$ is selected from the group consisting of hydrogen, alkyl, cycloalkyl, heterocyclyl, aryl and heteroaryl, wherein the alkyl, cycloalkyl, heterocyclyl, aryl or heteroaryl is each independently optionally substituted with one or more substituents selected from the group consisting of alkyl, halogen, hydroxy, alkoxy, cycloalkyl, heterocyclyl, aryl and heteroaryl;
$R^7$ and $R^8$ are identical or different and are each independently selected from the group consisting of hydrogen, alkyl, cycloalkyl, heterocyclyl, aryl, heteroaryl, —C(O)$R^6$ and —S(O)$_r R^6$, wherein the alkyl, cycloalkyl, heterocyclyl, aryl and heteroaryl are each independently optionally substituted with one or more substituents selected from the group consisting of alkyl, halogen, hydroxy, alkoxy, cycloalkyl, heterocyclyl, aryl and heteroaryl;

m is 0, 1, 2, 3, 4, 5 or 6;

n is 0, 1, 2, 3, 4 or 5; and r is 0, 1 or 2.

13. The compound of general formula (IA) or the atropisomer, tautomer, mesomer, racemate, enantiomer, diastereomer thereof or the mixture thereof, or the pharmaceutically acceptable salt thereof according to claim 12, wherein the compound or the pharmaceutically acceptable salt thereof is selected from the group consisting of:

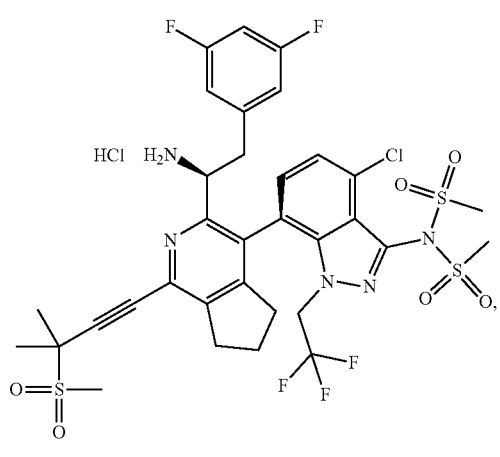

1n-1

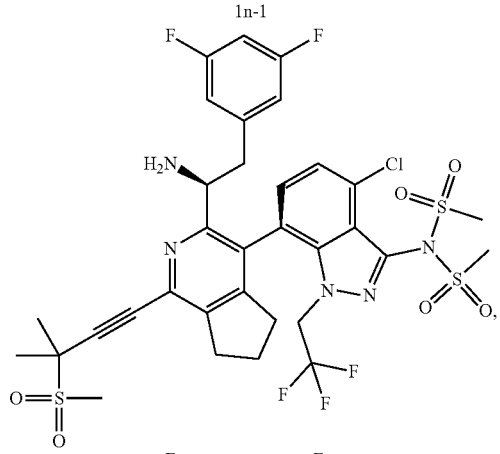

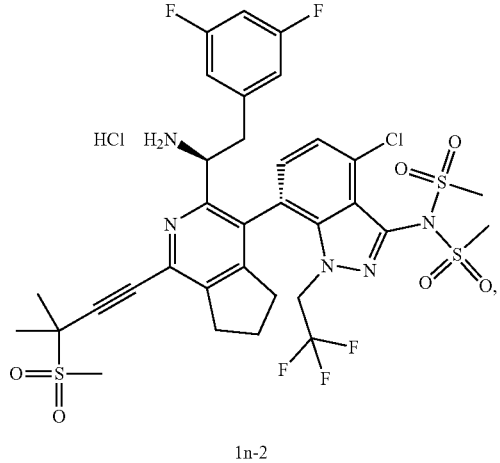

1n-2

-continued

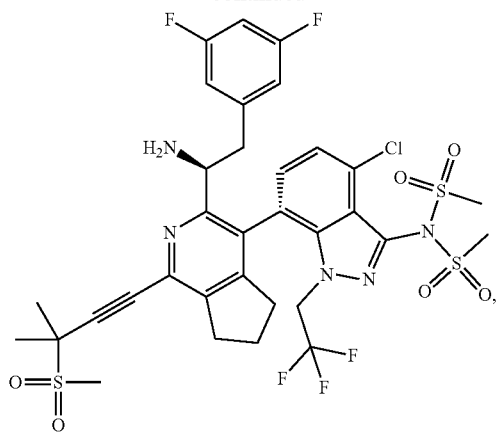

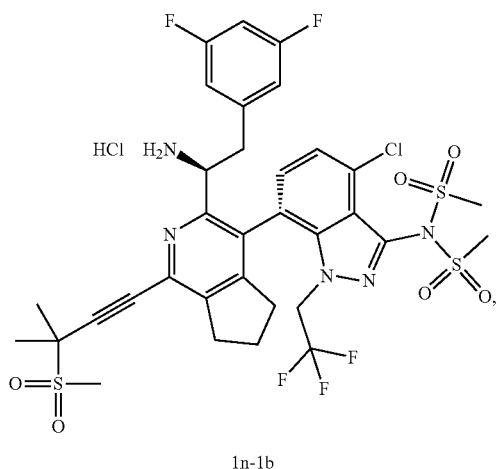

1n-1b

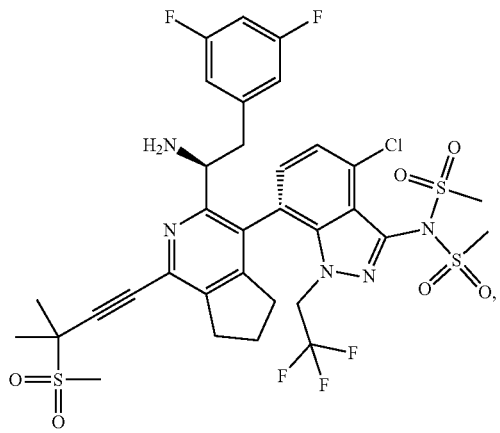

219
-continued
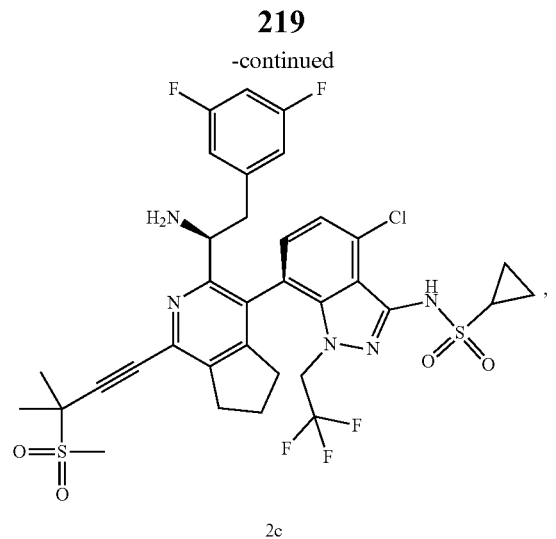
2c
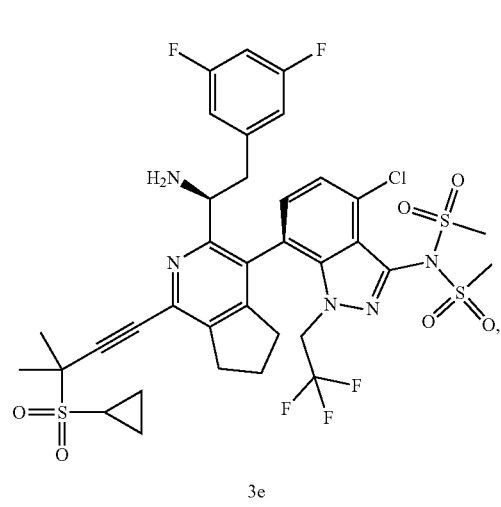
3e
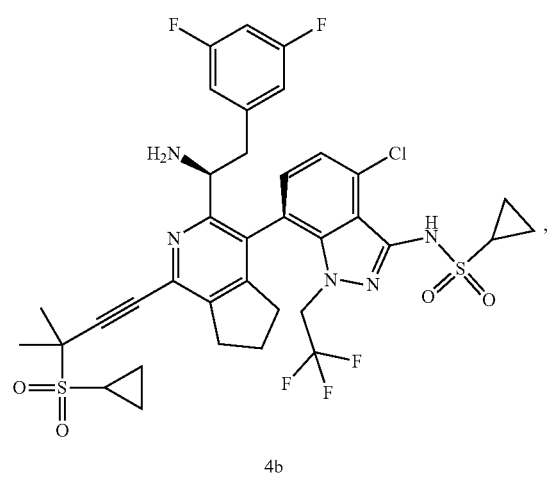
4b
220
-continued
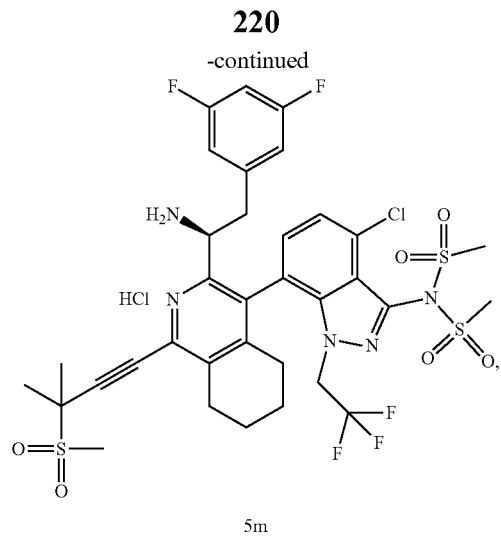
5m
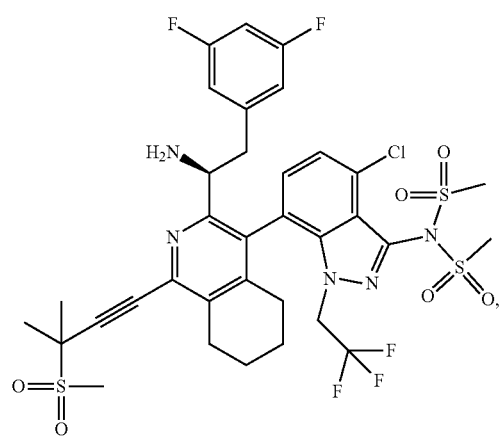
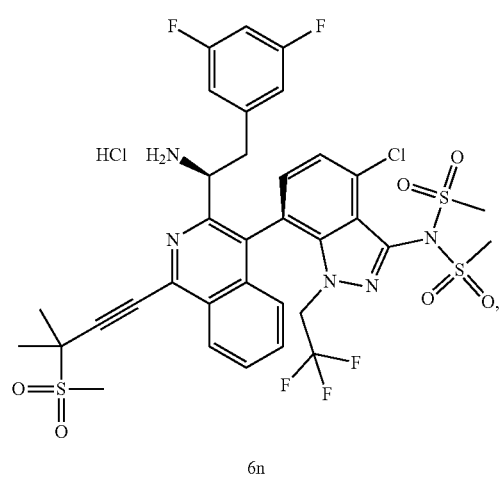
6n 221
-continued
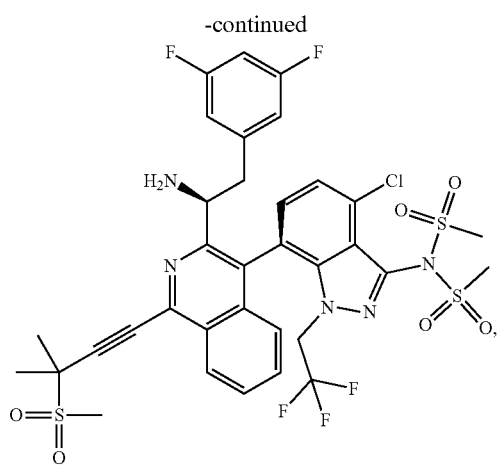
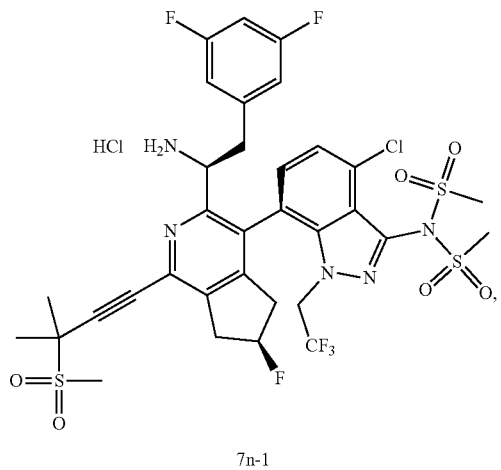
7n-1
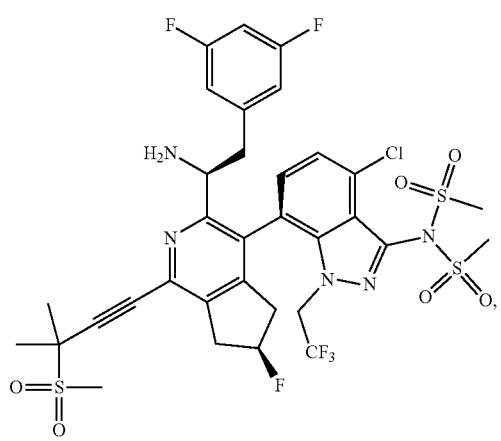
222
-continued
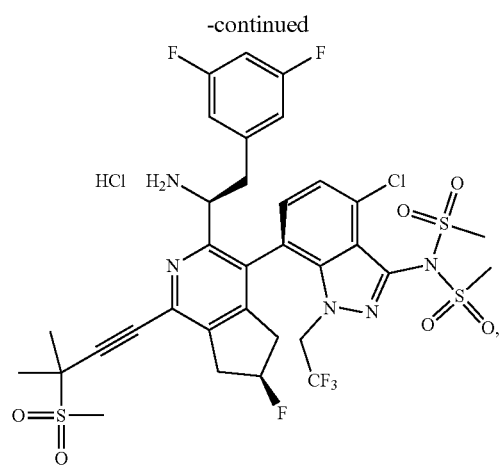
7n-2
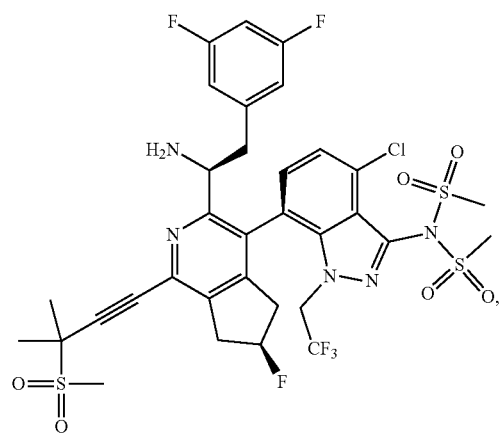
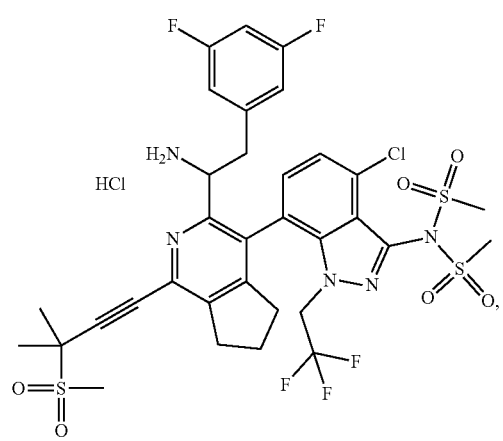

223
-continued
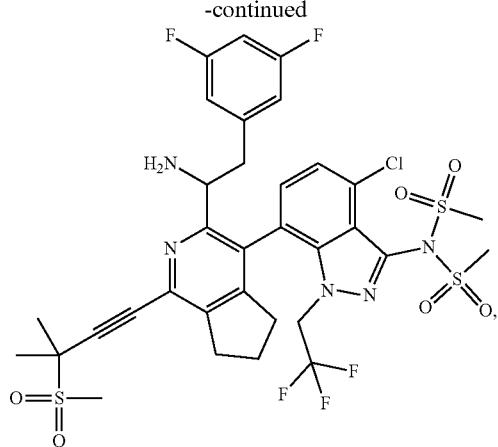
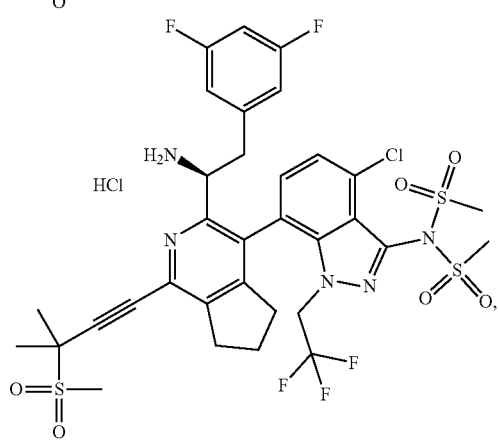
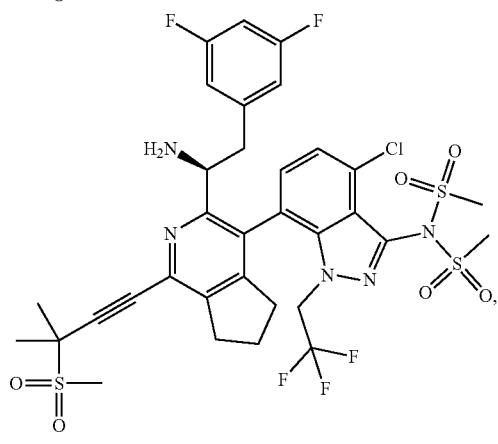
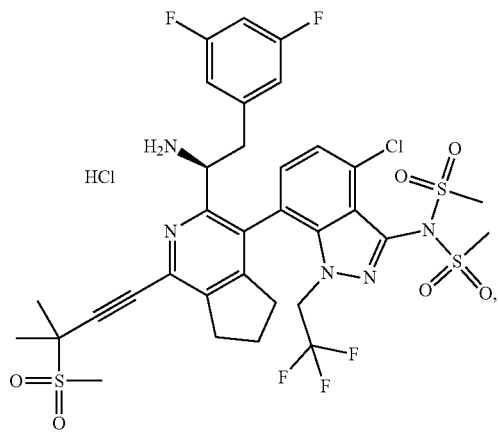
224
-continued
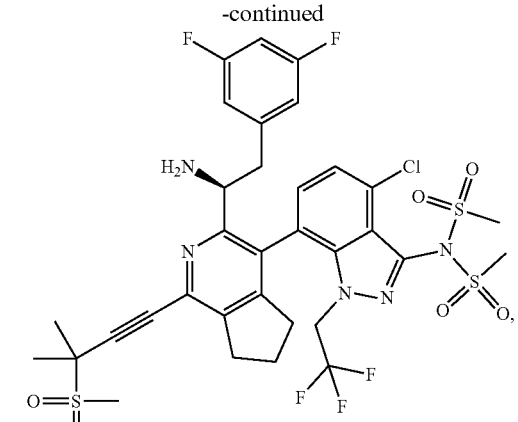
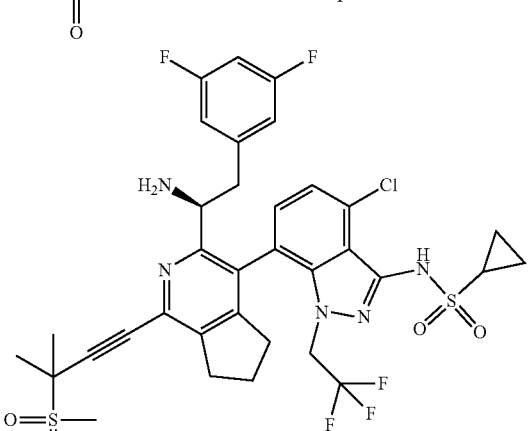
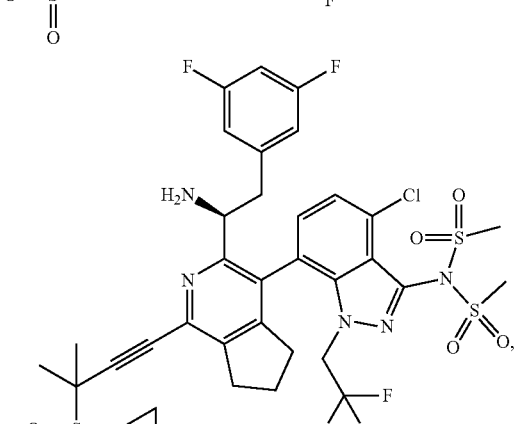
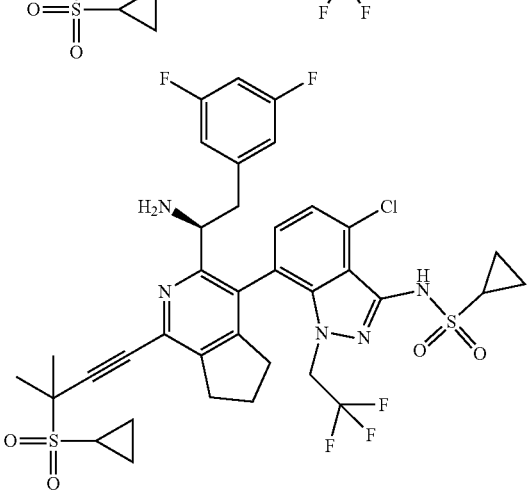

225
-continued
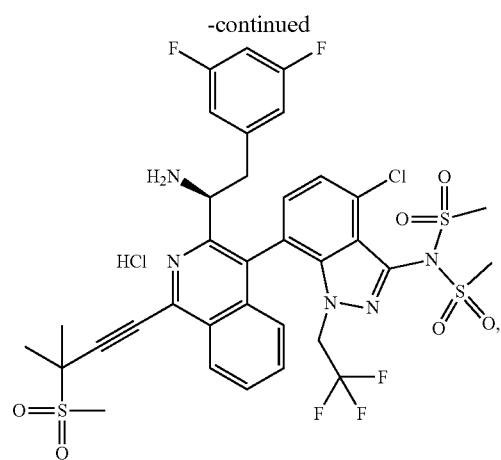
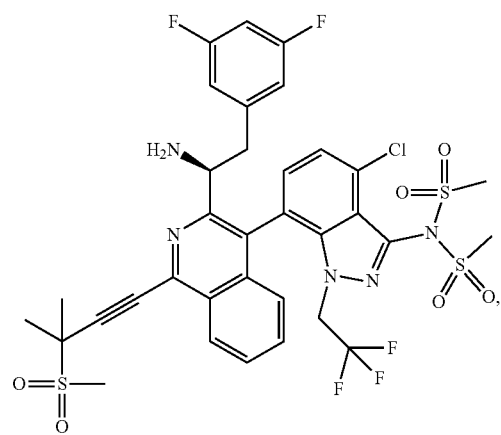
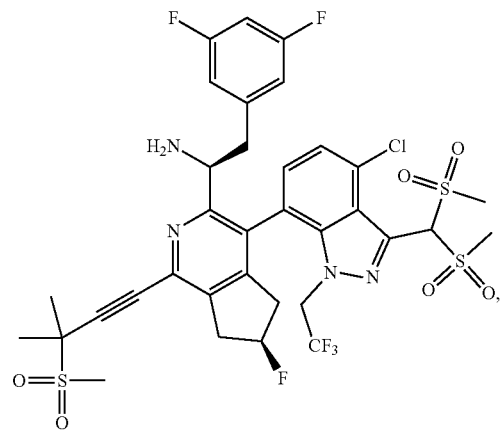
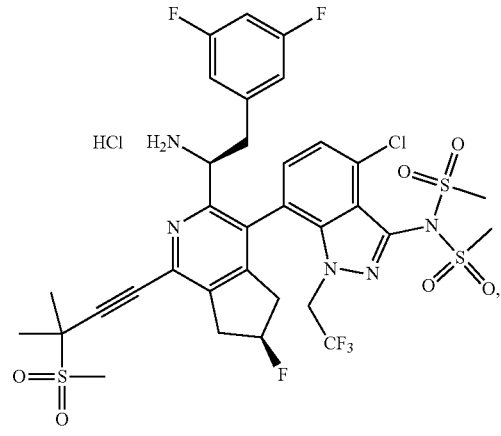
226
-continued
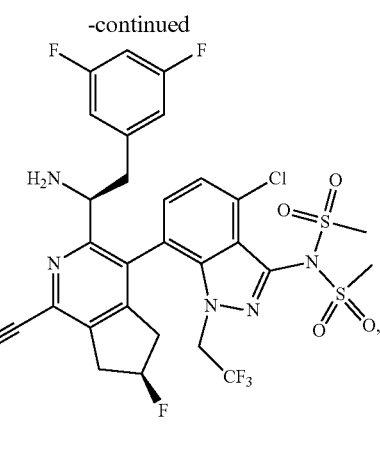
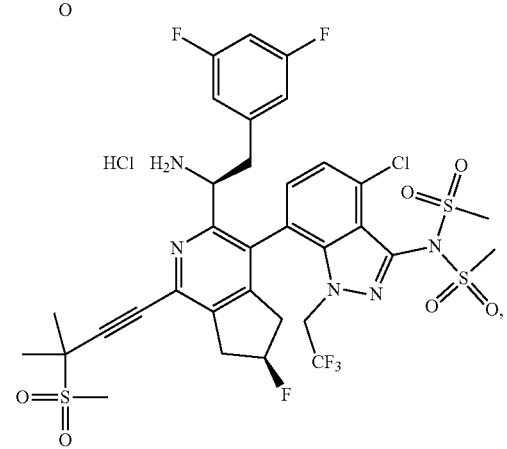
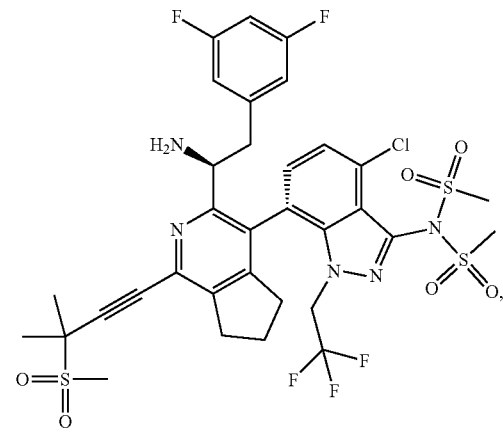
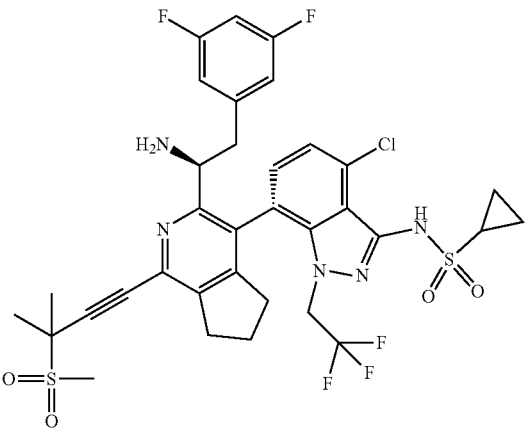

227
-continued
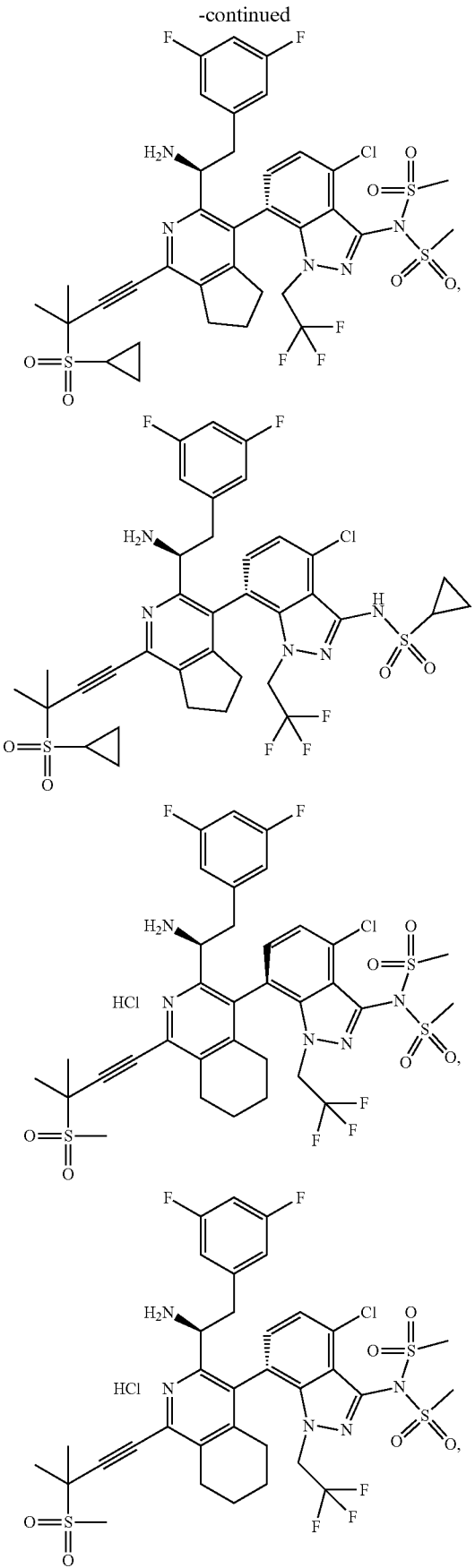
228
-continued
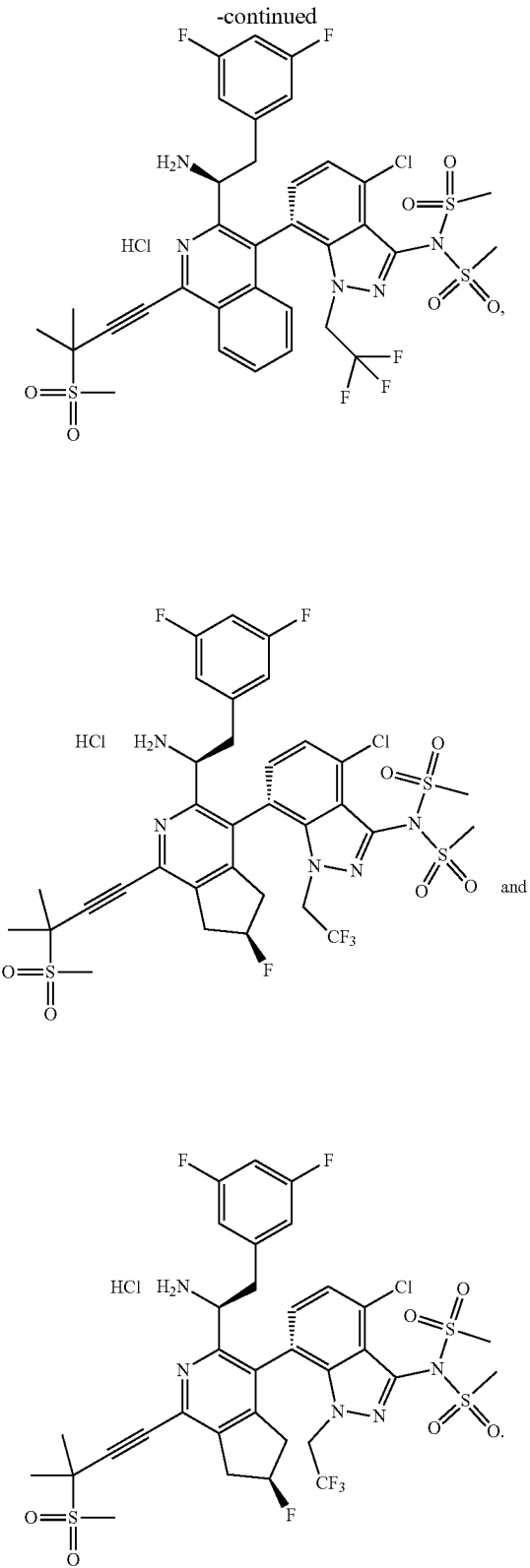
and
14. A method for preparing the compound of general formula (I) or the atropisomer, tautomer, mesomer, racemate, enantiomer, diastereomer thereof or the mixture thereof, or the pharmaceutically acceptable salt thereof according to claim 1, comprising the following steps:

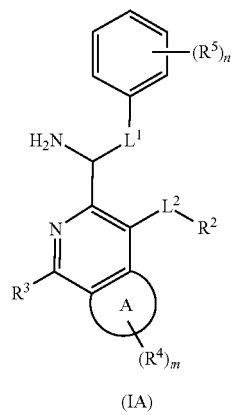

(IA)

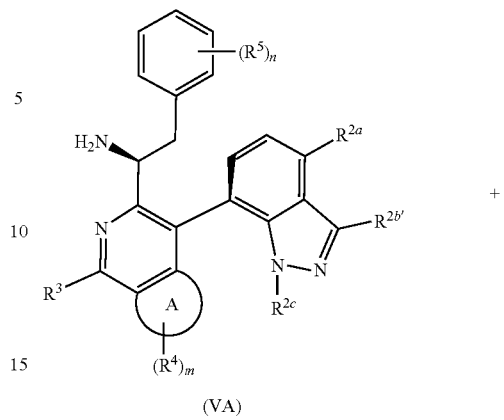

(VA)

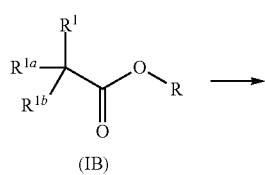

(IB)

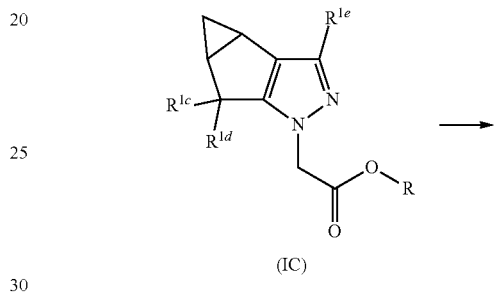

(IC)

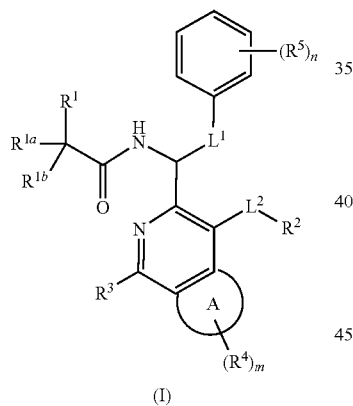

(I)

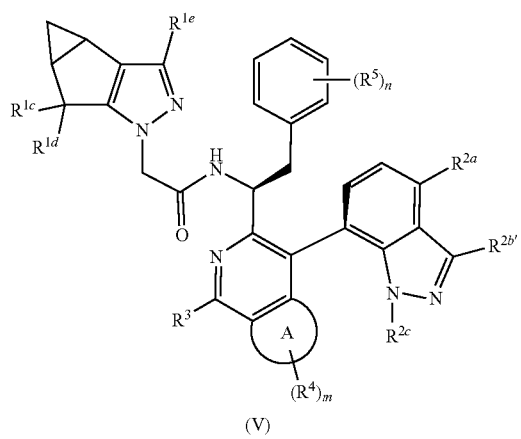

(V)

reacting a compound of general formula (IA) or a pharmaceutically acceptable salt thereof with a compound of general formula (IB) to give the compound of general formula (I) or the atropisomer, tautomer, mesomer, racemate, enantiomer, diastereomer thereof or the mixture thereof, or the pharmaceutically acceptable salt thereof, wherein, R is hydrogen or alkyl; and ring A, $L^1$, $L^2$, $R^1$-$R^5$, $R^{1a}$, $R^{1b}$, m and n are as defined in claim 1.

15. A method for preparing the compound of general formula (III-1a) or the atropisomer, tautomer, mesomer, racemate, enantiomer, diastereomer thereof or the mixture thereof, or the pharmaceutically acceptable salt thereof according to claim 6, comprising the following steps:

when $R^{2b'}$ in general formula (III-1A'a) and $R^{2b}$ in the final product are identical, subjecting a compound of general formula (III-1A'a) or a pharmaceutically acceptable salt thereof and a compound of general formula (IC) to a condensation reaction to give the compound of general formula (III-1a) or the atropisomer, tautomer, mesomer, racemate, enantiomer, diastereomer thereof or the mixture thereof, or the pharmaceutically acceptable salt thereof, wherein $R^{2b'}$ is selected from the group consisting of hydrogen, halogen, alkyl, alkenyl, alkynyl, alkoxy, haloalkyl, cyano, amino, nitro, hydroxy, hydroxyalkyl, cycloalkyl, heterocyclyl, aryl, heteroaryl, —$OR^6$, —$OC(O) R^6$, —$OC(O)NR^7R^8$, —$NHS(O)_rR^6$, —$NHS(O)_2OR^6$, —$NHS(O)_2NR^7R^8$, —$C(O)R^6$, —$C(O)OR^6$, —$C(O)NR^7R^8$, —$S(O)_rR^6$, —$S(O)_rNR^7R^8$, —$NR^7R^8$, —$NHC(O)R^6$, —$NHC(O)OR^6$, —$NHC(O)NR^7R^8$ and —$NHC(O)NHOR^6$;

when $R^{2b'}$ in general formula (III-1A'a) is

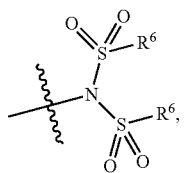

subjecting a compound of general formula (III-1A'a) or a pharmaceutically acceptable salt thereof and a compound of general formula (IC) to a condensation reaction, and meanwhile removing one —$S(O)_2R^6$ group to give the compound of general formula (III-1a) or the atropisomer, tautomer, mesomer, racemate, enantiomer, diastereomer thereof or the mixture thereof, or the pharmaceutically acceptable salt thereof,
wherein,
the pharmaceutically acceptable salt of the compound of general formula (III-1A'a) is hydrochloride;
R is hydrogen or alkyl; and
ring A, $R^{1c}$, $R^{1d}$, $R^{1e}$, $R^{2a}$, $R^{2b}$, $R^{2c}$, $R^3$, $R^4$, $R^5$, n and m are as defined in claim 6.

16. A pharmaceutical composition, comprising the compound of general formula (I) or the atropisomer, tautomer, mesomer, racemate, enantiomer, diastereomer thereof or the mixture thereof, or the pharmaceutically acceptable salt thereof according to claim 1, and one or more pharmaceutically acceptable carriers, diluents or excipients.

17. A method for inhibiting HIV capsid protein in a subject in need thereof, the method comprising administering to the subject an effective amount of the pharmaceutical composition according to claim 16.

18. A method for preventing and/or treating a viral infection disease in a subject in need thereof, the method comprising administering to the subject an effective amount of the pharmaceutical composition according to claim 16.

19. The method of claim 18, wherein the viral infection is an HIV infection.

* * * * *